US012668801B2

(12) United States Patent
Krishnamurthy et al.

(10) Patent No.: US 12,668,801 B2
(45) Date of Patent: *Jun. 30, 2026

(54) RNA-EDITING OLIGONUCLEOTIDES AND USES THEREOF

(71) Applicant: KORRO BIO, INC., Cambridge, MA (US)

(72) Inventors: Venkat Krishnamurthy, Holliston, MA (US); Christopher Brown, Ashland, MA (US); Tyson Moyer, Cambridge, MA (US); Mallikarjuna Reddy Putta, Lexington, MA (US); Mateusz Maciejewski, Boston, MA (US)

(73) Assignee: KORRO BIO, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/039,578

(22) Filed: Jan. 28, 2025

(65) Prior Publication Data

US 2025/0340876 A1 Nov. 6, 2025

Related U.S. Application Data

(63) Continuation of application No. PCT/US2024/038051, filed on Jul. 15, 2024.

(60) Provisional application No. 63/513,526, filed on Jul. 13, 2023.

(51) Int. Cl.
*C12N 15/113* (2010.01)
*A61K 9/51* (2006.01)
*C12N 15/88* (2006.01)

(52) U.S. Cl.
CPC .......... *C12N 15/113* (2013.01); *A61K 9/5123* (2013.01); *C12N 15/88* (2013.01); *C12N 2310/11* (2013.01); *C12N 2310/314* (2013.01); *C12N 2310/315* (2013.01); *C12N 2310/321* (2013.01); *C12N 2310/322* (2013.01)

(58) Field of Classification Search
CPC .............. C12N 15/113; C12N 2310/11; C12N 2310/346
See application file for complete search history.

(56) References Cited

U.S. PATENT DOCUMENTS

| | | | |
|---|---|---|---|
| 3,687,808 | A | 8/1972 | Merigan, Jr. et al. |
| 4,469,863 | A | 9/1984 | Ts'o et al. |
| 4,476,301 | A | 10/1984 | Imbach et al. |
| 4,587,044 | A | 5/1986 | Miller et al. |
| 4,605,735 | A | 8/1986 | Miyoshi et al. |
| 4,667,025 | A | 5/1987 | Miyoshi et al. |
| 4,683,202 | A | 7/1987 | Mullis |
| 4,762,779 | A | 8/1988 | Snitman |
| 4,789,737 | A | 12/1988 | Miyoshi et al. |
| 4,824,941 | A | 4/1989 | Gordon et al. |
| 4,828,979 | A | 5/1989 | Klevan et al. |
| 4,835,263 | A | 5/1989 | Nguyen et al. |
| 4,837,028 | A | 6/1989 | Allen |
| 4,845,205 | A | 7/1989 | Huynh Dinh et al. |
| 4,876,335 | A | 10/1989 | Yamane et al. |
| 4,897,355 | A | 1/1990 | Eppstein et al. |
| 4,904,582 | A | 2/1990 | Tullis |
| 4,948,882 | A | 8/1990 | Ruth |
| 4,958,013 | A | 9/1990 | Letsinger |
| 4,981,957 | A | 1/1991 | Lebleu et al. |
| 5,023,243 | A | 6/1991 | Tullis |
| 5,034,506 | A | 7/1991 | Summerton et al. |
| 5,082,830 | A | 1/1992 | Brakel et al. |
| 5,109,124 | A | 4/1992 | Ramachandran et al. |
| 5,112,963 | A | 5/1992 | Pieles et al. |
| 5,118,800 | A | 6/1992 | Smith et al. |
| 5,118,802 | A | 6/1992 | Smith et al. |
| 5,134,066 | A | 7/1992 | Rogers et al. |
| 5,138,045 | A | 8/1992 | Cook et al. |
| 5,166,315 | A | 11/1992 | Summerton et al. |
| 5,171,678 | A | 12/1992 | Behr et al. |
| 5,175,273 | A | 12/1992 | Bischofberger et al. |
| 5,177,195 | A | 1/1993 | Gregory et al. |
| 5,185,444 | A | 2/1993 | Summerton et al. |
| 5,188,897 | A | 2/1993 | Suhadolnik et al. |
| 5,214,134 | A | 5/1993 | Weis et al. |
| 5,214,136 | A | 5/1993 | Lin et al. |
| 5,216,141 | A | 6/1993 | Benner |
| 5,218,105 | A | 6/1993 | Cook et al. |
| 5,235,033 | A | 8/1993 | Summerton et al. |
| 5,245,022 | A | 9/1993 | Weis et al. |
| 5,254,469 | A | 10/1993 | Warren, III et al. |

(Continued)

FOREIGN PATENT DOCUMENTS

| | | | |
|---|---|---|---|
| WO | WO-88/04924 | A1 | 7/1988 |
| WO | WO-90/15065 | A1 | 12/1990 |

(Continued)

OTHER PUBLICATIONS

U.S. Appl. No. 19/051,812 (Krishnamurthy), filed Feb. 12, 2025 (Year: 2025).*

Sproat, Chemistry and applications of oligonucleotide analogues, J. Biotechnol., 41(2): 221-238, (Jul. 1995).

Monian et al., Endogenous ADAR-mediated RNA editing in non-human primates using stereopure chemically modified oligonucleotides, Nat. Biotechnol., 40(7): 1093-1102, (Mar. 2022).

Kandasamy et al., Control of backbone chemistry and chirality boost oligonucleotide splice switching activity, Nuc. Acids Res., 50(10): 5443-5466, (Jun. 2022).

Cook et al., Medicinal chemistry of antisense oligonucleotides-future opportunities, Anti-Canc. Drug Des., 6: 585-607, (Dec. 1991).

(Continued)

*Primary Examiner* — J. E. Angell
(74) *Attorney, Agent, or Firm* — MARSHALL, GERSTEIN & BORUN LLP

(57) ABSTRACT

The present disclosure features useful compositions and methods to treat disorders for which deamination of an adenosine in an RNA produces a therapeutic result in a subject in need thereof.

29 Claims, 22 Drawing Sheets

Specification includes a Sequence Listing.

(56) References Cited

U.S. PATENT DOCUMENTS

| | | | |
|---|---|---|---|
| 5,258,506 | A | 11/1993 | Urdea et al. |
| 5,262,536 | A | 11/1993 | Hobbs, Jr. |
| 5,264,423 | A | 11/1993 | Cohen et al. |
| 5,264,562 | A | 11/1993 | Matteucci |
| 5,264,564 | A | 11/1993 | Matteucci |
| 5,272,250 | A | 12/1993 | Spielvogel et al. |
| 5,276,019 | A | 1/1994 | Cohen et al. |
| 5,278,302 | A | 1/1994 | Caruthers et al. |
| 5,283,185 | A | 2/1994 | Epand et al. |
| 5,286,717 | A | 2/1994 | Cohen et al. |
| 5,292,873 | A | 3/1994 | Rokita et al. |
| 5,317,098 | A | 5/1994 | Shizuya et al. |
| 5,319,080 | A | 6/1994 | Leumann |
| 5,321,131 | A | 6/1994 | Agrawal et al. |
| 5,359,044 | A | 10/1994 | Cook et al. |
| 5,367,066 | A | 11/1994 | Urdea et al. |
| 5,371,241 | A | 12/1994 | Brush |
| 5,391,723 | A | 2/1995 | Priest |
| 5,393,878 | A | 2/1995 | Leumann |
| 5,399,676 | A | 3/1995 | Froehler |
| 5,405,938 | A | 4/1995 | Summerton et al. |
| 5,405,939 | A | 4/1995 | Suhadolnik et al. |
| 5,414,077 | A | 5/1995 | Lin et al. |
| 5,416,203 | A | 5/1995 | Letsinger |
| 5,432,272 | A | 7/1995 | Benner |
| 5,434,257 | A | 7/1995 | Matteucci et al. |
| 5,445,934 | A | 8/1995 | Fodor et al. |
| 5,446,137 | A | 8/1995 | Maag et al. |
| 5,451,463 | A | 9/1995 | Nelson et al. |
| 5,453,496 | A | 9/1995 | Caruthers et al. |
| 5,455,233 | A | 10/1995 | Spielvogel et al. |
| 5,457,187 | A | 10/1995 | Gmeiner et al. |
| 5,459,255 | A | 10/1995 | Cook et al. |
| 5,466,677 | A | 11/1995 | Baxter et al. |
| 5,466,786 | A | 11/1995 | Buhr et al. |
| 5,470,967 | A | 11/1995 | Huie et al. |
| 5,476,925 | A | 12/1995 | Letsinger et al. |
| 5,484,908 | A | 1/1996 | Froehler et al. |
| 5,486,603 | A | 1/1996 | Buhr |
| 5,489,677 | A | 2/1996 | Sanghvi et al. |
| 5,502,177 | A | 3/1996 | Matteucci et al. |
| 5,510,475 | A | 4/1996 | Agrawal et al. |
| 5,512,439 | A | 4/1996 | Hornes et al. |
| 5,512,667 | A | 4/1996 | Reed et al. |
| 5,514,785 | A | 5/1996 | Van Ness et al. |
| 5,519,126 | A | 5/1996 | Hecht |
| 5,519,134 | A | 5/1996 | Acevedo et al. |
| 5,525,465 | A | 6/1996 | Haralambidis et al. |
| 5,525,711 | A | 6/1996 | Hawkins et al. |
| 5,536,821 | A | 7/1996 | Agrawal et al. |
| 5,539,082 | A | 7/1996 | Nielsen et al. |
| 5,541,307 | A | 7/1996 | Cook et al. |
| 5,541,313 | A | 7/1996 | Ruth |
| 5,541,316 | A | 7/1996 | Engelskirchen et al. |
| 5,543,152 | A | 8/1996 | Webb et al. |
| 5,545,730 | A | 8/1996 | Urdea et al. |
| 5,550,111 | A | 8/1996 | Suhadolnik et al. |
| 5,552,538 | A | 9/1996 | Urdea et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,552 | A | 10/1996 | Magda et al. |
| 5,567,810 | A | 10/1996 | Weis et al. |
| 5,567,811 | A | 10/1996 | Misiura et al. |
| 5,571,799 | A | 11/1996 | Tkachuk et al. |
| 5,574,142 | A | 11/1996 | Meyer, Jr. et al. |
| 5,576,427 | A | 11/1996 | Cook et al. |
| 5,578,717 | A | 11/1996 | Urdea et al. |
| 5,578,718 | A | 11/1996 | Cook et al. |
| 5,580,731 | A | 12/1996 | Chang et al. |
| 5,585,481 | A | 12/1996 | Arnold, Jr. et al. |
| 5,587,361 | A | 12/1996 | Cook et al. |
| 5,587,371 | A | 12/1996 | Sessler et al. |
| 5,587,469 | A | 12/1996 | Cook et al. |
| 5,591,584 | A | 1/1997 | Chang et al. |
| 5,591,722 | A | 1/1997 | Montgomery et al. |
| 5,594,121 | A | 1/1997 | Froehler et al. |
| 5,595,726 | A | 1/1997 | Magda et al. |
| 5,596,086 | A | 1/1997 | Matteucci et al. |
| 5,597,696 | A | 1/1997 | Linn et al. |
| 5,597,909 | A | 1/1997 | Urdea et al. |
| 5,599,923 | A | 2/1997 | Sessler et al. |
| 5,599,928 | A | 2/1997 | Hemmi et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,610,300 | A | 3/1997 | Altmann et al. |
| 5,614,617 | A | 3/1997 | Cook et al. |
| 5,618,704 | A | 4/1997 | Sanghvi et al. |
| 5,623,070 | A | 4/1997 | Cook et al. |
| 5,627,053 | A | 5/1997 | Usman et al. |
| 5,633,360 | A | 5/1997 | Bischofberger et al. |
| 5,639,873 | A | 6/1997 | Barascut et al. |
| 5,646,265 | A | 7/1997 | McGee |
| 5,658,873 | A | 8/1997 | Bertsch-Frank et al. |
| 5,663,312 | A | 9/1997 | Chaturvedula |
| 5,670,633 | A | 9/1997 | Cook et al. |
| 5,677,195 | A | 10/1997 | Winkler et al. |
| 5,677,437 | A | 10/1997 | Teng et al. |
| 5,677,439 | A | 10/1997 | Weis et al. |
| 5,681,941 | A | 10/1997 | Cook et al. |
| 5,700,920 | A | 12/1997 | Altmann et al. |
| 5,714,331 | A | 2/1998 | Buchardt et al. |
| 5,719,262 | A | 2/1998 | Buchardt et al. |
| 5,744,305 | A | 4/1998 | Fodor et al. |
| 5,750,692 | A | 5/1998 | Cook et al. |
| 5,770,722 | A | 6/1998 | Lockhart et al. |
| 5,854,033 | A | 12/1998 | Lizardi |
| 5,874,219 | A | 2/1999 | Rava et al. |
| 5,976,567 | A | 11/1999 | Wheeler et al. |
| 5,981,501 | A | 11/1999 | Wheeler et al. |
| 6,015,886 | A | 1/2000 | Dale et al. |
| 6,028,188 | A | 2/2000 | Arnold, Jr. et al. |
| 6,124,445 | A | 9/2000 | Imbach et al. |
| 6,147,200 | A | 11/2000 | Manoharan et al. |
| 6,160,109 | A | 12/2000 | Just et al. |
| 6,166,197 | A | 12/2000 | Cook et al. |
| 6,169,170 | B1 | 1/2001 | Gryaznov et al. |
| 6,172,209 | B1 | 1/2001 | Manoharan et al. |
| 6,222,025 | B1 | 4/2001 | Cook et al. |
| 6,235,887 | B1 | 5/2001 | Froehler et al. |
| 6,239,265 | B1 | 5/2001 | Cook |
| 6,268,490 | B1 | 7/2001 | Imanishi et al. |
| 6,277,603 | B1 | 8/2001 | Cook |
| 6,294,664 | B1 | 9/2001 | Ravikumar et al. |
| 6,320,017 | B1 | 11/2001 | Ansell |
| 6,326,199 | B1 | 12/2001 | Cook et al. |
| 6,346,614 | B1 | 2/2002 | Metelev et al. |
| 6,380,368 | B1 | 4/2002 | Froehler et al. |
| 6,444,423 | B1 | 9/2002 | Meade et al. |
| 6,525,191 | B1 | 2/2003 | Ramasamy |
| 6,528,640 | B1 | 3/2003 | Beigelman et al. |
| 6,531,590 | B1 | 3/2003 | Manoharan et al. |
| 6,534,484 | B1 | 3/2003 | Wheeler et al. |
| 6,534,639 | B1 | 3/2003 | Manoharan et al. |
| 6,576,752 | B1 | 6/2003 | Manoharan et al. |
| 6,586,410 | B1 | 7/2003 | Wheeler et al. |
| 6,608,035 | B1 | 8/2003 | Agrawal et al. |
| 6,617,438 | B1 | 9/2003 | Beigelman et al. |
| 6,639,062 | B2 | 10/2003 | Manoharan et al. |
| 6,670,461 | B1 | 12/2003 | Wengel et al. |
| 6,683,167 | B2 | 1/2004 | Metelev et al. |
| 6,770,748 | B2 | 8/2004 | Imanishi et al. |
| 6,783,931 | B1 | 8/2004 | Cook et al. |
| 6,794,499 | B2 | 9/2004 | Wengel et al. |
| 6,815,432 | B2 | 11/2004 | Wheeler et al. |
| 6,858,225 | B2 | 2/2005 | Semple et al. |
| 6,858,715 | B2 | 2/2005 | Ravikumar et al. |
| 6,867,294 | B1 | 3/2005 | Sanghvi et al. |
| 6,878,805 | B2 | 4/2005 | Manoharan et al. |
| 6,900,297 | B1 | 5/2005 | Cook et al. |
| 6,998,484 | B2 | 2/2006 | Koch et al. |
| 7,015,315 | B1 | 3/2006 | Cook et al. |
| 7,034,133 | B2 | 4/2006 | Wengel et al. |

(56) References Cited

U.S. PATENT DOCUMENTS

| | | | |
|---|---|---|---|
| 7,037,646 | B1 | 5/2006 | Cook et al. |
| 7,041,816 | B2 | 5/2006 | Ravikumar et al. |
| 7,045,610 | B2 | 5/2006 | Dempcy et al. |
| 7,053,207 | B2 | 5/2006 | Wengel |
| 7,084,125 | B2 | 8/2006 | Wengel |
| RE39,464 | E | 1/2007 | Cook et al. |
| 7,273,933 | B1 | 9/2007 | Krotz et al. |
| 7,321,029 | B2 | 1/2008 | Gryaznov et al. |
| 7,399,845 | B2 | 7/2008 | Seth et al. |
| 7,427,605 | B2 | 9/2008 | Davis et al. |
| 7,427,672 | B2 | 9/2008 | Imanishi et al. |
| 7,495,088 | B1 | 2/2009 | Brakel et al. |
| 7,569,686 | B1 | 8/2009 | Bhat et al. |
| 7,741,457 | B2 | 6/2010 | Seth et al. |
| 8,022,193 | B2 | 9/2011 | Seth et al. |
| 8,030,467 | B2 | 10/2011 | Seth et al. |
| 8,058,069 | B2 | 11/2011 | Yaworski et al. |
| 8,106,022 | B2 | 1/2012 | Manoharan et al. |
| 8,158,601 | B2 | 4/2012 | Chen et al. |
| 8,278,283 | B2 | 10/2012 | Seth et al. |
| 8,278,425 | B2 | 10/2012 | Prakash et al. |
| 8,278,426 | B2 | 10/2012 | Seth et al. |
| 8,314,227 | B2 | 11/2012 | Wengel |
| 9,394,333 | B2 | 7/2016 | Wada et al. |
| 9,598,458 | B2 | 3/2017 | Shimizu et al. |
| 9,605,019 | B2 | 3/2017 | Verdine et al. |
| 9,744,183 | B2 | 8/2017 | Verdine et al. |
| 9,982,257 | B2 | 5/2018 | Butler et al. |
| 2004/0171570 | A1 | 9/2004 | Allerson et al. |
| 2006/0058255 | A1 | 3/2006 | Chen et al. |
| 2008/0039618 | A1 | 2/2008 | Allerson et al. |
| 2009/0012281 | A1 | 1/2009 | Swayze et al. |
| 2010/0324120 | A1 | 12/2010 | Chen et al. |
| 2011/0313020 | A1 | 12/2011 | Templin et al. |
| 2012/0157511 | A1 | 6/2012 | Manoharan et al. |
| 2013/0011922 | A1 | 1/2013 | Quay et al. |
| 2013/0096289 | A1 | 4/2013 | Wengel |
| 2013/0190383 | A1 | 7/2013 | Vaish et al. |
| 2013/0317086 | A1 | 11/2013 | Guire et al. |
| 2014/0135376 | A1 | 5/2014 | Engbersen et al. |
| 2014/0342003 | A1 | 11/2014 | Saltzman et al. |
| 2015/0174549 | A1 | 6/2015 | Lim et al. |
| 2015/0307554 | A1 | 10/2015 | Castillo Rodriguez |
| 2015/0335764 | A1 | 11/2015 | Martinez Fong |
| 2016/0230189 | A1 | 8/2016 | Kotha et al. |
| 2016/0251478 | A1 | 9/2016 | Saltzman et al. |
| 2016/0279256 | A1 | 9/2016 | Wang et al. |
| 2016/0369269 | A1 | 12/2016 | Shen et al. |
| 2017/0037399 | A1 | 2/2017 | . et al. |
| 2017/0121454 | A1 | 5/2017 | Saltzman et al. |
| 2018/0216107 | A1 | 8/2018 | Frank-Kamenetsky et al. |
| 2018/0216108 | A1 | 8/2018 | Vargeese et al. |

FOREIGN PATENT DOCUMENTS

| | | | |
|---|---|---|---|
| WO | WO-91/16024 | A1 | 10/1991 |
| WO | WO-93/24640 | A2 | 12/1993 |
| WO | WO-94/00569 | A1 | 1/1994 |
| WO | WO-96/37194 | A1 | 11/1996 |
| WO | WO-97/13499 | A1 | 4/1997 |
| WO | WO-98/39359 | A1 | 9/1998 |
| WO | WO-99/14226 | A2 | 3/1999 |
| WO | WO-00/03683 | A2 | 1/2000 |
| WO | WO-2008/042973 | A2 | 4/2008 |
| WO | WO-2009/086558 | A1 | 7/2009 |
| WO | WO-2009/088891 | A1 | 7/2009 |
| WO | WO-2011/005861 | A1 | 1/2011 |
| WO | WO-2012/177906 | A1 | 12/2012 |
| WO | WO-2013/036868 | A1 | 3/2013 |
| WO | WO-2014/066851 | A1 | 5/2014 |
| WO | WO-2014/179620 | A1 | 11/2014 |
| WO | WO-2014/179627 | A2 | 11/2014 |
| WO | WO-2017/062862 | A2 | 4/2017 |
| WO | WO-2017/160741 | A1 | 9/2017 |
| WO | WO-2017/192679 | A1 | 11/2017 |
| WO | WO-2017/210647 | A1 | 12/2017 |
| WO | WO-2018/022473 | A1 | 2/2018 |
| WO | WO-2018/041973 | A1 | 3/2018 |
| WO | WO-2018/067973 | A1 | 4/2018 |
| WO | WO-2018/098264 | A1 | 5/2018 |
| WO | WO-2018/195165 | A1 | 10/2018 |
| WO | WO-2018/223056 | A1 | 12/2018 |
| WO | WO-2018/223073 | A1 | 12/2018 |
| WO | WO-2018/223081 | A1 | 12/2018 |
| WO | WO-2018/237194 | A1 | 12/2018 |
| WO | WO-2019/032607 | A1 | 2/2019 |
| WO | WO-2019/032612 | A1 | 2/2019 |
| WO | WO-2019/055951 | A1 | 3/2019 |
| WO | WO-2019/075357 | A1 | 4/2019 |
| WO | WO-2019/200185 | A1 | 10/2019 |
| WO | WO-2019/217784 | A1 | 11/2019 |
| WO | WO-2020/154342 | A1 | 7/2020 |
| WO | WO-2020/191252 | A1 | 9/2020 |
| WO | WO-2021/071858 | A1 | 4/2021 |
| WO | WO-2021/243023 | A1 | 12/2021 |
| WO | WO-2023/278410 | A1 | 1/2023 |
| WO | WO-2024/200278 | A1 | 10/2024 |

OTHER PUBLICATIONS

International Search Report and Written Opinion for PCT Application No. PCT/US2024/038051 mailed Nov. 25, 2024.

Weiner et al., Liposomes: A Novel Topical Delivery System for Pharmaceutical and Cosmetic Applications, J. Drug Targeting, 2: 405-410 , (1994).

Aigner, Delivery systems for the direct application of siRNAs to induce RNA interference (RNAi) in vivo, J. Biomed. Biotechnol., 2006: 71659, (May 2006).

Allen et al., Large unilamellar liposomes with low uptake into the reticuloendothelial system, FEBS Letters, 223: 42-46, (Oct. 1987).

Arnold et al., Specific ß1-adrenergic receptor silencing with small interfering RNA lowers high blood pressure and improves cardiac function in myocardial ischemia, J. Hypertens., 25: 197-205, (2007).

Bangham et al., Diffusion of univalent ions across the lamellae of swollen phospholipids, M. Mol. Biol. 23: 238-252, (1965).

Barany, Genetic disease detection and DNA amplification using cloned thermostable ligase, Proc. Natl. Acad. Sci. USA, 88: 189-193, (Jan. 1991).

Berge et al., Pharmaceutical salts, J. Pharmaceutical Sci., 66:1-19, (Jan. 1977).

Bergstrom, Unnatural Nucleosides with Unusual Base Pairing Properties, Current Protocols in Nucleic Acid Chemistry, Suppl. 37: 1.4.1-1.4.32, (Jun. 2009).

Bonnet et al., Systemic delivery of DNA or siRNA mediated by linear polyethylenimine (L-PEI) does not induce an inflammatory response, Pharm. Res., 25(12): 2972-2082, (Dec. 2008).

Zhou et al., Fine Tuning of Electrostatics around the Internucleotidic Phosphate through Incorporation of Modified 2',4'-Carbocyclic-LNAs and -ENAs Leads to Significant Modulation of Antisense Properties, J. Org. Chem., 74: 118-134, (2009).

Chien et al., Novel cationic cardiolipin analogue-based liposome for efficient DNA and small interfering RNA delivery in vitro and in vivo, Cancer Gene Ther., 12: 321-328, (Mar. 2005).

Crooke et al., Pharmacokinetic properties of several novel oligonucleotide analogs in mice, J. Pharmacol. Exp. Ther., 277: 923-937, (May 1996).

Du Plessis et al., Topical delivery of liposomally encapsulated gamma-interferon, Antiviral Research, 18: 259-265, (Jun. 1992).

Eggington et al., Predicting sites of ADAR editing in double-stranded RNA, Nat. Commun., 319: 1-9, (May 2011).

Eifler et al., RNA-Seq Analysis Identifies a Novel Set of Editing Substrates for Human ADAR2 Present in *Saccharomyces cerevisiae*, Biochemistry, 52(45): 7857-7869, (Oct. 2013).

Englisch et al., Chemically modified oligonucleotides as probes and inhibitors, Angewandte Chemie, International Edition, 30(6): 613-722, (Jun. 1991).

Felgner et al., Enhanced gene delivery and mechanism studies with a novel series of cationic lipid formulations, J. Biol. Chem., 269: 2550-2561, (Jan. 1994).

(56) References Cited

OTHER PUBLICATIONS

Felgner et al., Lipofection: a highly efficient, lipid-mediated DNA-transfection procedure, Proc. Natl. Acad. Sci. USA, 84: 7413-7417, (1987).
Fluiter et al., Filling the gap in LNA antisense oligo gapmers: the effects of unlocked nucleic acid (UNA) and 4'-C-hydroxymethyl-DNA modifications on RNase H recruitment and efficacy of an LNA gapmer, Mol. Biosyst., 5: 838-843, (2009).
Fukunaga et al., Liposome entrapment enhances the hypocalcemic action of parenterally administered calcitonin, Endocrinol. 115(2): 757-761, (Aug. 1984).
Gabizon et al., Liposome formulations with prolonged circulation time in blood and enhanced uptake by tumors, Proc. Natl. Acad. Sci. U.S.A., 85(18): 6949-6953, (Sep. 1988).
Gao et al., A novel cationic liposome reagent for efficient transfection of mammalian cells, Biochem. Biophys. Res. Commun., 179(1): 280-285, (Aug. 1991).
Gershon et al., Mode of formation and structural features of DNA-cationic liposome complexes used for transfection, Biochem., 32(28): 7143-7151, (Jul. 1993).
Grunweller et al., Comparison of different antisense strategies in mammalian cells using locked nucleic acids, 2'-O-methyl RNA, phosphorothioates and small interfering RNA, Nucleic Acids Res., 31(12): 3185-3193, (2003).
Guatelli et al., Isothermal, in vitro amplification of nucleic acids by a multienzyme reaction modeled after retroviral replication, Proc. Natl. Acad. Sci. USA, 87: 1874-1878, (Mar. 1990).
Hirao et al., Natural versus Artificial Creation of Base Pairs in DNA: Origin of Nucleobases from the Perspectives of Unnatural Base Pair Studies, Acc. Chem. Res., 45(12): 2055-2065, (Jan. 2012).
Hu et al., (1994) S.T.P.Pharma. Sci., 4(6):466).
Itani et al., A simple and efficient liposome method for transfection of DNA into mammalian cells grown in suspension, Gene, 56(2-3): 267-276, (1987).
Kabanov et al., A new class of antivirals: antisense oligonucleotides combined with a hydrophobic substituent effectively inhibit influenza virus reproduction and synthesis of virus-specific proteins in MDCK cells, FEBS Lett., 259: 327-330, (Jan. 1990).
Kim et al., Preparation of multivesicular liposomes, Biochim. Biophys. Acta, 728(3): 339-348, (Mar. 1983).
Kubo et al., Distinct induction pathways of heat shock protein 27 in human keratinocytes: Heat stimulation or capsaicin through phosphorylation of heat shock factor 1 at serine 326 and/or suppression of ?Np63, Biochem. Biophys. Res. Comm., 365(1): 54-61, (2007).
Kwoh et al., Transcription-based amplification system and detection of amplified human immunodeficiency virus type 1 with a bead-based sandwich hybridization format, Proc. Natl. Acad. Sci. USA 86: 1173-1177, (Feb. 1989).
Letsinger et al., Cholesteryl-conjugated oligonucleotides: synthesis, properties, and activity as inhibitors of replication of human immunodeficiency virus in cell culture, Proc. Natl. Acad. Sci. USA, 86: 6553-6556, (Sep. 1989).
Liu, Radiolabeled multimeric cyclic RGD peptides as integrin alphavbeta3 targeted radiotracers for tumor imaging, Mol. Pharm., 3: 472-487, (Sep. 2006).
Lizardi et al., Exponential Amplification of Recombinant-RNA Hybridization Probes, Bio/Technol., 6: 1197-1202, (1988).
Mannino et al., Liposome mediated gene transfer, Biotechniques 6: 682-690, (1998).
Manoharan et al., Chemical modifications to improve uptake and bioavailability of antisense oligonucleotides, Ann. N.Y. Acad. Sci., 660: 306-309, (1992).
Manoharan et al., Introduction of a lipophilic thioether tether in the minor groove of nucleic acids for antisense applications, Biorg. Med. Chem. Let., 3(12): 2765-2770, (1993).
Manoharan et al., Cholic acid-oligonucleotide conjugates for antisense applications, Biorg. Med. Chem. Let., 4: 1053-1060, (Apr. 1994).
Manoharan et al., Oligonucleotide Conjugates: Alteration of the Pharmacokinetic Properties of Antisense Agents, Nucleosides & Nucleotides, 14(3-5): 969-973, (1995).
Manoharan et al., Lipidic nucleic acids, Tetrahedron Lett., 36(21): 3651-3654, (May 1995).
Martin et al., Ein neuer Zugang zu 2'-O-Alkylribonucleosiden und Eigenschaften deren Oligonucleotide, Helv. Chin. Acta, 78: 486-504, (Mar. 1995).
Mayer et al., Vesicles of variable sizes produced by a rapid extrusion procedure, Biochim. Biophys. Acta, 858: 161-168, (Jun. 1986).
Mayhew et al., Characterization of liposomes prepared using a microemulsifier, Biochim. Biophys. Acta, 775(2): 169-174, (Aug. 1984).
Mishra et al., Improved leishmanicidal effect of phosphorotioate antisense oligonucleotides by LDL-mediated delivery, Biochim. Biophys. Acta, 1264(2): 229-237, (Nov. 1995).
Nabel et al., Gene Transfer In Vivo with DNA-Liposome Complexes: Lack of Autoimmunity and Gonadal Localization, Human Gene Ther., 3: 649-656, (1992).
Nabel, Direct gene transfer with DNA-liposome complexes in melanoma: expression, biologic activity, and lack of toxicity in humans, Proc. Natl. Acad. Sci., 90: 11307-11311, (Dec. 1993).
Nicolau et al., Liposomes as carriers for in vivo gene transfer and expression, Meth. Enzymol. 149: 157-176, (1987).
Nielsen et al., Sequence-selective recognition of DNA by strand displacement with a thymine-substituted polyamid, Science, 254: 1497-1500, (1991).
Jensen et al., Unlocked nucleic acid (UNA) and UNA derivatives: Thermal denaturation studies, Nuc. Acids Symp. Series, 52(1): 133-134, (Sep. 2008).
Oberhauser et al., Effective incorporation of 2'-O-methyl-oligoribonuclectides into liposomes and enhanced cell association through modification with thiocholesterol, Nucl. Acids Res., 20(3): 533-538, (1992).
Olson et al., Preparation of liposomes of defined size distribution by extrusion through polycarbonate membranes, Biochim. Biophys. Acta, 557: 9-23, (1979).
Pal et al., Systemic delivery of RafsiRNA using cationic cardiolipin liposomes silences Raf-1 expression and inhibits tumor growth in xenograft model of human prostate cancer, Int. J. Oncol., 26: 1087-1091, (2005).
Saison-Behmoaras et al., Short modified antisense oligonucleotides directed against Ha-ras point mutation induce selective cleavage of the mRNA and inhibit T24 cells proliferation, EMBO J, 10(5): 1111-1118, (1991).
Shea et al., Synthesis, hybridization properties and antiviral activity of lipid-oligodeoxynucleotide conjugates, Nucl. Acids Res., 18(13): 3777-3783, (Jul. 1990).
Simeoni et al., Insight into the mechanism of the peptide-based gene delivery system MPG: implications for delivery of siRNA into mammalian cells, Nucl. Acids Res., 31: 2717-2724, (Jun. 2003).
Sorensen et al., Gene silencing by systemic delivery of synthetic siRNAs in adult mice, J. Mol. Biol., 327(4): 761-766, (Apr. 2003).
Straubinger et al., Liposomes as carriers for intracellular delivery of nucleic acids, Meth. Enzymol. 101: 512-527, (1983).
Strauss et al., Molecular complementation of a collagen mutation in mammalian cells using yeast artificial chromosomes, EMBO J., 11: 417-422, (Feb. 1992).
Summerton et al., Morpholino and phosphorothioate antisense oligomers compared in cell-free and in-cell systems, Antisense Nucleic Acid Drug Dev., 7: 63-70, (Apr. 1997).
Svinarchuk et al., Inhibition of HIV proliferation in MT-4 cells by antisense oligonucleotide conjugated to lipophilic groups, Biochimie, 75(1-2): 49-54, (1993).
Szoka et al., Procedure for preparation of liposomes with large internal aqueous space and high capture by reverse-phase evaporation, Proc. Natl. Acad. Sci., 75(9): 4194-4198, (Sep. 1978).
Tomalia et al., Dendrimers as multi-purpose nanodevices for oncology drug delivery and diagnostic imaging, Biochem. Soc. Trans., 35: 61-67, (2007).
Verma et al., Small interfering RNAs directed against beta-catenin inhibit the in vitro and in vivo growth of colon cancer cells, Clin. Cancer Res. 9: 1291-1300, (Apr. 2003).

(56) References Cited

OTHER PUBLICATIONS

Wang et al., Plasmid DNA adsorbed to pH-sensitive liposomes efficiently transforms the target cells, Biochem. Biophys. Res. Commun., 147: 980-985, (Sep. 1987).
Wang et al., Selective Recognition of RNA Substrates by ADAR Deaminase Domains, Biochemistry, 57(10): 1640-1651, (Mar. 2018).
Wang et al., pH-sensitive immunoliposomes mediate target-cell-specific delivery and controlled expression of a foreign gene in mouse, Proc. Natl. Acad. Sci. USA, 84: 7851-7855, (Nov. 1987).
Wu et al., Increased microvascular permeability contributes to preferential accumulation of Stealth liposomes in tumor tissue., Cancer Research, 53: 3765-3770, (Aug. 1993).
Yoo et al., PAMAM dendrimers as delivery agents for antisense oligonucleotide, Pharm. Res., 16: 1799-1804, (Dec. 1999).
Zhang et al., HELM: a hierarchical notation language for complex biomolecule structure representation, J. Chem. Inf. Model., 52(10): 2796-2806, (Oct. 2012).
Zhou et al., Targeted Delivery of DNA by Liposomes and Polymers, J. Controlled Release, 19:269-274, (Mar. 1992).
Zhou et al., Lipophilic polylysines mediate efficient DNA transfection in mammalian cells, Biochim. Biophys. Acta, 1065: 8-14, (May 1991).
Zimmermann et al., RNAi-mediated gene silencing in non-human primates, Nature, 441: 111-114, (May 2006).

* cited by examiner

A

SEQ ID NO: 1
SEQ ID NO: 3
SEQ ID NO: 4

B

Mesyl Phosphoramidate (PA-1)

C

| | % Editing (B601) | | |
|---|---|---|---|
| Oligo # | Day-1 | Day-4 | Day-7 |
| 1 | 45.5 | 22.7 | 15.6 |
| 2 | 40.3 | 22.8 | 14 |
| 3 | 55.3 | 62.5 | 41.3 |

| Oligo # | % Editing (B586) Day-1 | Day-4 |
|---|---|---|
| 4 | 28.7 | 20.4 |
| 5 | 23.4 | 23 |
| 6 | 48.5 | 43.3 |

| B433 | % Editing (FU) | | % Editing (LPO) | |
|---|---|---|---|---|
| | 100 nM | 1000 nM | 100 nM | 1000 nM |
| #7 | 16 | 19 | 39 | 50 |
| #8 | 3 | 7 | 14 | 32 |
| #9 | 3 | 6 | 31 | 41 |
| #10 | 1 | 1 | 11 | 16 |

B

A

| | # | Compound ID | 5' C | 5' L | -29 | -28 | -27 | -26 | -25 | -24 | -23 | -22 | -21 | -20 | -19 | -18 |
|---|---|---|---|---|---|---|---|---|---|---|---|---|---|---|---|---|
| SEQ ID NO: 20 | 1 | #15 | TriGal... | P | | | | | | | C | C | C | A | G | [illegible] |

B

| | # | Compound ID | 5' C | 5' L | -29 | -28 | -27 | -26 | -25 | -24 | -23 | -22 | -21 | -20 | -19 | -18 |
|---|---|---|---|---|---|---|---|---|---|---|---|---|---|---|---|---|
| SEQ ID NO: 62 | | #40 | TriGal... | P | | | | | | | C | C | C | A | G | [illegible] |
| SEQ ID NO: 63 | | #41 | TriGal... | P | | | | | | | C | C | C | A | G | [illegible] |
| SEQ ID NO: 64 | | #42 | TriGal... | P | | | | | | | C | C | C | A | G | [illegible] |
| SEQ ID NO: 65 | | #43 | TriGal... | P | | | | | | | C | C | C | A | G | [illegible] |
| SEQ ID NO: 66 | | #44 | TriGal... | P | | | | | | | C | C | C | A | G | [illegible] |
| SEQ ID NO: 67 | | #45 | TriGal... | P | | | | | | | C | C | C | A | G | [illegible] |
| SEQ ID NO: 68 | | #46 | TriGal... | P | | | | | | | C | C | C | A | G | [illegible] |
| SEQ ID NO: 69 | | #47 | TriGal... | P | | | | | | | C | C | C | A | G | [illegible] |
| SEQ ID NO: 70 | | #48 | TriGal... | P | | | | | | | C | C | C | A | G | [illegible] |
| SEQ ID NO: 71 | | #49 | TriGal... | P | | | | | | | C | C | C | A | G | [illegible] |
| SEQ ID NO: 72 | | #50 | TriGal... | P | | | | | | | C | C | C | A | G | [illegible] |
| SEQ ID NO: 73 | | #51 | TriGal... | P | | | | | | | C | C | C | A | G | [illegible] |
| SEQ ID NO: 74 | | #52 | TriGal... | P | | | | | | | C | C | C | A | G | [illegible] |
| SEQ ID NO: 75 | | #53 | TriGal... | P | | | | | | | C | C | C | A | G | [illegible] |
| SEQ ID NO: 76 | | #54 | TriGal... | P | | | | | | | C | C | C | A | G | [illegible] |
| SEQ ID NO: 77 | | #55 | TriGal... | P | | | | | | | C | C | C | A | G | [illegible] |
| SEQ ID NO: 78 | | #56 | TriGal... | P | | | | | | | C | C | C | A | G | [illegible] |
| SEQ ID NO: 79 | | #57 | TriGal... | P | | | | | | | C | C | C | A | G | [illegible] |
| SEQ ID NO: 80 | | #58 | TriGal... | P | | | | | | | C | C | C | A | G | [illegible] |
| SEQ ID NO: 81 | | #59 | TriGal... | P | | | | | | | C | C | C | A | G | [illegible] |
| SEQ ID NO: 82 | | #60 | TriGal... | P | | | | | | | C | C | C | A | G | [illegible] |

| | # | Compound ID | 5' C | 5' L | -29 | -28 | -27 | -26 | -25 | -24 | -23 | -22 | -21 | -20 | -19 | -18 | -17 |
|---|---|---|---|---|---|---|---|---|---|---|---|---|---|---|---|---|---|
| SEQ ID NO: 83 | | #61 | TriGal... | P | | | | | | | C | C | C | A | G | [illegible] | A |
| SEQ ID NO: 84 | | #62 | TriGal... | P | | | | | | | C | C | C | A | G | [illegible] | A |
| SEQ ID NO: 85 | | #63 | TriGal... | P | | | | | | | C | C | C | A | G | C | A |
| SEQ ID NO: 86 | | #64 | TriGal... | P | | | | | | | C | C | C | A | G | [illegible] | A |
| SEQ ID NO: 87 | | #65 | TriGal... | P | | | | | | | C | C | C | A | G | [illegible] | A |
| SEQ ID NO: 88 | | #66 | TriGal... | P | | | | | | | C | C | C | A | G | [illegible] | A |
| SEQ ID NO: 89 | | #67 | TriGal... | P | | | | | | | C | C | C | A | G | [illegible] | A |
| SEQ ID NO: 90 | | #68 | TriGal... | P | | | | | | | C | C | C | A | G | [illegible] | A |
| SEQ ID NO: 91 | | #69 | TriGal... | P | | | | | | | C | C | C | A | G | [illegible] | A |
| SEQ ID NO: 92 | | #70 | TriGal... | P | | | | | | | C | C | C | A | G | [illegible] | A |
| SEQ ID NO: 93 | | #71 | TriGal... | P | | | | | | | C | C | C | A | G | [illegible] | A |
| SEQ ID NO: 94 | | #72 | TriGal... | P | | | | | | | C | C | C | A | G | [illegible] | A |
| SEQ ID NO: 95 | | #73 | TriGal... | P | | | | | | | C | C | C | A | G | [illegible] | A |
| SEQ ID NO: 96 | | #74 | TriGal... | P | | | | | | | C | C | C | A | G | [illegible] | A |
| SEQ ID NO: 98 | | #75 | TriGal... | P | | | | | | | C | C | C | A | G | [illegible] | A |
| SEQ ID NO: 100 | | #76 | TriGal... | P | | | | | | | C | C | C | A | G | [illegible] | A |
| SEQ ID NO: 101 | | #77 | TriGal... | P | | | | | | | C | C | C | A | G | [illegible] | A |
| SEQ ID NO: 102 | | #78 | TriGal... | P | | | | | | | C | C | C | A | G | C | A |
| SEQ ID NO: 103 | | #79 | TriGal... | P | | | | | | | C | C | C | A | G | [illegible] | A |
| SEQ ID NO: 104 | | #80 | TriGal... | P | | | | | | | C | C | C | A | G | [illegible] | A |
| SEQ ID NO: 105 | | #81 | TriGal... | P | | | | | | | C | C | C | A | G | [illegible] | A |
| SEQ ID NO: 107 | | #82 | TriGal... | P | | | | | | | C | C | C | A | G | C | A |

FIG. 8

SEQUENCE LISTING

```
Sequence total quantity: 309
SEQ ID NO: 1            moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotide
modified_base           33
                        mod_base = i
modified_base           order(1..2,4..12,14..18,21..35,39..41)
                        mod_base = OTHER
                        note = Phosphorothioate internucleoside linkage
modified_base           order(3,13,19..20,36..38)
                        mod_base = OTHER
                        note = Phosphate internucleoside linkage
SEQUENCE: 1
aacatggccc cagcagcttc agtccctttc tcntcgatgg tc                42

SEQ ID NO: 2            moltype = RNA  length = 42
FEATURE                 Location/Qualifiers
source                  1..42
                        mol_type = other RNA
                        organism = synthetic construct
modified_base           33
                        mod_base = i
modified_base           31
                        mod_base = OTHER
                        note = Thymidine
SEQUENCE: 2
aacatggccc cagcagcttc agtccctttc tcntcgatgg tc                42

SEQ ID NO: 3            moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
```

-continued

```
modified_base          order(1,2,5..8,10,12,15,16,18,22,23,25..27,29,35,40,41)
                       mod_base = OTHER
                       note = 2-Prime-deoxy-2-Prime-fluororibose nucleotides
modified_base          31
                       mod_base = OTHER
                       note = Deoxyribose Thymidine
modified_base          32
                       mod_base = OTHER
                       note = Beta-homoDNA
modified_base          33
                       mod_base = OTHER
                       note = 2-Prime-fluroarabinose nucleotides
modified_base          33
                       mod_base = i
modified_base          32
                       mod_base = OTHER
                       note = Mesyl phosphroamidate internucleoside linkage
modified_base          order(1..2,4..12,14..18,21..31,33..35,39..41)
                       mod_base = OTHER
                       note = Phosphorothioate internucleoside linkage
modified_base          order(3,13,19..20,36..38)
                       mod_base = OTHER
                       note = Phosphate internucleoside linkage
SEQUENCE: 3
aacatggccc cagcagcttc agtcccttc tcntcgatgg tc                     42

SEQ ID NO: 4           moltype = RNA  length = 42
FEATURE                Location/Qualifiers
source                 1..42
                       mol_type = other RNA
                       organism = synthetic construct
modified_base          order(3,4,9,11,13,14,17,19..21,24,28,30,34,36..39,42)
                       mod_base = OTHER
                       note = 2-Prime-methoxyribose nucleotides
modified_base          order(1,2,5..8,10,12,15,16,18,22,23,25..27,29,35,40,41)
                       mod_base = OTHER
                       note = 2-Prime-deoxy-2-Prime-fluororibose nucleotides
modified_base          31
                       mod_base = OTHER
                       note = Deoxyribose Thymidine
modified_base          32
                       mod_base = OTHER
                       note = Beta-homoDNA
modified_base          33
                       mod_base = i
modified_base          33
                       mod_base = OTHER
                       note = 2-Prime-fluroarabinose nucleotides
modified_base          order(1,21,23,33,41)
                       mod_base = OTHER
                       note = Mesyl phosphroamidate internucleoside linkage
modified_base          order(2,4..12,14..18,22,24..32,34..35,39..40)
                       mod_base = OTHER
                       note = Phosphorothioate internucleoside linkage
modified_base          order(3,13,19..20,36..38)
                       mod_base = OTHER
                       note = Phosphate internucleoside linkage
SEQUENCE: 4
aacatggccc cagcagcttc agtcccttc tcntcgatgg tc                     42

SEQ ID NO: 5           moltype = RNA  length = 30
FEATURE                Location/Qualifiers
source                 1..30
                       mol_type = other RNA
                       organism = synthetic construct
modified_base          order(1,4,5,7,9,12..14,17,20,21,23,27,29,30)
                       mod_base = OTHER
                       note = 2-Prime-methoxyribose nucleotides
modified_base          order(2,3,6,8,10,11,15,16,18,19,22,28)
                       mod_base = OTHER
                       note = 2-Prime-deoxy-2-Prime-fluororibose nucleotides
modified_base          24
                       mod_base = OTHER
                       note = Deoxyribose Thymidine
modified_base          25
                       mod_base = OTHER
                       note = Beta-homoDNA
modified_base          26
                       mod_base = i
```

```
modified_base          26
                       mod_base = OTHER
                       note = Deoxyribose
modified_base          order(1,14,16,26,29)
                       mod_base = OTHER
                       note = Mesyl phosphroamidate internucleoside linkage
modified_base          order(2..3,6,8,10..11,15,18..19,22,24..25,28)
                       mod_base = OTHER
                       note = Phosphorothioate internucleoside linkage
modified_base          order(4..5,7,9,12..13,17,20..21,23,27)
                       mod_base = OTHER
                       note = Phosphate internucleoside linkage
SEQUENCE: 5
ccccagcagc ttcagtccct ttctcntcga                                   30

SEQ ID NO: 6           moltype = RNA  length = 30
FEATURE                Location/Qualifiers
source                 1..30
                       mol_type = other RNA
                       organism = synthetic construct
modified_base          26
                       mod_base = i
modified_base          24
                       mod_base = OTHER
                       note = Thymidine
SEQUENCE: 6
ccccagcagc ttcagtccct ttctcntcga                                   30

SEQ ID NO: 7           moltype = RNA  length = 30
FEATURE                Location/Qualifiers
source                 1..30
                       mol_type = other RNA
                       organism = synthetic construct
modified_base          order(5,6,8,9,14,15,29,30)
                       mod_base = OTHER
                       note = 2-Prime-methoxyribose nucleotides
modified_base          order(1..4,7,10..13,16..23,27,28)
                       mod_base = OTHER
                       note = 2-Prime-deoxy-2-Prime-fluororibose nucleotides
modified_base          24
                       mod_base = OTHER
                       note = Deoxyribose Thymidine
modified_base          25
                       mod_base = OTHER
                       note = Beta-homoDNA
modified_base          26
                       mod_base = i
modified_base          26
                       mod_base = OTHER
                       note = Deoxyribose
modified_base          order(1,14,16,26,29)
                       mod_base = OTHER
                       note = Mesyl phosphroamidate internucleoside linkage
modified_base          order(2..13,15,17..25,27..28)
                       mod_base = OTHER
                       note = Phosphorothioate internucleoside linkage
SEQUENCE: 7
ccccagcagc ttcagtccct ttctcntcga                                   30

SEQ ID NO: 8           moltype = RNA  length = 30
FEATURE                Location/Qualifiers
source                 1..30
                       mol_type = other RNA
                       organism = synthetic construct
modified_base          order(1,5,9,13,17,21,27,29,30)
                       mod_base = OTHER
                       note = 2-Prime-methoxyribose nucleotides
modified_base          order(2..4,6..8,10..12,14..16,18..20,22..24,28)
                       mod_base = OTHER
                       note = 2-Prime-deoxy-2-Prime-fluororibose nucleotides
modified_base          25
                       mod_base = OTHER
                       note = Beta-homoDNA
modified_base          26
                       mod_base = OTHER
                       note = Deoxyribose
modified_base          26
                       mod_base = i
modified_base          order(1,14,16,26,29)
```

```
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 8
ccccagcagc ttcagtccct ttctcntcga                                    30

SEQ ID NO: 9            moltype = RNA  length = 30
FEATURE                 Location/Qualifiers
source                  1..30
                        mol_type = other RNA
                        organism = synthetic construct
modified_base           26
                        mod_base = i
SEQUENCE: 9
ccccagcagc ttcagtccct ttctcntcga                                    30

SEQ ID NO: 10           moltype = RNA  length = 30
FEATURE                 Location/Qualifiers
source                  1..30
                        mol_type = other RNA
                        organism = synthetic construct
modified_base           order(1..15,24)
                        mod_base = OTHER
                        note = 2-Prime-deoxy-2-Prime-fluororibose nucleotides
modified_base           order(16..23,27..30)
                        mod_base = OTHER
                        note = 2-Prime-methoxyribose nucleotides
modified_base           25..26
                        mod_base = OTHER
                        note = Deoxyribose
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 10
acataattta cacgaaagca atgccatcac                                    30

SEQ ID NO: 11           moltype = RNA  length = 30
FEATURE                 Location/Qualifiers
source                  1..30
                        mol_type = other RNA
                        organism = synthetic construct
SEQUENCE: 11
acataattta cacgaaagca atgccatcac                                    30

SEQ ID NO: 12           moltype = RNA  length = 30
FEATURE                 Location/Qualifiers
source                  1..30
                        mol_type = other RNA
                        organism = synthetic construct
modified_base           order(16..23,27..30)
                        mod_base = OTHER
                        note = 2-Prime-methoxyribose nucleotides
modified_base           order(1..15,24)
                        mod_base = OTHER
                        note = 2-Prime-deoxy-2-Prime-fluororibose nucleotides
modified_base           25..26
                        mod_base = OTHER
                        note = Deoxyribose
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
modified_base           30
                        mod_base = OTHER
                        note = Phosphate internucleoside linkage
SEQUENCE: 12
acataattta cacgaaagca atgccatcac                                    30

SEQ ID NO: 13           moltype = RNA  length = 30
FEATURE                 Location/Qualifiers
source                  1..30
                        mol_type = other RNA
```

```
                         organism = synthetic construct
modified_base            order(1..15,24)
                         mod_base = OTHER
                         note = 2-Prime-deoxy-2-Prime-fluororibose nucleotides
modified_base            order(16..23,27..30)
                         mod_base = OTHER
                         note = 2-Prime-methoxyribose nucleotides
modified_base            25..26
                         mod_base = OTHER
                         note = Deoxyribose
modified_base            1..29
                         mod_base = OTHER
                         note = Phosphorothioate internucleoside linkage
SEQUENCE: 13
acataattta cacgaaagca atgccatcac                                   30

SEQ ID NO: 14            moltype = RNA  length = 30
FEATURE                  Location/Qualifiers
source                   1..30
                         mol_type = other RNA
                         organism = synthetic construct
modified_base            order(1..15,24)
                         mod_base = OTHER
                         note = 2-Prime-deoxy-2-Prime-fluororibose nucleotides
modified_base            order(16..23,27..30)
                         mod_base = OTHER
                         note = 2-Prime-methoxyribose nucleotides
modified_base            25..26
                         mod_base = OTHER
                         note = Deoxyribose
modified_base            1..29
                         mod_base = OTHER
                         note = Phosphorothioate internucleoside linkage
modified_base            30
                         mod_base = OTHER
                         note = Phosphate internucleoside linkage
SEQUENCE: 14
acataattta cacgaaagca atgccatcac                                   30

SEQ ID NO: 15            moltype = RNA  length = 30
FEATURE                  Location/Qualifiers
source                   1..30
                         mol_type = other RNA
                         organism = synthetic construct
modified_base            order(1..15,24)
                         mod_base = OTHER
                         note = 2-Prime-deoxy-2-Prime-fluororibose nucleotides
modified_base            order(16..23,27..30)
                         mod_base = OTHER
                         note = 2-Prime-methoxyribose nucleotides
modified_base            25..26
                         mod_base = OTHER
                         note = Deoxyribose
modified_base            order(1,14,16,26,29)
                         mod_base = OTHER
                         note = Mesyl phosphroamidate internucleoside linkage
modified_base            order(2..13,15,17..25,27..28)
                         mod_base = OTHER
                         note = Phosphorothioate internucleoside linkage
SEQUENCE: 15
gtctactgta cagaatactg ccgccagctg                                   30

SEQ ID NO: 16            moltype = RNA  length = 30
FEATURE                  Location/Qualifiers
source                   1..30
                         mol_type = other RNA
                         organism = synthetic construct
SEQUENCE: 16
gtctactgta cagaatactg ccgccagctg                                   30

SEQ ID NO: 17            moltype = RNA  length = 30
FEATURE                  Location/Qualifiers
source                   1..30
                         mol_type = other RNA
                         organism = synthetic construct
modified_base            order(1..15,24)
                         mod_base = OTHER
                         note = 2-Prime-deoxy-2-Prime-fluororibose nucleotides
modified_base            order(16..23,27..30)
```

```
                         mod_base = OTHER
                         note = 2-Prime-methoxyribose nucleotides
modified_base            25..26
                         mod_base = OTHER
                         note = Deoxyribose
modified_base            order(1,14,16,26,29)
                         mod_base = OTHER
                         note = Mesyl phosphroamidate internucleoside linkage
modified_base            order(2..13,15,17..25,27..28)
                         mod_base = OTHER
                         note = Phosphorothioate internucleoside linkage
modified_base            30
                         mod_base = OTHER
                         note = Phosphate internucleoside linkage
SEQUENCE: 17
gtctactgta cagaatactg ccgccagctg                                   30

SEQ ID NO: 18            moltype = RNA  length = 30
FEATURE                  Location/Qualifiers
source                   1..30
                         mol_type = other RNA
                         organism = synthetic construct
modified_base            order(1..15,24)
                         mod_base = OTHER
                         note = 2-Prime-deoxy-2-Prime-fluororibose nucleotides
modified_base            order(16..23,27..30)
                         mod_base = OTHER
                         note = 2-Prime-methoxyribose nucleotides
modified_base            25..26
                         mod_base = OTHER
                         note = Deoxyribose
modified_base            1..29
                         mod_base = OTHER
                         note = Phosphorothioate internucleoside linkage
SEQUENCE: 18
gtctactgta cagaatactg ccgccagctg                                   30

SEQ ID NO: 19            moltype = RNA  length = 30
FEATURE                  Location/Qualifiers
source                   1..30
                         mol_type = other RNA
                         organism = synthetic construct
modified_base            order(1..15,24)
                         mod_base = OTHER
                         note = 2-Prime-deoxy-2-Prime-fluororibose nucleotides
modified_base            order(16..23,27..30)
                         mod_base = OTHER
                         note = 2-Prime-methoxyribose nucleotides
modified_base            25..26
                         mod_base = OTHER
                         note = Deoxyribose
modified_base            1..29
                         mod_base = OTHER
                         note = Phosphorothioate internucleoside linkage
modified_base            30
                         mod_base = OTHER
                         note = Phosphate internucleoside linkage
SEQUENCE: 19
gtctactgta cagaatactg ccgccagctg                                   30

SEQ ID NO: 20            moltype = RNA  length = 30
FEATURE                  Location/Qualifiers
source                   1..30
                         mol_type = other RNA
                         organism = synthetic construct
modified_base            order(1..3,12,14,16,26,28..30)
                         mod_base = OTHER
                         note = 2-Prime-methoxyribose nucleotides
modified_base            order(4,5,8,9,11,13,15,17..19,22,27)
                         mod_base = OTHER
                         note = 2-Prime-deoxy-2-Prime-fluororibose nucleotides
modified_base            order(6,7,10,20,21)
                         mod_base = OTHER
                         note = 2-Prime-MOEribose nucleotides
modified_base            order(10,20,21,23)
                         mod_base = OTHER
                         note = Thymidine
modified_base            23
                         mod_base = OTHER
```

-continued

```
                      note = Deoxyribose Thymidine
modified_base         24
                      mod_base = OTHER
                      note = Beta-homoDNA
modified_base         25
                      mod_base = OTHER
                      note = Deoxyribose
modified_base         25
                      mod_base = i
modified_base         order(1,11,14,25,29)
                      mod_base = OTHER
                      note = Mesyl phosphroamidate internucleoside linkage
modified_base         order(2..5,8..9,13,16..19,22..24,27..28)
                      mod_base = OTHER
                      note = Phosphorothioate internucleoside linkage
modified_base         order(6..7,10,12,15,20..21,26)
                      mod_base = OTHER
                      note = Phosphate internucleoside linkage
modified_base         6
                      mod_base = m5c
SEQUENCE: 20
cccagnagct tcagtccctt tctcntcgat                                   30

SEQ ID NO: 21         moltype = RNA  length = 29
FEATURE               Location/Qualifiers
source                1..29
                      mol_type = other RNA
                      organism = synthetic construct
modified_base         24
                      mod_base = i
modified_base         order(9,19,20,22)
                      mod_base = OTHER
                      note = Thymidine
SEQUENCE: 21
cccagagctt cagtcccttt ctcntcgat                                    29

SEQ ID NO: 22         moltype = RNA  length = 29
FEATURE               Location/Qualifiers
source                1..29
                      mol_type = other RNA
                      organism = synthetic construct
modified_base         order(1..3,12,14,16,26,28,29)
                      mod_base = OTHER
                      note = 2-Prime-methoxyribose nucleotides
modified_base         order(4,5,8,9,11,13,15,17..19,22,27)
                      mod_base = OTHER
                      note = 2-Prime-deoxy-2-Prime-fluororibose nucleotides
modified_base         order(6,7,10,20,21)
                      mod_base = OTHER
                      note = 2-Prime-MOEribose nucleotides
modified_base         order(10,20,21,23)
                      mod_base = OTHER
                      note = Thymidine
modified_base         24
                      mod_base = OTHER
                      note = Beta-homoDNA
modified_base         25
                      mod_base = OTHER
                      note = Deoxyribose
modified_base         25
                      mod_base = i
modified_base         order(1,11,14,25,28)
                      mod_base = OTHER
                      note = Mesyl phosphroamidate internucleoside linkage
modified_base         order(2..5,8..9,13,16..19,22..24,27)
                      mod_base = OTHER
                      note = Phosphorothioate internucleoside linkage
modified_base         order(6..7,10,12,15,20..21,26)
                      mod_base = OTHER
                      note = Phosphate internucleoside linkage
modified_base         6
                      mod_base = m5c
SEQUENCE: 22
cccagnagct tcagtccctt tctcntcga                                    29

SEQ ID NO: 23         moltype = RNA  length = 28
FEATURE               Location/Qualifiers
source                1..28
                      mol_type = other RNA
```

-continued

```
                         organism = synthetic construct
modified_base            24
                         mod_base = i
modified_base            order(9,19,20,22)
                         mod_base = OTHER
                         note = Thymidine
SEQUENCE: 23
cccagagctt cagtcccttt ctcntcga                                     28

SEQ ID NO: 24            moltype = RNA  length = 28
FEATURE                  Location/Qualifiers
source                   1..28
                         mol_type = other RNA
                         organism = synthetic construct
modified_base            order(1..3,12,14,16,26,28)
                         mod_base = OTHER
                         note = 2-Prime-methoxyribose nucleotides
modified_base            order(4,5,8,9,11,13,15,17..19,22,27)
                         mod_base = OTHER
                         note = 2-Prime-deoxy-2-Prime-fluororibose nucleotides
modified_base            order(6,7,10,20,21)
                         mod_base = OTHER
                         note = 2-Prime-MOEribose nucleotides
modified_base            order(10,20,21,23)
                         mod_base = OTHER
                         note = Thymidine
modified_base            24
                         mod_base = OTHER
                         note = Beta-homoDNA
modified_base            25
                         mod_base = OTHER
                         note = Deoxyribose
modified_base            25
                         mod_base = i
modified_base            order(1,11,14,25,27)
                         mod_base = OTHER
                         note = Mesyl phosphroamidate internucleoside linkage
modified_base            order(2..5,8..9,13,16..19,22..24,26)
                         mod_base = OTHER
                         note = Phosphorothioate internucleoside linkage
modified_base            order(6..7,10,12,15,20..21)
                         mod_base = OTHER
                         note = Phosphate internucleoside linkage
modified_base            6
                         mod_base = m5c
SEQUENCE: 24
cccagnagct tcagtccctt tctcntcg                                     28

SEQ ID NO: 25            moltype = RNA  length = 27
FEATURE                  Location/Qualifiers
source                   1..27
                         mol_type = other RNA
                         organism = synthetic construct
modified_base            order(9,19,20,22)
                         mod_base = OTHER
                         note = Thymidine
modified_base            24
                         mod_base = i
SEQUENCE: 25
cccagagctt cagtcccttt ctcntcg                                      27

SEQ ID NO: 26            moltype = RNA  length = 36
FEATURE                  Location/Qualifiers
source                   1..36
                         mol_type = other RNA
                         organism = synthetic construct
modified_base            order(1..9,18,20,22,32,34..36)
                         mod_base = OTHER
                         note = 2-Prime-methoxyribose nucleotides
modified_base            order(10,11,14,15,17,19,21,23..25,28,33)
                         mod_base = OTHER
                         note = 2-Prime-deoxy-2-Prime-fluororibose nucleotides
modified_base            order(12,13,16,26,27)
                         mod_base = OTHER
                         note = 2-Prime-MOEribose nucleotides
modified_base            12
                         mod_base = OTHER
                         note = m5c
modified_base            order(16,26,27)
```

-continued

```
                          mod_base = OTHER
                          note = Thymidine
modified_base             29
                          mod_base = OTHER
                          note = Deoxyribose Thymidine
modified_base             30
                          mod_base = OTHER
                          note = Beta-homoDNA
modified_base             31
                          mod_base = OTHER
                          note = Deoxyribose
modified_base             31
                          mod_base = i
modified_base             order(1,17,20,31,35)
                          mod_base = OTHER
                          note = Mesyl phosphroamidate internucleoside linkage
modified_base             order(2..4,10..11,14..15,19,22..25,28..30,33..34)
                          mod_base = OTHER
                          note = Phosphorothioate internucleoside linkage
modified_base             order(5..9,12..13,16,18,21,26..27,32)
                          mod_base = OTHER
                          note = Phosphate internucleoside linkage
SEQUENCE: 26
catggcccca gnagcttcag tccctttctc ntcgat                           36

SEQ ID NO: 27             moltype = RNA  length = 35
FEATURE                   Location/Qualifiers
source                    1..35
                          mol_type = other RNA
                          organism = synthetic construct
modified_base             30
                          mod_base = i
modified_base             order(15,25,26,28)
                          mod_base = OTHER
                          note = Thymidine
SEQUENCE: 27
catggcccca gagcttcagt ccctttctcn tcgat                            35

SEQ ID NO: 28             moltype = RNA  length = 35
FEATURE                   Location/Qualifiers
source                    1..35
                          mol_type = other RNA
                          organism = synthetic construct
modified_base             order(1..8,17,19,21,31,33..35)
                          mod_base = OTHER
                          note = 2-Prime-methoxyribose nucleotides
modified_base             order(9,10,13,14,16,18,20,22..24,27,32)
                          mod_base = OTHER
                          note = 2-Prime-deoxy-2-Prime-fluororibose nucleotides
modified_base             order(11,12,15,25,26)
                          mod_base = OTHER
                          note = 2-Prime-MOEribose nucleotides
modified_base             order(15,25,26)
                          mod_base = OTHER
                          note = Thymidine
modified_base             28
                          mod_base = OTHER
                          note = Deoxyribose Thymidine
modified_base             29
                          mod_base = OTHER
                          note = Beta-homoDNA
modified_base             30
                          mod_base = i
modified_base             30
                          mod_base = OTHER
                          note = Deoxyribose
modified_base             order(1,16,19,30,34)
                          mod_base = OTHER
                          note = Mesyl phosphroamidate internucleoside linkage
modified_base             order(2..4,9..10,13..14,18,21..24,27..29,32..33)
                          mod_base = OTHER
                          note = Phosphorothioate internucleoside linkage
modified_base             order(5..8,11..12,15,17,20,25..26,31)
                          mod_base = OTHER
                          note = Phosphate internucleoside linkage
modified_base             11
                          mod_base = m5c
SEQUENCE: 28
atggccccag nagcttcagt ccctttctcn tcgat                            35
```

```
SEQ ID NO: 29          moltype = RNA  length = 34
FEATURE                Location/Qualifiers
source                 1..34
                       mol_type = other RNA
                       organism = synthetic construct
modified_base          29
                       mod_base = i
modified_base          order(14,24,25,27)
                       mod_base = OTHER
                       note = Thymidine
SEQUENCE: 29
atggccccag agcttcagtc cctttctcnt cgat                              34

SEQ ID NO: 30          moltype = RNA  length = 34
FEATURE                Location/Qualifiers
source                 1..34
                       mol_type = other RNA
                       organism = synthetic construct
modified_base          order(1..7,16,18,20,30,32..34)
                       mod_base = OTHER
                       note = 2-Prime-methoxyribose nucleotides
modified_base          order(8,9,12,13,15,17,19,21..23,26,31)
                       mod_base = OTHER
                       note = 2-Prime-deoxy-2-Prime-fluororibose nucleotides
modified_base          order(10,11,14,24,25)
                       mod_base = OTHER
                       note = 2-Prime-MOEribose nucleotides
modified_base          order(14,24,25)
                       mod_base = OTHER
                       note = Thymidine
modified_base          27
                       mod_base = OTHER
                       note = Deoxyribose Thymidine
modified_base          29
                       mod_base = OTHER
                       note = Deoxyribose
modified_base          29
                       mod_base = i
modified_base          28
                       mod_base = OTHER
                       note = Beta-homoDNA
modified_base          10
                       mod_base = m5c
modified_base          order(1,15,18,29,33)
                       mod_base = OTHER
                       note = Mesyl phosphroamidate internucleoside linkage
modified_base          order(2..4,8..9,12..13,17,20..23,26..28,31..32)
                       mod_base = OTHER
                       note = Phosphorothioate internucleoside linkage
modified_base          order(5..7,10..11,14,16,19,24..25,30)
                       mod_base = OTHER
                       note = Phosphate internucleoside linkage
SEQUENCE: 30
tggccccagn agcttcagtc cctttctcnt cgat                              34

SEQ ID NO: 31          moltype = RNA  length = 33
FEATURE                Location/Qualifiers
source                 1..33
                       mol_type = other RNA
                       organism = synthetic construct
modified_base          29
                       mod_base = i
modified_base          order(14,24,25,27)
                       mod_base = OTHER
                       note = Thymidine
SEQUENCE: 31
tggccccaga gcttcagtcc ctttctcntc gat                               33

SEQ ID NO: 32          moltype = RNA  length = 33
FEATURE                Location/Qualifiers
source                 1..33
                       mol_type = other RNA
                       organism = synthetic construct
modified_base          order(1..6,15,17,19,29,31..33)
                       mod_base = OTHER
                       note = 2-Prime-methoxyribose nucleotides
modified_base          order(7,8,11,12,14,16,18,20..22,25,30)
                       mod_base = OTHER
```

```
                         note = 2-Prime-deoxy-2-Prime-fluororibose nucleotides
modified_base            order(9,10,13,23,24)
                         mod_base = OTHER
                         note = 2-Prime-MOEribose nucleotides
modified_base            9
                         mod_base = OTHER
                         note = m5C
modified_base            order(13,23,24)
                         mod_base = OTHER
                         note = Thymidine
modified_base            26
                         mod_base = OTHER
                         note = Deoxyribose Thymidine
modified_base            27
                         mod_base = OTHER
                         note = Beta-homoDNA
modified_base            28
                         mod_base = OTHER
                         note = Deoxyribose
modified_base            28
                         mod_base = i
modified_base            order(1,14,17,28,32)
                         mod_base = OTHER
                         note = Mesyl phosphroamidate internucleoside linkage
modified_base            order(2..4,7..8,11..12,16,19..22,25..27,30..31)
                         mod_base = OTHER
                         note = Phosphorothioate internucleoside linkage
modified_base            order(5..6,9..10,13,15,18,23..24,29)
                         mod_base = OTHER
                         note = Phosphate internucleoside linkage
SEQUENCE: 32
cgccccagna gcttcagtcc ctttctcntc gat                                33

SEQ ID NO: 33            moltype = RNA  length = 32
FEATURE                  Location/Qualifiers
source                   1..32
                         mol_type = other RNA
                         organism = synthetic construct
modified_base            27
                         mod_base = i
modified_base            order(12,22,23,25)
                         mod_base = OTHER
                         note = Thymidine
SEQUENCE: 33
cgccccagag cttcagtccc tttctcntcg at                                 32

SEQ ID NO: 34            moltype = RNA  length = 32
FEATURE                  Location/Qualifiers
source                   1..32
                         mol_type = other RNA
                         organism = synthetic construct
modified_base            order(1..5,14,16,18,28,30..32)
                         mod_base = OTHER
                         note = 2-Prime-methoxyribose nucleotides
modified_base            order(6,7,10,11,13,15,17,19..21,24,29)
                         mod_base = OTHER
                         note = 2-Prime-deoxy-2-Prime-fluororibose nucleotides
modified_base            order(8,9,12,22,23)
                         mod_base = OTHER
                         note = 2-Prime-MOEribose nucleotides
modified_base            8
                         mod_base = m5c
modified_base            order(12,22,23)
                         mod_base = OTHER
                         note = Thymidine
modified_base            25
                         mod_base = OTHER
                         note = Deoxyribose Thymidine
modified_base            26
                         mod_base = OTHER
                         note = Beta-homoDNA
modified_base            27
                         mod_base = OTHER
                         note = Deoxyribose
modified_base            27
                         mod_base = i
modified_base            order(1,13,16,27,31)
                         mod_base = OTHER
                         note = Mesyl phosphroamidate internucleoside linkage
```

-continued

```
modified_base          order(2..4,6..7,10..11,15,18..21,24..26,29..30)
                       mod_base = OTHER
                       note = Phosphorothioate internucleoside linkage
modified_base          order(5,8..9,12,14,17,22..23,28)
                       mod_base = OTHER
                       note = Phosphate internucleoside linkage
SEQUENCE: 34
gccccagnag cttcagtccc tttctcntcg at                              32

SEQ ID NO: 35          moltype = RNA  length = 31
FEATURE                Location/Qualifiers
source                 1..31
                       mol_type = other RNA
                       organism = synthetic construct
modified_base          26
                       mod_base = i
modified_base          order(11,21,22,24)
                       mod_base = OTHER
                       note = Thymidine
SEQUENCE: 35
gccccagagc ttcagtccct ttctcntcga t                               31

SEQ ID NO: 36          moltype = RNA  length = 31
FEATURE                Location/Qualifiers
source                 1..31
                       mol_type = other RNA
                       organism = synthetic construct
modified_base          order(1..4,13,15,17,27,29..31)
                       mod_base = OTHER
                       note = 2-Prime-methoxyribose nucleotides
modified_base          order(5,6,9,10,12,14,16,18..20,23,28)
                       mod_base = OTHER
                       note = 2-Prime-deoxy-2-Prime-fluororibose nucleotides
modified_base          order(8,11,21,22)
                       mod_base = OTHER
                       note = 2-Prime-MOEribose nucleotides
modified_base          7
                       mod_base = m5c
modified_base          order(11,21,22)
                       mod_base = OTHER
                       note = Thymidine
modified_base          24
                       mod_base = OTHER
                       note = Deoxyribose Thymidine
modified_base          25
                       mod_base = OTHER
                       note = Beta-homoDNA
modified_base          26
                       mod_base = OTHER
                       note = Deoxyribose
modified_base          26
                       mod_base = i
modified_base          order(1,12,15,26,30)
                       mod_base = OTHER
                       note = Mesyl phosphroamidate internucleoside linkage
modified_base          order(2..6,9..10,14,17..20,23..25,28..29)
                       mod_base = OTHER
                       note = Phosphorothioate internucleoside linkage
modified_base          order(7..8,11,13,16,21..22,27)
                       mod_base = OTHER
                       note = Phosphate internucleoside linkage
SEQUENCE: 36
ccccagnagc ttcagtccct ttctcntcga t                               31

SEQ ID NO: 37          moltype = RNA  length = 30
FEATURE                Location/Qualifiers
source                 1..30
                       mol_type = other RNA
                       organism = synthetic construct
modified_base          25
                       mod_base = i
modified_base          order(10,20,21,23)
                       mod_base = OTHER
                       note = Thymidine
SEQUENCE: 37
ccccagagct tcagtccctt tctcntcgat                                 30

SEQ ID NO: 38          moltype = RNA  length = 29
FEATURE                Location/Qualifiers
```

-continued

```
source                1..29
                      mol_type = other RNA
                      organism = synthetic construct
modified_base         order(1,2,11,13,15,25,27..29)
                      mod_base = OTHER
                      note = 2-Prime-methoxyribose nucleotides
modified_base         order(3,4,7,8,10,12,14,16..18,21,26)
                      mod_base = OTHER
                      note = 2-Prime-deoxy-2-Prime-fluororibose nucleotides
modified_base         order(5,6,9,19..20)
                      mod_base = OTHER
                      note = 2-Prime-MOEribose nucleotides
modified_base         5
                      mod_base = m5c
modified_base         order(9,19,20)
                      mod_base = OTHER
                      note = Thymidine
modified_base         22
                      mod_base = OTHER
                      note = Deoxyribose Thymidine
modified_base         23
                      mod_base = OTHER
                      note = Beta-homoDNA
modified_base         24
                      mod_base = OTHER
                      note = Deoxyribose
modified_base         24
                      mod_base = i
modified_base         order(1,10,13,24,28)
                      mod_base = OTHER
                      note = Mesyl phosphroamidate internucleoside linkage
modified_base         order(2..4,7..8,12,15..18,21..23,26..27)
                      mod_base = OTHER
                      note = Phosphorothioate internucleoside linkage
modified_base         order(5..6,9,11,14,19..20,25)
                      mod_base = OTHER
                      note = Phosphate internucleoside linkage
SEQUENCE: 38
ccagnagctt cagtcccttt ctcntcgat                                    29

SEQ ID NO: 39         moltype = RNA  length = 28
FEATURE               Location/Qualifiers
source                1..28
                      mol_type = other RNA
                      organism = synthetic construct
modified_base         23
                      mod_base = i
modified_base         order(9,18,19,21)
                      mod_base = OTHER
                      note = Thymidine
SEQUENCE: 39
ccagagcttc agtccctttc tcntcgat                                     28

SEQ ID NO: 40         moltype = RNA  length = 28
FEATURE               Location/Qualifiers
source                1..28
                      mol_type = other RNA
                      organism = synthetic construct
modified_base         order(1,10,12,14,24,26..28)
                      mod_base = OTHER
                      note = 2-Prime-methoxyribose nucleotides
modified_base         order(2,3,6,7,9,11,13,15..17,20,25)
                      mod_base = OTHER
                      note = 2-Prime-deoxy-2-Prime-fluororibose nucleotides
modified_base         order(4,5,8,18,19)
                      mod_base = OTHER
                      note = 2-Prime-MOEribose nucleotides
modified_base         4
                      mod_base = m5c
modified_base         order(8,18,19)
                      mod_base = OTHER
                      note = Thymidine
modified_base         21
                      mod_base = OTHER
                      note = Deoxyribose Thymidine
modified_base         22
                      mod_base = OTHER
                      note = Beta-homoDNA
modified_base         23
```

```
                        mod_base = OTHER
                        note = Deoxyribose
modified_base           23
                        mod_base = i
modified_base           order(1,9,12,23,27)
                        mod_base = OTHER
                        note = Mesyl phosphroamidate internucleoside linkage
modified_base           order(2..3,6..7,11,14..17,20..22,25..26)
                        mod_base = OTHER
                        note = Phosphorothioate internucleoside linkage
modified_base           order(4..5,8,10,13,18..19,24)
                        mod_base = OTHER
                        note = Phosphate internucleoside linkage
SEQUENCE: 40
cagnagcttc agtccctttc tcntcgat                                        28

SEQ ID NO: 41           moltype = RNA  length = 27
FEATURE                 Location/Qualifiers
source                  1..27
                        mol_type = other RNA
                        organism = synthetic construct
modified_base           22
                        mod_base = i
modified_base           order(7,17,18,20)
                        mod_base = OTHER
                        note = Thymidine
SEQUENCE: 41
cagagcttca gtccctttct cntcgat                                         27

SEQ ID NO: 42           moltype = RNA  length = 27
FEATURE                 Location/Qualifiers
source                  1..27
                        mol_type = other RNA
                        organism = synthetic construct
modified_base           order(1,9,11,13,23,25..27)
                        mod_base = OTHER
                        note = 2-Prime-methoxyribose nucleotides
modified_base           order(2,5,6,8,10,12,14..16,19,24)
                        mod_base = OTHER
                        note = 2-Prime-deoxy-2-Prime-fluororibose nucleotides
modified_base           order(3,4,7,17,18)
                        mod_base = OTHER
                        note = 2-Prime-MOEribose nucleotides
modified_base           3
                        mod_base = m5c
modified_base           order(7,17,18)
                        mod_base = OTHER
                        note = Thymidine
modified_base           20
                        mod_base = OTHER
                        note = Deoxyribose Thymidine
modified_base           21
                        mod_base = OTHER
                        note = Beta-homoDNA
modified_base           22
                        mod_base = OTHER
                        note = Deoxyribose
modified_base           22
                        mod_base = i
modified_base           order(1,8,11,22,26)
                        mod_base = OTHER
                        note = Mesyl phosphroamidate internucleoside linkage
modified_base           order(2..3,5..6,10,13..16,19..21,24..25)
                        mod_base = OTHER
                        note = Phosphorothioate internucleoside linkage
modified_base           order(4,7,9,12,17..18,23)
                        mod_base = OTHER
                        note = Phosphate internucleoside linkage
SEQUENCE: 42
agnagcttca gtccctttct cntcgat                                         27

SEQ ID NO: 43           moltype = RNA  length = 26
FEATURE                 Location/Qualifiers
source                  1..26
                        mol_type = other RNA
                        organism = synthetic construct
modified_base           21
                        mod_base = i
modified_base           order(6,16,17,19)
```

```
                        mod_base = OTHER
                        note = Thymidine
SEQUENCE: 43
agagcttcag tccctttctc ntcgat                                              26

SEQ ID NO: 44           moltype = RNA  length = 26
FEATURE                 Location/Qualifiers
source                  1..26
                        mol_type = other RNA
                        organism = synthetic construct
modified_base           order(1,8,10,12,22,24..26)
                        mod_base = OTHER
                        note = 2-Prime-methoxyribose nucleotides
modified_base           order(4,5,7,9,11,13..15,18,23)
                        mod_base = OTHER
                        note = 2-Prime-deoxy-2-Prime-fluororibose nucleotides
modified_base           order(2,3,6,16,17)
                        mod_base = OTHER
                        note = 2-Prime-MOEribose nucleotides
modified_base           2
                        mod_base = m5c
modified_base           order(6,16,17)
                        mod_base = OTHER
                        note = Thymidine
modified_base           19
                        mod_base = OTHER
                        note = Deoxyribose Thymidine
modified_base           20
                        mod_base = OTHER
                        note = Beta-homoDNA
modified_base           21
                        mod_base = i
modified_base           21
                        mod_base = OTHER
                        note = Deoxyribose
modified_base           order(1,7,10,21,25)
                        mod_base = OTHER
                        note = Mesyl phosphroamidate internucleoside linkage
modified_base           order(2..5,9,12..15,18..20,23..24)
                        mod_base = OTHER
                        note = Phosphorothioate internucleoside linkage
modified_base           order(6,8,11,16..17,22)
                        mod_base = OTHER
                        note = Phosphate internucleoside linkage
SEQUENCE: 44
gnagcttcag tccctttctc ntcgat                                              26

SEQ ID NO: 45           moltype = RNA  length = 25
FEATURE                 Location/Qualifiers
source                  1..25
                        mol_type = other RNA
                        organism = synthetic construct
modified_base           20
                        mod_base = i
modified_base           order(5,15,16,18)
                        mod_base = OTHER
                        note = Thymidine
SEQUENCE: 45
gagcttcagt ccctttctcn tcgat                                               25

SEQ ID NO: 46           moltype = RNA  length = 25
FEATURE                 Location/Qualifiers
source                  1..25
                        mol_type = other RNA
                        organism = synthetic construct
modified_base           order(7,9,11,21,23,24..25)
                        mod_base = OTHER
                        note = 2-Prime-methoxyribose nucleotides
modified_base           order(3,4,6,8,10,12..14,17,22)
                        mod_base = OTHER
                        note = 2-Prime-deoxy-2-Prime-fluororibose nucleotides
modified_base           order(1,2,5,15,16)
                        mod_base = OTHER
                        note = 2-Prime-MOEribose nucleotides
modified_base           1
                        mod_base = m5c
modified_base           order(5,15,16)
                        mod_base = OTHER
                        note = Thymidine
```

```
modified_base          18
                       mod_base = OTHER
                       note = Deoxyribose Thymidine
modified_base          19
                       mod_base = OTHER
                       note = Beta-homoDNA
modified_base          20
                       mod_base = OTHER
                       note = Deoxyribose
modified_base          20
                       mod_base = i
modified_base          order(1,6,9,20,24)
                       mod_base = OTHER
                       note = Mesyl phosphroamidate internucleoside linkage
modified_base          order(2..4,8,11..14,17..19,22..23)
                       mod_base = OTHER
                       note = Phosphorothioate internucleoside linkage
modified_base          order(5,7,10,15..16,21)
                       mod_base = OTHER
                       note = Phosphate internucleoside linkage
SEQUENCE: 46
nagcttcagt ccctttctcn tcgat                                        25

SEQ ID NO: 47          moltype = RNA  length = 24
FEATURE                Location/Qualifiers
source                 1..24
                       mol_type = other RNA
                       organism = synthetic construct
modified_base          19
                       mod_base = i
modified_base          order(4,14,15,17)
                       mod_base = OTHER
                       note = Thymidine
SEQUENCE: 47
agcttcagtc cctttctcnt cgat                                         24

SEQ ID NO: 48          moltype = RNA  length = 24
FEATURE                Location/Qualifiers
source                 1..24
                       mol_type = other RNA
                       organism = synthetic construct
modified_base          order(6,8,10,20,22..24)
                       mod_base = OTHER
                       note = 2-Prime-methoxyribose nucleotides
modified_base          order(2,3,5,7,9,11..13,16,21)
                       mod_base = OTHER
                       note = 2-Prime-deoxy-2-Prime-fluororibose nucleotides
modified_base          order(1,4,14,15)
                       mod_base = OTHER
                       note = 2-Prime-MOEribose nucleotides
modified_base          order(4,14,15)
                       mod_base = OTHER
                       note = Thymidine
modified_base          17
                       mod_base = OTHER
                       note = Deoxyribose Thymidine
modified_base          18
                       mod_base = OTHER
                       note = Beta-homoDNA
modified_base          19
                       mod_base = OTHER
                       note = Deoxyribose
modified_base          19
                       mod_base = i
modified_base          order(1,5,8,19,23)
                       mod_base = OTHER
                       note = Mesyl phosphroamidate internucleoside linkage
modified_base          order(2..3,7,10..13,16..18,21..22)
                       mod_base = OTHER
                       note = Phosphorothioate internucleoside linkage
modified_base          order(4,6,9,14..15,20)
                       mod_base = OTHER
                       note = Phosphate internucleoside linkage
SEQUENCE: 48
agcttcagtc cctttctcnt cgat                                         24

SEQ ID NO: 49          moltype = RNA  length = 24
FEATURE                Location/Qualifiers
source                 1..24
```

```
                         mol_type = other RNA
                         organism = synthetic construct
modified_base            19
                         mod_base = i
modified_base            order(4,14,15,17)
                         mod_base = OTHER
                         note = Thymidine
SEQUENCE: 49
agcttcagtc cctttctcnt cgat                                          24

SEQ ID NO: 50            moltype = RNA  length = 23
FEATURE                  Location/Qualifiers
source                   1..23
                         mol_type = other RNA
                         organism = synthetic construct
modified_base            order(5,7,9,19,21..23)
                         mod_base = OTHER
                         note = 2-Prime-methoxyribose nucleotides
modified_base            order(1,2,4,6,8,10..12,15,20)
                         mod_base = OTHER
                         note = 2-Prime-deoxy-2-Prime-fluororibose nucleotides
modified_base            order(3,13,14)
                         mod_base = OTHER
                         note = 2-Prime-MOEribose nucleotides
modified_base            order(3,13,14)
                         mod_base = OTHER
                         note = Thymidine
modified_base            16
                         mod_base = OTHER
                         note = Deoxyribose Thymidine
modified_base            17
                         mod_base = OTHER
                         note = Beta-homoDNA
modified_base            18
                         mod_base = OTHER
                         note = Deoxyribose
modified_base            18
                         mod_base = i
modified_base            order(1,4,7,18,22)
                         mod_base = OTHER
                         note = Mesyl phosphroamidate internucleoside linkage
modified_base            order(2,6,9..12,15..17,20..21)
                         mod_base = OTHER
                         note = Phosphorothioate internucleoside linkage
modified_base            order(3,5,8,13..14,19)
                         mod_base = OTHER
                         note = Phosphate internucleoside linkage
SEQUENCE: 50
gcttcagtcc ctttctcntc gat                                           23

SEQ ID NO: 51            moltype = RNA  length = 23
FEATURE                  Location/Qualifiers
source                   1..23
                         mol_type = other RNA
                         organism = synthetic construct
modified_base            18
                         mod_base = i
modified_base            order(3,13,14,16)
                         mod_base = OTHER
                         note = Thymidine
SEQUENCE: 51
gcttcagtcc ctttctcntc gat                                           23

SEQ ID NO: 52            moltype = RNA  length = 30
FEATURE                  Location/Qualifiers
source                   1..30
                         mol_type = other RNA
                         organism = synthetic construct
modified_base            order(1..3,12,14,16,26,28..30)
                         mod_base = OTHER
                         note = 2-Prime-methoxyribose nucleotides
modified_base            order(4,5,8,9,11,13,15,17..19,22,27)
                         mod_base = OTHER
                         note = 2-Prime-deoxy-2-Prime-fluororibose nucleotides
modified_base            order(6,7,10,20,21)
                         mod_base = OTHER
                         note = 2-Prime-MOEribose nucleotides
modified_base            6
                         mod_base = m5c
```

-continued

```
modified_base          order(10,20,21)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
modified_base          25
                       mod_base = i
modified_base          order(1,11,14,19,25,29)
                       mod_base = OTHER
                       note = Mesyl phosphroamidate internucleoside linkage
modified_base          order(2..5,8..9,13,16..18,22..24,27..28)
                       mod_base = OTHER
                       note = Phosphorothioate internucleoside linkage
modified_base          order(6..7,10,12,15,20..21,26)
                       mod_base = OTHER
                       note = Phosphate internucleoside linkage
SEQUENCE: 52
cccagnagct tcagtccctt tctcntcgat                                   30

SEQ ID NO: 53          moltype = RNA  length = 30
FEATURE                Location/Qualifiers
source                 1..30
                       mol_type = other RNA
                       organism = synthetic construct
modified_base          25
                       mod_base = i
modified_base          order(10,20,21,23)
                       mod_base = OTHER
                       note = Thymidine
SEQUENCE: 53
cccagcagct tcagtccctt tctcntcgat                                   30

SEQ ID NO: 54          moltype = RNA  length = 30
FEATURE                Location/Qualifiers
source                 1..30
                       mol_type = other RNA
                       organism = synthetic construct
modified_base          order(1..3,12,14,16,26,28..30)
                       mod_base = OTHER
                       note = 2-Prime-methoxyribose nucleotides
modified_base          order(4,5,8,9,11,13,15,17..19,22,27)
                       mod_base = OTHER
                       note = 2-Prime-deoxy-2-Prime-fluororibose nucleotides
modified_base          order(6,7,10,20,21)
                       mod_base = OTHER
                       note = 2-Prime-MOEribose nucleotides
modified_base          6
                       mod_base = m5c
modified_base          order(10,20,21)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
modified_base          25
                       mod_base = i
modified_base          order(1..5,8..9,11,13..14,16..19,22..25,27..29)
                       mod_base = OTHER
                       note = Phosphorothioate internucleoside linkage
modified_base          order(6..7,10,12,15,20..21,26)
                       mod_base = OTHER
                       note = Phosphate internucleoside linkage
SEQUENCE: 54
cccagnagct tcagtccctt tctcntcgat                                   30

SEQ ID NO: 55          moltype = RNA  length = 30
```

-continued

```
FEATURE               Location/Qualifiers
source                1..30
                      mol_type = other RNA
                      organism = synthetic construct
modified_base         order(1..3,12,14,16,26,28..30)
                      mod_base = OTHER
                      note = 2-Prime-methoxyribose nucleotides
modified_base         order(4,5,8,9,11,13,15,17..19,22,27)
                      mod_base = OTHER
                      note = 2-Prime-deoxy-2-Prime-fluororibose nucleotides
modified_base         order(6,7,10,20,21)
                      mod_base = OTHER
                      note = 2-Prime-MOEribose nucleotides
modified_base         6
                      mod_base = m5c
modified_base         order(10,20,21)
                      mod_base = OTHER
                      note = Thymidine
modified_base         23
                      mod_base = OTHER
                      note = Deoxyribose Thymidine
modified_base         24
                      mod_base = OTHER
                      note = Beta-homoDNA
modified_base         25
                      mod_base = OTHER
                      note = Deoxyribose
modified_base         25
                      mod_base = i
modified_base         order(1,11,14,25,29)
                      mod_base = OTHER
                      note = Mesyl phosphroamidate internucleoside linkage
modified_base         order(2..10,12..13,15..24,26..28)
                      mod_base = OTHER
                      note = Phosphorothioate internucleoside linkage
SEQUENCE: 55
cccagnagct tcagtccctt tctcntcgat                                   30

SEQ ID NO: 56         moltype = RNA  length = 30
FEATURE               Location/Qualifiers
source                1..30
                      mol_type = other RNA
                      organism = synthetic construct
modified_base         order(1..3,12,14,16,26,28..30)
                      mod_base = OTHER
                      note = 2-Prime-methoxyribose nucleotides
modified_base         order(4,5,8,9,11,13,15,17..19,22,27)
                      mod_base = OTHER
                      note = 2-Prime-deoxy-2-Prime-fluororibose nucleotides
modified_base         order(6,7,10,20,21)
                      mod_base = OTHER
                      note = 2-Prime-MOEribose nucleotides
modified_base         6
                      mod_base = m5c
modified_base         order(10,20,21)
                      mod_base = OTHER
                      note = Thymidine
modified_base         23
                      mod_base = OTHER
                      note = Deoxyribose Thymidine
modified_base         24
                      mod_base = OTHER
                      note = Beta-homoDNA
modified_base         25
                      mod_base = OTHER
                      note = Deoxyribose
modified_base         25
                      mod_base = i
modified_base         order(1,10,12,14,25,29)
                      mod_base = OTHER
                      note = Mesyl phosphroamidate internucleoside linkage
modified_base         order(2..5,8..9,11,13,16..19,22..24,27..28)
                      mod_base = OTHER
                      note = Phosphorothioate internucleoside linkage
modified_base         order(6..7,15,20..21,26)
                      mod_base = OTHER
                      note = Phosphate internucleoside linkage
SEQUENCE: 56
cccagnagct tcagtccctt tctcntcgat                                   30
```

```
SEQ ID NO: 57           moltype = RNA  length = 30
FEATURE                 Location/Qualifiers
source                  1..30
                        mol_type = other RNA
                        organism = synthetic construct
modified_base           order(1..3,12,14,16,26,28..30)
                        mod_base = OTHER
                        note = 2-Prime-methoxyribose nucleotides
modified_base           order(4,5,8,9,11,13,15,17..19,22,27)
                        mod_base = OTHER
                        note = 2-Prime-deoxy-2-Prime-fluororibose nucleotides
modified_base           order(6,7,10,20,21)
                        mod_base = OTHER
                        note = 2-Prime-MOEribose nucleotides
modified_base           6
                        mod_base = m5c
modified_base           order(10,20,21)
                        mod_base = OTHER
                        note = Thymidine
modified_base           23
                        mod_base = OTHER
                        note = Deoxyribose Thymidine
modified_base           24
                        mod_base = OTHER
                        note = Beta-homoDNA
modified_base           25
                        mod_base = OTHER
                        note = Deoxyribose
modified_base           25
                        mod_base = i
modified_base           order(11,14,25,29)
                        mod_base = OTHER
                        note = Mesyl phosphroamidate internucleoside linkage
modified_base           order(1..5,8..9,13,16..19,22..24,27..28)
                        mod_base = OTHER
                        note = Phosphorothioate internucleoside linkage
modified_base           order(6..7,10,12,15,20..21,26)
                        mod_base = OTHER
                        note = Phosphate internucleoside linkage
SEQUENCE: 57
cccagnagct tcagtccctt tctcntcgat                                   30

SEQ ID NO: 58           moltype = RNA  length = 30
FEATURE                 Location/Qualifiers
source                  1..30
                        mol_type = other RNA
                        organism = synthetic construct
modified_base           order(1..3,12,14,16,26,28..30)
                        mod_base = OTHER
                        note = 2-Prime-methoxyribose nucleotides
modified_base           order(4,5,8,9,11,13,15,17..19,22,27)
                        mod_base = OTHER
                        note = 2-Prime-deoxy-2-Prime-fluororibose nucleotides
modified_base           order(6,7,10,20,21)
                        mod_base = OTHER
                        note = 2-Prime-MOEribose nucleotides
modified_base           6
                        mod_base = m5c
modified_base           order(10,20,21)
                        mod_base = OTHER
                        note = Thymidine
modified_base           23
                        mod_base = OTHER
                        note = Deoxyribose Thymidine
modified_base           24
                        mod_base = OTHER
                        note = Beta-homoDNA
modified_base           25
                        mod_base = OTHER
                        note = Deoxyribose
modified_base           25
                        mod_base = i
modified_base           order(1,14,25,29)
                        mod_base = OTHER
                        note = Mesyl phosphroamidate internucleoside linkage
modified_base           order(2..5,8..9,11,13,16..19,22..24,27..28)
                        mod_base = OTHER
                        note = Phosphorothioate internucleoside linkage
```

```
modified_base          order(6..7,10,12,15,20..21,26)
                       mod_base = OTHER
                       note = Phosphate internucleoside linkage
SEQUENCE: 58
cccagnagct tcagtccctt tctcntcgat                                   30

SEQ ID NO: 59          moltype = RNA  length = 30
FEATURE                Location/Qualifiers
source                 1..30
                       mol_type = other RNA
                       organism = synthetic construct
modified_base          order(1..3,12,14,16,26,28..30)
                       mod_base = OTHER
                       note = 2-Prime-methoxyribose nucleotides
modified_base          order(4,5,8,9,11,13,15,17..19,22,27)
                       mod_base = OTHER
                       note = 2-Prime-deoxy-2-Prime-fluororibose nucleotides
modified_base          order(6,7,10,20,21)
                       mod_base = OTHER
                       note = 2-Prime-MOEribose nucleotides
modified_base          6
                       mod_base = m5c
modified_base          order(10,20,21)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
modified_base          25
                       mod_base = i
modified_base          order(1,11,25,29)
                       mod_base = OTHER
                       note = Mesyl phosphroamidate internucleoside linkage
modified_base          order(2..5,8..9,13..14,16..19,22..24,27..28)
                       mod_base = OTHER
                       note = Phosphorothioate internucleoside linkage
modified_base          order(6..7,10,12,15,20..21,26)
                       mod_base = OTHER
                       note = Phosphate internucleoside linkage
SEQUENCE: 59
cccagnagct tcagtccctt tctcntcgat                                   30

SEQ ID NO: 60          moltype = RNA  length = 30
FEATURE                Location/Qualifiers
source                 1..30
                       mol_type = other RNA
                       organism = synthetic construct
modified_base          order(1..3,12,14,16,26,28..30)
                       mod_base = OTHER
                       note = 2-Prime-methoxyribose nucleotides
modified_base          order(4,5,8,9,11,13,15,17..19,22,27)
                       mod_base = OTHER
                       note = 2-Prime-deoxy-2-Prime-fluororibose nucleotides
modified_base          order(6,7,10,20,21)
                       mod_base = OTHER
                       note = 2-Prime-MOEribose nucleotides
modified_base          6
                       mod_base = m5c
modified_base          order(10,20,21)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
modified_base          25
                       mod_base = i
modified_base          order(1,11,14,29)
```

```
                        mod_base = OTHER
                        note = Mesyl phosphroamidate internucleoside linkage
modified_base           order(2..5,8..9,13,16..19,22..25,27..28)
                        mod_base = OTHER
                        note = Phosphorothioate internucleoside linkage
modified_base           order(6..7,10,12,15,20..21,26)
                        mod_base = OTHER
                        note = Phosphate internucleoside linkage
SEQUENCE: 60
cccagnagct tcagtccctt tctcntcgat                                   30

SEQ ID NO: 61           moltype = RNA  length = 30
FEATURE                 Location/Qualifiers
source                  1..30
                        mol_type = other RNA
                        organism = synthetic construct
modified_base           order(1..3,12,14,16,26,28..30)
                        mod_base = OTHER
                        note = 2-Prime-methoxyribose nucleotides
modified_base           order(4,5,8,9,11,13,15,17..19,22,27)
                        mod_base = OTHER
                        note = 2-Prime-deoxy-2-Prime-fluororibose nucleotides
modified_base           order(6,7,10,20,21)
                        mod_base = OTHER
                        note = 2-Prime-MOEribose nucleotides
modified_base           6
                        mod_base = m5c
modified_base           order(10,20,21)
                        mod_base = OTHER
                        note = Thymidine
modified_base           23
                        mod_base = OTHER
                        note = Deoxyribose Thymidine
modified_base           24
                        mod_base = OTHER
                        note = Beta-homoDNA
modified_base           25
                        mod_base = OTHER
                        note = Deoxyribose
modified_base           25
                        mod_base = i
modified_base           order(1,11,14,25)
                        mod_base = OTHER
                        note = Mesyl phosphroamidate internucleoside linkage
modified_base           order(2..5,8..9,13,16..19,22..24,27..29)
                        mod_base = OTHER
                        note = Phosphorothioate internucleoside linkage
modified_base           order(6..7,10,12,15,20..21,26)
                        mod_base = OTHER
                        note = Phosphate internucleoside linkage
SEQUENCE: 61
cccagnagct tcagtccctt tctcntcgat                                   30

SEQ ID NO: 62           moltype = RNA  length = 30
FEATURE                 Location/Qualifiers
source                  1..30
                        mol_type = other RNA
                        organism = synthetic construct
modified_base           order(1..3,12,14,16,26,28..30)
                        mod_base = OTHER
                        note = 2-Prime-methoxyribose nucleotides
modified_base           order(4,5,8,9,11,13,15,17..19,22,27)
                        mod_base = OTHER
                        note = 2-Prime-deoxy-2-Prime-fluororibose nucleotides
modified_base           order(6,7,10,20,21)
                        mod_base = OTHER
                        note = 2-Prime-MOEribose nucleotides
modified_base           6
                        mod_base = m5c
modified_base           order(10,20,21)
                        mod_base = OTHER
                        note = Thymidine
modified_base           23
                        mod_base = OTHER
                        note = Deoxyribose Thymidine
modified_base           24
                        mod_base = OTHER
                        note = Beta-homoDNA
modified_base           25
```

-continued

```
                        mod_base = OTHER
                        note = Deoxyribose
modified_base           25
                        mod_base = i
modified_base           order(1..2,11,14,25,29)
                        mod_base = OTHER
                        note = Mesyl phosphroamidate internucleoside linkage
modified_base           order(3..5,8..9,13,16..19,22..24,27..28)
                        mod_base = OTHER
                        note = Phosphorothioate internucleoside linkage
modified_base           order(6..7,10,12,15,20..21,26)
                        mod_base = OTHER
                        note = Phosphate internucleoside linkage
SEQUENCE: 62
cccagnagct tcagtccctt tctcntcgat                                      30

SEQ ID NO: 63           moltype = RNA  length = 30
FEATURE                 Location/Qualifiers
source                  1..30
                        mol_type = other RNA
                        organism = synthetic construct
modified_base           order(1..3,12,14,16,26,28..30)
                        mod_base = OTHER
                        note = 2-Prime-methoxyribose nucleotides
modified_base           order(4,5,8,9,11,13,15,17..19,22,27)
                        mod_base = OTHER
                        note = 2-Prime-deoxy-2-Prime-fluororibose nucleotides
modified_base           order(6,7,10,20,21)
                        mod_base = OTHER
                        note = 2-Prime-MOEribose nucleotides
modified_base           6
                        mod_base = m5c
modified_base           order(10,20,21)
                        mod_base = OTHER
                        note = Thymidine
modified_base           23
                        mod_base = OTHER
                        note = Deoxyribose Thymidine
modified_base           24
                        mod_base = OTHER
                        note = Beta-homoDNA
modified_base           25
                        mod_base = OTHER
                        note = Deoxyribose
modified_base           25
                        mod_base = i
modified_base           order(1,3,11,14,25,29)
                        mod_base = OTHER
                        note = Mesyl phosphroamidate internucleoside linkage
modified_base           order(2,4..5,8..9,13,16..19,22..24,27..28)
                        mod_base = OTHER
                        note = Phosphorothioate internucleoside linkage
modified_base           order(6..7,10,12,15,20..21,26)
                        mod_base = OTHER
                        note = Phosphate internucleoside linkage
SEQUENCE: 63
cccagnagct tcagtccctt tctcntcgat                                      30

SEQ ID NO: 64           moltype = RNA  length = 30
FEATURE                 Location/Qualifiers
source                  1..30
                        mol_type = other RNA
                        organism = synthetic construct
modified_base           order(1..3,12,14,16,26,28..30)
                        mod_base = OTHER
                        note = 2-Prime-methoxyribose nucleotides
modified_base           order(4,5,8,9,11,13,15,17..19,22,27)
                        mod_base = OTHER
                        note = 2-Prime-deoxy-2-Prime-fluororibose nucleotides
modified_base           order(6,7,10,20,21)
                        mod_base = OTHER
                        note = 2-Prime-MOEribose nucleotides
modified_base           6
                        mod_base = m5c
modified_base           order(10,20,21)
                        mod_base = OTHER
                        note = Thymidine
modified_base           23
                        mod_base = OTHER
```

-continued

```
                        note = Deoxyribose Thymidine
modified_base           24
                        mod_base = OTHER
                        note = Beta-homoDNA
modified_base           25
                        mod_base = OTHER
                        note = Deoxyribose
modified_base           25
                        mod_base = i
modified_base           order(1,4,11,14,25,29)
                        mod_base = OTHER
                        note = Mesyl phosphroamidate internucleoside linkage
modified_base           order(2..3,5,8..9,13,16..19,22..24,27..28)
                        mod_base = OTHER
                        note = Phosphorothioate internucleoside linkage
modified_base           order(6..7,10,12,15,20..21,26)
                        mod_base = OTHER
                        note = Phosphate internucleoside linkage
SEQUENCE: 64
cccagnagct tcagtccctt tctcntcgat                                   30

SEQ ID NO: 65           moltype = RNA  length = 30
FEATURE                 Location/Qualifiers
source                  1..30
                        mol_type = other RNA
                        organism = synthetic construct
modified_base           order(1..3,12,14,16,26,28..30)
                        mod_base = OTHER
                        note = 2-Prime-methoxyribose nucleotides
modified_base           order(4,5,8,9,11,13,15,17..19,22,27)
                        mod_base = OTHER
                        note = 2-Prime-deoxy-2-Prime-fluororibose nucleotides
modified_base           order(6,7,10,20,21)
                        mod_base = OTHER
                        note = 2-Prime-MOEribose nucleotides
modified_base           6
                        mod_base = m5c
modified_base           order(10,20,21)
                        mod_base = OTHER
                        note = Thymidine
modified_base           23
                        mod_base = OTHER
                        note = Deoxyribose Thymidine
modified_base           24
                        mod_base = OTHER
                        note = Beta-homoDNA
modified_base           25
                        mod_base = OTHER
                        note = Deoxyribose
modified_base           25
                        mod_base = i
modified_base           order(1,5,11,14,25,29)
                        mod_base = OTHER
                        note = Mesyl phosphroamidate internucleoside linkage
modified_base           order(2..4,8..9,13,16..19,22..24,27..28)
                        mod_base = OTHER
                        note = Phosphorothioate internucleoside linkage
modified_base           order(6..7,10,12,15,20..21,26)
                        mod_base = OTHER
                        note = Phosphate internucleoside linkage
SEQUENCE: 65
cccagnagct tcagtccctt tctcntcgat                                   30

SEQ ID NO: 66           moltype = RNA  length = 30
FEATURE                 Location/Qualifiers
source                  1..30
                        mol_type = other RNA
                        organism = synthetic construct
modified_base           order(1..3,12,14,16,26,28..30)
                        mod_base = OTHER
                        note = 2-Prime-methoxyribose nucleotides
modified_base           order(4,5,8,9,11,13,15,17..19,22,27)
                        mod_base = OTHER
                        note = 2-Prime-deoxy-2-Prime-fluororibose nucleotides
modified_base           order(6,7,10,20,21)
                        mod_base = OTHER
                        note = 2-Prime-MOEribose nucleotides
modified_base           6
                        mod_base = m5c
```

```
modified_base           order(10,20,21)
                        mod_base = OTHER
                        note = Thymidine
modified_base           23
                        mod_base = OTHER
                        note = Deoxyribose Thymidine
modified_base           24
                        mod_base = OTHER
                        note = Beta-homoDNA
modified_base           25
                        mod_base = OTHER
                        note = Deoxyribose
modified_base           25
                        mod_base = i
modified_base           order(1,6,11,14,25,29)
                        mod_base = OTHER
                        note = Mesyl phosphroamidate internucleoside linkage
modified_base           order(2..5,8..9,13,16..19,22..24,27..28)
                        mod_base = OTHER
                        note = Phosphorothioate internucleoside linkage
modified_base           order(7,10,12,15,20..21,26)
                        mod_base = OTHER
                        note = Phosphate internucleoside linkage
SEQUENCE: 66
cccagnagct tcagtccctt tctcntcgat                                       30

SEQ ID NO: 67           moltype = RNA  length = 30
FEATURE                 Location/Qualifiers
source                  1..30
                        mol_type = other RNA
                        organism = synthetic construct
modified_base           order(1..3,12,14,16,26,28..30)
                        mod_base = OTHER
                        note = 2-Prime-methoxyribose nucleotides
modified_base           order(4,5,8,9,11,13,15,17..19,22,27)
                        mod_base = OTHER
                        note = 2-Prime-deoxy-2-Prime-fluororibose nucleotides
modified_base           order(6,7,10,20,21)
                        mod_base = OTHER
                        note = 2-Prime-MOEribose nucleotides
modified_base           6
                        mod_base = m5c
modified_base           order(10,20,21)
                        mod_base = OTHER
                        note = Thymidine
modified_base           23
                        mod_base = OTHER
                        note = Deoxyribose Thymidine
modified_base           24
                        mod_base = OTHER
                        note = Beta-homoDNA
modified_base           25
                        mod_base = OTHER
                        note = Deoxyribose
modified_base           25
                        mod_base = i
modified_base           order(1,7,11,14,25,29)
                        mod_base = OTHER
                        note = Mesyl phosphroamidate internucleoside linkage
modified_base           order(2..5,8..9,13,16..19,22..24,27..28)
                        mod_base = OTHER
                        note = Phosphorothioate internucleoside linkage
modified_base           order(6,10,12,15,20..21,26)
                        mod_base = OTHER
                        note = Phosphate internucleoside linkage
SEQUENCE: 67
cccagnagct tcagtccctt tctcntcgat                                       30

SEQ ID NO: 68           moltype = RNA  length = 30
FEATURE                 Location/Qualifiers
source                  1..30
                        mol_type = other RNA
                        organism = synthetic construct
modified_base           order(1..3,12,14,16,26,28..30)
                        mod_base = OTHER
                        note = 2-Prime-methoxyribose nucleotides
modified_base           order(4,5,8,9,11,13,15,17..19,22,27)
                        mod_base = OTHER
                        note = 2-Prime-deoxy-2-Prime-fluororibose nucleotides
```

-continued

```
modified_base          order(6,7,10,20,21)
                       mod_base = OTHER
                       note = 2-Prime-MOEribose nucleotides
modified_base          6
                       mod_base = m5c
modified_base          order(10,20,21)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
modified_base          25
                       mod_base = i
modified_base          order(1,8,11,14,25,29)
                       mod_base = OTHER
                       note = Mesyl phosphroamidate internucleoside linkage
modified_base          order(2..5,9,13,16..19,22..24,27..28)
                       mod_base = OTHER
                       note = Phosphorothioate internucleoside linkage
modified_base          order(6..7,10,12,15,20..21,26)
                       mod_base = OTHER
                       note = Phosphate internucleoside linkage
SEQUENCE: 68
cccagnagct tcagtccctt tctcntcgat                                   30

SEQ ID NO: 69          moltype = RNA  length = 30
FEATURE                Location/Qualifiers
source                 1..30
                       mol_type = other RNA
                       organism = synthetic construct
modified_base          order(1..3,12,14,16,26,28..30)
                       mod_base = OTHER
                       note = 2-Prime-methoxyribose nucleotides
modified_base          order(4,5,8,9,11,13,15,17..19,22,27)
                       mod_base = OTHER
                       note = 2-Prime-deoxy-2-Prime-fluororibose nucleotides
modified_base          order(6,7,10,20,21)
                       mod_base = OTHER
                       note = 2-Prime-MOEribose nucleotides
modified_base          6
                       mod_base = m5c
modified_base          order(10,20,21)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
modified_base          25
                       mod_base = i
modified_base          order(1,9,11,14,25,29)
                       mod_base = OTHER
                       note = Mesyl phosphroamidate internucleoside linkage
modified_base          order(2..5,8,13,16..19,22..24,27..28)
                       mod_base = OTHER
                       note = Phosphorothioate internucleoside linkage
modified_base          order(6..7,10,12,15,20..21,26)
                       mod_base = OTHER
                       note = Phosphate internucleoside linkage
SEQUENCE: 69
cccagnagct tcagtccctt tctcntcgat                                   30

SEQ ID NO: 70          moltype = RNA  length = 30
FEATURE                Location/Qualifiers
source                 1..30
                       mol_type = other RNA
                       organism = synthetic construct
modified_base          order(1..3,12,14,16,26,28..30)
```

```
                          mod_base = OTHER
                          note = 2-Prime-methoxyribose nucleotides
modified_base             order(4,5,8,9,11,13,15,17..19,22,27)
                          mod_base = OTHER
                          note = 2-Prime-deoxy-2-Prime-fluororibose nucleotides
modified_base             order(6,7,10,20,21)
                          mod_base = OTHER
                          note = 2-Prime-MOEribose nucleotides
modified_base             6
                          mod_base = m5c
modified_base             order(10,20,21)
                          mod_base = OTHER
                          note = Thymidine
modified_base             23
                          mod_base = OTHER
                          note = Deoxyribose Thymidine
modified_base             24
                          mod_base = OTHER
                          note = Beta-homoDNA
modified_base             25
                          mod_base = OTHER
                          note = Deoxyribose
modified_base             25
                          mod_base = i
modified_base             order(1,10..11,14,25,29)
                          mod_base = OTHER
                          note = Mesyl phosphroamidate internucleoside linkage
modified_base             order(2..5,8..9,13,16..19,22..24,27..28)
                          mod_base = OTHER
                          note = Phosphorothioate internucleoside linkage
modified_base             order(6..7,12,15,20..21,26)
                          mod_base = OTHER
                          note = Phosphate internucleoside linkage
SEQUENCE: 70
cccagnagct tcagtccctt tctcntcgat                                   30

SEQ ID NO: 71             moltype = RNA  length = 30
FEATURE                   Location/Qualifiers
source                    1..30
                          mol_type = other RNA
                          organism = synthetic construct
modified_base             order(1..3,12,14,16,26,28..30)
                          mod_base = OTHER
                          note = 2-Prime-methoxyribose nucleotides
modified_base             order(4,5,8,9,11,13,15,17..19,22,27)
                          mod_base = OTHER
                          note = 2-Prime-deoxy-2-Prime-fluororibose nucleotides
modified_base             order(6,7,10,20,21)
                          mod_base = OTHER
                          note = 2-Prime-MOEribose nucleotides
modified_base             6
                          mod_base = m5c
modified_base             order(10,20,21)
                          mod_base = OTHER
                          note = Thymidine
modified_base             23
                          mod_base = OTHER
                          note = Deoxyribose Thymidine
modified_base             24
                          mod_base = OTHER
                          note = Beta-homoDNA
modified_base             25
                          mod_base = OTHER
                          note = Deoxyribose
modified_base             25
                          mod_base = i
modified_base             order(1,11..12,14,25,29)
                          mod_base = OTHER
                          note = Mesyl phosphroamidate internucleoside linkage
modified_base             order(2..5,8..9,13,16..19,22..24,27..28)
                          mod_base = OTHER
                          note = Phosphorothioate internucleoside linkage
modified_base             order(6..7,10,15,20..21,26)
                          mod_base = OTHER
                          note = Phosphate internucleoside linkage
SEQUENCE: 71
cccagnagct tcagtccctt tctcntcgat                                   30

SEQ ID NO: 72             moltype = RNA  length = 30
```

-continued

```
FEATURE                Location/Qualifiers
source                 1..30
                       mol_type = other RNA
                       organism = synthetic construct
modified_base          order(1..3,12,14,16,26,28..30)
                       mod_base = OTHER
                       note = 2-Prime-methoxyribose nucleotides
modified_base          order(4,5,8,9,11,13,15,17..19,22,27)
                       mod_base = OTHER
                       note = 2-Prime-deoxy-2-Prime-fluororibose nucleotides
modified_base          order(6,7,10,20,21)
                       mod_base = OTHER
                       note = 2-Prime-MOEribose nucleotides
modified_base          6
                       mod_base = m5c
modified_base          order(10,20,21)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
modified_base          25
                       mod_base = i
modified_base          order(1,11,13..14,25,29)
                       mod_base = OTHER
                       note = Mesyl phosphroamidate internucleoside linkage
modified_base          order(2..5,8..9,16..19,22..24,27..28)
                       mod_base = OTHER
                       note = Phosphorothioate internucleoside linkage
modified_base          order(6..7,10,12,15,20..21,26)
                       mod_base = OTHER
                       note = Phosphate internucleoside linkage
SEQUENCE: 72
cccagnagct tcagtccctt tctcntcgat                                   30

SEQ ID NO: 73          moltype = RNA  length = 30
FEATURE                Location/Qualifiers
source                 1..30
                       mol_type = other RNA
                       organism = synthetic construct
modified_base          order(1..3,12,14,16,26,28..30)
                       mod_base = OTHER
                       note = 2-Prime-methoxyribose nucleotides
modified_base          order(4,5,8,9,11,13,15,17..19,22,27)
                       mod_base = OTHER
                       note = 2-Prime-deoxy-2-Prime-fluororibose nucleotides
modified_base          order(6,7,10,20,21)
                       mod_base = OTHER
                       note = 2-Prime-MOEribose nucleotides
modified_base          6
                       mod_base = m5c
modified_base          order(10,20,21)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
modified_base          25
                       mod_base = i
modified_base          order(1,11,14..15,25,29)
                       mod_base = OTHER
                       note = Mesyl phosphroamidate internucleoside linkage
modified_base          order(2..5,8..9,13,16..19,22..24,27..28)
                       mod_base = OTHER
                       note = Phosphorothioate internucleoside linkage
modified_base          order(6..7,10,12,20..21,26)
                       mod_base = OTHER
```

```
                       note = Phosphate internucleoside linkage
SEQUENCE: 73
cccagnagct tcagtccctt tctcntcgat                                   30

SEQ ID NO: 74          moltype = RNA  length = 30
FEATURE                Location/Qualifiers
source                 1..30
                       mol_type = other RNA
                       organism = synthetic construct
modified_base          order(1..3,12,14,16,26,28..30)
                       mod_base = OTHER
                       note = 2-Prime-methoxyribose nucleotides
modified_base          order(4,5,8,9,11,13,15,17..19,22,27)
                       mod_base = OTHER
                       note = 2-Prime-deoxy-2-Prime-fluororibose nucleotides
modified_base          order(6,7,10,20,21)
                       mod_base = OTHER
                       note = 2-Prime-MOEribose nucleotides
modified_base          6
                       mod_base = m5c
modified_base          order(10,20,21)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
modified_base          25
                       mod_base = i
modified_base          order(1,11,14,16,25,29)
                       mod_base = OTHER
                       note = Mesyl phosphroamidate internucleoside linkage
modified_base          order(2..5,8..9,13,17..19,22..24,27..28)
                       mod_base = OTHER
                       note = Phosphorothioate internucleoside linkage
modified_base          order(6..7,10,12,15,20..21,26)
                       mod_base = OTHER
                       note = Phosphate internucleoside linkage
SEQUENCE: 74
cccagnagct tcagtccctt tctcntcgat                                   30

SEQ ID NO: 75          moltype = RNA  length = 30
FEATURE                Location/Qualifiers
source                 1..30
                       mol_type = other RNA
                       organism = synthetic construct
modified_base          order(1..3,12,14,16,26,28..30)
                       mod_base = OTHER
                       note = 2-Prime-methoxyribose nucleotides
modified_base          order(4,5,8,9,11,13,15,17..19,22,27)
                       mod_base = OTHER
                       note = 2-Prime-deoxy-2-Prime-fluororibose nucleotides
modified_base          order(6,7,10,20,21)
                       mod_base = OTHER
                       note = 2-Prime-MOEribose nucleotides
modified_base          6
                       mod_base = m5c
modified_base          order(10,20,21)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
modified_base          25
                       mod_base = i
modified_base          order(1,11,14,17,25,29)
                       mod_base = OTHER
                       note = Mesyl phosphroamidate internucleoside linkage
```

-continued

```
modified_base          order(2..5,8..9,13,16,18..19,22..24,27..28)
                       mod_base = OTHER
                       note = Phosphorothioate internucleoside linkage
modified_base          order(6..7,10,12,15,20..21,26)
                       mod_base = OTHER
                       note = Phosphate internucleoside linkage
SEQUENCE: 75
cccagnagct tcagtccctt tctcntcgat                                   30

SEQ ID NO: 76          moltype = RNA  length = 30
FEATURE                Location/Qualifiers
source                 1..30
                       mol_type = other RNA
                       organism = synthetic construct
modified_base          order(1..3,12,14,16,26,28..30)
                       mod_base = OTHER
                       note = 2-Prime-methoxyribose nucleotides
modified_base          order(4,5,8,9,11,13,15,17..19,22,27)
                       mod_base = OTHER
                       note = 2-Prime-deoxy-2-Prime-fluororibose nucleotides
modified_base          order(6,7,10,20,21)
                       mod_base = OTHER
                       note = 2-Prime-MOEribose nucleotides
modified_base          6
                       mod_base = m5c
modified_base          order(10,20,21)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
modified_base          25
                       mod_base = i
modified_base          order(1,11,14,18,25,29)
                       mod_base = OTHER
                       note = Mesyl phosphroamidate internucleoside linkage
modified_base          order(2..5,8..9,13,16..17,19,22..24,27..28)
                       mod_base = OTHER
                       note = Phosphorothioate internucleoside linkage
modified_base          order(6..7,10,12,15,20..21,26)
                       mod_base = OTHER
                       note = Phosphate internucleoside linkage
SEQUENCE: 76
cccagnagct tcagtccctt tctcntcgat                                   30

SEQ ID NO: 77          moltype = RNA  length = 30
FEATURE                Location/Qualifiers
source                 1..30
                       mol_type = other RNA
                       organism = synthetic construct
modified_base          order(1..3,12,14,16,26,28..30)
                       mod_base = OTHER
                       note = 2-Prime-methoxyribose nucleotides
modified_base          order(4,5,8,9,11,13,15,17..19,22,27)
                       mod_base = OTHER
                       note = 2-Prime-deoxy-2-Prime-fluororibose nucleotides
modified_base          order(6,7,10,20,21)
                       mod_base = OTHER
                       note = 2-Prime-MOEribose nucleotides
modified_base          6
                       mod_base = m5c
modified_base          order(10,20,21)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
```

-continued

```
modified_base          25
                       mod_base = i
modified_base          order(1,11,14,20,25,29)
                       mod_base = OTHER
                       note = Mesyl phosphroamidate internucleoside linkage
modified_base          order(2..5,8..9,13,16..19,22..24,27..28)
                       mod_base = OTHER
                       note = Phosphorothioate internucleoside linkage
modified_base          order(6..7,10,12,15,21,26)
                       mod_base = OTHER
                       note = Phosphate internucleoside linkage
SEQUENCE: 77
cccagnagct tcagtccctt tctcntcgat                                    30

SEQ ID NO: 78          moltype = RNA  length = 30
FEATURE                Location/Qualifiers
source                 1..30
                       mol_type = other RNA
                       organism = synthetic construct
modified_base          order(1..3,12,14,16,26,28..30)
                       mod_base = OTHER
                       note = 2-Prime-methoxyribose nucleotides
modified_base          order(4,5,8,9,11,13,15,17..19,22,27)
                       mod_base = OTHER
                       note = 2-Prime-deoxy-2-Prime-fluororibose nucleotides
modified_base          order(6,7,10,20,21)
                       mod_base = OTHER
                       note = 2-Prime-MOEribose nucleotides
modified_base          6
                       mod_base = m5c
modified_base          order(10,20,21)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
modified_base          25
                       mod_base = i
modified_base          order(1,11,14,21,25,29)
                       mod_base = OTHER
                       note = Mesyl phosphroamidate internucleoside linkage
modified_base          order(2..5,8..9,13,16..19,22..24,27..28)
                       mod_base = OTHER
                       note = Phosphorothioate internucleoside linkage
modified_base          order(6..7,10,12,15,20,26)
                       mod_base = OTHER
                       note = Phosphate internucleoside linkage
SEQUENCE: 78
cccagnagct tcagtccctt tctcntcgat                                    30

SEQ ID NO: 79          moltype = RNA  length = 30
FEATURE                Location/Qualifiers
source                 1..30
                       mol_type = other RNA
                       organism = synthetic construct
modified_base          order(1..3,12,14,16,26,28..30)
                       mod_base = OTHER
                       note = 2-Prime-methoxyribose nucleotides
modified_base          order(4,5,8,9,11,13,15,17..19,22,27)
                       mod_base = OTHER
                       note = 2-Prime-deoxy-2-Prime-fluororibose nucleotides
modified_base          order(6,7,10,20,21)
                       mod_base = OTHER
                       note = 2-Prime-MOEribose nucleotides
modified_base          6
                       mod_base = m5c
modified_base          order(10,20,21)
                       mod_base = OTHER
                       note = Thymidine
modified_base          23
                       mod_base = OTHER
                       note = Deoxyribose Thymidine
modified_base          24
```

```
                          mod_base = OTHER
                          note = Beta-homoDNA
modified_base             25
                          mod_base = OTHER
                          note = Deoxyribose
modified_base             25
                          mod_base = i
modified_base             order(1,11,14,22,25,29)
                          mod_base = OTHER
                          note = Mesyl phosphroamidate internucleoside linkage
modified_base             order(2..5,8..9,13,16..19,23..24,27..28)
                          mod_base = OTHER
                          note = Phosphorothioate internucleoside linkage
modified_base             order(6..7,10,12,15,20..21,26)
                          mod_base = OTHER
                          note = Phosphate internucleoside linkage
SEQUENCE: 79
cccagnagct tcagtccctt tctcntcgat                                     30

SEQ ID NO: 80             moltype = RNA  length = 30
FEATURE                   Location/Qualifiers
source                    1..30
                          mol_type = other RNA
                          organism = synthetic construct
modified_base             order(1..3,12,14,16,26,28..30)
                          mod_base = OTHER
                          note = 2-Prime-methoxyribose nucleotides
modified_base             order(4,5,8,9,11,13,15,17..19,22,27)
                          mod_base = OTHER
                          note = 2-Prime-deoxy-2-Prime-fluororibose nucleotides
modified_base             order(6,7,10,20,21)
                          mod_base = OTHER
                          note = 2-Prime-MOEribose nucleotides
modified_base             6
                          mod_base = m5c
modified_base             order(10,20,21)
                          mod_base = OTHER
                          note = Thymidine
modified_base             23
                          mod_base = OTHER
                          note = Deoxyribose Thymidine
modified_base             24
                          mod_base = OTHER
                          note = Beta-homoDNA
modified_base             25
                          mod_base = OTHER
                          note = Deoxyribose
modified_base             25
                          mod_base = i
modified_base             order(1,11,14,25..26,29)
                          mod_base = OTHER
                          note = Mesyl phosphroamidate internucleoside linkage
modified_base             order(2..5,8..9,13,16..19,22..24,27..28)
                          mod_base = OTHER
                          note = Phosphorothioate internucleoside linkage
modified_base             order(6..7,10,12,15,20..21)
                          mod_base = OTHER
                          note = Phosphate internucleoside linkage
SEQUENCE: 80
cccagnagct tcagtccctt tctcntcgat                                     30

SEQ ID NO: 81             moltype = RNA  length = 30
FEATURE                   Location/Qualifiers
source                    1..30
                          mol_type = other RNA
                          organism = synthetic construct
modified_base             order(1..3,12,14,16,26,28..30)
                          mod_base = OTHER
                          note = 2-Prime-methoxyribose nucleotides
modified_base             order(4,5,8,9,11,13,15,17..19,22,27)
                          mod_base = OTHER
                          note = 2-Prime-deoxy-2-Prime-fluororibose nucleotides
modified_base             order(6,7,10,20,21)
                          mod_base = OTHER
                          note = 2-Prime-MOEribose nucleotides
modified_base             6
                          mod_base = m5c
modified_base             order(10,20,21)
                          mod_base = OTHER
```

```
                        note = Thymidine
modified_base           23
                        mod_base = OTHER
                        note = Deoxyribose Thymidine
modified_base           24
                        mod_base = OTHER
                        note = Beta-homoDNA
modified_base           25
                        mod_base = OTHER
                        note = Deoxyribose
modified_base           25
                        mod_base = i
modified_base           order(1,11,14,25,27,29)
                        mod_base = OTHER
                        note = Mesyl phosphroamidate internucleoside linkage
modified_base           order(2..5,8..9,13,16..19,22..24,28)
                        mod_base = OTHER
                        note = Phosphorothioate internucleoside linkage
modified_base           order(6..7,10,12,15,20..21,26)
                        mod_base = OTHER
                        note = Phosphate internucleoside linkage
SEQUENCE: 81
cccagnagct tcagtccctt tctcntcgat                                   30

SEQ ID NO: 82           moltype = RNA  length = 30
FEATURE                 Location/Qualifiers
source                  1..30
                        mol_type = other RNA
                        organism = synthetic construct
modified_base           order(1..3,12,14,16,26,28..30)
                        mod_base = OTHER
                        note = 2-Prime-methoxyribose nucleotides
modified_base           order(4,5,8,9,11,13,15,17..19,22,27)
                        mod_base = OTHER
                        note = 2-Prime-deoxy-2-Prime-fluororibose nucleotides
modified_base           order(6,7,10,20,21)
                        mod_base = OTHER
                        note = 2-Prime-MOEribose nucleotides
modified_base           6
                        mod_base = m5c
modified_base           order(10,20,21)
                        mod_base = OTHER
                        note = Thymidine
modified_base           23
                        mod_base = OTHER
                        note = Deoxyribose Thymidine
modified_base           24
                        mod_base = OTHER
                        note = Beta-homoDNA
modified_base           25
                        mod_base = OTHER
                        note = Deoxyribose
modified_base           25
                        mod_base = i
modified_base           order(1,11,14,25,28..29)
                        mod_base = OTHER
                        note = Mesyl phosphroamidate internucleoside linkage
modified_base           order(2..5,8..9,13,16..19,22..24,27)
                        mod_base = OTHER
                        note = Phosphorothioate internucleoside linkage
modified_base           order(6..7,10,12,15,20..21,26)
                        mod_base = OTHER
                        note = Phosphate internucleoside linkage
SEQUENCE: 82
cccagnagct tcagtccctt tctcntcgat                                   30

SEQ ID NO: 83           moltype = RNA  length = 30
FEATURE                 Location/Qualifiers
source                  1..30
                        mol_type = other RNA
                        organism = synthetic construct
modified_base           order(1..4,12,14,16,26,28..30)
                        mod_base = OTHER
                        note = 2-Prime-methoxyribose nucleotides
modified_base           order(5,8,9,11,13,15,17..19,22,27)
                        mod_base = OTHER
                        note = 2-Prime-deoxy-2-Prime-fluororibose nucleotides
modified_base           order(6,7,10,20,21)
                        mod_base = OTHER
```

```
                        note = 2-Prime-MOEribose nucleotides
modified_base           6
                        mod_base = m5c
modified_base           order(10,20,21)
                        mod_base = OTHER
                        note = Thymidine
modified_base           23
                        mod_base = OTHER
                        note = Deoxyribose Thymidine
modified_base           24
                        mod_base = OTHER
                        note = Beta-homoDNA
modified_base           25
                        mod_base = OTHER
                        note = Deoxyribose
modified_base           25
                        mod_base = i
modified_base           order(1,11,14,25,29)
                        mod_base = OTHER
                        note = Mesyl phosphroamidate internucleoside linkage
modified_base           order(2..5,8..9,13,16..19,22..24,27..28)
                        mod_base = OTHER
                        note = Phosphorothioate internucleoside linkage
modified_base           order(6..7,10,12,15,20..21,26)
                        mod_base = OTHER
                        note = Phosphate internucleoside linkage
SEQUENCE: 83
cccagnagct tcagtccctt tctcntcgat                                   30

SEQ ID NO: 84           moltype = RNA  length = 30
FEATURE                 Location/Qualifiers
source                  1..30
                        mol_type = other RNA
                        organism = synthetic construct
modified_base           order(1..3,5,12,14,16,26,28..30)
                        mod_base = OTHER
                        note = 2-Prime-methoxyribose nucleotides
modified_base           order(4,8,9,11,15,17..19,22,27)
                        mod_base = OTHER
                        note = 2-Prime-deoxy-2-Prime-fluororibose nucleotides
modified_base           order(6,7,10,20,21)
                        mod_base = OTHER
                        note = 2-Prime-MOEribose nucleotides
modified_base           6
                        mod_base = m5c
modified_base           order(10,20,21)
                        mod_base = OTHER
                        note = Thymidine
modified_base           23
                        mod_base = OTHER
                        note = Deoxyribose Thymidine
modified_base           24
                        mod_base = OTHER
                        note = Beta-homoDNA
modified_base           25
                        mod_base = OTHER
                        note = Deoxyribose
modified_base           25
                        mod_base = i
modified_base           order(1,11,14,25,29)
                        mod_base = OTHER
                        note = Mesyl phosphroamidate internucleoside linkage
modified_base           order(2..5,8..9,13,16..19,22..24,27..28)
                        mod_base = OTHER
                        note = Phosphorothioate internucleoside linkage
modified_base           order(6..7,10,12,15,20..21,26)
                        mod_base = OTHER
                        note = Phosphate internucleoside linkage
SEQUENCE: 84
cccagnagct tcagtccctt tctcntcgat                                   30

SEQ ID NO: 85           moltype = RNA  length = 30
FEATURE                 Location/Qualifiers
source                  1..30
                        mol_type = other RNA
                        organism = synthetic construct
modified_base           order(1..3,6,12,14,16,26,28..30)
                        mod_base = OTHER
                        note = 2-Prime-methoxyribose nucleotides
```

-continued

```
modified_base          order(4,5,8,9,11,13,15,17..19,22,27)
                       mod_base = OTHER
                       note = 2-Prime-deoxy-2-Prime-fluororibose nucleotides
modified_base          order(7,10,20,21)
                       mod_base = OTHER
                       note = 2-Prime-MOEribose nucleotides
modified_base          order(10,20,21)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
modified_base          order(1,11,14,25,29)
                       mod_base = OTHER
                       note = Mesyl phosphroamidate internucleoside linkage
modified_base          order(2..5,8..9,13,16..19,22..24,27..28)
                       mod_base = OTHER
                       note = Phosphorothioate internucleoside linkage
modified_base          order(6..7,10,12,15,20..21,26)
                       mod_base = OTHER
                       note = Phosphate internucleoside linkage
SEQUENCE: 85
cccagcagct tcagtccctt tctcntcgat                                    30

SEQ ID NO: 86          moltype = RNA  length = 30
FEATURE                Location/Qualifiers
source                 1..30
                       mol_type = other RNA
                       organism = synthetic construct
modified_base          order(1..3,7,12,14,16,26,28..30)
                       mod_base = OTHER
                       note = 2-Prime-methoxyribose nucleotides
modified_base          order(4,5,8,9,11,15,17..19,22,27)
                       mod_base = OTHER
                       note = 2-Prime-deoxy-2-Prime-fluororibose nucleotides
modified_base          order(6,10,20,21)
                       mod_base = OTHER
                       note = 2-Prime-MOEribose nucleotides
modified_base          6
                       mod_base = m5c
modified_base          order(10,20,21)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
modified_base          25
                       mod_base = i
modified_base          order(1,11,14,25,29)
                       mod_base = OTHER
                       note = Mesyl phosphroamidate internucleoside linkage
modified_base          order(2..5,8..9,13,16..19,22..24,27..28)
                       mod_base = OTHER
                       note = Phosphorothioate internucleoside linkage
modified_base          order(6..7,10,12,15,20..21,26)
                       mod_base = OTHER
                       note = Phosphate internucleoside linkage
SEQUENCE: 86
cccagnagct tcagtccctt tctcntcgat                                    30

SEQ ID NO: 87          moltype = RNA  length = 30
FEATURE                Location/Qualifiers
source                 1..30
                       mol_type = other RNA
                       organism = synthetic construct
modified_base          order(1..3,8,12,14,16,26,28..30)
                       mod_base = OTHER
```

```
                        note = 2-Prime-methoxyribose nucleotides
modified_base           order(4,5,9,11,13,15,17..19,22,27)
                        mod_base = OTHER
                        note = 2-Prime-deoxy-2-Prime-fluororibose nucleotides
modified_base           order(6,7,10,20,21)
                        mod_base = OTHER
                        note = 2-Prime-MOEribose nucleotides
modified_base           6
                        mod_base = m5c
modified_base           order(10,20,21)
                        mod_base = OTHER
                        note = Thymidine
modified_base           23
                        mod_base = OTHER
                        note = Deoxyribose Thymidine
modified_base           24
                        mod_base = OTHER
                        note = Beta-homoDNA
modified_base           25
                        mod_base = OTHER
                        note = Deoxyribose
modified_base           order(1,11,14,25,29)
                        mod_base = OTHER
                        note = Mesyl phosphroamidate internucleoside linkage
modified_base           order(2..5,8..9,13,16..19,22..24,27..28)
                        mod_base = OTHER
                        note = Phosphorothioate internucleoside linkage
modified_base           order(6..7,10,12,15,20..21,26)
                        mod_base = OTHER
                        note = Phosphate internucleoside linkage
SEQUENCE: 87
cccagnagct tcagtccctt tctcntcgat                                   30

SEQ ID NO: 88           moltype = RNA  length = 30
FEATURE                 Location/Qualifiers
source                  1..30
                        mol_type = other RNA
                        organism = synthetic construct
modified_base           order(1..3,9,12,14,16,26,28..30)
                        mod_base = OTHER
                        note = 2-Prime-methoxyribose nucleotides
modified_base           order(4,5,8,11,13,15,17..19,22,27)
                        mod_base = OTHER
                        note = 2-Prime-deoxy-2-Prime-fluororibose nucleotides
modified_base           order(6,7,10,20,21)
                        mod_base = OTHER
                        note = 2-Prime-MOEribose nucleotides
modified_base           6
                        mod_base = m5c
modified_base           order(10,20,21)
                        mod_base = OTHER
                        note = Thymidine
modified_base           23
                        mod_base = OTHER
                        note = Deoxyribose Thymidine
modified_base           24
                        mod_base = OTHER
                        note = Beta-homoDNA
modified_base           25
                        mod_base = OTHER
                        note = Deoxyribose
modified_base           25
                        mod_base = i
modified_base           order(1,11,14,25,29)
                        mod_base = OTHER
                        note = Mesyl phosphroamidate internucleoside linkage
modified_base           order(2..5,8..9,13,16..19,22..24,27..28)
                        mod_base = OTHER
                        note = Phosphorothioate internucleoside linkage
modified_base           order(6..7,10,12,15,20..21,26)
                        mod_base = OTHER
                        note = Phosphate internucleoside linkage
SEQUENCE: 88
cccagnagct tcagtccctt tctcntcgat                                   30

SEQ ID NO: 89           moltype = RNA  length = 30
FEATURE                 Location/Qualifiers
source                  1..30
                        mol_type = other RNA
```

```
                       organism = synthetic construct
modified_base          order(1..3,10,12,14,16,26,28..30)
                       mod_base = OTHER
                       note = 2-Prime-methoxyribose nucleotides
modified_base          order(4,5,8,9,11,13,15,17..19,22,27)
                       mod_base = OTHER
                       note = 2-Prime-deoxy-2-Prime-fluororibose nucleotides
modified_base          order(6,7,20,21)
                       mod_base = OTHER
                       note = 2-Prime-MOEribose nucleotides
modified_base          6
                       mod_base = m5c
modified_base          order(20,21)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
modified_base          25
                       mod_base = i
modified_base          order(1,11,14,25,29)
                       mod_base = OTHER
                       note = Mesyl phosphroamidate internucleoside linkage
modified_base          order(2..5,8..9,13,16..19,22..24,27..28)
                       mod_base = OTHER
                       note = Phosphorothioate internucleoside linkage
modified_base          order(6..7,10,12,15,20..21,26)
                       mod_base = OTHER
                       note = Phosphate internucleoside linkage
SEQUENCE: 89
cccagnagct tcagtccctt tctcntcgat                                   30

SEQ ID NO: 90          moltype = RNA  length = 30
FEATURE                Location/Qualifiers
source                 1..30
                       mol_type = other RNA
                       organism = synthetic construct
modified_base          order(1..3,7,11,12,14,16,26,28..30)
                       mod_base = OTHER
                       note = 2-Prime-methoxyribose nucleotides
modified_base          order(4,5,8,9,13,15,17..19,22,27)
                       mod_base = OTHER
                       note = 2-Prime-deoxy-2-Prime-fluororibose nucleotides
modified_base          order(6,7,10,20,21)
                       mod_base = OTHER
                       note = 2-Prime-MOEribose nucleotides
modified_base          6
                       mod_base = m5c
modified_base          order(10,20,21)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
modified_base          25
                       mod_base = i
modified_base          order(1,11,14,25,29)
                       mod_base = OTHER
                       note = Mesyl phosphroamidate internucleoside linkage
modified_base          order(2..5,8..9,13,16..19,22..24,27..28)
                       mod_base = OTHER
                       note = Phosphorothioate internucleoside linkage
modified_base          order(6..7,10,12,15,20..21,26)
                       mod_base = OTHER
                       note = Phosphate internucleoside linkage
SEQUENCE: 90
cccagnagct tcagtccctt tctcntcgat                                   30
```

-continued

```
SEQ ID NO: 91           moltype = RNA  length = 30
FEATURE                 Location/Qualifiers
source                  1..30
                        mol_type = other RNA
                        organism = synthetic construct
modified_base           order(1..3,7,12..14,16,26,28..30)
                        mod_base = OTHER
                        note = 2-Prime-methoxyribose nucleotides
modified_base           order(4,5,8,9,11,15,17..19,22,27)
                        mod_base = OTHER
                        note = 2-Prime-deoxy-2-Prime-fluororibose nucleotides
modified_base           order(6,7,10,20,21)
                        mod_base = OTHER
                        note = 2-Prime-MOEribose nucleotides
modified_base           order(10,20,21)
                        mod_base = OTHER
                        note = Thymidine
modified_base           23
                        mod_base = OTHER
                        note = Deoxyribose Thymidine
modified_base           24
                        mod_base = OTHER
                        note = Beta-homoDNA
modified_base           25
                        mod_base = OTHER
                        note = Deoxyribose
modified_base           25
                        mod_base = i
modified_base           order(1,11,14,25,29)
                        mod_base = OTHER
                        note = Mesyl phosphroamidate internucleoside linkage
modified_base           order(2..5,8..9,13,16..19,22..24,27..28)
                        mod_base = OTHER
                        note = Phosphorothioate internucleoside linkage
modified_base           order(6..7,10,12,15,20..21,26)
                        mod_base = OTHER
                        note = Phosphate internucleoside linkage
SEQUENCE: 91
cccagnagct tcagtccctt tctcntcgat                                   30

SEQ ID NO: 92           moltype = RNA  length = 30
FEATURE                 Location/Qualifiers
source                  1..30
                        mol_type = other RNA
                        organism = synthetic construct
modified_base           order(1..3,7,12,14..16,26,28..30)
                        mod_base = OTHER
                        note = 2-Prime-methoxyribose nucleotides
modified_base           order(4,5,8,9,11,13,17..19,22,27)
                        mod_base = OTHER
                        note = 2-Prime-deoxy-2-Prime-fluororibose nucleotides
modified_base           order(6,7,10,20,21)
                        mod_base = OTHER
                        note = 2-Prime-MOEribose nucleotides
modified_base           6
                        mod_base = m5c
modified_base           order(10,20,21)
                        mod_base = OTHER
                        note = Thymidine
modified_base           23
                        mod_base = OTHER
                        note = Deoxyribose Thymidine
modified_base           24
                        mod_base = OTHER
                        note = Beta-homoDNA
modified_base           25
                        mod_base = OTHER
                        note = Deoxyribose
modified_base           25
                        mod_base = i
modified_base           order(1,11,14,25,29)
                        mod_base = OTHER
                        note = Mesyl phosphroamidate internucleoside linkage
modified_base           order(2..5,8..9,13,16..19,22..24,27..28)
                        mod_base = OTHER
                        note = Phosphorothioate internucleoside linkage
modified_base           order(6..7,10,12,15,20..21,26)
                        mod_base = OTHER
```

```
                         note = Phosphate internucleoside linkage
SEQUENCE: 92
cccagnagct tcagtccctt tctcntcgat                                    30

SEQ ID NO: 93            moltype = RNA  length = 30
FEATURE                  Location/Qualifiers
source                   1..30
                         mol_type = other RNA
                         organism = synthetic construct
modified_base            order(1..3,7,12,14,16,17,26,28..30)
                         mod_base = OTHER
                         note = 2-Prime-methoxyribose nucleotides
modified_base            order(4,5,8,9,11,13,15,18,19,22,27)
                         mod_base = OTHER
                         note = 2-Prime-deoxy-2-Prime-fluororibose nucleotides
modified_base            order(6,7,10,20,21)
                         mod_base = OTHER
                         note = 2-Prime-MOEribose nucleotides
modified_base            6
                         mod_base = m5c
modified_base            order(10,20,21)
                         mod_base = OTHER
                         note = Thymidine
modified_base            23
                         mod_base = OTHER
                         note = Deoxyribose Thymidine
modified_base            24
                         mod_base = OTHER
                         note = Beta-homoDNA
modified_base            25
                         mod_base = OTHER
                         note = Deoxyribose
modified_base            25
                         mod_base = i
modified_base            order(1,11,14,25,29)
                         mod_base = OTHER
                         note = Mesyl phosphroamidate internucleoside linkage
modified_base            order(2..5,8..9,13,16..19,22..24,27..28)
                         mod_base = OTHER
                         note = Phosphorothioate internucleoside linkage
modified_base            order(6..7,10,12,15,20..21,26)
                         mod_base = OTHER
                         note = Phosphate internucleoside linkage
SEQUENCE: 93
cccagnagct tcagtccctt tctcntcgat                                    30

SEQ ID NO: 94            moltype = RNA  length = 30
FEATURE                  Location/Qualifiers
source                   1..30
                         mol_type = other RNA
                         organism = synthetic construct
modified_base            order(1..3,7,12,14,16,18,26,28..30)
                         mod_base = OTHER
                         note = 2-Prime-methoxyribose nucleotides
modified_base            order(4,5,8,9,11,13,15,17,19,22,27)
                         mod_base = OTHER
                         note = 2-Prime-deoxy-2-Prime-fluororibose nucleotides
modified_base            order(6,7,10,20,21)
                         mod_base = OTHER
                         note = 2-Prime-MOEribose nucleotides
modified_base            6
                         mod_base = m5c
modified_base            order(10,20,21)
                         mod_base = OTHER
                         note = Thymidine
modified_base            23
                         mod_base = OTHER
                         note = Deoxyribose Thymidine
modified_base            24
                         mod_base = OTHER
                         note = Beta-homoDNA
modified_base            25
                         mod_base = OTHER
                         note = Deoxyribose
modified_base            25
                         mod_base = i
modified_base            order(1,11,14,25,29)
                         mod_base = OTHER
                         note = Mesyl phosphroamidate internucleoside linkage
```

```
modified_base          order(2..5,8..9,13,16..19,22..24,27..28)
                       mod_base = OTHER
                       note = Phosphorothioate internucleoside linkage
modified_base          order(6..7,10,12,15,20..21,26)
                       mod_base = OTHER
                       note = Phosphate internucleoside linkage
SEQUENCE: 94
cccagnagct tcagtccctt tctcntcgat                                   30

SEQ ID NO: 95          moltype = RNA  length = 30
FEATURE                Location/Qualifiers
source                 1..30
                       mol_type = other RNA
                       organism = synthetic construct
modified_base          order(1..3,7,12,14,16,19,26,28..30)
                       mod_base = OTHER
                       note = 2-Prime-methoxyribose nucleotides
modified_base          order(4,5,8,9,11,13,15,17,18,22,27)
                       mod_base = OTHER
                       note = 2-Prime-deoxy-2-Prime-fluororibose nucleotides
modified_base          order(6,7,10,20,21)
                       mod_base = OTHER
                       note = 2-Prime-MOEribose nucleotides
modified_base          6
                       mod_base = m5c
modified_base          order(10,20,21)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
modified_base          25
                       mod_base = i
modified_base          order(1,11,14,25,29)
                       mod_base = OTHER
                       note = Mesyl phosphroamidate internucleoside linkage
modified_base          order(2..5,8..9,13,16..19,22..24,27..28)
                       mod_base = OTHER
                       note = Phosphorothioate internucleoside linkage
modified_base          order(6..7,10,12,15,20..21,26)
                       mod_base = OTHER
                       note = Phosphate internucleoside linkage
SEQUENCE: 95
cccagnagct tcagtccctt tctcntcgat                                   30

SEQ ID NO: 96          moltype = RNA  length = 30
FEATURE                Location/Qualifiers
source                 1..30
                       mol_type = other RNA
                       organism = synthetic construct
modified_base          order(1..3,7,12,14,16,20,26,28..30)
                       mod_base = OTHER
                       note = 2-Prime-methoxyribose nucleotides
modified_base          order(4,5,8,9,11,13,15,17..19,22,27)
                       mod_base = OTHER
                       note = 2-Prime-deoxy-2-Prime-fluororibose nucleotides
modified_base          order(6,7,10,21)
                       mod_base = OTHER
                       note = 2-Prime-MOEribose nucleotides
modified_base          6
                       mod_base = m5c
modified_base          order(10,21)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
```

```
modified_base          25
                       mod_base = i
modified_base          order(1,11,14,25,29)
                       mod_base = OTHER
                       note = Mesyl phosphroamidate internucleoside linkage
modified_base          order(2..5,8..9,13,16..19,22..24,27..28)
                       mod_base = OTHER
                       note = Phosphorothioate internucleoside linkage
modified_base          order(6..7,10,12,15,20..21,26)
                       mod_base = OTHER
                       note = Phosphate internucleoside linkage
SEQUENCE: 96
cccagnagct tcagtccctt tctcntcgat                                   30

SEQ ID NO: 97          moltype = RNA  length = 30
FEATURE                Location/Qualifiers
source                 1..30
                       mol_type = other RNA
                       organism = synthetic construct
modified_base          25
                       mod_base = i
modified_base          order(10,21,23)
                       mod_base = OTHER
                       note = Thymidine
SEQUENCE: 97
cccacgagct tcagtccctt tctcntcgat                                   30

SEQ ID NO: 98          moltype = RNA  length = 30
FEATURE                Location/Qualifiers
source                 1..30
                       mol_type = other RNA
                       organism = synthetic construct
modified_base          order(1..3,12,14,16,21,26,28..30)
                       mod_base = OTHER
                       note = 2-Prime-methoxyribose nucleotides
modified_base          order(4,5,8,9,11,13,15,17..19,22,27)
                       mod_base = OTHER
                       note = 2-Prime-deoxy-2-Prime-fluororibose nucleotides
modified_base          order(6,7,10,20)
                       mod_base = OTHER
                       note = 2-Prime-MOEribose nucleotides
modified_base          6
                       mod_base = m5c
modified_base          order(10,20)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
modified_base          25
                       mod_base = i
modified_base          order(1,11,14,25,29)
                       mod_base = OTHER
                       note = Mesyl phosphroamidate internucleoside linkage
modified_base          order(2..5,8..9,13,16..19,22..24,27..28)
                       mod_base = OTHER
                       note = Phosphorothioate internucleoside linkage
modified_base          order(6..7,10,12,15,20..21,26)
                       mod_base = OTHER
                       note = Phosphate internucleoside linkage
SEQUENCE: 98
cccagnagct tcagtccctt tctcntcgat                                   30

SEQ ID NO: 99          moltype = RNA  length = 30
FEATURE                Location/Qualifiers
source                 1..30
                       mol_type = other RNA
                       organism = synthetic construct
modified_base          25
                       mod_base = i
modified_base          order(10,20,23)
                       mod_base = OTHER
                       note = Thymidine
```

-continued

```
SEQUENCE: 99
cccacgagct tcagtccctt tctcntcgat                                   30

SEQ ID NO: 100         moltype = RNA  length = 30
FEATURE                Location/Qualifiers
source                 1..30
                       mol_type = other RNA
                       organism = synthetic construct
modified_base          order(1..3,7,12,14,16,21,26,28..30)
                       mod_base = OTHER
                       note = 2-Prime-methoxyribose nucleotides
modified_base          order(4,5,8,9,11,13,15,17..19,22,27)
                       mod_base = OTHER
                       note = 2-Prime-deoxy-2-Prime-fluororibose nucleotides
modified_base          order(6,7,10,20)
                       mod_base = OTHER
                       note = 2-Prime-MOEribose nucleotides
modified_base          6
                       mod_base = m5c
modified_base          order(10,20)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
modified_base          25
                       mod_base = i
modified_base          order(1,11,14,25,29)
                       mod_base = OTHER
                       note = Mesyl phosphroamidate internucleoside linkage
modified_base          order(2..5,8..9,13,16..19,22..24,27..28)
                       mod_base = OTHER
                       note = Phosphorothioate internucleoside linkage
modified_base          order(6..7,10,12,15,20..21,26)
                       mod_base = OTHER
                       note = Phosphate internucleoside linkage
SEQUENCE: 100
cccagnagct tcagtccctt tctcntcgat                                   30

SEQ ID NO: 101         moltype = RNA  length = 30
FEATURE                Location/Qualifiers
source                 1..30
                       mol_type = other RNA
                       organism = synthetic construct
modified_base          order(1..3,12,14,16,22,26,28..30)
                       mod_base = OTHER
                       note = 2-Prime-methoxyribose nucleotides
modified_base          order(4,5,8,9,11,13,15,17..19,27)
                       mod_base = OTHER
                       note = 2-Prime-deoxy-2-Prime-fluororibose nucleotides
modified_base          order(6,7,10,20,21)
                       mod_base = OTHER
                       note = 2-Prime-MOEribose nucleotides
modified_base          6
                       mod_base = m5c
modified_base          order(10,20,21)
                       mod_base = OTHER
                       note = Thymidine
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
modified_base          25
                       mod_base = i
modified_base          order(1,11,14,25,29)
                       mod_base = OTHER
                       note = Mesyl phosphroamidate internucleoside linkage
modified_base          order(2..5,8..9,13,16..19,22..24,27..28)
```

-continued

```
                         mod_base = OTHER
                         note = Phosphorothioate internucleoside linkage
modified_base            order(6..7,10,12,15,20..21,26)
                         mod_base = OTHER
                         note = Phosphate internucleoside linkage
SEQUENCE: 101
cccagnagct tcagtccctt tctcntcgat                                   30

SEQ ID NO: 102           moltype = RNA  length = 30
FEATURE                  Location/Qualifiers
source                   1..30
                         mol_type = other RNA
                         organism = synthetic construct
modified_base            order(1..3,12,14,16,26..30)
                         mod_base = OTHER
                         note = 2-Prime-methoxyribose nucleotides
modified_base            order(4,5,8,9,11,13,15,17..19,27)
                         mod_base = OTHER
                         note = 2-Prime-deoxy-2-Prime-fluororibose nucleotides
modified_base            6
                         mod_base = m5c
modified_base            order(6,7,10,20,21)
                         mod_base = OTHER
                         note = 2-Prime-MOEribose nucleotides
modified_base            order(10,20,21)
                         mod_base = OTHER
                         note = Thymidine
modified_base            23
                         mod_base = OTHER
                         note = Deoxyribose Thymidine
modified_base            24
                         mod_base = OTHER
                         note = Beta-homoDNA
modified_base            25
                         mod_base = OTHER
                         note = Deoxyribose
modified_base            25
                         mod_base = i
modified_base            order(1,11,14,25,29)
                         mod_base = OTHER
                         note = Mesyl phosphroamidate internucleoside linkage
modified_base            order(2..5,8..9,13,16..19,22..24,27..28)
                         mod_base = OTHER
                         note = Phosphorothioate internucleoside linkage
modified_base            order(6..7,10,12,15,20..21,26)
                         mod_base = OTHER
                         note = Phosphate internucleoside linkage
SEQUENCE: 102
cccagnagct tcagtccctt tctcntcgat                                   30

SEQ ID NO: 103           moltype = RNA  length = 30
FEATURE                  Location/Qualifiers
source                   1..30
                         mol_type = other RNA
                         organism = synthetic construct
modified_base            order(1..7,12,14,16,26,28..30)
                         mod_base = OTHER
                         note = 2-Prime-methoxyribose nucleotides
modified_base            order(8,9,11,13,15,17..19,22,27)
                         mod_base = OTHER
                         note = 2-Prime-deoxy-2-Prime-fluororibose nucleotides
modified_base            order(10,20,21)
                         mod_base = OTHER
                         note = 2-Prime-MOEribose nucleotides
modified_base            order(10,20,21)
                         mod_base = OTHER
                         note = Thymidine
modified_base            23
                         mod_base = OTHER
                         note = Deoxyribose Thymidine
modified_base            24
                         mod_base = OTHER
                         note = Beta-homoDNA
modified_base            25
                         mod_base = OTHER
                         note = Deoxyribose
modified_base            25
                         mod_base = i
modified_base            order(1,11,14,25,29)
```

```
                        mod_base = OTHER
                        note = Mesyl phosphroamidate internucleoside linkage
modified_base           order(2..5,8..9,13,16..19,22..24,27..28)
                        mod_base = OTHER
                        note = Phosphorothioate internucleoside linkage
modified_base           order(6..7,10,12,15,20..21,26)
                        mod_base = OTHER
                        note = Phosphate internucleoside linkage
SEQUENCE: 103
cccacgagct tcagtccctt tctcntcgat                                    30

SEQ ID NO: 104          moltype = RNA  length = 30
FEATURE                 Location/Qualifiers
source                  1..30
                        mol_type = other RNA
                        organism = synthetic construct
modified_base           order(1..3,8..12,14,16,26,28..30)
                        mod_base = OTHER
                        note = 2-Prime-methoxyribose nucleotides
modified_base           order(4,5,13,15,17..19,22,27)
                        mod_base = OTHER
                        note = 2-Prime-deoxy-2-Prime-fluororibose nucleotides
modified_base           order(6,7,20,21)
                        mod_base = OTHER
                        note = 2-Prime-MOEribose nucleotides
modified_base           6
                        mod_base = m5c
modified_base           order(20,21)
                        mod_base = OTHER
                        note = Thymidine
modified_base           23
                        mod_base = OTHER
                        note = Deoxyribose Thymidine
modified_base           24
                        mod_base = OTHER
                        note = Beta-homoDNA
modified_base           25
                        mod_base = OTHER
                        note = Deoxyribose
modified_base           25
                        mod_base = i
modified_base           order(1,11,14,25,29)
                        mod_base = OTHER
                        note = Mesyl phosphroamidate internucleoside linkage
modified_base           order(2..5,8..9,13,16..19,22..24,27..28)
                        mod_base = OTHER
                        note = Phosphorothioate internucleoside linkage
modified_base           order(6..7,10,12,15,20..21,26)
                        mod_base = OTHER
                        note = Phosphate internucleoside linkage
SEQUENCE: 104
cccagnagct tcagtccctt tctcntcgat                                    30

SEQ ID NO: 105          moltype = RNA  length = 30
FEATURE                 Location/Qualifiers
source                  1..30
                        mol_type = other RNA
                        organism = synthetic construct
modified_base           order(1..3,12,14,16..19,26,28..30)
                        mod_base = OTHER
                        note = 2-Prime-methoxyribose nucleotides
modified_base           order(4,5,8,9,11,13,15,22,27)
                        mod_base = OTHER
                        note = 2-Prime-deoxy-2-Prime-fluororibose nucleotides
modified_base           order(6,7,10,20,21)
                        mod_base = OTHER
                        note = 2-Prime-MOEribose nucleotides
modified_base           6
                        mod_base = m5c
modified_base           order(10,20,21)
                        mod_base = OTHER
                        note = Thymidine
modified_base           23
                        mod_base = OTHER
                        note = Deoxyribose Thymidine
modified_base           24
                        mod_base = OTHER
                        note = Beta-homoDNA
modified_base           25
```

-continued

```
                        mod_base = OTHER
                        note = Deoxyribose
modified_base           25
                        mod_base = i
modified_base           order(1,11,14,25,29)
                        mod_base = OTHER
                        note = Mesyl phosphroamidate internucleoside linkage
modified_base           order(2..5,8..9,13,16..19,22..24,27..28)
                        mod_base = OTHER
                        note = Phosphorothioate internucleoside linkage
modified_base           order(6..7,10,12,15,20..21,26)
                        mod_base = OTHER
                        note = Phosphate internucleoside linkage
SEQUENCE: 105
cccagnagct tcagtccctt tctcntcgat                                   30

SEQ ID NO: 106          moltype = RNA  length = 30
FEATURE                 Location/Qualifiers
source                  1..30
                        mol_type = other RNA
                        organism = synthetic construct
modified_base           25
                        mod_base = i
modified_base           order(10,23)
                        mod_base = OTHER
                        note = Thymidine
SEQUENCE: 106
cccagcagct tcagtccctt tctcntcgat                                   30

SEQ ID NO: 107          moltype = RNA  length = 30
FEATURE                 Location/Qualifiers
source                  1..30
                        mol_type = other RNA
                        organism = synthetic construct
modified_base           order(1..3,6,7,10,12,14,16,20,21,26,28..30)
                        mod_base = OTHER
                        note = 2-Prime-methoxyribose nucleotides
modified_base           order(4,5,8,9,11,13,15,17..19,22,27)
                        mod_base = OTHER
                        note = 2-Prime-deoxy-2-Prime-fluororibose nucleotides
modified_base           23
                        mod_base = OTHER
                        note = Deoxyribose Thymidine
modified_base           24
                        mod_base = OTHER
                        note = Beta-homoDNA
modified_base           25
                        mod_base = OTHER
                        note = Deoxyribose
modified_base           25
                        mod_base = i
modified_base           order(1,11,14,25,29)
                        mod_base = OTHER
                        note = Mesyl phosphroamidate internucleoside linkage
modified_base           order(2..5,8..9,13,16..19,22..24,27..28)
                        mod_base = OTHER
                        note = Phosphorothioate internucleoside linkage
modified_base           order(6..7,10,12,15,20..21,26)
                        mod_base = OTHER
                        note = Phosphate internucleoside linkage
SEQUENCE: 107
cccagcagct tcagtccctt tctcntcgat                                   30

SEQ ID NO: 108          moltype = RNA  length = 30
FEATURE                 Location/Qualifiers
source                  1..30
                        mol_type = other RNA
                        organism = synthetic construct
modified_base           25
                        mod_base = i
modified_base           23
                        mod_base = OTHER
                        note = Thymidine
SEQUENCE: 108
cccagcagct tcagtccctt tctcntcgat                                   30

SEQ ID NO: 109          moltype = RNA  length = 42
FEATURE                 Location/Qualifiers
source                  1..42
```

```
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotides
modified_base           33
                        mod_base = i
modified_base           order(1..2,21,23,33,41)
                        mod_base = OTHER
                        note = Mesyl phosphroamidate internucleoside linkage
modified_base           order(4..12,14..18,22,24..32,34..35,39..40)
                        mod_base = OTHER
                        note = Phosphorothioate internucleoside linkage
modified_base           order(3,13,19..20,36..38)
                        mod_base = OTHER
                        note = Phosphate internucleoside linkage
SEQUENCE: 109
aacatggccc cagcagcttc agtccctttc tcntcgatgg tc                    42

SEQ ID NO: 110          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotides
modified_base           33
                        mod_base = i
modified_base           order(1,3,21,23,33,41)
                        mod_base = OTHER
                        note = Mesyl phosphroamidate internucleoside linkage
modified_base           order(2,4..12,14..18,22,24..32,34..35,39..40)
                        mod_base = OTHER
                        note = Phosphorothioate internucleoside linkage
modified_base           order(13,19..20,36..38)
                        mod_base = OTHER
                        note = Phosphate internucleoside linkage
SEQUENCE: 110
aacatggccc cagcagcttc agtccctttc tcntcgatgg tc                    42

SEQ ID NO: 111          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
```

```
modified_base          32
                       mod_base = OTHER
                       note = Beta-homoDNA
modified_base          33
                       mod_base = OTHER
                       note = 2-Prime-fluroarabinose nucleotides
modified_base          33
                       mod_base = i
modified_base          order(1,4,21,23,33,41)
                       mod_base = OTHER
                       note = Mesyl phosphroamidate internucleoside linkage
modified_base          order(2,5..12,14..18,22,24..32,34..35,39..40)
                       mod_base = OTHER
                       note = Phosphorothioate internucleoside linkage
modified_base          order(3,13,19..20,36..38)
                       mod_base = OTHER
                       note = Phosphate internucleoside linkage
SEQUENCE: 111
aacatggccc cagcagcttc agtccctttc tcntcgatgg tc                     42

SEQ ID NO: 112         moltype = RNA  length = 42
FEATURE                Location/Qualifiers
source                 1..42
                       mol_type = other RNA
                       organism = synthetic construct
modified_base          order(3,4,9,11,13,14,17,19..21,24,28,30,34,36..39,42)
                       mod_base = OTHER
                       note = 2-Prime-methoxyribose nucleotides
modified_base          order(1,2,5..8,10,12,15,16,18,22,23,25..27,29,35,40,41)
                       mod_base = OTHER
                       note = 2-Prime-deoxy-2-Prime-fluororibose nucleotides
modified_base          31
                       mod_base = OTHER
                       note = Deoxyribose Thymidine
modified_base          32
                       mod_base = OTHER
                       note = Beta-homoDNA
modified_base          33
                       mod_base = OTHER
                       note = 2-Prime-fluroarabinose nucleotides
modified_base          33
                       mod_base = i
modified_base          order(1,5,21,23,33,41)
                       mod_base = OTHER
                       note = Mesyl phosphroamidate internucleoside linkage
modified_base          order(2,4,6..12,14..18,22,24..32,34..35,39..40)
                       mod_base = OTHER
                       note = Phosphorothioate internucleoside linkage
modified_base          order(3,13,19..20,36..38)
                       mod_base = OTHER
                       note = Phosphate internucleoside linkage
SEQUENCE: 112
aacatggccc cagcagcttc agtccctttc tcntcgatgg tc                     42

SEQ ID NO: 113         moltype = RNA  length = 42
FEATURE                Location/Qualifiers
source                 1..42
                       mol_type = other RNA
                       organism = synthetic construct
modified_base          order(3,4,9,11,13,14,17,19..21,24,28,30,34,36..39,42)
                       mod_base = OTHER
                       note = 2-Prime-methoxyribose nucleotides
modified_base          order(1,2,5..8,10,12,15,16,18,22,23,25..27,29,35,40,41)
                       mod_base = OTHER
                       note = 2-Prime-deoxy-2-Prime-fluororibose nucleotides
modified_base          31
                       mod_base = OTHER
                       note = Deoxyribose Thymidine
modified_base          32
                       mod_base = OTHER
                       note = Beta-homoDNA
modified_base          33
                       mod_base = OTHER
                       note = 2-Prime-fluroarabinose nucleotides
modified_base          33
                       mod_base = i
modified_base          order(1,6,21,23,33,41)
                       mod_base = OTHER
                       note = Mesyl phosphroamidate internucleoside linkage
```

```
modified_base          order(2,4..5,7..12,14..18,22,24..32,34..35,39..40)
                       mod_base = OTHER
                       note = Phosphorothioate internucleoside linkage
modified_base          order(3,13,19..20,36..38)
                       mod_base = OTHER
                       note = Phosphate internucleoside linkage
SEQUENCE: 113
aacatggccc cagcagcttc agtccctttc tcntcgatgg tc                    42

SEQ ID NO: 114         moltype = RNA  length = 42
FEATURE                Location/Qualifiers
source                 1..42
                       mol_type = other RNA
                       organism = synthetic construct
modified_base          order(3,4,9,11,13,14,17,19..21,24,28,30,34,36..39,42)
                       mod_base = OTHER
                       note = 2-Prime-methoxyribose nucleotides
modified_base          order(1,2,5..8,10,12,15,16,18,22,23,25..27,29,35,40,41)
                       mod_base = OTHER
                       note = 2-Prime-deoxy-2-Prime-fluororibose nucleotides
modified_base          31
                       mod_base = OTHER
                       note = Deoxyribose Thymidine
modified_base          32
                       mod_base = OTHER
                       note = Beta-homoDNA
modified_base          33
                       mod_base = OTHER
                       note = 2-Prime-fluroarabinose nucleotides
modified_base          33
                       mod_base = i
modified_base          order(1,7,21,23,33,41)
                       mod_base = OTHER
                       note = Mesyl phosphroamidate internucleoside linkage
modified_base          order(2,4..6,8..12,14..18,22,24..32,34..35,39..40)
                       mod_base = OTHER
                       note = Phosphorothioate internucleoside linkage
modified_base          order(3,13,19..20,36..38)
                       mod_base = OTHER
                       note = Phosphate internucleoside linkage
SEQUENCE: 114
aacatggccc cagcagcttc agtccctttc tcntcgatgg tc                    42

SEQ ID NO: 115         moltype = RNA  length = 42
FEATURE                Location/Qualifiers
source                 1..42
                       mol_type = other RNA
                       organism = synthetic construct
modified_base          order(3,4,9,11,13,14,17,19..21,24,28,30,34,36..39,42)
                       mod_base = OTHER
                       note = 2-Prime-methoxyribose nucleotides
modified_base          order(1,2,5..8,10,12,15,16,18,22,23,25..27,29,35,40,41)
                       mod_base = OTHER
                       note = 2-Prime-deoxy-2-Prime-fluororibose nucleotides
modified_base          31
                       mod_base = OTHER
                       note = Deoxyribose Thymidine
modified_base          32
                       mod_base = OTHER
                       note = Beta-homoDNA
modified_base          33
                       mod_base = OTHER
                       note = 2-Prime-fluroarabinose nucleotides
modified_base          33
                       mod_base = i
modified_base          order(1,8,21,23,33,41)
                       mod_base = OTHER
                       note = Mesyl phosphroamidate internucleoside linkage
modified_base          order(2,4..7,9..12,14..18,22,24..32,34..35,39..40)
                       mod_base = OTHER
                       note = Phosphorothioate internucleoside linkage
modified_base          order(3,13,19..20,36..38)
                       mod_base = OTHER
                       note = Phosphate internucleoside linkage
SEQUENCE: 115
aacatggccc cagcagcttc agtccctttc tcntcgatgg tc                    42

SEQ ID NO: 116         moltype = RNA  length = 42
FEATURE                Location/Qualifiers
```

```
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotides
modified_base           33
                        mod_base = i
modified_base           order(1,9,21,23,33,41)
                        mod_base = OTHER
                        note = Mesyl phosphroamidate internucleoside linkage
modified_base           order(2,4..8,10..12,14..18,22,24..32,34..35,39..40)
                        mod_base = OTHER
                        note = Phosphorothioate internucleoside linkage
modified_base           order(3,13,19..20,36..38)
                        mod_base = OTHER
                        note = Phosphate internucleoside linkage
SEQUENCE: 116
aacatggccc cagcagcttc agtcccttc tcntcgatgg tc                      42

SEQ ID NO: 117          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotides
modified_base           33
                        mod_base = i
modified_base           order(1,10,21,23,33,41)
                        mod_base = OTHER
                        note = Mesyl phosphroamidate internucleoside linkage
modified_base           order(2,4..9,11..12,14..18,22,24..32,34..35,39..40)
                        mod_base = OTHER
                        note = Phosphorothioate internucleoside linkage
modified_base           order(3,13,19..20,36..38)
                        mod_base = OTHER
                        note = Phosphate internucleoside linkage
SEQUENCE: 117
aacatggccc cagcagcttc agtcccttc tcntcgatgg tc                      42

SEQ ID NO: 118          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
```

```
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotides
modified_base           33
                        mod_base = i
modified_base           order(1,11,21,23,33,41)
                        mod_base = OTHER
                        note = Mesyl phosphroamidate internucleoside linkage
modified_base           order(2,4..10,12,14..18,22,24..32,34..35,39..40)
                        mod_base = OTHER
                        note = Phosphorothioate internucleoside linkage
modified_base           order(3,13,19..20,36..38)
                        mod_base = OTHER
                        note = Phosphate internucleoside linkage
SEQUENCE: 118
aacatggccc cagcagcttc agtccctttc tcntcgatgg tc                      42

SEQ ID NO: 119          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotides
modified_base           33
                        mod_base = i
modified_base           order(1,12,21,23,33,41)
                        mod_base = OTHER
                        note = Mesyl phosphroamidate internucleoside linkage
modified_base           order(2,4..11,14..18,22,24..32,34..35,39..40)
                        mod_base = OTHER
                        note = Phosphorothioate internucleoside linkage
modified_base           order(3,13,19..20,36..38)
                        mod_base = OTHER
                        note = Phosphate internucleoside linkage
SEQUENCE: 119
aacatggccc cagcagcttc agtccctttc tcntcgatgg tc                      42

SEQ ID NO: 120          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotides
modified_base           33
                        mod_base = i
modified_base           order(1,13,21,23,33,41)
                        mod_base = OTHER
```

```
                        note = Mesyl phosphroamidate internucleoside linkage
modified_base           order(2,4..12,14..18,22,24..32,34..35,39..40)
                        mod_base = OTHER
                        note = Phosphorothioate internucleoside linkage
modified_base           order(3,19..20,36..38)
                        mod_base = OTHER
                        note = Phosphate internucleoside linkage
SEQUENCE: 120
aacatggccc cagcagcttc agtccctttc tcntcgatgg tc                    42

SEQ ID NO: 121          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotides
modified_base           33
                        mod_base = i
modified_base           order(1,14,21,23,33,41)
                        mod_base = OTHER
                        note = Mesyl phosphroamidate internucleoside linkage
modified_base           order(2,4..12,15..18,22,24..32,34..35,39..40)
                        mod_base = OTHER
                        note = Phosphorothioate internucleoside linkage
modified_base           order(3,13,19..20,36..38)
                        mod_base = OTHER
                        note = Phosphate internucleoside linkage
SEQUENCE: 121
aacatggccc cagcagcttc agtccctttc tcntcgatgg tc                    42

SEQ ID NO: 122          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotides
modified_base           33
                        mod_base = i
modified_base           order(1,15,21,23,33,41)
                        mod_base = OTHER
                        note = Mesyl phosphroamidate internucleoside linkage
modified_base           order(2,4..12,14,16..18,22,24..32,34..35,39..40)
                        mod_base = OTHER
                        note = Phosphorothioate internucleoside linkage
modified_base           order(3,13,19..20,36..38)
                        mod_base = OTHER
                        note = Phosphate internucleoside linkage
SEQUENCE: 122
aacatggccc cagcagcttc agtccctttc tcntcgatgg tc                    42

SEQ ID NO: 123          moltype = RNA  length = 42
```

-continued

```
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotides
modified_base           33
                        mod_base = i
modified_base           order(1,16,21,23,33,41)
                        mod_base = OTHER
                        note = Mesyl phosphroamidate internucleoside linkage
modified_base           order(2,4..12,14..15,17..18,22,24..32,34..35,39..40)
                        mod_base = OTHER
                        note = Phosphorothioate internucleoside linkage
modified_base           order(3,13,19..20,36..38)
                        mod_base = OTHER
                        note = Phosphate internucleoside linkage
SEQUENCE: 123
aacatggccc cagcagcttc agtccctttc tcntcgatgg tc                    42

SEQ ID NO: 124          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotides
modified_base           33
                        mod_base = i
modified_base           order(1,17,21,23,33,41)
                        mod_base = OTHER
                        note = Mesyl phosphroamidate internucleoside linkage
modified_base           order(2,4..12,14..16,18,22,24..32,34..35,39..40)
                        mod_base = OTHER
                        note = Phosphorothioate internucleoside linkage
modified_base           order(3,13,19..20,36..38)
                        mod_base = OTHER
                        note = Phosphate internucleoside linkage
SEQUENCE: 124
aacatggccc cagcagcttc agtccctttc tcntcgatgg tc                    42

SEQ ID NO: 125          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
```

```
                         mod_base = OTHER
                         note = Deoxyribose Thymidine
modified_base            32
                         mod_base = OTHER
                         note = Beta-homoDNA
modified_base            33
                         mod_base = OTHER
                         note = 2-Prime-fluroarabinose nucleotides
modified_base            33
                         mod_base = i
modified_base            order(1,18,21,23,33,41)
                         mod_base = OTHER
                         note = Mesyl phosphroamidate internucleoside linkage
modified_base            order(2,4..12,14..17,22,24..32,34..35,39..40)
                         mod_base = OTHER
                         note = Phosphorothioate internucleoside linkage
modified_base            order(3,13,19..20,36..38)
                         mod_base = OTHER
                         note = Phosphate internucleoside linkage
SEQUENCE: 125
aacatggccc cagcagcttc agtccctttc tcntcgatgg tc                       42

SEQ ID NO: 126           moltype = RNA  length = 42
FEATURE                  Location/Qualifiers
source                   1..42
                         mol_type = other RNA
                         organism = synthetic construct
modified_base            order(3,4,9,11,13,14,17,19..21,24,28,30,34,36..39,42)
                         mod_base = OTHER
                         note = 2-Prime-methoxyribose nucleotides
modified_base            order(1,2,5..8,10,12,15,16,18,22,23,25..27,29,35,40,41)
                         mod_base = OTHER
                         note = 2-Prime-deoxy-2-Prime-fluororibose nucleotides
modified_base            31
                         mod_base = OTHER
                         note = Deoxyribose Thymidine
modified_base            32
                         mod_base = OTHER
                         note = Beta-homoDNA
modified_base            33
                         mod_base = OTHER
                         note = 2-Prime-fluroarabinose nucleotides
modified_base            33
                         mod_base = i
modified_base            order(1,19,21,23,33,41)
                         mod_base = OTHER
                         note = Mesyl phosphroamidate internucleoside linkage
modified_base            order(2,4..12,14..18,22,24..32,34..35,39..40)
                         mod_base = OTHER
                         note = Phosphorothioate internucleoside linkage
modified_base            order(3,13,20,36..38)
                         mod_base = OTHER
                         note = Phosphate internucleoside linkage
SEQUENCE: 126
aacatggccc cagcagcttc agtccctttc tcntcgatgg tc                       42

SEQ ID NO: 127           moltype = RNA  length = 42
FEATURE                  Location/Qualifiers
source                   1..42
                         mol_type = other RNA
                         organism = synthetic construct
modified_base            order(3,4,9,11,13,14,17,19..21,24,28,30,34,36..39,42)
                         mod_base = OTHER
                         note = 2-Prime-methoxyribose nucleotides
modified_base            order(1,2,5..8,10,12,15,16,18,22,23,25..27,29,35,40,41)
                         mod_base = OTHER
                         note = 2-Prime-deoxy-2-Prime-fluororibose nucleotides
modified_base            31
                         mod_base = OTHER
                         note = Deoxyribose Thymidine
modified_base            32
                         mod_base = OTHER
                         note = Beta-homoDNA
modified_base            33
                         mod_base = OTHER
                         note = 2-Prime-fluroarabinose nucleotides
modified_base            33
                         mod_base = i
modified_base            order(1,20..21,23,33,41)
```

```
                         mod_base = OTHER
                         note = Mesyl phosphroamidate internucleoside linkage
modified_base            order(2,4..12,14..18,22,24..32,34..35,39..40)
                         mod_base = OTHER
                         note = Phosphorothioate internucleoside linkage
modified_base            order(3,13,19,36..38)
                         mod_base = OTHER
                         note = Phosphate internucleoside linkage
SEQUENCE: 127
aacatggccc cagcagcttc agtccctttc tcntcgatgg tc                    42

SEQ ID NO: 128           moltype = RNA  length = 42
FEATURE                  Location/Qualifiers
source                   1..42
                         mol_type = other RNA
                         organism = synthetic construct
modified_base            order(3,4,9,11,13,14,17,19..21,24,28,30,34,36..39,42)
                         mod_base = OTHER
                         note = 2-Prime-methoxyribose nucleotides
modified_base            order(1,2,5..8,10,12,15,16,18,22,23,25..27,29,35,40,41)
                         mod_base = OTHER
                         note = 2-Prime-deoxy-2-Prime-fluororibose nucleotides
modified_base            31
                         mod_base = OTHER
                         note = Deoxyribose Thymidine
modified_base            32
                         mod_base = OTHER
                         note = Beta-homoDNA
modified_base            33
                         mod_base = OTHER
                         note = 2-Prime-fluroarabinose nucleotides
modified_base            33
                         mod_base = i
modified_base            order(1,21..23,33,41)
                         mod_base = OTHER
                         note = Mesyl phosphroamidate internucleoside linkage
modified_base            order(2,4..12,14..18,24..32,34..35,39..40)
                         mod_base = OTHER
                         note = Phosphorothioate internucleoside linkage
modified_base            order(3,13,19..20,36..38)
                         mod_base = OTHER
                         note = Phosphate internucleoside linkage
SEQUENCE: 128
aacatggccc cagcagcttc agtccctttc tcntcgatgg tc                    42

SEQ ID NO: 129           moltype = RNA  length = 42
FEATURE                  Location/Qualifiers
source                   1..42
                         mol_type = other RNA
                         organism = synthetic construct
modified_base            order(3,4,9,11,13,14,17,19..21,24,28,30,34,36..39,42)
                         mod_base = OTHER
                         note = 2-Prime-methoxyribose nucleotides
modified_base            order(1,2,5..8,10,12,15,16,18,22,23,25..27,29,35,40,41)
                         mod_base = OTHER
                         note = 2-Prime-deoxy-2-Prime-fluororibose nucleotides
modified_base            31
                         mod_base = OTHER
                         note = Deoxyribose Thymidine
modified_base            32
                         mod_base = OTHER
                         note = Beta-homoDNA
modified_base            33
                         mod_base = OTHER
                         note = 2-Prime-fluroarabinose nucleotides
modified_base            33
                         mod_base = i
modified_base            order(1,21,23..24,33,41)
                         mod_base = OTHER
                         note = Mesyl phosphroamidate internucleoside linkage
modified_base            order(2,4..12,14..18,22,25..32,34..35,39..40)
                         mod_base = OTHER
                         note = Phosphorothioate internucleoside linkage
modified_base            order(3,13,19..20,36..38)
                         mod_base = OTHER
                         note = Phosphate internucleoside linkage
SEQUENCE: 129
aacatggccc cagcagcttc agtccctttc tcntcgatgg tc                    42
```

-continued

```
SEQ ID NO: 130          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotides
modified_base           33
                        mod_base = i
modified_base           order(1,21,23,25,33,41)
                        mod_base = OTHER
                        note = Mesyl phosphroamidate internucleoside linkage
modified_base           order(2,4..12,14..18,22,24,26..32,34..35,39..40)
                        mod_base = OTHER
                        note = Phosphorothioate internucleoside linkage
modified_base           order(3,13,19..20,36..38)
                        mod_base = OTHER
                        note = Phosphate internucleoside linkage
SEQUENCE: 130
aacatggccc cagcagcttc agtccctttc tcntcgatgg tc                    42

SEQ ID NO: 131          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotides
modified_base           33
                        mod_base = i
modified_base           order(1,21,23,26,33,41)
                        mod_base = OTHER
                        note = Mesyl phosphroamidate internucleoside linkage
modified_base           order(2,4..12,14..18,22,24..25,27..32,34..35,39..40)
                        mod_base = OTHER
                        note = Phosphorothioate internucleoside linkage
modified_base           order(3,13,19..20,36..38)
                        mod_base = OTHER
                        note = Phosphate internucleoside linkage
SEQUENCE: 131
aacatggccc cagcagcttc agtccctttc tcntcgatgg tc                    42

SEQ ID NO: 132          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
```

```
modified_base          31
                       mod_base = OTHER
                       note = Deoxyribose Thymidine
modified_base          32
                       mod_base = OTHER
                       note = Beta-homoDNA
modified_base          33
                       mod_base = OTHER
                       note = 2-Prime-fluroarabinose nucleotides
modified_base          33
                       mod_base = i
modified_base          order(1,21,23,27,33,41)
                       mod_base = OTHER
                       note = Mesyl phosphroamidate internucleoside linkage
modified_base          order(2,4..12,14..18,22,24..26,28..32,34..35,39..40)
                       mod_base = OTHER
                       note = Phosphorothioate internucleoside linkage
modified_base          order(3,13,19..20,36..38)
                       mod_base = OTHER
                       note = Phosphate internucleoside linkage
SEQUENCE: 132
aacatggccc cagcagcttc agtccctttc tcntcgatgg tc                     42

SEQ ID NO: 133         moltype = RNA  length = 42
FEATURE                Location/Qualifiers
source                 1..42
                       mol_type = other RNA
                       organism = synthetic construct
modified_base          order(3,4,9,11,13,14,17,19..21,24,28,30,34,36..39,42)
                       mod_base = OTHER
                       note = 2-Prime-methoxyribose nucleotides
modified_base          order(1,2,5..8,10,12,15,16,18,22,23,25..27,29,35,40,41)
                       mod_base = OTHER
                       note = 2-Prime-deoxy-2-Prime-fluororibose nucleotides
modified_base          31
                       mod_base = OTHER
                       note = Deoxyribose Thymidine
modified_base          32
                       mod_base = OTHER
                       note = Beta-homoDNA
modified_base          33
                       mod_base = OTHER
                       note = 2-Prime-fluroarabinose nucleotides
modified_base          33
                       mod_base = i
modified_base          order(1,21,23,28,33,41)
                       mod_base = OTHER
                       note = Mesyl phosphroamidate internucleoside linkage
modified_base          order(2,4..12,14..18,22,24..27,29..32,34..35,39..40)
                       mod_base = OTHER
                       note = Phosphorothioate internucleoside linkage
modified_base          order(3,13,19..20,36..38)
                       mod_base = OTHER
                       note = Phosphate internucleoside linkage
SEQUENCE: 133
aacatggccc cagcagcttc agtccctttc tcntcgatgg tc                     42

SEQ ID NO: 134         moltype = RNA  length = 42
FEATURE                Location/Qualifiers
source                 1..42
                       mol_type = other RNA
                       organism = synthetic construct
modified_base          order(3,4,9,11,13,14,17,19..21,24,28,30,34,36..39,42)
                       mod_base = OTHER
                       note = 2-Prime-methoxyribose nucleotides
modified_base          order(1,2,5..8,10,12,15,16,18,22,23,25..27,29,35,40,41)
                       mod_base = OTHER
                       note = 2-Prime-deoxy-2-Prime-fluororibose nucleotides
modified_base          31
                       mod_base = OTHER
                       note = Deoxyribose Thymidine
modified_base          32
                       mod_base = OTHER
                       note = Beta-homoDNA
modified_base          33
                       mod_base = OTHER
                       note = 2-Prime-fluroarabinose nucleotides
modified_base          33
                       mod_base = i
```

```
modified_base          order(1,21,23,29,33,41)
                       mod_base = OTHER
                       note = Mesyl phosphroamidate internucleoside linkage
modified_base          order(2,4..12,14..18,22,24..28,30..32,34..35,39..40)
                       mod_base = OTHER
                       note = Phosphorothioate internucleoside linkage
modified_base          order(3,13,19..20,36..38)
                       mod_base = OTHER
                       note = Phosphate internucleoside linkage
SEQUENCE: 134
aacatggccc cagcagcttc agtccctttc tcntcgatgg tc                     42

SEQ ID NO: 135         moltype = RNA  length = 42
FEATURE                Location/Qualifiers
source                 1..42
                       mol_type = other RNA
                       organism = synthetic construct
modified_base          order(3,4,9,11,13,14,17,19..21,24,28,30,34,36..39,42)
                       mod_base = OTHER
                       note = 2-Prime-methoxyribose nucleotides
modified_base          order(1,2,5..8,10,12,15,16,18,22,23,25..27,29,35,40,41)
                       mod_base = OTHER
                       note = 2-Prime-deoxy-2-Prime-fluororibose nucleotides
modified_base          31
                       mod_base = OTHER
                       note = Deoxyribose Thymidine
modified_base          32
                       mod_base = OTHER
                       note = Beta-homoDNA
modified_base          33
                       mod_base = OTHER
                       note = 2-Prime-fluroarabinose nucleotides
modified_base          33
                       mod_base = i
modified_base          order(1,21,23,30,33,41)
                       mod_base = OTHER
                       note = Mesyl phosphroamidate internucleoside linkage
modified_base          order(2,4..12,14..18,22,24..29,31..32,34..35,39..40)
                       mod_base = OTHER
                       note = Phosphorothioate internucleoside linkage
modified_base          order(3,13,19..20,36..38)
                       mod_base = OTHER
                       note = Phosphate internucleoside linkage
SEQUENCE: 135
aacatggccc cagcagcttc agtccctttc tcntcgatgg tc                     42

SEQ ID NO: 136         moltype = RNA  length = 42
FEATURE                Location/Qualifiers
source                 1..42
                       mol_type = other RNA
                       organism = synthetic construct
modified_base          order(3,4,9,11,13,14,17,19..21,24,28,30,34,36..39,42)
                       mod_base = OTHER
                       note = 2-Prime-methoxyribose nucleotides
modified_base          order(1,2,5..8,10,12,15,16,18,22,23,25..27,29,35,40,41)
                       mod_base = OTHER
                       note = 2-Prime-deoxy-2-Prime-fluororibose nucleotides
modified_base          31
                       mod_base = OTHER
                       note = Deoxyribose Thymidine
modified_base          32
                       mod_base = OTHER
                       note = Beta-homoDNA
modified_base          33
                       mod_base = OTHER
                       note = 2-Prime-fluroarabinose nucleotides
modified_base          33
                       mod_base = i
modified_base          order(1,21,23,31,33,41)
                       mod_base = OTHER
                       note = Mesyl phosphroamidate internucleoside linkage
modified_base          order(2,4..12,14..18,22,24..30,32,34..35,39..40)
                       mod_base = OTHER
                       note = Phosphorothioate internucleoside linkage
modified_base          order(3,13,19..20,36..38)
                       mod_base = OTHER
                       note = Phosphate internucleoside linkage
SEQUENCE: 136
aacatggccc cagcagcttc agtccctttc tcntcgatgg tc                     42
```

```
SEQ ID NO: 137          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotides
modified_base           33
                        mod_base = i
modified_base           order(1,21,23,32..33,41)
                        mod_base = OTHER
                        note = Mesyl phosphroamidate internucleoside linkage
modified_base           order(2,4..12,14..18,22,24..31,34..35,39..40)
                        mod_base = OTHER
                        note = Phosphorothioate internucleoside linkage
modified_base           order(3,13,19..20,36..38)
                        mod_base = OTHER
                        note = Phosphate internucleoside linkage
SEQUENCE: 137
aacatggccc cagcagcttc agtccctttc tcntcgatgg tc                    42

SEQ ID NO: 138          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotides
modified_base           33
                        mod_base = i
modified_base           order(1,21,23,33..34,41)
                        mod_base = OTHER
                        note = Mesyl phosphroamidate internucleoside linkage
modified_base           order(2,4..12,14..18,22,24..32,35,39..40)
                        mod_base = OTHER
                        note = Phosphorothioate internucleoside linkage
modified_base           order(3,13,19..20,36..38)
                        mod_base = OTHER
                        note = Phosphate internucleoside linkage
SEQUENCE: 138
aacatggccc cagcagcttc agtccctttc tcntcgatgg tc                    42

SEQ ID NO: 139          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
```

```
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotides
modified_base           33
                        mod_base = i
modified_base           order(1,21,23,33,35,41)
                        mod_base = OTHER
                        note = Mesyl phosphroamidate internucleoside linkage
modified_base           order(2,4..12,14..18,22,24..32,34,39..40)
                        mod_base = OTHER
                        note = Phosphorothioate internucleoside linkage
modified_base           order(3,13,19..20,36..38)
                        mod_base = OTHER
                        note = Phosphate internucleoside linkage
SEQUENCE: 139
aacatggccc cagcagcttc agtccctttc tcntcgatgg tc                    42

SEQ ID NO: 140          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotides
modified_base           33
                        mod_base = i
modified_base           order(1,21,23,33,36,41)
                        mod_base = OTHER
                        note = Mesyl phosphroamidate internucleoside linkage
modified_base           order(2,4..12,14..18,22,24..32,34..35,39..40)
                        mod_base = OTHER
                        note = Phosphorothioate internucleoside linkage
modified_base           order(3,13,19..20,37..38)
                        mod_base = OTHER
                        note = Phosphate internucleoside linkage
SEQUENCE: 140
aacatggccc cagcagcttc agtccctttc tcntcgatgg tc                    42

SEQ ID NO: 141          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotides
modified_base           33
```

```
                        mod_base = i
modified_base           order(1,21,23,33,37,41)
                        mod_base = OTHER
                        note = Mesyl phosphroamidate internucleoside linkage
modified_base           order(2,4..12,14..18,22,24..32,34..35,39..40)
                        mod_base = OTHER
                        note = Phosphorothioate internucleoside linkage
modified_base           order(3,13,19..20,36,38)
                        mod_base = OTHER
                        note = Phosphate internucleoside linkage
SEQUENCE: 141
aacatggccc cagcagcttc agtccctttc tcntcgatgg tc                    42

SEQ ID NO: 142          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotides
modified_base           33
                        mod_base = i
modified_base           order(1,21,23,33,38,41)
                        mod_base = OTHER
                        note = Mesyl phosphroamidate internucleoside linkage
modified_base           order(2,4..12,14..18,22,24..32,34..35,39..40)
                        mod_base = OTHER
                        note = Phosphorothioate internucleoside linkage
modified_base           order(3,13,19..20,36..37)
                        mod_base = OTHER
                        note = Phosphate internucleoside linkage
SEQUENCE: 142
aacatggccc cagcagcttc agtccctttc tcntcgatgg tc                    42

SEQ ID NO: 143          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotides
modified_base           33
                        mod_base = i
modified_base           order(1,21,23,33,39,41)
                        mod_base = OTHER
                        note = Mesyl phosphroamidate internucleoside linkage
modified_base           order(2,4..12,14..18,22,24..32,34..35,40)
                        mod_base = OTHER
                        note = Phosphorothioate internucleoside linkage
modified_base           order(3,13,19..20,36..38)
                        mod_base = OTHER
                        note = Phosphate internucleoside linkage
SEQUENCE: 143
```

```
aacatggccc cagcagcttc agtccctttc tcntcgatgg tc                    42

SEQ ID NO: 144          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotides
modified_base           33
                        mod_base = i
modified_base           order(1,21,23,33,40..41)
                        mod_base = OTHER
                        note = Mesyl phosphroamidate internucleoside linkage
modified_base           order(2,4..12,14..18,22,24..32,34..35,39)
                        mod_base = OTHER
                        note = Phosphorothioate internucleoside linkage
modified_base           order(3,13,19..20,36..38)
                        mod_base = OTHER
                        note = Phosphate internucleoside linkage
SEQUENCE: 144
aacatggccc cagcagcttc agtccctttc tcntcgatgg tc                    42

SEQ ID NO: 145          moltype = RNA  length = 42
FEATURE                 Location/Qualifiers
source                  1..42
                        mol_type = other RNA
                        organism = synthetic construct
modified_base           order(1,3,4,9..11,13,14,18,20,21,24,25,30,34,36..40,42)
                        mod_base = OTHER
                        note = 2-Prime-methoxyribose nucleotides
modified_base           order(2,5..8,12,15..17,19,22,23,26..29,35,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = Deoxyribose
modified_base           33
                        mod_base = i
modified_base           order(1..8,12..13,15..20,22..24,26..29,31..33,35,38..41)
                        mod_base = OTHER
                        note = Phosphorothioate internucleoside linkage
modified_base           order(9..11,14,21,25,30,34,36..37)
                        mod_base = OTHER
                        note = Phosphate internucleoside linkage
SEQUENCE: 145
ttgcagtaca taatttacac agaagcaatg ccntcacctt cc                    42

SEQ ID NO: 146          moltype = RNA  length = 42
FEATURE                 Location/Qualifiers
source                  1..42
                        mol_type = other RNA
                        organism = synthetic construct
modified_base           33
                        mod_base = i
SEQUENCE: 146
ttgcagtaca taatttacac agaagcaatg ccntcacctt cc                    42

SEQ ID NO: 147          moltype = RNA  length = 42
FEATURE                 Location/Qualifiers
```

-continued

```
source                  1..42
                        mol_type = other RNA
                        organism = synthetic construct
modified_base           order(1,3,4,9..11,13,14,18,20,21,24,25,30,34,36..40,42)
                        mod_base = OTHER
                        note = 2-Prime-methoxyribose nucleotides
modified_base           order(2,5..8,12,15..17,19,22,23,26..29,35,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = Deoxyribose
modified_base           33
                        mod_base = i
modified_base           order(1,41)
                        mod_base = OTHER
                        note = Mesyl phosphroamidate internucleoside linkage
modified_base           order(2..8,12..13,15..20,22..24,26..29,31..33,35,38..40)
                        mod_base = OTHER
                        note = Phosphorothioate internucleoside linkage
modified_base           order(9..11,14,21,25,30,34,36..37)
                        mod_base = OTHER
                        note = Phosphate internucleoside linkage
SEQUENCE: 147
ttgcagtaca taatttacac agaagcaatg ccntcacctt cc                    42

SEQ ID NO: 148          moltype = RNA  length = 42
FEATURE                 Location/Qualifiers
source                  1..42
                        mol_type = other RNA
                        organism = synthetic construct
modified_base           order(1,3,4,9..11,13,14,18,20,21,24,25,30,34,36..40,42)
                        mod_base = OTHER
                        note = 2-Prime-methoxyribose nucleotides
modified_base           order(2,5..8,12,15..17,19,22,23,26..29,35,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = Deoxyribose
modified_base           33
                        mod_base = i
modified_base           order(1,21,23,33,41)
                        mod_base = OTHER
                        note = Mesyl phosphroamidate internucleoside linkage
modified_base           order(2..8,12..13,15..20,22,24,26..29,31..32,35,38..40)
                        mod_base = OTHER
                        note = Phosphorothioate internucleoside linkage
modified_base           order(9..11,14,25,30,34,36..37)
                        mod_base = OTHER
                        note = Phosphate internucleoside linkage
SEQUENCE: 148
ttgcagtaca taatttacac agaagcaatg ccntcacctt cc                    42

SEQ ID NO: 149          moltype = RNA  length = 30
FEATURE                 Location/Qualifiers
source                  1..30
                        mol_type = other RNA
                        organism = synthetic construct
modified_base           order(2,4,7..9,11,13,19,22,27,29,30)
                        mod_base = OTHER
                        note = 2-Prime-methoxyribose nucleotides
modified_base           order(1,3,5,6,10,12,14..18,20,21,23,28)
                        mod_base = OTHER
                        note = 2-Prime-deoxy-2-Prime-fluororibose nucleotides
modified_base           order(24,26)
                        mod_base = OTHER
```

-continued

```
                        note = Deoxyribose
modified_base           25
                        mod_base = OTHER
                        note = Beta-homoDNA
modified_base           26
                        mod_base = i
modified_base           1..29
                        mod_base = OTHER
                        note = Phosphorothioate internucleoside linkage
SEQUENCE: 149
acataattta cacagaagca atgccntcac                                   30

SEQ ID NO: 150          moltype = RNA  length = 30
FEATURE                 Location/Qualifiers
source                  1..30
                        mol_type = other RNA
                        organism = synthetic construct
modified_base           26
                        mod_base = i
SEQUENCE: 150
acataattta cacagaagca atgccntcac                                   30

SEQ ID NO: 151          moltype = RNA  length = 30
FEATURE                 Location/Qualifiers
source                  1..30
                        mol_type = other RNA
                        organism = synthetic construct
modified_base           order(2,4,7..9,11,13,19,22,27,29,30)
                        mod_base = OTHER
                        note = 2-Prime-methoxyribose nucleotides
modified_base           order(1,3,5,6,10,12,14..18,20,21,23,28)
                        mod_base = OTHER
                        note = 2-Prime-deoxy-2-Prime-fluororibose nucleotides
modified_base           order(24,26)
                        mod_base = OTHER
                        note = Deoxyribose
modified_base           25
                        mod_base = OTHER
                        note = Beta-homoDNA
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 151
acataattta cacagaagca atgccntcac                                   30

SEQ ID NO: 152          moltype = RNA  length = 30
FEATURE                 Location/Qualifiers
source                  1..30
                        mol_type = other RNA
                        organism = synthetic construct
modified_base           26
                        mod_base = i
modified_base           24
                        mod_base = OTHER
                        note = Thymidine
SEQUENCE: 152
ccccagcagc ttcagtccct ttctcntcga                                   30

SEQ ID NO: 153          moltype =   length =
SEQUENCE: 153
000

SEQ ID NO: 154          moltype =   length =
SEQUENCE: 154
000

SEQ ID NO: 155          moltype =   length =
SEQUENCE: 155
000

SEQ ID NO: 156          moltype = DNA  length = 23
FEATURE                 Location/Qualifiers
source                  1..23
                        mol_type = other DNA
```

```
                        organism = synthetic construct
SEQUENCE: 156
acctatgatc tgaagagcgt cct                                     23

SEQ ID NO: 157          moltype = DNA  length = 25
FEATURE                 Location/Qualifiers
source                  1..25
                        mol_type = other DNA
                        organism = synthetic construct
SEQUENCE: 157
ttcaatcatt aagaagacaa agggt                                   25

SEQ ID NO: 158          moltype = DNA  length = 24
FEATURE                 Location/Qualifiers
source                  1..24
                        mol_type = other DNA
                        organism = synthetic construct
SEQUENCE: 158
gatgcattgt tacaggaagt ccct                                    24

SEQ ID NO: 159          moltype = DNA  length = 25
FEATURE                 Location/Qualifiers
source                  1..25
                        mol_type = other DNA
                        organism = synthetic construct
SEQUENCE: 159
agggggcatg aaggctcatt attca                                   25

SEQ ID NO: 160          moltype = DNA  length = 24
FEATURE                 Location/Qualifiers
source                  1..24
                        mol_type = other DNA
                        organism = synthetic construct
SEQUENCE: 160
taagtggtta caggaagtcc ctca                                    24

SEQ ID NO: 161          moltype = DNA  length = 21
FEATURE                 Location/Qualifiers
source                  1..21
                        mol_type = other DNA
                        organism = synthetic construct
SEQUENCE: 161
ggaggcctca gacctgggcc a                                       21

SEQ ID NO: 162          moltype = RNA  length = 30
FEATURE                 Location/Qualifiers
source                  1..30
                        mol_type = other RNA
                        organism = synthetic construct
modified_base           order(1,5,9,13,17,21,27,29,30)
                        mod_base = OTHER
                        note = 2-Prime-methoxyribose nucleotides
modified_base           order(2..4,6..8,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 162
ccccagcagc ttcagtccct ttctcntcga                              30

SEQ ID NO: 163          moltype = RNA  length = 30
FEATURE                 Location/Qualifiers
source                  1..30
                        mol_type = other RNA
```

```
                        organism = synthetic construct
modified_base           25
                        mod_base = i
SEQUENCE: 163
ccccagcagc ttcagtccct ttctcntcga                                      30

SEQ ID NO: 164          moltype = RNA  length = 30
FEATURE                 Location/Qualifiers
source                  1..30
                        mol_type = other RNA
                        organism = synthetic construct
modified_base           order(1,5,9,13,17,21,27,29,30)
                        mod_base = OTHER
                        note = 2-Prime-methoxyribose nucleotides
modified_base           order(2..4,6..8,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           1..29
                        mod_base = OTHER
                        note = Phosphorothioate internucleoside linkage
SEQUENCE: 164
ccccagcagc ttcagtccct ttctcntcga                                      30

SEQ ID NO: 165          moltype = RNA  length = 30
FEATURE                 Location/Qualifiers
source                  1..30
                        mol_type = other RNA
                        organism = synthetic construct
modified_base           order(1,5,9,13,17,21,27,29,30)
                        mod_base = OTHER
                        note = 2-Prime-methoxyribose nucleotides
modified_base           order(2..4,6..8,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(14,16,26,29)
                        mod_base = OTHER
                        note = Mesyl phosphroamidate internucleoside linkage
modified_base           order(1..13,15,17..25,27..28)
                        mod_base = OTHER
                        note = Phosphorothioate internucleoside linkage
SEQUENCE: 165
ccccagcagc ttcagtccct ttctcntcga                                      30

SEQ ID NO: 166          moltype = RNA  length = 30
FEATURE                 Location/Qualifiers
source                  1..30
                        mol_type = other RNA
                        organism = synthetic construct
modified_base           order(1,5,9,13,17,21,27,29,30)
                        mod_base = OTHER
                        note = 2-Prime-methoxyribose nucleotides
modified_base           order(2..4,6..8,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
```

-continued

```
modified_base          25
                       mod_base = OTHER
                       note = Beta-homoDNA
modified_base          26
                       mod_base = OTHER
                       note = Deoxyribose
modified_base          26
                       mod_base = i
modified_base          order(1,16,26,29)
                       mod_base = OTHER
                       note = Mesyl phosphroamidate internucleoside linkage
modified_base          order(2..15,17..25,27..28)
                       mod_base = OTHER
                       note = Phosphorothioate internucleoside linkage
SEQUENCE: 166
ccccagcagc ttcagtccct ttctcntcga                                   30

SEQ ID NO: 167         moltype = RNA  length = 30
FEATURE                Location/Qualifiers
source                 1..30
                       mol_type = other RNA
                       organism = synthetic construct
modified_base          order(1,5,9,13,17,21,27,29,30)
                       mod_base = OTHER
                       note = 2-Prime-methoxyribose nucleotides
modified_base          order(2..4,6..8,10..12,14..16,18..20,22,23,28)
                       mod_base = OTHER
                       note = 2-Prime-deoxy-2-Prime-fluororibose nucleotides
modified_base          24
                       mod_base = OTHER
                       note = Deoxyribose Thymidine
modified_base          25
                       mod_base = OTHER
                       note = Beta-homoDNA
modified_base          26
                       mod_base = OTHER
                       note = Deoxyribose
modified_base          26
                       mod_base = i
modified_base          order(1,14,26,29)
                       mod_base = OTHER
                       note = Mesyl phosphroamidate internucleoside linkage
modified_base          order(2..13,15..25,27..28)
                       mod_base = OTHER
                       note = Phosphorothioate internucleoside linkage
SEQUENCE: 167
ccccagcagc ttcagtccct ttctcntcga                                   30

SEQ ID NO: 168         moltype = RNA  length = 30
FEATURE                Location/Qualifiers
source                 1..30
                       mol_type = other RNA
                       organism = synthetic construct
modified_base          order(1,5,9,13,17,21,27,29,30)
                       mod_base = OTHER
                       note = 2-Prime-methoxyribose nucleotides
modified_base          order(2..4,6..8,10..12,14..16,18..20,22,23,28)
                       mod_base = OTHER
                       note = 2-Prime-deoxy-2-Prime-fluororibose nucleotides
modified_base          24
                       mod_base = OTHER
                       note = Deoxyribose Thymidine
modified_base          25
                       mod_base = OTHER
                       note = Beta-homoDNA
modified_base          26
                       mod_base = OTHER
                       note = Deoxyribose
modified_base          26
                       mod_base = i
modified_base          order(1,14,16,29)
                       mod_base = OTHER
                       note = Mesyl phosphroamidate internucleoside linkage
modified_base          order(2..13,15,17..28)
                       mod_base = OTHER
                       note = Phosphorothioate internucleoside linkage
SEQUENCE: 168
ccccagcagc ttcagtccct ttctcntcga                                   30
```

-continued

```
SEQ ID NO: 169         moltype = RNA  length = 30
FEATURE                Location/Qualifiers
source                 1..30
                       mol_type = other RNA
                       organism = synthetic construct
modified_base          order(1,5,9,13,17,21,27,29,30)
                       mod_base = OTHER
                       note = 2-Prime-methoxyribose nucleotides
modified_base          order(2..4,6..8,10..12,14..16,18..20,22,23,28)
                       mod_base = OTHER
                       note = 2-Prime-deoxy-2-Prime-fluororibose nucleotides
modified_base          24
                       mod_base = OTHER
                       note = Deoxyribose Thymidine
modified_base          25
                       mod_base = OTHER
                       note = Beta-homoDNA
modified_base          26
                       mod_base = OTHER
                       note = Deoxyribose
modified_base          26
                       mod_base = i
modified_base          order(1,14,16,26)
                       mod_base = OTHER
                       note = Mesyl phosphroamidate internucleoside linkage
modified_base          order(2..13,15,17..25,27..29)
                       mod_base = OTHER
                       note = Phosphorothioate internucleoside linkage
SEQUENCE: 169
ccccagcagc ttcagtccct ttctcntcga                                   30

SEQ ID NO: 170         moltype = RNA  length = 30
FEATURE                Location/Qualifiers
source                 1..30
                       mol_type = other RNA
                       organism = synthetic construct
modified_base          order(1,5,9,13,17,21,27,29,30)
                       mod_base = OTHER
                       note = 2-Prime-methoxyribose nucleotides
modified_base          order(2..4,6..8,10..12,14..16,18..20,22,23,28)
                       mod_base = OTHER
                       note = 2-Prime-deoxy-2-Prime-fluororibose nucleotides
modified_base          24
                       mod_base = OTHER
                       note = Deoxyribose Thymidine
modified_base          25
                       mod_base = OTHER
                       note = Beta-homoDNA
modified_base          26
                       mod_base = OTHER
                       note = Deoxyribose
modified_base          26
                       mod_base = i
modified_base          order(1..2,14,16,26,29)
                       mod_base = OTHER
                       note = Mesyl phosphroamidate internucleoside linkage
modified_base          order(3..13,15,17..25,27..28)
                       mod_base = OTHER
                       note = Phosphorothioate internucleoside linkage
SEQUENCE: 170
ccccagcagc ttcagtccct ttctcntcga                                   30

SEQ ID NO: 171         moltype = RNA  length = 30
FEATURE                Location/Qualifiers
source                 1..30
                       mol_type = other RNA
                       organism = synthetic construct
modified_base          order(1,5,9,13,17,21,27,29,30)
                       mod_base = OTHER
                       note = 2-Prime-methoxyribose nucleotides
modified_base          order(2..4,6..8,10..12,14..16,18..20,22,23,28)
                       mod_base = OTHER
                       note = 2-Prime-deoxy-2-Prime-fluororibose nucleotides
modified_base          24
                       mod_base = OTHER
                       note = Deoxyribose Thymidine
modified_base          25
                       mod_base = OTHER
                       note = Beta-homoDNA
```

```
modified_base          26
                       mod_base = OTHER
                       note = Deoxyribose
modified_base          26
                       mod_base = i
modified_base          order(1,3,14,16,26,29)
                       mod_base = OTHER
                       note = Mesyl phosphroamidate internucleoside linkage
modified_base          order(2,4..13,15,17..25,27..28)
                       mod_base = OTHER
                       note = Phosphorothioate internucleoside linkage
SEQUENCE: 171
ccccagcagc ttcagtccct ttctcntcga                                   30

SEQ ID NO: 172         moltype = RNA  length = 30
FEATURE                Location/Qualifiers
source                 1..30
                       mol_type = other RNA
                       organism = synthetic construct
modified_base          order(1,5,9,13,17,21,27,29,30)
                       mod_base = OTHER
                       note = 2-Prime-methoxyribose nucleotides
modified_base          order(2..4,6..8,10..12,14..16,18..20,22,23,28)
                       mod_base = OTHER
                       note = 2-Prime-deoxy-2-Prime-fluororibose nucleotides
modified_base          24
                       mod_base = OTHER
                       note = Deoxyribose Thymidine
modified_base          25
                       mod_base = OTHER
                       note = Beta-homoDNA
modified_base          26
                       mod_base = OTHER
                       note = Deoxyribose
modified_base          26
                       mod_base = i
modified_base          order(1,4,14,16,26,29)
                       mod_base = OTHER
                       note = Mesyl phosphroamidate internucleoside linkage
modified_base          order(2..3,5..13,15,17..25,27..28)
                       mod_base = OTHER
                       note = Phosphorothioate internucleoside linkage
SEQUENCE: 172
ccccagcagc ttcagtccct ttctcntcga                                   30

SEQ ID NO: 173         moltype = RNA  length = 30
FEATURE                Location/Qualifiers
source                 1..30
                       mol_type = other RNA
                       organism = synthetic construct
modified_base          order(1,5,9,13,17,21,27,29,30)
                       mod_base = OTHER
                       note = 2-Prime-methoxyribose nucleotides
modified_base          order(2..4,6..8,10..12,14..16,18..20,22,23,28)
                       mod_base = OTHER
                       note = 2-Prime-deoxy-2-Prime-fluororibose nucleotides
modified_base          24
                       mod_base = OTHER
                       note = Deoxyribose Thymidine
modified_base          25
                       mod_base = OTHER
                       note = Beta-homoDNA
modified_base          26
                       mod_base = OTHER
                       note = Deoxyribose
modified_base          26
                       mod_base = i
modified_base          order(1,5,14,16,26,29)
                       mod_base = OTHER
                       note = Mesyl phosphroamidate internucleoside linkage
modified_base          order(2..4,6..13,15,17..25,27..28)
                       mod_base = OTHER
                       note = Phosphorothioate internucleoside linkage
SEQUENCE: 173
ccccagcagc ttcagtccct ttctcntcga                                   30

SEQ ID NO: 174         moltype = RNA  length = 30
FEATURE                Location/Qualifiers
source                 1..30
```

```
                        mol_type = other RNA
                        organism = synthetic construct
modified_base           order(1,5,9,13,17,21,27,29,30)
                        mod_base = OTHER
                        note = 2-Prime-methoxyribose nucleotides
modified_base           order(2..4,6..8,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,6,14,16,26,29)
                        mod_base = OTHER
                        note = Mesyl phosphroamidate internucleoside linkage
modified_base           order(2..5,7..13,15,17..25,27..28)
                        mod_base = OTHER
                        note = Phosphorothioate internucleoside linkage
SEQUENCE: 174
ccccagcagc ttcagtccct ttctcntcga                                   30

SEQ ID NO: 175          moltype = RNA  length = 30
FEATURE                 Location/Qualifiers
source                  1..30
                        mol_type = other RNA
                        organism = synthetic construct
modified_base           order(1,5,9,13,17,21,27,29,30)
                        mod_base = OTHER
                        note = 2-Prime-methoxyribose nucleotides
modified_base           order(2..4,6..8,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,7,14,16,26,29)
                        mod_base = OTHER
                        note = Mesyl phosphroamidate internucleoside linkage
modified_base           order(2..6,8..13,15,17..25,27..28)
                        mod_base = OTHER
                        note = Phosphorothioate internucleoside linkage
SEQUENCE: 175
ccccagcagc ttcagtccct ttctcntcga                                   30

SEQ ID NO: 176          moltype = RNA  length = 30
FEATURE                 Location/Qualifiers
source                  1..30
                        mol_type = other RNA
                        organism = synthetic construct
modified_base           order(1,5,9,13,17,21,27,29,30)
                        mod_base = OTHER
                        note = 2-Prime-methoxyribose nucleotides
modified_base           order(2..4,6..8,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
```

```
modified_base          26
                       mod_base = i
modified_base          order(1,8,14,16,26,29)
                       mod_base = OTHER
                       note = Mesyl phosphroamidate internucleoside linkage
modified_base          order(2..7,9..13,15,17..25,27..28)
                       mod_base = OTHER
                       note = Phosphorothioate internucleoside linkage
SEQUENCE: 176
ccccagcagc ttcagtccct ttctcntcga                                   30

SEQ ID NO: 177         moltype = RNA  length = 30
FEATURE                Location/Qualifiers
source                 1..30
                       mol_type = other RNA
                       organism = synthetic construct
modified_base          order(1,5,9,13,17,21,27,29,30)
                       mod_base = OTHER
                       note = 2-Prime-methoxyribose nucleotides
modified_base          order(2..4,6..8,10..12,14..16,18..20,22,23,28)
                       mod_base = OTHER
                       note = 2-Prime-deoxy-2-Prime-fluororibose nucleotides
modified_base          24
                       mod_base = OTHER
                       note = Deoxyribose Thymidine
modified_base          25
                       mod_base = OTHER
                       note = Beta-homoDNA
modified_base          26
                       mod_base = OTHER
                       note = Deoxyribose
modified_base          26
                       mod_base = i
modified_base          order(1,9,14,16,26,29)
                       mod_base = OTHER
                       note = Mesyl phosphroamidate internucleoside linkage
modified_base          order(2..8,10..13,15,17..25,27..28)
                       mod_base = OTHER
                       note = Phosphorothioate internucleoside linkage
SEQUENCE: 177
ccccagcagc ttcagtccct ttctcntcga                                   30

SEQ ID NO: 178         moltype = RNA  length = 30
FEATURE                Location/Qualifiers
source                 1..30
                       mol_type = other RNA
                       organism = synthetic construct
modified_base          order(1,5,9,13,17,21,27,29,30)
                       mod_base = OTHER
                       note = 2-Prime-methoxyribose nucleotides
modified_base          order(2..4,6..8,10..12,14..16,18..20,22,23,28)
                       mod_base = OTHER
                       note = 2-Prime-deoxy-2-Prime-fluororibose nucleotides
modified_base          24
                       mod_base = OTHER
                       note = Deoxyribose Thymidine
modified_base          25
                       mod_base = OTHER
                       note = Beta-homoDNA
modified_base          26
                       mod_base = OTHER
                       note = Deoxyribose
modified_base          26
                       mod_base = i
modified_base          order(1,10,14,16,26,29)
                       mod_base = OTHER
                       note = Mesyl phosphroamidate internucleoside linkage
modified_base          order(2..9,11..13,15,17..25,27..28)
                       mod_base = OTHER
                       note = Phosphorothioate internucleoside linkage
SEQUENCE: 178
ccccagcagc ttcagtccct ttctcntcga                                   30

SEQ ID NO: 179         moltype = RNA  length = 30
FEATURE                Location/Qualifiers
source                 1..30
                       mol_type = other RNA
                       organism = synthetic construct
modified_base          order(1,5,9,13,17,21,27,29,30)
```

```
                         mod_base = OTHER
                         note = 2-Prime-methoxyribose nucleotides
modified_base            order(2..4,6..8,10..12,14..16,18..20,22,23,28)
                         mod_base = OTHER
                         note = 2-Prime-deoxy-2-Prime-fluororibose nucleotides
modified_base            24
                         mod_base = OTHER
                         note = Deoxyribose Thymidine
modified_base            25
                         mod_base = OTHER
                         note = Beta-homoDNA
modified_base            26
                         mod_base = OTHER
                         note = Deoxyribose
modified_base            26
                         mod_base = i
modified_base            order(1,11,14,16,26,29)
                         mod_base = OTHER
                         note = Mesyl phosphroamidate internucleoside linkage
modified_base            order(2..10,12..13,15,17..25,27..28)
                         mod_base = OTHER
                         note = Phosphorothioate internucleoside linkage
SEQUENCE: 179
ccccagcagc ttcagtccct ttctcntcga                                   30

SEQ ID NO: 180           moltype = RNA  length = 30
FEATURE                  Location/Qualifiers
source                   1..30
                         mol_type = other RNA
                         organism = synthetic construct
modified_base            order(1,5,9,13,17,21,27,29,30)
                         mod_base = OTHER
                         note = 2-Prime-methoxyribose nucleotides
modified_base            order(2..4,6..8,10..12,14..16,18..20,22,23,28)
                         mod_base = OTHER
                         note = 2-Prime-deoxy-2-Prime-fluororibose nucleotides
modified_base            24
                         mod_base = OTHER
                         note = Deoxyribose Thymidine
modified_base            25
                         mod_base = OTHER
                         note = Beta-homoDNA
modified_base            26
                         mod_base = OTHER
                         note = Deoxyribose
modified_base            26
                         mod_base = i
modified_base            order(1,12,14,16,26,29)
                         mod_base = OTHER
                         note = Mesyl phosphroamidate internucleoside linkage
modified_base            order(2..11,13,15,17..25,27..28)
                         mod_base = OTHER
                         note = Phosphorothioate internucleoside linkage
SEQUENCE: 180
ccccagcagc ttcagtccct ttctcntcga                                   30

SEQ ID NO: 181           moltype = RNA  length = 30
FEATURE                  Location/Qualifiers
source                   1..30
                         mol_type = other RNA
                         organism = synthetic construct
modified_base            order(1,5,9,13,17,21,27,29,30)
                         mod_base = OTHER
                         note = 2-Prime-methoxyribose nucleotides
modified_base            order(2..4,6..8,10..12,14..16,18..20,22,23,28)
                         mod_base = OTHER
                         note = 2-Prime-deoxy-2-Prime-fluororibose nucleotides
modified_base            24
                         mod_base = OTHER
                         note = Deoxyribose Thymidine
modified_base            25
                         mod_base = OTHER
                         note = Beta-homoDNA
modified_base            26
                         mod_base = OTHER
                         note = Deoxyribose
modified_base            26
                         mod_base = i
modified_base            order(1,13..14,16,26,29)
```

-continued

```
                         mod_base = OTHER
                         note = Mesyl phosphroamidate internucleoside linkage
modified_base            order(2..12,15,17..25,27..28)
                         mod_base = OTHER
                         note = Phosphorothioate internucleoside linkage
SEQUENCE: 181
ccccagcagc ttcagtccct ttctcntcga                                   30

SEQ ID NO: 182           moltype = RNA  length = 30
FEATURE                  Location/Qualifiers
source                   1..30
                         mol_type = other RNA
                         organism = synthetic construct
modified_base            order(1,5,9,13,17,21,27,29,30)
                         mod_base = OTHER
                         note = 2-Prime-methoxyribose nucleotides
modified_base            order(2..4,6..8,10..12,14..16,18..20,22,23,28)
                         mod_base = OTHER
                         note = 2-Prime-deoxy-2-Prime-fluororibose nucleotides
modified_base            24
                         mod_base = OTHER
                         note = Deoxyribose Thymidine
modified_base            25
                         mod_base = OTHER
                         note = Beta-homoDNA
modified_base            26
                         mod_base = OTHER
                         note = Deoxyribose
modified_base            26
                         mod_base = i
modified_base            order(1,14..16,26,29)
                         mod_base = OTHER
                         note = Mesyl phosphroamidate internucleoside linkage
modified_base            order(2..13,17..25,27..28)
                         mod_base = OTHER
                         note = Phosphorothioate internucleoside linkage
SEQUENCE: 182
ccccagcagc ttcagtccct ttctcntcga                                   30

SEQ ID NO: 183           moltype = RNA  length = 30
FEATURE                  Location/Qualifiers
source                   1..30
                         mol_type = other RNA
                         organism = synthetic construct
modified_base            order(1,5,9,13,17,21,27,29,30)
                         mod_base = OTHER
                         note = 2-Prime-methoxyribose nucleotides
modified_base            order(2..4,6..8,10..12,14..16,18..20,22,23,28)
                         mod_base = OTHER
                         note = 2-Prime-deoxy-2-Prime-fluororibose nucleotides
modified_base            24
                         mod_base = OTHER
                         note = Deoxyribose Thymidine
modified_base            25
                         mod_base = OTHER
                         note = Beta-homoDNA
modified_base            26
                         mod_base = OTHER
                         note = Deoxyribose
modified_base            26
                         mod_base = i
modified_base            order(1,14,16..17,26,29)
                         mod_base = OTHER
                         note = Mesyl phosphroamidate internucleoside linkage
modified_base            order(2..13,15,18..25,27..28)
                         mod_base = OTHER
                         note = Phosphorothioate internucleoside linkage
SEQUENCE: 183
ccccagcagc ttcagtccct ttctcntcga                                   30

SEQ ID NO: 184           moltype = RNA  length = 30
FEATURE                  Location/Qualifiers
source                   1..30
                         mol_type = other RNA
                         organism = synthetic construct
modified_base            order(1,5,9,13,17,21,27,29,30)
                         mod_base = OTHER
                         note = 2-Prime-methoxyribose nucleotides
modified_base            order(2..4,6..8,10..12,14..16,18..20,22,23,28)
```

```
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,18,26,29)
                        mod_base = OTHER
                        note = Mesyl phosphroamidate internucleoside linkage
modified_base           order(2..13,15,17,19..25,27..28)
                        mod_base = OTHER
                        note = Phosphorothioate internucleoside linkage
SEQUENCE: 184
ccccagcagc ttcagtccct ttctcntcga                                    30

SEQ ID NO: 185          moltype = RNA  length = 30
FEATURE                 Location/Qualifiers
source                  1..30
                        mol_type = other RNA
                        organism = synthetic construct
modified_base           order(1,5,9,13,17,21,27,29,30)
                        mod_base = OTHER
                        note = 2-Prime-methoxyribose nucleotides
modified_base           order(2..4,6..8,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,19,26,29)
                        mod_base = OTHER
                        note = Mesyl phosphroamidate internucleoside linkage
modified_base           order(2..13,15,17..18,20..25,27..28)
                        mod_base = OTHER
                        note = Phosphorothioate internucleoside linkage
SEQUENCE: 185
ccccagcagc ttcagtccct ttctcntcga                                    30

SEQ ID NO: 186          moltype = RNA  length = 30
FEATURE                 Location/Qualifiers
source                  1..30
                        mol_type = other RNA
                        organism = synthetic construct
modified_base           order(1,5,9,13,17,21,27,29,30)
                        mod_base = OTHER
                        note = 2-Prime-methoxyribose nucleotides
modified_base           order(2..4,6..8,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,20,26,29)
                        mod_base = OTHER
                        note = Mesyl phosphroamidate internucleoside linkage
modified_base           order(2..13,15,17..19,21..25,27..28)
```

```
                         mod_base = OTHER
                         note = Phosphorothioate internucleoside linkage
SEQUENCE: 186
ccccagcagc ttcagtccct ttctcntcga                                30

SEQ ID NO: 187           moltype = RNA  length = 30
FEATURE                  Location/Qualifiers
source                   1..30
                         mol_type = other RNA
                         organism = synthetic construct
modified_base            order(1,5,9,13,17,21,27,29,30)
                         mod_base = OTHER
                         note = 2-Prime-methoxyribose nucleotides
modified_base            order(2..4,6..8,10..12,14..16,18..20,22,23,28)
                         mod_base = OTHER
                         note = 2-Prime-deoxy-2-Prime-fluororibose nucleotides
modified_base            24
                         mod_base = OTHER
                         note = Deoxyribose Thymidine
modified_base            25
                         mod_base = OTHER
                         note = Beta-homoDNA
modified_base            26
                         mod_base = OTHER
                         note = Deoxyribose
modified_base            26
                         mod_base = i
modified_base            order(1,14,16,21,26,29)
                         mod_base = OTHER
                         note = Mesyl phosphroamidate internucleoside linkage
modified_base            order(2..13,15,17..20,22..25,27..28)
                         mod_base = OTHER
                         note = Phosphorothioate internucleoside linkage
SEQUENCE: 187
ccccagcagc ttcagtccct ttctcntcga                                30

SEQ ID NO: 188           moltype = RNA  length = 30
FEATURE                  Location/Qualifiers
source                   1..30
                         mol_type = other RNA
                         organism = synthetic construct
modified_base            order(1,5,9,13,17,21,27,29,30)
                         mod_base = OTHER
                         note = 2-Prime-methoxyribose nucleotides
modified_base            order(2..4,6..8,10..12,14..16,18..20,22,23,28)
                         mod_base = OTHER
                         note = 2-Prime-deoxy-2-Prime-fluororibose nucleotides
modified_base            24
                         mod_base = OTHER
                         note = Deoxyribose Thymidine
modified_base            25
                         mod_base = OTHER
                         note = Beta-homoDNA
modified_base            26
                         mod_base = OTHER
                         note = Deoxyribose
modified_base            26
                         mod_base = i
modified_base            order(1,14,16,22,26,29)
                         mod_base = OTHER
                         note = Mesyl phosphroamidate internucleoside linkage
modified_base            order(2..13,15,17..21,23..25,27..28)
                         mod_base = OTHER
                         note = Phosphorothioate internucleoside linkage
SEQUENCE: 188
ccccagcagc ttcagtccct ttctcntcga                                30

SEQ ID NO: 189           moltype = RNA  length = 30
FEATURE                  Location/Qualifiers
source                   1..30
                         mol_type = other RNA
                         organism = synthetic construct
modified_base            order(1,5,9,13,17,21,27,29,30)
                         mod_base = OTHER
                         note = 2-Prime-methoxyribose nucleotides
modified_base            order(2..4,6..8,10..12,14..16,18..20,22,23,28)
                         mod_base = OTHER
                         note = 2-Prime-deoxy-2-Prime-fluororibose nucleotides
modified_base            24
```

```
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,23,26,29)
                        mod_base = OTHER
                        note = Mesyl phosphroamidate internucleoside linkage
modified_base           order(2..13,15,17..22,24..25,27..28)
                        mod_base = OTHER
                        note = Phosphorothioate internucleoside linkage
SEQUENCE: 189
ccccagcagc ttcagtccct ttctcntcga                                        30

SEQ ID NO: 190          moltype = RNA  length = 30
FEATURE                 Location/Qualifiers
source                  1..30
                        mol_type = other RNA
                        organism = synthetic construct
modified_base           order(1,5,9,13,17,21,27,29,30)
                        mod_base = OTHER
                        note = 2-Prime-methoxyribose nucleotides
modified_base           order(2..4,6..8,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26..27,29)
                        mod_base = OTHER
                        note = Mesyl phosphroamidate internucleoside linkage
modified_base           order(2..13,15,17..25,28)
                        mod_base = OTHER
                        note = Phosphorothioate internucleoside linkage
SEQUENCE: 190
ccccagcagc ttcagtccct ttctcntcga                                        30

SEQ ID NO: 191          moltype = RNA  length = 30
FEATURE                 Location/Qualifiers
source                  1..30
                        mol_type = other RNA
                        organism = synthetic construct
modified_base           order(1,5,9,13,17,21,27,29,30)
                        mod_base = OTHER
                        note = 2-Prime-methoxyribose nucleotides
modified_base           order(2..4,6..8,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,28..29)
                        mod_base = OTHER
                        note = Mesyl phosphroamidate internucleoside linkage
modified_base           order(2..13,15,17..25,27)
                        mod_base = OTHER
                        note = Phosphorothioate internucleoside linkage
SEQUENCE: 191
```

```
ccccagcagc ttcagtccct ttctcntcga                                   30

SEQ ID NO: 192          moltype = RNA  length = 30
FEATURE                 Location/Qualifiers
source                  1..30
                        mol_type = other RNA
                        organism = synthetic construct
modified_base           order(5,9,13,17,21,27,29,30)
                        mod_base = OTHER
                        note = 2-Prime-methoxyribose nucleotides
modified_base           order(1..4,6..8,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 192
ccccagcagc ttcagtccct ttctcntcga                                   30

SEQ ID NO: 193          moltype = RNA  length = 30
FEATURE                 Location/Qualifiers
source                  1..30
                        mol_type = other RNA
                        organism = synthetic construct
modified_base           order(1,2,5,9,13,17,21,27,29,30)
                        mod_base = OTHER
                        note = 2-Prime-methoxyribose nucleotides
modified_base           order(3,4,6..8,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 193
ccccagcagc ttcagtccct ttctcntcga                                   30

SEQ ID NO: 194          moltype = RNA  length = 30
FEATURE                 Location/Qualifiers
source                  1..30
                        mol_type = other RNA
                        organism = synthetic construct
modified_base           order(1,3,5,9,13,17,21,27,29,30)
                        mod_base = OTHER
                        note = 2-Prime-methoxyribose nucleotides
modified_base           order(2,4,6..8,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
```

```
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 194
ccccagcagc ttcagtccct ttctcntcga                                   30

SEQ ID NO: 195          moltype = RNA  length = 30
FEATURE                 Location/Qualifiers
source                  1..30
                        mol_type = other RNA
                        organism = synthetic construct
modified_base           order(1,4,5,9,13,17,21,27,29,30)
                        mod_base = OTHER
                        note = 2-Prime-methoxyribose nucleotides
modified_base           order(2,3,6..8,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 195
ccccagcagc ttcagtccct ttctcntcga                                   30

SEQ ID NO: 196          moltype = RNA  length = 30
FEATURE                 Location/Qualifiers
source                  1..30
                        mol_type = other RNA
                        organism = synthetic construct
modified_base           order(1,9,13,17,21,27,29,30)
                        mod_base = OTHER
                        note = 2-Prime-methoxyribose nucleotides
modified_base           order(2..8,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 196
ccccagcagc ttcagtccct ttctcntcga                                   30

SEQ ID NO: 197          moltype = RNA  length = 30
```

-continued

```
FEATURE                Location/Qualifiers
source                 1..30
                       mol_type = other RNA
                       organism = synthetic construct
modified_base          order(1,5,6,9,13,17,21,27,29,30)
                       mod_base = OTHER
                       note = 2-Prime-methoxyribose nucleotides
modified_base          order(2..4,7,8,10..12,14..16,18..20,22,23,28)
                       mod_base = OTHER
                       note = 2-Prime-deoxy-2-Prime-fluororibose nucleotides
modified_base          24
                       mod_base = OTHER
                       note = Deoxyribose Thymidine
modified_base          25
                       mod_base = OTHER
                       note = Beta-homoDNA
modified_base          26
                       mod_base = OTHER
                       note = Deoxyribose
modified_base          26
                       mod_base = i
modified_base          order(1,14,16,26,29)
                       mod_base = OTHER
                       note = Mesyl phosphroamidate internucleoside linkage
modified_base          order(2..13,15,17..25,27..28)
                       mod_base = OTHER
                       note = Phosphorothioate internucleoside linkage
SEQUENCE: 197
ccccagcagc ttcagtccct ttctcntcga                                   30

SEQ ID NO: 198         moltype = RNA  length = 30
FEATURE                Location/Qualifiers
source                 1..30
                       mol_type = other RNA
                       organism = synthetic construct
modified_base          order(1,5,7,9,13,17,21,27,29,30)
                       mod_base = OTHER
                       note = 2-Prime-methoxyribose nucleotides
modified_base          order(2..4,6,8,10..12,14..16,18..20,22,23,28)
                       mod_base = OTHER
                       note = 2-Prime-deoxy-2-Prime-fluororibose nucleotides
modified_base          24
                       mod_base = OTHER
                       note = Deoxyribose Thymidine
modified_base          25
                       mod_base = OTHER
                       note = Beta-homoDNA
modified_base          26
                       mod_base = OTHER
                       note = Deoxyribose
modified_base          26
                       mod_base = i
modified_base          order(1,14,16,26,29)
                       mod_base = OTHER
                       note = Mesyl phosphroamidate internucleoside linkage
modified_base          order(2..13,15,17..25,27..28)
                       mod_base = OTHER
                       note = Phosphorothioate internucleoside linkage
SEQUENCE: 198
ccccagcagc ttcagtccct ttctcntcga                                   30

SEQ ID NO: 199         moltype = RNA  length = 30
FEATURE                Location/Qualifiers
source                 1..30
                       mol_type = other RNA
                       organism = synthetic construct
modified_base          order(1,5,8,9,13,17,21,27,29,30)
                       mod_base = OTHER
                       note = 2-Prime-methoxyribose nucleotides
modified_base          order(2..4,6,7,10..12,14..16,18..20,22,23,28)
                       mod_base = OTHER
                       note = 2-Prime-deoxy-2-Prime-fluororibose nucleotides
modified_base          24
                       mod_base = OTHER
                       note = Deoxyribose Thymidine
modified_base          25
                       mod_base = OTHER
                       note = Beta-homoDNA
modified_base          26
```

```
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 199
ccccagcagc ttcagtccct ttctcntcga                                   30

SEQ ID NO: 200          moltype = RNA  length = 30
FEATURE                 Location/Qualifiers
source                  1..30
                        mol_type = other RNA
                        organism = synthetic construct
modified_base           order(1,5,13,17,21,27,29,30)
                        mod_base = OTHER
                        note = 2-Prime-methoxyribose nucleotides
modified_base           order(2..4,6..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 200
ccccagcagc ttcagtccct ttctcntcga                                   30

SEQ ID NO: 201          moltype = RNA  length = 30
FEATURE                 Location/Qualifiers
source                  1..30
                        mol_type = other RNA
                        organism = synthetic construct
modified_base           order(1,5,9,10,13,17,21,27,29,30)
                        mod_base = OTHER
                        note = 2-Prime-methoxyribose nucleotides
modified_base           order(2..4,6..8,11,12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 201
ccccagcagc ttcagtccct ttctcntcga                                   30

SEQ ID NO: 202          moltype = RNA  length = 30
FEATURE                 Location/Qualifiers
source                  1..30
                        mol_type = other RNA
```

```
                        organism = synthetic construct
modified_base           order(1,5,9,11,13,17,21,27,29,30)
                        mod_base = OTHER
                        note = 2-Prime-methoxyribose nucleotides
modified_base           order(2..4,6..8,10,12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 202
ccccagcagc ttcagtccct ttctcntcga                                   30

SEQ ID NO: 203          moltype = RNA  length = 30
FEATURE                 Location/Qualifiers
source                  1..30
                        mol_type = other RNA
                        organism = synthetic construct
modified_base           order(1,5,9,12,13,17,21,27,29,30)
                        mod_base = OTHER
                        note = 2-Prime-methoxyribose nucleotides
modified_base           order(2..4,6..8,10,11,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 203
ccccagcagc ttcagtccct ttctcntcga                                   30

SEQ ID NO: 204          moltype = RNA  length = 30
FEATURE                 Location/Qualifiers
source                  1..30
                        mol_type = other RNA
                        organism = synthetic construct
modified_base           order(1,5,9,17,21,27,29,30)
                        mod_base = OTHER
                        note = 2-Prime-methoxyribose nucleotides
modified_base           order(2..4,6..8,10..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
```

```
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 204
ccccagcagc ttcagtccct ttctcntcga                                   30

SEQ ID NO: 205          moltype = RNA  length = 30
FEATURE                 Location/Qualifiers
source                  1..30
                        mol_type = other RNA
                        organism = synthetic construct
modified_base           order(1,5,9,13,14,17,21,27,29,30)
                        mod_base = OTHER
                        note = 2-Prime-methoxyribose nucleotides
modified_base           order(2..4,6..8,10..12,15,16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 205
ccccagcagc ttcagtccct ttctcntcga                                   30

SEQ ID NO: 206          moltype = RNA  length = 30
FEATURE                 Location/Qualifiers
source                  1..30
                        mol_type = other RNA
                        organism = synthetic construct
modified_base           order(1,5,9,13,17,21,27,29,30)
                        mod_base = OTHER
                        note = 2-Prime-methoxyribose nucleotides
modified_base           order(2..4,6..8,10..12,14,16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 206
ccccagcagc ttcagtccct ttctcntcga                                   30

SEQ ID NO: 207          moltype = RNA  length = 30
FEATURE                 Location/Qualifiers
source                  1..30
                        mol_type = other RNA
                        organism = synthetic construct
modified_base           order(1,5,9,13,16,17,21,27,29,30)
                        mod_base = OTHER
```

```
                        note = 2-Prime-methoxyribose nucleotides
modified_base           order(2..4,6..8,10..12,14,15,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 207
ccccagcagc ttcagtccct ttctcntcga                                    30

SEQ ID NO: 208          moltype = RNA  length = 30
FEATURE                 Location/Qualifiers
source                  1..30
                        mol_type = other RNA
                        organism = synthetic construct
modified_base           order(1,5,9,13,21,27,29,30)
                        mod_base = OTHER
                        note = 2-Prime-methoxyribose nucleotides
modified_base           order(2..4,6..8,10..12,14..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 208
ccccagcagc ttcagtccct ttctcntcga                                    30

SEQ ID NO: 209          moltype = RNA  length = 30
FEATURE                 Location/Qualifiers
source                  1..30
                        mol_type = other RNA
                        organism = synthetic construct
modified_base           order(1,5,9,13,17,18,21,27,29,30)
                        mod_base = OTHER
                        note = 2-Prime-methoxyribose nucleotides
modified_base           order(2..4,6..8,10..12,14..16,19,20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
```

-continued

```
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 209
ccccagcagc ttcagtccct ttctcntcga                                   30

SEQ ID NO: 210          moltype = RNA  length = 30
FEATURE                 Location/Qualifiers
source                  1..30
                        mol_type = other RNA
                        organism = synthetic construct
modified_base           order(1,5,9,13,17,19,21,27,29,30)
                        mod_base = OTHER
                        note = 2-Prime-methoxyribose nucleotides
modified_base           order(2..4,6..8,10..12,14..16,18,20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 210
ccccagcagc ttcagtccct ttctcntcga                                   30

SEQ ID NO: 211          moltype = RNA  length = 30
FEATURE                 Location/Qualifiers
source                  1..30
                        mol_type = other RNA
                        organism = synthetic construct
modified_base           order(1,5,9,13,17,20,21,27,29,30)
                        mod_base = OTHER
                        note = 2-Prime-methoxyribose nucleotides
modified_base           order(2..4,6..8,10..12,14..16,18,19,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 211
ccccagcagc ttcagtccct ttctcntcga                                   30

SEQ ID NO: 212          moltype = RNA  length = 30
FEATURE                 Location/Qualifiers
source                  1..30
                        mol_type = other RNA
                        organism = synthetic construct
modified_base           order(1,5,9,13,17,27,29,30)
                        mod_base = OTHER
                        note = 2-Prime-methoxyribose nucleotides
modified_base           order(2..4,6..8,10..12,14..16,18..23,28)
                        mod_base = OTHER
```

```
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 212
ccccagcagc ttcagtccct ttctcntcga                                   30

SEQ ID NO: 213          moltype = RNA  length = 30
FEATURE                 Location/Qualifiers
source                  1..30
                        mol_type = other RNA
                        organism = synthetic construct
modified_base           order(1,5,9,13,17,21,22,27,29,30)
                        mod_base = OTHER
                        note = 2-Prime-methoxyribose nucleotides
modified_base           order(2..4,6..8,10..12,14..16,18..20,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 213
ccccagcagc ttcagtccct ttctcntcga                                   30

SEQ ID NO: 214          moltype = RNA  length = 30
FEATURE                 Location/Qualifiers
source                  1..30
                        mol_type = other RNA
                        organism = synthetic construct
modified_base           order(1,5,9,13,17,21,23,27,29,30)
                        mod_base = OTHER
                        note = 2-Prime-methoxyribose nucleotides
modified_base           order(2..4,6..8,10..12,14..16,18..20,22,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
```

```
                       note = Phosphorothioate internucleoside linkage
SEQUENCE: 214
ccccagcagc ttcagtccct ttctcntcga                                   30

SEQ ID NO: 215         moltype = RNA  length = 30
FEATURE                Location/Qualifiers
source                 1..30
                       mol_type = other RNA
                       organism = synthetic construct
modified_base          order(1,5,9,13,17,21,30)
                       mod_base = OTHER
                       note = 2-Prime-methoxyribose nucleotides
modified_base          order(2..4,6..8,10..12,14..16,18..20,22,23,27,28)
                       mod_base = OTHER
                       note = 2-Prime-deoxy-2-Prime-fluororibose nucleotides
modified_base          24
                       mod_base = OTHER
                       note = Deoxyribose Thymidine
modified_base          25
                       mod_base = OTHER
                       note = Beta-homoDNA
modified_base          26
                       mod_base = OTHER
                       note = Deoxyribose
modified_base          26
                       mod_base = i
modified_base          order(1,14,16,26,29)
                       mod_base = OTHER
                       note = Mesyl phosphroamidate internucleoside linkage
modified_base          order(2..13,15,17..25,27..28)
                       mod_base = OTHER
                       note = Phosphorothioate internucleoside linkage
SEQUENCE: 215
ccccagcagc ttcagtccct ttctcntcga                                   30

SEQ ID NO: 216         moltype = RNA  length = 30
FEATURE                Location/Qualifiers
source                 1..30
                       mol_type = other RNA
                       organism = synthetic construct
modified_base          order(1,5,9,13,17,21,27..30)
                       mod_base = OTHER
                       note = 2-Prime-methoxyribose nucleotides
modified_base          order(2..4,6..8,10..12,14..16,18..20,22,23)
                       mod_base = OTHER
                       note = 2-Prime-deoxy-2-Prime-fluororibose nucleotides
modified_base          24
                       mod_base = OTHER
                       note = Deoxyribose Thymidine
modified_base          25
                       mod_base = OTHER
                       note = Beta-homoDNA
modified_base          26
                       mod_base = OTHER
                       note = Deoxyribose
modified_base          26
                       mod_base = i
modified_base          order(1,14,16,26,29)
                       mod_base = OTHER
                       note = Mesyl phosphroamidate internucleoside linkage
modified_base          order(2..13,15,17..25,27..28)
                       mod_base = OTHER
                       note = Phosphorothioate internucleoside linkage
SEQUENCE: 216
ccccagcagc ttcagtccct ttctcntcga                                   30

SEQ ID NO: 217         moltype = RNA  length = 30
FEATURE                Location/Qualifiers
source                 1..30
                       mol_type = other RNA
                       organism = synthetic construct
modified_base          order(1,5,9,13,17,21,27,30)
                       mod_base = OTHER
                       note = 2-Prime-methoxyribose nucleotides
modified_base          order(2..4,6..8,10..12,14..16,18..20,22,23,28,29)
                       mod_base = OTHER
                       note = 2-Prime-deoxy-2-Prime-fluororibose nucleotides
modified_base          24
                       mod_base = OTHER
```

-continued

```
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 217
ccccagcagc ttcagtccct ttctcntcga                                  30

SEQ ID NO: 218          moltype = RNA  length = 30
FEATURE                 Location/Qualifiers
source                  1..30
                        mol_type = other RNA
                        organism = synthetic construct
modified_base           order(1,5,9,13,17,21,27,29,30)
                        mod_base = OTHER
                        note = 2-Prime-methoxyribose nucleotides
modified_base           order(2..4,6..8,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 218
ccccagcagc ttcagtccct ttctcntcga                                  30

SEQ ID NO: 219          moltype = RNA  length = 30
FEATURE                 Location/Qualifiers
source                  1..30
                        mol_type = other RNA
                        organism = synthetic construct
modified_base           order(1,5,9,13,17,21,27,29,30)
                        mod_base = OTHER
                        note = 2-Prime-methoxyribose nucleotides
modified_base           order(2..4,6..8,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,12,15,26,29)
                        mod_base = OTHER
                        note = Mesyl phosphroamidate internucleoside linkage
modified_base           order(2..11,13..14,16..25,27..28)
                        mod_base = OTHER
                        note = Phosphorothioate internucleoside linkage
SEQUENCE: 219
ccccagcagc ttcagtccct ttctcntcga                                  30
```

```
SEQ ID NO: 220          moltype = RNA  length = 30
FEATURE                 Location/Qualifiers
source                  1..30
                        mol_type = other RNA
                        organism = synthetic construct
modified_base           order(1,5,9,13,17,21,27,29,30)
                        mod_base = OTHER
                        note = 2-Prime-methoxyribose nucleotides
modified_base           order(2..4,6..8,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,12,15,20,26,29)
                        mod_base = OTHER
                        note = Mesyl phosphroamidate internucleoside linkage
modified_base           order(2..11,13..14,16..19,21..25,27..28)
                        mod_base = OTHER
                        note = Phosphorothioate internucleoside linkage
SEQUENCE: 220
ccccagcagc ttcagtccct ttctcntcga                                   30

SEQ ID NO: 221          moltype = RNA  length = 30
FEATURE                 Location/Qualifiers
source                  1..30
                        mol_type = other RNA
                        organism = synthetic construct
modified_base           order(1,5,9,13,17,21,27,29,30)
                        mod_base = OTHER
                        note = 2-Prime-methoxyribose nucleotides
modified_base           order(2..4,6..8,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..4,6..8,10..12,15,18..20,22..25,27..28)
                        mod_base = OTHER
                        note = Phosphorothioate internucleoside linkage
modified_base           order(5,9,13,17,21)
                        mod_base = OTHER
                        note = Phosphate internucleoside linkage
SEQUENCE: 221
ccccagcagc ttcagtccct ttctcntcga                                   30

SEQ ID NO: 222          moltype = RNA  length = 30
FEATURE                 Location/Qualifiers
source                  1..30
                        mol_type = other RNA
                        organism = synthetic construct
modified_base           order(1..5,9,13,17,21,27,29,30)
                        mod_base = OTHER
                        note = 2-Prime-methoxyribose nucleotides
modified_base           order(6..8,10..12,14..16,18..20,22,23,28)
                        mod_base = OTHER
                        note = 2-Prime-deoxy-2-Prime-fluororibose nucleotides
modified_base           24
                        mod_base = OTHER
```

```
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 222
ccccagcagc ttcagtccct ttctcntcga                                   30

SEQ ID NO: 223          moltype = RNA  length = 30
FEATURE                 Location/Qualifiers
source                  1..30
                        mol_type = other RNA
                        organism = synthetic construct
modified_base           order(1,5..9,13,17,21,27,29,30)
                        mod_base = OTHER
                        note = 2-Prime-methoxyribose nucleotides
modified_base           order(2..4,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 223
ccccagcagc ttcagtccct ttctcntcga                                   30

SEQ ID NO: 224          moltype = RNA  length = 30
FEATURE                 Location/Qualifiers
source                  1..30
                        mol_type = other RNA
                        organism = synthetic construct
modified_base           order(1,5,9,13..17,21,27,29,30)
                        mod_base = OTHER
                        note = 2-Prime-methoxyribose nucleotides
modified_base           order(2..4,6..8,10..12,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 224
ccccagcagc ttcagtccct ttctcntcga                                   30
```

```
SEQ ID NO: 225          moltype = RNA  length = 30
FEATURE                 Location/Qualifiers
source                  1..30
                        mol_type = other RNA
                        organism = synthetic construct
modified_base           order(1,5,9,13,17..21,27,29,30)
                        mod_base = OTHER
                        note = 2-Prime-methoxyribose nucleotides
modified_base           order(2..4,6..8,10..12,14..16,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 225
ccccagcagc ttcagtccct ttctcntcga                                   30

SEQ ID NO: 226          moltype = RNA  length = 30
FEATURE                 Location/Qualifiers
source                  1..30
                        mol_type = other RNA
                        organism = synthetic construct
modified_base           order(1,5,9,13,17,21..23,27,29,30)
                        mod_base = OTHER
                        note = 2-Prime-methoxyribose nucleotides
modified_base           order(2..4,6..8,10..12,14..16,18..20,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..13,15,17..25,27..28)
                        mod_base = OTHER
                        note = Phosphorothioate internucleoside linkage
SEQUENCE: 226
ccccagcagc ttcagtccct ttctcntcga                                   30

SEQ ID NO: 227          moltype = RNA  length = 30
FEATURE                 Location/Qualifiers
source                  1..30
                        mol_type = other RNA
                        organism = synthetic construct
modified_base           order(1..5,9,13,17,21,27,29,30)
                        mod_base = OTHER
                        note = 2-Prime-methoxyribose nucleotides
modified_base           order(6..8,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
```

```
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..4,6..8,10..12,15,18..20,22..25,27..28)
                        mod_base = OTHER
                        note = Phosphorothioate internucleoside linkage
modified_base           order(5,9,13,17,21)
                        mod_base = OTHER
                        note = Phosphate internucleoside linkage
SEQUENCE: 227
ccccagcagc ttcagtccct ttctcntcga                                   30

SEQ ID NO: 228          moltype = RNA  length = 30
FEATURE                 Location/Qualifiers
source                  1..30
                        mol_type = other RNA
                        organism = synthetic construct
modified_base           order(1,5..9,13,17,21,27,29,30)
                        mod_base = OTHER
                        note = 2-Prime-methoxyribose nucleotides
modified_base           order(2..4,10..12,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..4,10..12,15,18..20,22..25,27..28)
                        mod_base = OTHER
                        note = Phosphorothioate internucleoside linkage
modified_base           order(5..9,13,17,21)
                        mod_base = OTHER
                        note = Phosphate internucleoside linkage
SEQUENCE: 228
ccccagcagc ttcagtccct ttctcntcga                                   30

SEQ ID NO: 229          moltype = RNA  length = 30
FEATURE                 Location/Qualifiers
source                  1..30
                        mol_type = other RNA
                        organism = synthetic construct
modified_base           order(1,5,9..13,17,21,27,29,30)
                        mod_base = OTHER
                        note = 2-Prime-methoxyribose nucleotides
modified_base           order(2..4,6..8,14..16,18..20,22,23,28)
                        mod_base = OTHER
                        note = 2-Prime-deoxy-2-Prime-fluororibose nucleotides
modified_base           24
                        mod_base = OTHER
                        note = Deoxyribose Thymidine
modified_base           25
                        mod_base = OTHER
                        note = Beta-homoDNA
modified_base           26
                        mod_base = OTHER
                        note = Deoxyribose
modified_base           26
                        mod_base = i
modified_base           order(1,14,16,26,29)
                        mod_base = OTHER
                        note = Mesyl phosphroamidate internucleoside linkage
modified_base           order(2..4,6..8,15,18..20,22..25,27..28)
                        mod_base = OTHER
```

-continued

```
                         note = Phosphorothioate internucleoside linkage
modified_base            order(5,9..13,17,21)
                         mod_base = OTHER
                         note = Phosphate internucleoside linkage
SEQUENCE: 229
ccccagcagc ttcagtccct ttctcntcga                                   30

SEQ ID NO: 230           moltype = RNA  length = 30
FEATURE                  Location/Qualifiers
source                   1..30
                         mol_type = other RNA
                         organism = synthetic construct
modified_base            order(1,5,9,13..17,21,27,29,30)
                         mod_base = OTHER
                         note = 2-Prime-methoxyribose nucleotides
modified_base            order(2..4,6..8,10..12,18..20,22,23,28)
                         mod_base = OTHER
                         note = 2-Prime-deoxy-2-Prime-fluororibose nucleotides
modified_base            24
                         mod_base = OTHER
                         note = Deoxyribose Thymidine
modified_base            25
                         mod_base = OTHER
                         note = Beta-homoDNA
modified_base            26
                         mod_base = OTHER
                         note = Deoxyribose
modified_base            26
                         mod_base = i
modified_base            order(1,14,16,26,29)
                         mod_base = OTHER
                         note = Mesyl phosphroamidate internucleoside linkage
modified_base            order(2..4,6..8,10..12,18..20,22..25,27..28)
                         mod_base = OTHER
                         note = Phosphorothioate internucleoside linkage
modified_base            order(5,9,13,15,17,21)
                         mod_base = OTHER
                         note = Phosphate internucleoside linkage
SEQUENCE: 230
ccccagcagc ttcagtccct ttctcntcga                                   30

SEQ ID NO: 231           moltype = RNA  length = 30
FEATURE                  Location/Qualifiers
source                   1..30
                         mol_type = other RNA
                         organism = synthetic construct
modified_base            order(1,5,9,13,17..21,27,29,30)
                         mod_base = OTHER
                         note = 2-Prime-methoxyribose nucleotides
modified_base            order(2..4,6..8,10..12,14..16,22,23,28)
                         mod_base = OTHER
                         note = 2-Prime-deoxy-2-Prime-fluororibose nucleotides
modified_base            24
                         mod_base = OTHER
                         note = Deoxyribose Thymidine
modified_base            25
                         mod_base = OTHER
                         note = Beta-homoDNA
modified_base            26
                         mod_base = OTHER
                         note = Deoxyribose
modified_base            26
                         mod_base = i
modified_base            order(1,14,16,26,29)
                         mod_base = OTHER
                         note = Mesyl phosphroamidate internucleoside linkage
modified_base            order(2..4,6..8,10..12,15,22..25,27..28)
                         mod_base = OTHER
                         note = Phosphorothioate internucleoside linkage
modified_base            order(5,9,13,17..21)
                         mod_base = OTHER
                         note = Phosphate internucleoside linkage
SEQUENCE: 231
ccccagcagc ttcagtccct ttctcntcga                                   30

SEQ ID NO: 232           moltype = RNA  length = 30
FEATURE                  Location/Qualifiers
source                   1..30
                         mol_type = other RNA
```

-continued

```
                         organism = synthetic construct
modified_base            order(1,5,9,13,17,21..23,27,29,30)
                         mod_base = OTHER
                         note = 2-Prime-methoxyribose nucleotides
modified_base            order(2..4,6..8,10..12,14..16,18..20,28)
                         mod_base = OTHER
                         note = 2-Prime-deoxy-2-Prime-fluororibose nucleotides
modified_base            24
                         mod_base = OTHER
                         note = Deoxyribose Thymidine
modified_base            25
                         mod_base = OTHER
                         note = Beta-homoDNA
modified_base            26
                         mod_base = OTHER
                         note = Deoxyribose
modified_base            26
                         mod_base = i
modified_base            order(1,14,16,26,29)
                         mod_base = OTHER
                         note = Mesyl phosphroamidate internucleoside linkage
modified_base            order(2..4,6..8,10..12,15,18..20,24..25,27..28)
                         mod_base = OTHER
                         note = Phosphorothioate internucleoside linkage
modified_base            order(5,9,13,17,21..23)
                         mod_base = OTHER
                         note = Phosphate internucleoside linkage
SEQUENCE: 232
ccccagcagc ttcagtccct ttctcntcga                                   30

SEQ ID NO: 233           moltype = RNA  length = 30
FEATURE                  Location/Qualifiers
source                   1..30
                         mol_type = other RNA
                         organism = synthetic construct
modified_base            order(1,5,9..13,17,21,27,29,30)
                         mod_base = OTHER
                         note = order(1,5,9..13,17,21,27,29,30)
modified_base            order(2..4,6..8,14..16,18..20,22,23,28)
                         mod_base = OTHER
                         note = 2-Prime-deoxy-2-Prime-fluororibose nucleotides
modified_base            24
                         mod_base = OTHER
                         note = Deoxyribose Thymidine
modified_base            25
                         mod_base = OTHER
                         note = Beta-homoDNA
modified_base            26
                         mod_base = OTHER
                         note = Deoxyribose
modified_base            26
                         mod_base = i
modified_base            order(1,14,16,26,29)
                         mod_base = OTHER
                         note = Mesyl phosphroamidate internucleoside linkage
modified_base            order(2..13,15,17..25,27,28)
                         mod_base = OTHER
                         note = Phosphorothioate internucleoside linkage
SEQUENCE: 233
ccccagcagc ttcagtccct ttctcntcga                                   30

SEQ ID NO: 234           moltype = RNA  length = 42
FEATURE                  Location/Qualifiers
source                   1..42
                         mol_type = other RNA
                         organism = synthetic construct
SEQUENCE: 234
ttgcagtaca taatttacac agaagcaatg ccgtcacctt cc                     42

SEQ ID NO: 235           moltype = RNA  length = 42
FEATURE                  Location/Qualifiers
source                   1..42
                         mol_type = other RNA
                         organism = synthetic construct
modified_base            33
                         mod_base = i
SEQUENCE: 235
ttgcagtaca taatttacac agaagcaatg ccntcacctt cc                     42
```

```
SEQ ID NO: 236          moltype = RNA  length = 30
FEATURE                 Location/Qualifiers
source                  1..30
                        mol_type = other RNA
                        organism = synthetic construct
modified_base           25
                        mod_base = i
SEQUENCE: 236
cataatttac acagaagcaa tgccntcacc                                   30

SEQ ID NO: 237          moltype = RNA  length = 42
FEATURE                 Location/Qualifiers
source                  1..42
                        mol_type = other RNA
                        organism = synthetic construct
SEQUENCE: 237
tatacagatc cactgtggca cccagattat ccatgttaga ca                     42

SEQ ID NO: 238          moltype = RNA  length = 38
FEATURE                 Location/Qualifiers
source                  1..38
                        mol_type = other RNA
                        organism = synthetic construct
modified_base           28
                        mod_base = i
modified_base           17
                        mod_base = OTHER
                        note = Thymine
SEQUENCE: 238
gctgaattgg gagaaatcca cctgtccntt catctagt                          38

SEQ ID NO: 239          moltype = RNA  length = 42
FEATURE                 Location/Qualifiers
source                  1..42
                        mol_type = other RNA
                        organism = synthetic construct
modified_base           33
                        mod_base = i
modified_base           31
                        mod_base = OTHER
                        note = Thymine
SEQUENCE: 239
aacatggccc cagcagcttc agtccctttc tcntcgatgg tc                     42

SEQ ID NO: 240          moltype = RNA  length = 42
FEATURE                 Location/Qualifiers
source                  1..42
                        mol_type = other RNA
                        organism = synthetic construct
modified_base           33
                        mod_base = i
modified_base           order(18,28,29,31)
                        mod_base = OTHER
                        note = Thymine
SEQUENCE: 240
aacatggccc cagcagcttc agtccctttc tcntcgatgg tc                     42

SEQ ID NO: 241          moltype = RNA  length = 42
FEATURE                 Location/Qualifiers
source                  1..42
                        mol_type = other RNA
                        organism = synthetic construct
modified_base           33
                        mod_base = i
modified_base           order(18,28,29,31,41)
                        mod_base = OTHER
                        note = Thymine
SEQUENCE: 241
aacatggccc cagcagcttc agtccctttc tcntcgatgg tc                     42

SEQ ID NO: 242          moltype = RNA  length = 30
FEATURE                 Location/Qualifiers
source                  1..30
                        mol_type = other RNA
                        organism = synthetic construct
modified_base           25
                        mod_base = i
modified_base           23
                        mod_base = OTHER
```

```
                         note = Thymine
SEQUENCE: 242
cccagcagct tcagttcctt tctcntcgat                                       30

SEQ ID NO: 243           moltype = RNA  length = 42
FEATURE                  Location/Qualifiers
source                   1..42
                         mol_type = other RNA
                         organism = synthetic construct
modified_base            33
                         mod_base = i
modified_base            31
                         mod_base = OTHER
                         note = Thymine
SEQUENCE: 243
aacatggccc cagcagcttc agtccctttc tcntcgatgg tc                         42

SEQ ID NO: 244           moltype = RNA  length = 42
FEATURE                  Location/Qualifiers
source                   1..42
                         mol_type = other RNA
                         organism = synthetic construct
modified_base            order(1,3,4,9..11,13,14,18,20,21,24,25,30,34,36..40,42)
                         mod_base = OTHER
                         note = 2-Prime-methoxyribose nucleotides
modified_base            order(2,5..8,12,15..17,19,22,23,26..29,35,41)
                         mod_base = OTHER
                         note = 2-Prime-deoxy-2-Prime-fluororibose nucleotides
modified_base            31..33
                         mod_base = OTHER
                         note = Deoxyribose
modified_base            order(1..8,12..13,15..20,22..24,26..29,31..33,35,38..41)
                         mod_base = OTHER
                         note = Phosphorothioate internucleoside linkage
modified_base            order(9..11,14,21,25,30,34,36..37)
                         mod_base = OTHER
                         note = Phosphate internucleoside linkage
SEQUENCE: 244
ttgcagtaca taatttacac agaagcaatg ccgtcacctt cc                         42

SEQ ID NO: 245           moltype = RNA  length = 42
FEATURE                  Location/Qualifiers
source                   1..42
                         mol_type = other RNA
                         organism = synthetic construct
modified_base            order(1,3,4,9..11,13,14,18,20,21,24,25,27,30,34,36..40,42)
                         mod_base = OTHER
                         note = 2-Prime-methoxyribose nucleotides
modified_base            order(2,5..8,12,15..17,19,22,23,26,28,29,35,41)
                         mod_base = OTHER
                         note = 2-Prime-deoxy-2-Prime-fluororibose nucleotides
modified_base            order(31,33)
                         mod_base = OTHER
                         note = Deoxyribose
modified_base            33
                         mod_base = i
modified_base            32
                         mod_base = OTHER
                         note = Beta-homoDNA
modified_base            order(1,21,23,33,41)
                         mod_base = OTHER
                         note = Mesyl phosphroamidate internucleoside linkage
modified_base            order(2..8,12..13,15..20,22,24,26..29,31..32,35,38..40)
                         mod_base = OTHER
                         note = Phosphorothioate internucleoside linkage
modified_base            order(9..11,14,25,30,34,36..37)
                         mod_base = OTHER
                         note = Phosphate internucleoside linkage
SEQUENCE: 245
ttgcagtaca taatttacac agaagcaatg ccntcacctt cc                         42

SEQ ID NO: 246           moltype = RNA  length = 30
FEATURE                  Location/Qualifiers
source                   1..30
                         mol_type = other RNA
                         organism = synthetic construct
modified_base            order(1,3,6..8,10,12,18,21,26,28..30)
                         mod_base = OTHER
                         note = 2-Prime-methoxyribose nucleotides
```

```
modified_base          order(2,4,5,9,11,13..17,19,20,22,27)
                       mod_base = OTHER
                       note = 2-Prime-deoxy-2-Prime-fluororibose nucleotides
modified_base          order(23,25)
                       mod_base = OTHER
                       note = Deoxyribose
modified_base          25
                       mod_base = i
modified_base          24
                       mod_base = OTHER
                       note = Beta-homoDNA
modified_base          order(1,11,14,25,29)
                       mod_base = OTHER
                       note = Mesyl phosphroamidate internucleoside linkage
modified_base          order(2..10,12..13,15..24,26..28)
                       mod_base = OTHER
                       note = Phosphorothioate internucleoside linkage
SEQUENCE: 246
cataatttac acagaagcaa tgccntcacc                                   30

SEQ ID NO: 247         moltype = RNA  length = 42
FEATURE                Location/Qualifiers
source                 1..42
                       mol_type = other RNA
                       organism = synthetic construct
modified_base          order(1,3,4,9..11,13,14,18,20,21,24,25,30,34,36..40,42)
                       mod_base = OTHER
                       note = 2-Prime-methoxyribose nucleotides
modified_base          order(2,5..8,12,15..17,19,22,23,26..29,35,41)
                       mod_base = OTHER
                       note = 2-Prime-deoxy-2-Prime-fluororibose nucleotides
modified_base          order(31,33)
                       mod_base = OTHER
                       note = Deoxyribose
modified_base          32
                       mod_base = OTHER
                       note = Beta-homoDNA
modified_base          order(1..8,12..13,15..20,22..24,26..29,31..33,35,38..41)
                       mod_base = OTHER
                       note = Phosphorothioate internucleoside linkage
modified_base          order(9..11,14,21,25,30,34,36..37)
                       mod_base = OTHER
                       note = Phosphate internucleoside linkage
SEQUENCE: 247
tatacagatc cactgtggca cccagattat ccatgttaga ca                     42

SEQ ID NO: 248         moltype = RNA  length = 42
FEATURE                Location/Qualifiers
source                 1..42
                       mol_type = other RNA
                       organism = synthetic construct
modified_base          order(1,3,4,9..11,13,14,18,20,21,24,25,30,34,36..40,42)
                       mod_base = OTHER
                       note = 2-Prime-methoxyribose nucleotides
modified_base          order(2,5..8,12,15..17,19,22,23,26..29,35,41)
                       mod_base = OTHER
                       note = 2-Prime-deoxy-2-Prime-fluororibose nucleotides
modified_base          order(31,33)
                       mod_base = OTHER
                       note = Deoxyribose
modified_base          32
                       mod_base = OTHER
                       note = Beta-homoDNA
modified_base          order(1,21,23,33,41)
                       mod_base = OTHER
                       note = Mesyl phosphroamidate internucleoside linkage
modified_base          order(2..8,12..13,15..20,22,24,26..29,31..32,35,38..40)
                       mod_base = OTHER
                       note = Phosphorothioate internucleoside linkage
modified_base          order(9..11,14,25,30,34,36..37)
                       mod_base = OTHER
                       note = Phosphate internucleoside linkage
SEQUENCE: 248
tatacagatc cactgtggca cccagattat ccatgttaga ca                     42

SEQ ID NO: 249         moltype = RNA  length = 42
FEATURE                Location/Qualifiers
source                 1..42
                       mol_type = other RNA
```

```
                        organism = synthetic construct
modified_base           order(1,3,4,9..11,13,14,18,20,21,24,25,30,34,36..40,42)
                        mod_base = OTHER
                        note = 2-Prime-methoxyribose nucleotides
modified_base           order(2,5..8,12,15..17,19,22,23,26..29,35,41)
                        mod_base = OTHER
                        note = 2-Prime-deoxy-2-Prime-fluororibose nucleotides
modified_base           order(31,33)
                        mod_base = OTHER
                        note = Deoxyribose
modified_base           32
                        mod_base = OTHER
                        note = Beta-homoDNA
modified_base           order(1,21,23,27,33,41)
                        mod_base = OTHER
                        note = Mesyl phosphroamidate internucleoside linkage
modified_base           order(2..8,12..13,15..20,22,24,26,28..29,31..32,35,38..40)
                        mod_base = OTHER
                        note = Phosphorothioate internucleoside linkage
modified_base           order(9..11,14,25,30,34,36..37)
                        mod_base = OTHER
                        note = Phosphate internucleoside linkage
SEQUENCE: 249
tatacagatc cactgtggca cccagattat ccatgttaga ca                     42

SEQ ID NO: 250          moltype = RNA  length = 42
FEATURE                 Location/Qualifiers
source                  1..42
                        mol_type = other RNA
                        organism = synthetic construct
modified_base           order(1,3,4,9..11,13,14,18,20,21,24,25,30,34,36..40,42)
                        mod_base = OTHER
                        note = 2-Prime-methoxyribose nucleotides
modified_base           order(2,5..8,12,15..17,19,22,23,26..29,35,41)
                        mod_base = OTHER
                        note = 2-Prime-deoxy-2-Prime-fluororibose nucleotides
modified_base           order(31,33)
                        mod_base = OTHER
                        note = Deoxyribose
modified_base           32
                        mod_base = OTHER
                        note = Beta-homoDNA
modified_base           order(1,7,21,23,33,41)
                        mod_base = OTHER
                        note = Mesyl phosphroamidate internucleoside linkage
modified_base           order(2..6,8,12..13,15..20,22,24,26..29,31..32,35,38..40)
                        mod_base = OTHER
                        note = Phosphorothioate internucleoside linkage
modified_base           order(9..11,14,25,30,34,36..37)
                        mod_base = OTHER
                        note = Phosphate internucleoside linkage
SEQUENCE: 250
tatacagatc cactgtggca cccagattat ccatgttaga ca                     42

SEQ ID NO: 251          moltype = RNA  length = 42
FEATURE                 Location/Qualifiers
source                  1..42
                        mol_type = other RNA
                        organism = synthetic construct
modified_base           order(1,3,4,9..11,13,14,18,20,21,24,25,30,34,36..40,42)
                        mod_base = OTHER
                        note = 2-Prime-methoxyribose nucleotides
modified_base           order(2,5..8,12,15..17,19,22,23,26..29,35,41)
                        mod_base = OTHER
                        note = 2-Prime-deoxy-2-Prime-fluororibose nucleotides
modified_base           order(31,33)
                        mod_base = OTHER
                        note = Deoxyribose
modified_base           32
                        mod_base = OTHER
                        note = Beta-homoDNA
modified_base           order(1,10,13,21,23,33,41)
                        mod_base = OTHER
                        note = Mesyl phosphroamidate internucleoside linkage
modified_base           order(2..8,12,15..20,22,24,26..29,31..32,35,38..40)
                        mod_base = OTHER
                        note = Phosphorothioate internucleoside linkage
modified_base           order(9,11,14,25,30,34,36..37)
                        mod_base = OTHER
```

```
                         note = Phosphate internucleoside linkage
SEQUENCE: 251
tatacagatc cactgtggca cccagattat ccatgttaga ca                      42

SEQ ID NO: 252           moltype = RNA  length = 42
FEATURE                  Location/Qualifiers
source                   1..42
                         mol_type = other RNA
                         organism = synthetic construct
modified_base            order(1,3,4,9..11,13,14,18,20,21,24,25,30,34,36..40,42)
                         mod_base = OTHER
                         note = 2-Prime-methoxyribose nucleotides
modified_base            order(2,5..8,12,15..17,19,22,23,26..29,35,41)
                         mod_base = OTHER
                         note = 2-Prime-deoxy-2-Prime-fluororibose nucleotides
modified_base            order(31,33)
                         mod_base = OTHER
                         note = Deoxyribose
modified_base            32
                         mod_base = OTHER
                         note = Beta-homoDNA
modified_base            order(1,7,21,23,33,37,41)
                         mod_base = OTHER
                         note = Mesyl phosphroamidate internucleoside linkage
modified_base            order(2..6,8,12..13,15..20,22,24,26..29,31..32,35,38..40)
                         mod_base = OTHER
                         note = Phosphorothioate internucleoside linkage
modified_base            order(9..11,14,25,30,34,36)
                         mod_base = OTHER
                         note = Phosphate internucleoside linkage
SEQUENCE: 252
tatacagatc cactgtggca cccagattat ccatgttaga ca                      42

SEQ ID NO: 253           moltype = RNA  length = 42
FEATURE                  Location/Qualifiers
source                   1..42
                         mol_type = other RNA
                         organism = synthetic construct
modified_base            order(1,3,4,9..11,13,14,18,20,21,24,25,30,34,36..40,42)
                         mod_base = OTHER
                         note = 2-Prime-methoxyribose nucleotides
modified_base            order(2,5..8,12,15..17,19,22,23,26..29,35,41)
                         mod_base = OTHER
                         note = 2-Prime-deoxy-2-Prime-fluororibose nucleotides
modified_base            order(31,33)
                         mod_base = OTHER
                         note = Deoxyribose
modified_base            32
                         mod_base = OTHER
                         note = Beta-homoDNA
modified_base            order(1,7,13,21,23,33,37,41)
                         mod_base = OTHER
                         note = Mesyl phosphroamidate internucleoside linkage
modified_base            order(2..6,8,12,15..20,22,24,26..29,31..32,35,38..40)
                         mod_base = OTHER
                         note = Phosphorothioate internucleoside linkage
modified_base            order(9..11,14,25,30,34,36)
                         mod_base = OTHER
                         note = Phosphate internucleoside linkage
SEQUENCE: 253
tatacagatc cactgtggca cccagattat ccatgttaga ca                      42

SEQ ID NO: 254           moltype = RNA  length = 42
FEATURE                  Location/Qualifiers
source                   1..42
                         mol_type = other RNA
                         organism = synthetic construct
modified_base            order(1,3,4,9..11,13,14,18,20,21,24,25,30,34,36..40,42)
                         mod_base = OTHER
                         note = 2-Prime-methoxyribose nucleotides
modified_base            order(2,5..8,12,15..17,19,22,23,26..29,35,41)
                         mod_base = OTHER
                         note = 2-Prime-deoxy-2-Prime-fluororibose nucleotides
modified_base            order(31,33)
                         mod_base = OTHER
                         note = Deoxyribose
modified_base            32
                         mod_base = OTHER
                         note = Beta-homoDNA
```

-continued

```
modified_base          order(1,7,10,21,23,27,33,41)
                       mod_base = OTHER
                       note = Mesyl phosphroamidate internucleoside linkage
modified_base          order(2..6,8,12..13,15..20,22,24,26,28..29,31..32,35,38..40)
                       mod_base = OTHER
                       note = Phosphorothioate internucleoside linkage
modified_base          order(9,11,14,25,30,34,36..37)
                       mod_base = OTHER
                       note = Phosphate internucleoside linkage
SEQUENCE: 254
tatacagatc cactgtggca cccagattat ccatgttaga ca                    42

SEQ ID NO: 255         moltype = RNA  length = 42
FEATURE                Location/Qualifiers
source                 1..42
                       mol_type = other RNA
                       organism = synthetic construct
modified_base          order(1,3,4,9..11,13,14,18,20,21,24,25,30,34,36..40,42)
                       mod_base = OTHER
                       note = 2-Prime-methoxyribose nucleotides
modified_base          order(2,5..8,12,15..17,19,22,23,26..29,35,41)
                       mod_base = OTHER
                       note = 2-Prime-deoxy-2-Prime-fluororibose nucleotides
modified_base          order(31,33)
                       mod_base = OTHER
                       note = Deoxyribose
modified_base          32
                       mod_base = OTHER
                       note = Beta-homoDNA
modified_base          order(1,20,25,33,41)
                       mod_base = OTHER
                       note = Mesyl phosphroamidate internucleoside linkage
modified_base          order(2..8,12..13,15..19,22..24,26..29,31..32,35,38..40)
                       mod_base = OTHER
                       note = Phosphorothioate internucleoside linkage
modified_base          order(9..11,14,21,30,34,36..37)
                       mod_base = OTHER
                       note = Phosphate internucleoside linkage
SEQUENCE: 255
tatacagatc cactgtggca cccagattat ccatgttaga ca                    42

SEQ ID NO: 256         moltype = RNA  length = 42
FEATURE                Location/Qualifiers
source                 1..42
                       mol_type = other RNA
                       organism = synthetic construct
modified_base          order(1,3,4,9..11,13,14,18,20,21,24,25,30,34,36..40,42)
                       mod_base = OTHER
                       note = 2-Prime-methoxyribose nucleotides
modified_base          order(2,5..8,12,15..17,19,22,23,26..29,35,41)
                       mod_base = OTHER
                       note = 2-Prime-deoxy-2-Prime-fluororibose nucleotides
modified_base          order(31,33)
                       mod_base = OTHER
                       note = Deoxyribose
modified_base          32
                       mod_base = OTHER
                       note = Beta-homoDNA
modified_base          order(1,21,23,33,41)
                       mod_base = OTHER
                       note = Mesyl phosphroamidate internucleoside linkage
modified_base          order(2..20,22,24..32,34..40)
                       mod_base = OTHER
                       note = Phosphorothioate internucleoside linkage
SEQUENCE: 256
tatacagatc cactgtggca cccagattat ccatgttaga ca                    42

SEQ ID NO: 257         moltype = RNA  length = 42
FEATURE                Location/Qualifiers
source                 1..42
                       mol_type = other RNA
                       organism = synthetic construct
modified_base          order(1,3,4,9..11,13,14,18,20,21,24,25,30,34,36..40,42)
                       mod_base = OTHER
                       note = 2-Prime-methoxyribose nucleotides
modified_base          order(2,5..8,12,15..17,19,22,23,26..29,35,41)
                       mod_base = OTHER
                       note = 2-Prime-deoxy-2-Prime-fluororibose nucleotides
modified_base          order(31,33)
```

```
                         mod_base = OTHER
                         note = Deoxyribose
modified_base            32
                         mod_base = OTHER
                         note = Beta-homoDNA
modified_base            order(1,21,23,33,41)
                         mod_base = OTHER
                         note = Mesyl phosphroamidate internucleoside linkage
modified_base            order(2..9,12..13,15..20,22,24..29,31..32,35..36,38..40)
                         mod_base = OTHER
                         note = Phosphorothioate internucleoside linkage
modified_base            order(10..11,14,30,34,37)
                         mod_base = OTHER
                         note = Phosphate internucleoside linkage
SEQUENCE: 257
tatacagatc cactgtggca cccagattat ccatgttaga ca                    42

SEQ ID NO: 258           moltype = RNA  length = 42
FEATURE                  Location/Qualifiers
source                   1..42
                         mol_type = other RNA
                         organism = synthetic construct
modified_base            order(1,3,4,9..11,13,14,18,20,21,24,25,30,34,36..40,42)
                         mod_base = OTHER
                         note = 2-Prime-methoxyribose nucleotides
modified_base            order(2,5..8,12,15..17,19,22,23,26..29,35,41)
                         mod_base = OTHER
                         note = 2-Prime-deoxy-2-Prime-fluororibose nucleotides
modified_base            order(31,33)
                         mod_base = OTHER
                         note = Deoxyribose
modified_base            32
                         mod_base = OTHER
                         note = Beta-homoDNA
modified_base            order(1,21,23,33,41)
                         mod_base = OTHER
                         note = Mesyl phosphroamidate internucleoside linkage
modified_base            order(2..8,10,12..13,15..20,22,24..29,31..32,35,37..40)
                         mod_base = OTHER
                         note = Phosphorothioate internucleoside linkage
modified_base            order(9,11,14,30,34,36)
                         mod_base = OTHER
                         note = Phosphate internucleoside linkage
SEQUENCE: 258
tatacagatc cactgtggca cccagattat ccatgttaga ca                    42

SEQ ID NO: 259           moltype = RNA  length = 42
FEATURE                  Location/Qualifiers
source                   1..42
                         mol_type = other RNA
                         organism = synthetic construct
modified_base            order(1,3,4,9..11,13,14,18,20,21,24,25,30,34,36..40,42)
                         mod_base = OTHER
                         note = 2-Prime-methoxyribose nucleotides
modified_base            order(2,5..8,12,15..17,19,22,23,26..29,35,41)
                         mod_base = OTHER
                         note = 2-Prime-deoxy-2-Prime-fluororibose nucleotides
modified_base            order(31,33)
                         mod_base = OTHER
                         note = Deoxyribose
modified_base            32
                         mod_base = OTHER
                         note = Beta-homoDNA
modified_base            order(1,21,23,33,41)
                         mod_base = OTHER
                         note = Mesyl phosphroamidate internucleoside linkage
modified_base            order(2..8,11..20,22,24,26..29,31..32,35..36,38..40)
                         mod_base = OTHER
                         note = Phosphorothioate internucleoside linkage
modified_base            order(9..10,25,30,34,37)
                         mod_base = OTHER
                         note = Phosphate internucleoside linkage
SEQUENCE: 259
tatacagatc cactgtggca cccagattat ccatgttaga ca                    42

SEQ ID NO: 260           moltype = RNA  length = 42
FEATURE                  Location/Qualifiers
source                   1..42
                         mol_type = other RNA
```

```
                        organism = synthetic construct
modified_base           order(1,3,4,9..11,13,14,18,20,21,24,25,30,34,36..40,42)
                        mod_base = OTHER
                        note = 2-Prime-methoxyribose nucleotides
modified_base           order(2,5..8,12,15..17,19,22,23,26..29,35,41)
                        mod_base = OTHER
                        note = 2-Prime-deoxy-2-Prime-fluororibose nucleotides
modified_base           order(31,33)
                        mod_base = OTHER
                        note = Deoxyribose
modified_base           32
                        mod_base = OTHER
                        note = Beta-homoDNA
modified_base           order(1,21,23,33,41)
                        mod_base = OTHER
                        note = Mesyl phosphroamidate internucleoside linkage
modified_base           order(2,4..8,12..13,15,17..19,22,26,28..29,31..32,35,38,40)
                        mod_base = OTHER
                        note = Phosphorothioate internucleoside linkage
modified_base           order(3,9..11,14,16,20,24..25,27,30,34,36..37,39)
                        mod_base = OTHER
                        note = Phosphate internucleoside linkage
SEQUENCE: 260
tatacagatc cactgtggca cccagattat ccatgttaga ca                    42

SEQ ID NO: 261          moltype = RNA  length = 42
FEATURE                 Location/Qualifiers
source                  1..42
                        mol_type = other RNA
                        organism = synthetic construct
modified_base           order(1,3,4,9..11,13,14,18,20,21,24,25,30,34,36..40,42)
                        mod_base = OTHER
                        note = 2-Prime-methoxyribose nucleotides
modified_base           order(2,5..8,12,15..17,19,22,23,26..29,35,41)
                        mod_base = OTHER
                        note = 2-Prime-deoxy-2-Prime-fluororibose nucleotides
modified_base           order(31,33)
                        mod_base = OTHER
                        note = Deoxyribose
modified_base           32
                        mod_base = OTHER
                        note = Beta-homoDNA
modified_base           order(1,21,23,33,41)
                        mod_base = OTHER
                        note = Mesyl phosphroamidate internucleoside linkage
modified_base           order(2..3,5..8,12..13,16..19,22,26..27,29,31..32,35,39..40)
                        mod_base = OTHER
                        note = Phosphorothioate internucleoside linkage
modified_base           order(4,9..11,14..15,20,24..25,28,30,34,36..38)
                        mod_base = OTHER
                        note = Phosphate internucleoside linkage
SEQUENCE: 261
tatacagatc cactgtggca cccagattat ccatgttaga ca                    42

SEQ ID NO: 262          moltype = RNA  length = 42
FEATURE                 Location/Qualifiers
source                  1..42
                        mol_type = other RNA
                        organism = synthetic construct
modified_base           order(1,3,4,9..11,13,14,18,20,21,24,25,30,34,36..40,42)
                        mod_base = OTHER
                        note = 2-Prime-methoxyribose nucleotides
modified_base           order(2,5..8,12,15..17,19,22,23,26..29,35,41)
                        mod_base = OTHER
                        note = 2-Prime-deoxy-2-Prime-fluororibose nucleotides
modified_base           order(31,33)
                        mod_base = OTHER
                        note = Deoxyribose
modified_base           32
                        mod_base = OTHER
                        note = Beta-homoDNA
modified_base           order(1,21,23,33,41)
                        mod_base = OTHER
                        note = Mesyl phosphroamidate internucleoside linkage
modified_base           order(2..4,6..8,12..13,15..16,18..19,22,26..28,31..32,35,38..39)
                        mod_base = OTHER
                        note = Phosphorothioate internucleoside linkage
modified_base           order(5,9..11,14,17,20,24..25,29..30,34,36..37,40)
                        mod_base = OTHER
```

```
                         note = Phosphate internucleoside linkage
SEQUENCE: 262
tatacagatc cactgtggca cccagattat ccatgttaga ca                     42

SEQ ID NO: 263           moltype = RNA  length = 42
FEATURE                  Location/Qualifiers
source                   1..42
                         mol_type = other RNA
                         organism = synthetic construct
modified_base            order(1,3,4,9..11,13,14,18,20,21,24,25,30,34,36..40,42)
                         mod_base = OTHER
                         note = 2-Prime-methoxyribose nucleotides
modified_base            order(2,5..8,12,15..17,19,22,23,26..29,35,41)
                         mod_base = OTHER
                         note = 2-Prime-deoxy-2-Prime-fluororibose nucleotides
modified_base            order(31,33)
                         mod_base = OTHER
                         note = Deoxyribose
modified_base            32
                         mod_base = OTHER
                         note = Beta-homoDNA
modified_base            order(1,21,23,33,41)
                         mod_base = OTHER
                         note = Mesyl phosphroamidate internucleoside linkage
modified_base            order(2,5..6,8,12,15,17..18,20,22,27,29,31..32,35,38,40)
                         mod_base = OTHER
                         note = Phosphorothioate internucleoside linkage
modified_base            order(3..4,7,9..11,13..14,16,19,24..26,28,30,34,36..37,39)
                         mod_base = OTHER
                         note = Phosphate internucleoside linkage
SEQUENCE: 263
tatacagatc cactgtggca cccagattat ccatgttaga ca                     42

SEQ ID NO: 264           moltype = RNA  length = 42
FEATURE                  Location/Qualifiers
source                   1..42
                         mol_type = other RNA
                         organism = synthetic construct
modified_base            order(1,3,4,9..11,13,14,18,20,21,24,25,30,34,36..40,42)
                         mod_base = OTHER
                         note = 2-Prime-methoxyribose nucleotides
modified_base            order(2,5..8,12,15..17,19,22,23,26..29,35,41)
                         mod_base = OTHER
                         note = 2-Prime-deoxy-2-Prime-fluororibose nucleotides
modified_base            order(31,33)
                         mod_base = OTHER
                         note = Deoxyribose
modified_base            32
                         mod_base = OTHER
                         note = Beta-homoDNA
modified_base            order(1,21,23,33,41)
                         mod_base = OTHER
                         note = Mesyl phosphroamidate internucleoside linkage
modified_base            order(2,5,7,12,15..17,19..20,22,26,28,31..32,35,38,40)
                         mod_base = OTHER
                         note = Phosphorothioate internucleoside linkage
modified_base            order(3..4,6,8..11,13..14,18,24..25,27,29..30,34,36..37,39)
                         mod_base = OTHER
                         note = Phosphate internucleoside linkage
SEQUENCE: 264
tatacagatc cactgtggca cccagattat ccatgttaga ca                     42

SEQ ID NO: 265           moltype = RNA  length = 42
FEATURE                  Location/Qualifiers
source                   1..42
                         mol_type = other RNA
                         organism = synthetic construct
modified_base            order(1,3,4,9..11,13,14,18,20,21,24,25,30,34,36..40,42)
                         mod_base = OTHER
                         note = 2-Prime-methoxyribose nucleotides
modified_base            order(2,5..8,12,15..17,19,22,23,26..29,35,41)
                         mod_base = OTHER
                         note = 2-Prime-deoxy-2-Prime-fluororibose nucleotides
modified_base            order(31,33)
                         mod_base = OTHER
                         note = Deoxyribose
modified_base            32
                         mod_base = OTHER
                         note = Beta-homoDNA
```

```
modified_base          order(1,21,23,33,41)
                       mod_base = OTHER
                       note = Mesyl phosphroamidate internucleoside linkage
modified_base          order(2,6..7,12,15..16,18..20,22,27..28,31..32,35,39..40)
                       mod_base = OTHER
                       note = Phosphorothioate internucleoside linkage
modified_base          order(3..5,8..11,13..14,17,24..26,29..30,34,36..38)
                       mod_base = OTHER
                       note = Phosphate internucleoside linkage
SEQUENCE: 265
tatacagatc cactgtggca cccagattat ccatgttaga ca                    42

SEQ ID NO: 266         moltype = RNA  length = 38
FEATURE                Location/Qualifiers
source                 1..38
                       mol_type = other RNA
                       organism = synthetic construct
modified_base          order(1,3,6,7,9,11,14..16,22,23,25,29,31,32,35,38)
                       mod_base = OTHER
                       note = 2-Prime-methoxyribose nucleotides
modified_base          order(2,4,5,8,10,12,13,20,21,24,30,33,34,36,37)
                       mod_base = OTHER
                       note = 2-Prime-deoxy-2-Prime-fluororibose nucleotides
modified_base          17
                       mod_base = OTHER
                       note = Deoxyribose Thymidine
modified_base          order(18,19,26,28)
                       mod_base = OTHER
                       note = Deoxyribose
modified_base          28
                       mod_base = i
modified_base          27
                       mod_base = OTHER
                       note = Beta-homoDNA
modified_base          order(1..5,8,10,12..13,17..21,24,26..28,30,33..37)
                       mod_base = OTHER
                       note = Phosphorothioate internucleoside linkage
modified_base          order(6..7,9,11,14..16,22..23,25,29,31..32)
                       mod_base = OTHER
                       note = Phosphate internucleoside linkage
SEQUENCE: 266
gctgaattgg gagaaatcca cctgtccntt catctagt                         38

SEQ ID NO: 267         moltype = RNA  length = 38
FEATURE                Location/Qualifiers
source                 1..38
                       mol_type = other RNA
                       organism = synthetic construct
modified_base          order(1,3,6,7,9,11,14..16,22,23,25,29,31,32,35,38)
                       mod_base = OTHER
                       note = 2-Prime-methoxyribose nucleotides
modified_base          order(2,4,5,8,10,12,13,20,21,24,30,33,34,36,37)
                       mod_base = OTHER
                       note = 2-Prime-deoxy-2-Prime-fluororibose nucleotides
modified_base          order(18,19,26,28)
                       mod_base = OTHER
                       note = Deoxyribose
modified_base          27
                       mod_base = OTHER
                       note = Beta-homoDNA
modified_base          17
                       mod_base = OTHER
                       note = Deoxyribose Thymidine
modified_base          28
                       mod_base = i
modified_base          order(1,16,18,28,37)
                       mod_base = OTHER
                       note = Mesyl phosphroamidate internucleoside linkage
modified_base          order(2..5,8,10,12..13,17,19..21,24,26..27,30,33..36)
                       mod_base = OTHER
                       note = Phosphorothioate internucleoside linkage
modified_base          order(6..7,9,11,14..15,22..23,25,29,31..32)
                       mod_base = OTHER
                       note = Phosphate internucleoside linkage
SEQUENCE: 267
gctgaattgg gagaaatcca cctgtccntt catctagt                         38

SEQ ID NO: 268         moltype = RNA  length = 38
FEATURE                Location/Qualifiers
```

-continued

```
source                  1..38
                        mol_type = other RNA
                        organism = synthetic construct
modified_base           order(1,3,6,7,9,11,14..16,22,23,25,29,31,32,35,38)
                        mod_base = OTHER
                        note = 2-Prime-methoxyribose nucleotides
modified_base           order(2,4,5,8,10,12,13,20,21,24,30,33,34,36,37)
                        mod_base = OTHER
                        note = 2-Prime-deoxy-2-Prime-fluororibose nucleotides
modified_base           order(18,19,26,28)
                        mod_base = OTHER
                        note = Deoxyribose
modified_base           27
                        mod_base = OTHER
                        note = Beta-homoDNA
modified_base           17
                        mod_base = OTHER
                        note = Deoxyribose Thymidine
modified_base           28
                        mod_base = i
modified_base           order(1,28,37)
                        mod_base = OTHER
                        note = Mesyl phosphroamidate internucleoside linkage
modified_base           order(2..5,8,10,12..13,17..21,24,26..27,30,33..36)
                        mod_base = OTHER
                        note = Phosphorothioate internucleoside linkage
modified_base           order(6..7,9,11,14..16,22..23,25,29,31..32)
                        mod_base = OTHER
                        note = Phosphate internucleoside linkage
SEQUENCE: 268
gctgaattgg gagaaatcca cctgtccntt catctagt                          38

SEQ ID NO: 269          moltype = RNA  length = 38
FEATURE                 Location/Qualifiers
source                  1..38
                        mol_type = other RNA
                        organism = synthetic construct
modified_base           order(1,3,6,7,9,11,14..16,22,23,25,29,31,32,35,38)
                        mod_base = OTHER
                        note = 2-Prime-methoxyribose nucleotides
modified_base           order(2,4,5,8,10,12,13,20,21,24,30,33,34,36,37)
                        mod_base = OTHER
                        note = 2-Prime-deoxy-2-Prime-fluororibose nucleotides
modified_base           order(18,19,26,28)
                        mod_base = OTHER
                        note = Deoxyribose
modified_base           27
                        mod_base = OTHER
                        note = Beta-homoDNA
modified_base           17
                        mod_base = OTHER
                        note = Deoxyribose Thymidine
modified_base           28
                        mod_base = i
modified_base           order(1,37)
                        mod_base = OTHER
                        note = Mesyl phosphroamidate internucleoside linkage
modified_base           order(2..5,8,10,12..13,17..21,24,26..28,30,33..36)
                        mod_base = OTHER
                        note = Phosphorothioate internucleoside linkage
modified_base           order(6..7,9,11,14..16,22..23,25,29,31..32)
                        mod_base = OTHER
                        note = Phosphate internucleoside linkage
SEQUENCE: 269
gctgaattgg gagaaatcca cctgtccntt catctagt                          38

SEQ ID NO: 270          moltype = RNA  length = 38
FEATURE                 Location/Qualifiers
source                  1..38
                        mol_type = other RNA
                        organism = synthetic construct
modified_base           order(1,3,6,7,9,11,14..16,22,23,25,29,31,32,35,38)
                        mod_base = OTHER
                        note = 2-Prime-methoxyribose nucleotides
modified_base           order(2,4,5,8,10,12,13,20,21,24,30,33,34,36,37)
                        mod_base = OTHER
                        note = 2-Prime-deoxy-2-Prime-fluororibose nucleotides
modified_base           order(18,19,26,28)
                        mod_base = OTHER
```

```
                        note = Deoxyribose
modified_base           27
                        mod_base = OTHER
                        note = Beta-homoDNA
modified_base           17
                        mod_base = OTHER
                        note = Deoxyribose Thymidine
modified_base           28
                        mod_base = i
modified_base           1
                        mod_base = OTHER
                        note = Mesyl phosphroamidate internucleoside linkage
modified_base           order(2..5,8,10,12..13,17..21,24,26..28,30,33..37)
                        mod_base = OTHER
                        note = Phosphorothioate internucleoside linkage
modified_base           order(6..7,9,11,14..16,22..23,25,29,31..32)
                        mod_base = OTHER
                        note = Phosphate internucleoside linkage
SEQUENCE: 270
gctgaattgg gagaaatcca cctgtccntt catctagt                          38

SEQ ID NO: 271          moltype = RNA  length = 38
FEATURE                 Location/Qualifiers
source                  1..38
                        mol_type = other RNA
                        organism = synthetic construct
modified_base           order(1,3,6,7,9,11,14..16,22,23,25,29,31,32,35,38)
                        mod_base = OTHER
                        note = 2-Prime-methoxyribose nucleotides
modified_base           order(2,4,5,8,10,12,13,20,21,24,30,33,34,36,37)
                        mod_base = OTHER
                        note = 2-Prime-deoxy-2-Prime-fluororibose nucleotides
modified_base           order(18,19,26,28)
                        mod_base = OTHER
                        note = Deoxyribose
modified_base           27
                        mod_base = OTHER
                        note = Beta-homoDNA
modified_base           17
                        mod_base = OTHER
                        note = Deoxyribose Thymidine
modified_base           28
                        mod_base = i
modified_base           28
                        mod_base = OTHER
                        note = Mesyl phosphroamidate internucleoside linkage
modified_base           order(1..5,8,10,12..13,17..21,24,26..27,30,33..37)
                        mod_base = OTHER
                        note = Phosphorothioate internucleoside linkage
modified_base           order(6..7,9,11,14..16,22..23,25,29,31..32)
                        mod_base = OTHER
                        note = Phosphate internucleoside linkage
SEQUENCE: 271
gctgaattgg gagaaatcca cctgtccntt catctagt                          38

SEQ ID NO: 272          moltype = RNA  length = 38
FEATURE                 Location/Qualifiers
source                  1..38
                        mol_type = other RNA
                        organism = synthetic construct
modified_base           order(1,3,6,7,9,11,14..16,22,23,25,29,31,32,35,38)
                        mod_base = OTHER
                        note = 2-Prime-methoxyribose nucleotides
modified_base           order(2,4,5,8,10,12,13,20,21,24,30,33,34,36,37)
                        mod_base = OTHER
                        note = 2-Prime-deoxy-2-Prime-fluororibose nucleotides
modified_base           order(18,19,26,28)
                        mod_base = OTHER
                        note = Deoxyribose
modified_base           27
                        mod_base = OTHER
                        note = Beta-homoDNA
modified_base           17
                        mod_base = OTHER
                        note = Deoxyribose Thymidine
modified_base           28
                        mod_base = i
modified_base           37
                        mod_base = OTHER
```

```
                        note = Mesyl phosphroamidate internucleoside linkage
modified_base           order(1..5,8,10,12..13,17..21,24,26..28,30,33..36)
                        mod_base = OTHER
                        note = Phosphorothioate internucleoside linkage
modified_base           order(6..7,9,11,14..16,22..23,25,29,31..32)
                        mod_base = OTHER
                        note = Phosphate internucleoside linkage
SEQUENCE: 272
gctgaattgg gagaaatcca cctgtccntt catctagt                          38

SEQ ID NO: 273          moltype = RNA  length = 42
FEATURE                 Location/Qualifiers
source                  1..42
                        mol_type = other RNA
                        organism = synthetic construct
modified_base           order(1..11,14,15,18,20,24,26,28,29,34,36..42)
                        mod_base = OTHER
                        note = 2-Prime-methoxyribose nucleotides
modified_base           order(12,13,16,17,19,21..23,25,27,30,35)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = Deoxyribose
modified_base           33
                        mod_base = i
modified_base           order(1,19,22,33,41)
                        mod_base = OTHER
                        note = Mesyl phosphroamidate internucleoside linkage
modified_base           order(2..3,11..13,16,18,21,24..25,27,30..32,35,39..40)
                        mod_base = OTHER
                        note = Phosphorothioate internucleoside linkage
modified_base           order(4..10,14..15,17,20,23,26,28..29,34,36..38)
                        mod_base = OTHER
                        note = Phosphate internucleoside linkage
SEQUENCE: 273
aacatggccc cagcagcttc agtccctttc tcntcgatgg tc                     42

SEQ ID NO: 274          moltype = RNA  length = 42
FEATURE                 Location/Qualifiers
source                  1..42
                        mol_type = other RNA
                        organism = synthetic construct
modified_base           order(1..3,5,7..11,14,15,18,20,24,26,28,29,34,36..39,42)
                        mod_base = OTHER
                        note = 2-Prime-methoxyribose nucleotides
modified_base           order(4,6,12,13,16,17,19,21..23,25,27,30,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = Deoxyribose
modified_base           33
                        mod_base = i
modified_base           order(1,19,22,33,41)
                        mod_base = OTHER
                        note = Mesyl phosphroamidate internucleoside linkage
modified_base           order(2..4,6,11..13,16,18,21,24..25,27,30..32,35,39..40)
                        mod_base = OTHER
                        note = Phosphorothioate internucleoside linkage
modified_base           order(5,7..10,14..15,17,20,23,26,28..29,34,36..38)
                        mod_base = OTHER
                        note = Phosphate internucleoside linkage
SEQUENCE: 274
aacatggccc cagcagcttc agtccctttc tcntcgatgg tc                     42

SEQ ID NO: 275          moltype = RNA  length = 42
```

-continued

```
FEATURE                 Location/Qualifiers
source                  1..42
                        mol_type = other RNA
                        organism = synthetic construct
modified_base           order(1..5,9..11,14,15,18,20,24,26,28,29,34,36..40,42)
                        mod_base = OTHER
                        note = 2-Prime-methoxyribose nucleotides
modified_base           order(7,8,12,13,16,17,19,21..23,25,27,30,35)
                        mod_base = OTHER
                        note = 2-Prime-deoxy-2-Prime-fluororibose nucleotides
modified_base           order(6,33)
                        mod_base = OTHER
                        note = Deoxyribose
modified_base           33
                        mod_base = i
modified_base           order(31,41)
                        mod_base = OTHER
                        note = Deoxyribose Thymidine
modified_base           32
                        mod_base = OTHER
                        note = Beta-homoDNA
modified_base           order(1,19,22,33,41)
                        mod_base = OTHER
                        note = Mesyl phosphroamidate internucleoside linkage
modified_base           order(2..4,6..8,10..13,16,18,21,24..25,27,30..32,35,38..40)
                        mod_base = OTHER
                        note = Phosphorothioate internucleoside linkage
modified_base           order(5,9,14..15,17,20,23,26,28..29,34,36..37)
                        mod_base = OTHER
                        note = Phosphate internucleoside linkage
SEQUENCE: 275
aacatggccc cagcagcttc agtccctttc tcntcgatgg tc                    42

SEQ ID NO: 276          moltype = RNA  length = 42
FEATURE                 Location/Qualifiers
source                  1..42
                        mol_type = other RNA
                        organism = synthetic construct
modified_base           order(1..11,14,15,18,20,24,26,28,29,34,36..42)
                        mod_base = OTHER
                        note = 2-Prime-methoxyribose nucleotides
modified_base           order(12,13,16,17,19,21..23,25,27,30,35)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = Deoxyribose
modified_base           33
                        mod_base = i
modified_base           order(1..3,11..13,16,18..19,21..22,24..25,27,30..33,35,39..41)
                        mod_base = OTHER
                        note = Phosphorothioate internucleoside linkage
modified_base           order(4..10,14..15,17,20,23,26,28..29,34,36..38)
                        mod_base = OTHER
                        note = Phosphate internucleoside linkage
SEQUENCE: 276
aacatggccc cagcagcttc agtccctttc tcntcgatgg tc                    42

SEQ ID NO: 277          moltype = RNA  length = 42
FEATURE                 Location/Qualifiers
source                  1..42
                        mol_type = other RNA
                        organism = synthetic construct
modified_base           order(1..3,5,7..11,14,15,18,20,24,26,28,29,34,36..39,42)
                        mod_base = OTHER
                        note = 2-Prime-methoxyribose nucleotides
modified_base           order(4,6,12,13,16,17,19,21..23,25,27,30,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
```

```
                        mod_base = OTHER
                        note = Beta-homoDNA
modified_base           33
                        mod_base = OTHER
                        note = Deoxyribose
modified_base           33
                        mod_base = i
modified_base           order(1..4,6,11..13,16,18..19,21..22,24..25,27,30..33,35,39..41)
                        mod_base = OTHER
                        note = Phosphorothioate internucleoside linkage
modified_base           order(5,7..10,14..15,17,20,23,26,28..29,34,36..38)
                        mod_base = OTHER
                        note = Phosphate internucleoside linkage
SEQUENCE: 277
aacatggccc cagcagcttc agtccctttc tcntcgatgg tc                    42

SEQ ID NO: 278          moltype = RNA  length = 42
FEATURE                 Location/Qualifiers
source                  1..42
                        mol_type = other RNA
                        organism = synthetic construct
modified_base           order(1..5,9..11,14,15,18,20,24,26,28,29,34,36..40,42)
                        mod_base = OTHER
                        note = 2-Prime-methoxyribose nucleotides
modified_base           order(7,8,12,13,16,17,19,21..23,25,27,30,35)
                        mod_base = OTHER
                        note = 2-Prime-deoxy-2-Prime-fluororibose nucleotides
modified_base           order(6,33)
                        mod_base = OTHER
                        note = Deoxyribose
modified_base           order(31,41)
                        mod_base = OTHER
                        note = Deoxyribose Thymidine
modified_base           32
                        mod_base = OTHER
                        note = Beta-homoDNA
modified_base           33
                        mod_base = i
modified_base           order(1..4,6..8,11..13,16,18..19,21..22,24..25,27,30..33,35,38..41)
                        mod_base = OTHER
                        note = Phosphorothioate internucleoside linkage
modified_base           order(5,9..10,14..15,17,20,23,26,28..29,34,36..37)
                        mod_base = OTHER
                        note = Phosphate internucleoside linkage
SEQUENCE: 278
aacatggccc cagcagcttc agtccctttc tcntcgatgg tc                    42

SEQ ID NO: 279          moltype = RNA  length = 42
FEATURE                 Location/Qualifiers
source                  1..42
                        mol_type = other RNA
                        organism = synthetic construct
modified_base           order(1..11,20,22,24,34,36..42)
                        mod_base = OTHER
                        note = 2-Prime-methoxyribose nucleotides
modified_base           order(12,13,16,17,19,21,23,25..27,30,35)
                        mod_base = OTHER
                        note = 2-Prime-deoxy-2-Prime-fluororibose nucleotides
modified_base           order(14,15,18,28,29)
                        mod_base = OTHER
                        note = 2-Prime-MOEribose nucleotides
modified_base           order(18,28,29)
                        mod_base = OTHER
                        note = Thymidine
modified_base           14
                        mod_base = m5c
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = Deoxyribose
modified_base           33
                        mod_base = i
modified_base           order(1,19,22,33,41)
                        mod_base = OTHER
```

```
                        note = Mesyl phosphroamidate internucleoside linkage
modified_base           order(2..3,11..13,16..17,21,24..27,30..32,35,39..40)
                        mod_base = OTHER
                        note = Phosphorothioate internucleoside linkage
modified_base           order(4..10,14..15,18,20,23,28..29,34,36..38)
                        mod_base = OTHER
                        note = Phosphate internucleoside linkage
SEQUENCE: 279
aacatggccc cagnagcttc agtccctttc tcntcgatgg tc                     42

SEQ ID NO: 280          moltype = RNA  length = 42
FEATURE                 Location/Qualifiers
source                  1..42
                        mol_type = other RNA
                        organism = synthetic construct
modified_base           order(1..3,5,7..11,20,22,24,34,36..39,42)
                        mod_base = OTHER
                        note = 2-Prime-methoxyribose nucleotides
modified_base           order(4,6,12,13,16,17,19,21,23,25..27,30,35,40,41)
                        mod_base = OTHER
                        note = 2-Prime-deoxy-2-Prime-fluororibose nucleotides
modified_base           order(14,15,18,28,29)
                        mod_base = OTHER
                        note = 2-Prime-MOEribose nucleotides
modified_base           order(18,28,29)
                        mod_base = OTHER
                        note = Thymidine
modified_base           14
                        mod_base = m5c
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = Deoxyribose
modified_base           33
                        mod_base = i
modified_base           order(1,19,22,33,41)
                        mod_base = OTHER
                        note = Mesyl phosphroamidate internucleoside linkage
modified_base           order(2..4,6,11..13,16..17,21,24..27,30..32,35,39..40)
                        mod_base = OTHER
                        note = Phosphorothioate internucleoside linkage
modified_base           order(5,7..10,14..15,18,20,23,28..29,34,36..38)
                        mod_base = OTHER
                        note = Phosphate internucleoside linkage
SEQUENCE: 280
aacatggccc cagnagcttc agtccctttc tcntcgatgg tc                     42

SEQ ID NO: 281          moltype = RNA  length = 42
FEATURE                 Location/Qualifiers
source                  1..42
                        mol_type = other RNA
                        organism = synthetic construct
modified_base           order(1..5,9..11,20,22,24,34,36..40,42)
                        mod_base = OTHER
                        note = 2-Prime-methoxyribose nucleotides
modified_base           order(7,8,12,13,16,17,19,21,23,25..27,30,35)
                        mod_base = OTHER
                        note = 2-Prime-deoxy-2-Prime-fluororibose nucleotides
modified_base           order(6,33)
                        mod_base = OTHER
                        note = Deoxyribose
modified_base           order(14,15,18,28,29)
                        mod_base = OTHER
                        note = 2-Prime-MOEribose nucleotides
modified_base           order(18,28,29)
                        mod_base = OTHER
                        note = Thymidine
modified_base           14
                        mod_base = m5c
modified_base           order(31,41)
                        mod_base = OTHER
                        note = Deoxyribose Thymidine
modified_base           32
                        mod_base = OTHER
```

```
                        note = Beta-homoDNA
modified_base           33
                        mod_base = i
modified_base           order(1,19,22,33,41)
                        mod_base = OTHER
                        note = Mesyl phosphroamidate internucleoside linkage
modified_base           order(2..4,6..8,11..13,16..17,21,24..27,30..32,35,38..40)
                        mod_base = OTHER
                        note = Phosphorothioate internucleoside linkage
modified_base           order(5,9..10,14..15,18,20,23,28..29,34,36..37)
                        mod_base = OTHER
                        note = Phosphate internucleoside linkage
SEQUENCE: 281
aacatggccc cagnagcttc agtccctttc tcntcgatgg tc                    42

SEQ ID NO: 282          moltype = RNA  length = 42
FEATURE                 Location/Qualifiers
source                  1..42
                        mol_type = other RNA
                        organism = synthetic construct
modified_base           order(1..11,20,22,24,34,36..42)
                        mod_base = OTHER
                        note = 2-Prime-methoxyribose nucleotides
modified_base           order(12,13,16,17,19,21,23,25..27,30,35)
                        mod_base = OTHER
                        note = 2-Prime-deoxy-2-Prime-fluororibose nucleotides
modified_base           order(14,15,18,28,29)
                        mod_base = OTHER
                        note = 2-Prime-MOEribose nucleotides
modified_base           order(18,28,29)
                        mod_base = OTHER
                        note = Thymidine
modified_base           14
                        mod_base = m5c
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = Deoxyribose
modified_base           33
                        mod_base = i
modified_base           order(1..3,11..13,16..17,19,21..22,24..27,30..33,35,39..41)
                        mod_base = OTHER
                        note = Phosphorothioate internucleoside linkage
modified_base           order(4..10,14..15,18,20,23,28..29,34,36..38)
                        mod_base = OTHER
                        note = Phosphate internucleoside linkage
SEQUENCE: 282
aacatggccc cagnagcttc agtccctttc tcntcgatgg tc                    42

SEQ ID NO: 283          moltype = RNA  length = 42
FEATURE                 Location/Qualifiers
source                  1..42
                        mol_type = other RNA
                        organism = synthetic construct
modified_base           order(1..3,5,7..11,20,22,24,34,36..39,42)
                        mod_base = OTHER
                        note = 2-Prime-methoxyribose nucleotides
modified_base           order(4,6,12,13,16,17,19,21,23,25..27,30,35,40,41)
                        mod_base = OTHER
                        note = 2-Prime-deoxy-2-Prime-fluororibose nucleotides
modified_base           order(14,15,18,28,29)
                        mod_base = OTHER
                        note = 2-Prime-MOEribose nucleotides
modified_base           14
                        mod_base = m5c
modified_base           order(18,28,29)
                        mod_base = OTHER
                        note = Thymidine
modified_base           31
                        mod_base = OTHER
                        note = Deoxyribose Thymidine
modified_base           32
                        mod_base = OTHER
                        note = Beta-homoDNA
```

```
modified_base          33
                       mod_base = OTHER
                       note = Deoxyribose
modified_base          33
                       mod_base = i
modified_base          order(1..4,6,11..13,16..17,19,21..22,24..27,30..33,35,39..41)
                       mod_base = OTHER
                       note = Phosphorothioate internucleoside linkage
modified_base          order(5,7..10,14..15,18,20,23,28..29,34,36..38)
                       mod_base = OTHER
                       note = Phosphate internucleoside linkage
SEQUENCE: 283
aacatggccc cagnagcttc agtccctttc tcntcgatgg tc                    42

SEQ ID NO: 284         moltype = RNA  length = 42
FEATURE                Location/Qualifiers
source                 1..42
                       mol_type = other RNA
                       organism = synthetic construct
modified_base          order(1..5,9..11,20,22,24,34,36..40,42)
                       mod_base = OTHER
                       note = 2-Prime-methoxyribose nucleotides
modified_base          order(7,8,12,13,16,17,19,21,23,25..27,30,35)
                       mod_base = OTHER
                       note = 2-Prime-deoxy-2-Prime-fluororibose nucleotides
modified_base          order(14,15,18,28,29)
                       mod_base = OTHER
                       note = 2-Prime-MOEribose nucleotides
modified_base          order(18,28,29)
                       mod_base = OTHER
                       note = Thymidine
modified_base          order(6,33)
                       mod_base = OTHER
                       note = Deoxyribose
modified_base          order(31,41)
                       mod_base = OTHER
                       note = Deoxyribose Thymidine
modified_base          32
                       mod_base = OTHER
                       note = Beta-homoDNA
modified_base          33
                       mod_base = i
modified_base          14
                       mod_base = m5c
modified_base          order(1..4,6..8,11..13,16..17,19,21..22,24..27,30..33,35,38..41)
                       mod_base = OTHER
                       note = Phosphorothioate internucleoside linkage
modified_base          order(5,9..10,14..15,18,20,23,28..29,34,36..37)
                       mod_base = OTHER
                       note = Phosphate internucleoside linkage
SEQUENCE: 284
aacatggccc cagnagcttc agtccctttc tcntcgatgg tc                    42

SEQ ID NO: 285         moltype = RNA  length = 30
FEATURE                Location/Qualifiers
source                 1..30
                       mol_type = other RNA
                       organism = synthetic construct
modified_base          order(1..4,6,7,10..14,16,18,20,22,26,28..30)
                       mod_base = OTHER
                       note = 2-Prime-methoxyribose nucleotides
modified_base          order(5,8,9,15,17,19,21,27)
                       mod_base = OTHER
                       note = 2-Prime-deoxy-2-Prime-fluororibose nucleotides
modified_base          23
                       mod_base = OTHER
                       note = Deoxyribose Thymidine
modified_base          24
                       mod_base = OTHER
                       note = Beta-homoDNA
modified_base          25
                       mod_base = OTHER
                       note = Deoxyribose
modified_base          25
                       mod_base = i
modified_base          order(1,13,15,25,29)
                       mod_base = OTHER
                       note = Mesyl phosphroamidate internucleoside linkage
modified_base          order(2..3,5,8..9,17,19,21,23..24,27..28)
```

-continued

```
                        mod_base = OTHER
                        note = Phosphorothioate internucleoside linkage
modified_base           order(4,6..7,10..12,14,16,18,20,22,26)
                        mod_base = OTHER
                        note = Phosphate internucleoside linkage
SEQUENCE: 285
cccagcagct tcagttcctt tctcntcgat                                    30

SEQ ID NO: 286          moltype = RNA  length = 30
FEATURE                 Location/Qualifiers
source                  1..30
                        mol_type = other RNA
                        organism = synthetic construct
modified_base           order(1..4,6,7,10..14,16,18,20,22,26,28..30)
                        mod_base = OTHER
                        note = 2-Prime-methoxyribose nucleotides
modified_base           order(5,8,9,15,17,19,21,27)
                        mod_base = OTHER
                        note = 2-Prime-deoxy-2-Prime-fluororibose nucleotides
modified_base           25
                        mod_base = OTHER
                        note = Deoxyribose
modified_base           24
                        mod_base = OTHER
                        note = Beta-homoDNA
modified_base           23
                        mod_base = OTHER
                        note = Deoxyribose Thymidine
modified_base           25
                        mod_base = i
modified_base           order(1,3,8,15,25,29)
                        mod_base = OTHER
                        note = Mesyl phosphroamidate internucleoside linkage
modified_base           order(2,5,9,17,19,21,23..24,27..28)
                        mod_base = OTHER
                        note = Phosphorothioate internucleoside linkage
modified_base           order(4,6..7,10..14,16,18,20,22,26)
                        mod_base = OTHER
                        note = Phosphate internucleoside linkage
SEQUENCE: 286
cccagcagct tcagttcctt tctcntcgat                                    30

SEQ ID NO: 287          moltype = RNA  length = 30
FEATURE                 Location/Qualifiers
source                  1..30
                        mol_type = other RNA
                        organism = synthetic construct
modified_base           order(1..4,6,7,10..14,16,18,20,22,26,28..30)
                        mod_base = OTHER
                        note = 2-Prime-methoxyribose nucleotides
modified_base           order(5,8,9,15,17,19,21,27)
                        mod_base = OTHER
                        note = 2-Prime-deoxy-2-Prime-fluororibose nucleotides
modified_base           25
                        mod_base = OTHER
                        note = Deoxyribose
modified_base           25
                        mod_base = i
modified_base           24
                        mod_base = OTHER
                        note = Beta-homoDNA
modified_base           23
                        mod_base = OTHER
                        note = Deoxyribose Thymidine
modified_base           order(1,5,8,15,25,29)
                        mod_base = OTHER
                        note = Mesyl phosphroamidate internucleoside linkage
modified_base           order(2..3,9,17,19,21,23..24,27..28)
                        mod_base = OTHER
                        note = Phosphorothioate internucleoside linkage
modified_base           order(4,6..7,10..14,16,18,20,22,26)
                        mod_base = OTHER
                        note = Phosphate internucleoside linkage
SEQUENCE: 287
cccagcagct tcagttcctt tctcntcgat                                    30

SEQ ID NO: 288          moltype = RNA  length = 30
FEATURE                 Location/Qualifiers
source                  1..30
```

```
                         mol_type = other RNA
                         organism = synthetic construct
modified_base            order(1..4,6,7,10..14,16,18,20,22,26,28..30)
                         mod_base = OTHER
                         note = 2-Prime-methoxyribose nucleotides
modified_base            order(5,8,9,15,17,19,21,27)
                         mod_base = OTHER
                         note = 2-Prime-deoxy-2-Prime-fluororibose nucleotides
modified_base            25
                         mod_base = OTHER
                         note = Deoxyribose
modified_base            25
                         mod_base = i
modified_base            24
                         mod_base = OTHER
                         note = Beta-homoDNA
modified_base            23
                         mod_base = OTHER
                         note = Deoxyribose Thymidine
modified_base            order(1,5,8,15,25,29)
                         mod_base = OTHER
                         note = Mesyl phosphroamidate internucleoside linkage
modified_base            order(2,9,17,19,21,23..24,27..28)
                         mod_base = OTHER
                         note = Phosphorothioate internucleoside linkage
modified_base            order(3..4,6..7,10..14,16,18,20,22,26)
                         mod_base = OTHER
                         note = Phosphate internucleoside linkage
SEQUENCE: 288
cccagcagct tcagttcctt tctcntcgat                                   30

SEQ ID NO: 289           moltype = RNA  length = 30
FEATURE                  Location/Qualifiers
source                   1..30
                         mol_type = other RNA
                         organism = synthetic construct
modified_base            order(1..4,6,7,10..14,16,18,20,22,26,28..30)
                         mod_base = OTHER
                         note = 2-Prime-methoxyribose nucleotides
modified_base            order(5,8,9,15,17,19,21,27)
                         mod_base = OTHER
                         note = 2-Prime-deoxy-2-Prime-fluororibose nucleotides
modified_base            25
                         mod_base = OTHER
                         note = Deoxyribose
modified_base            25
                         mod_base = i
modified_base            24
                         mod_base = OTHER
                         note = Beta-homoDNA
modified_base            23
                         mod_base = OTHER
                         note = Deoxyribose Thymidine
modified_base            order(1,3,5,8,15,25,29)
                         mod_base = OTHER
                         note = Mesyl phosphroamidate internucleoside linkage
modified_base            order(2,9,17,19,21,23..24,27..28)
                         mod_base = OTHER
                         note = Phosphorothioate internucleoside linkage
modified_base            order(4,6..7,10..14,16,18,20,22,26)
                         mod_base = OTHER
                         note = Phosphate internucleoside linkage
SEQUENCE: 289
cccagcagct tcagttcctt tctcntcgat                                   30

SEQ ID NO: 290           moltype = RNA  length = 30
FEATURE                  Location/Qualifiers
source                   1..30
                         mol_type = other RNA
                         organism = synthetic construct
modified_base            order(1..4,6,7,10..14,16,18,20,22,26,28..30)
                         mod_base = OTHER
                         note = 2-Prime-methoxyribose nucleotides
modified_base            order(5,8,9,15,17,19,21,27)
                         mod_base = OTHER
                         note = 2-Prime-deoxy-2-Prime-fluororibose nucleotides
modified_base            25
                         mod_base = OTHER
                         note = Deoxyribose
```

```
modified_base          25
                       mod_base = i
modified_base          24
                       mod_base = OTHER
                       note = Beta-homoDNA
modified_base          23
                       mod_base = OTHER
                       note = Deoxyribose Thymidine
modified_base          order(1,3,5,8,15,19,25,29)
                       mod_base = OTHER
                       note = Mesyl phosphroamidate internucleoside linkage
modified_base          order(2,9,17,21,23..24,27..28)
                       mod_base = OTHER
                       note = Phosphorothioate internucleoside linkage
modified_base          order(4,6..7,10..14,16,18,20,22,26)
                       mod_base = OTHER
                       note = Phosphate internucleoside linkage
SEQUENCE: 290
cccagcagct tcagttcctt tctcntcgat                                   30

SEQ ID NO: 291         moltype = RNA  length = 30
FEATURE                Location/Qualifiers
source                 1..30
                       mol_type = other RNA
                       organism = synthetic construct
modified_base          order(1..4,6,7,10..14,16,18,20,22,26,28..30)
                       mod_base = OTHER
                       note = 2-Prime-methoxyribose nucleotides
modified_base          order(5,8,9,15,17,19,21,27)
                       mod_base = OTHER
                       note = 2-Prime-deoxy-2-Prime-fluororibose nucleotides
modified_base          25
                       mod_base = OTHER
                       note = Deoxyribose
modified_base          25
                       mod_base = i
modified_base          24
                       mod_base = OTHER
                       note = Beta-homoDNA
modified_base          23
                       mod_base = OTHER
                       note = Deoxyribose Thymidine
modified_base          order(1,29)
                       mod_base = OTHER
                       note = Mesyl phosphroamidate internucleoside linkage
modified_base          order(2..3,5,8..9,15..17,19,21,23..28)
                       mod_base = OTHER
                       note = Phosphorothioate internucleoside linkage
modified_base          order(4,6..7,10..14,18,20,22)
                       mod_base = OTHER
                       note = Phosphate internucleoside linkage
SEQUENCE: 291
cccagcagct tcagttcctt tctcntcgat                                   30

SEQ ID NO: 292         moltype = RNA  length = 30
FEATURE                Location/Qualifiers
source                 1..30
                       mol_type = other RNA
                       organism = synthetic construct
modified_base          order(1..4,6,7,10..14,16,18,20,22,26,28..30)
                       mod_base = OTHER
                       note = 2-Prime-methoxyribose nucleotides
modified_base          order(5,8,9,15,17,19,21,27)
                       mod_base = OTHER
                       note = 2-Prime-deoxy-2-Prime-fluororibose nucleotides
modified_base          25
                       mod_base = OTHER
                       note = Deoxyribose
modified_base          25
                       mod_base = i
modified_base          24
                       mod_base = OTHER
                       note = Beta-homoDNA
modified_base          23
                       mod_base = OTHER
                       note = Deoxyribose Thymidine
modified_base          order(1,3,5,7,29)
                       mod_base = OTHER
                       note = Mesyl phosphroamidate internucleoside linkage
```

```
modified_base          order(2,8..9,15..17,19,21,23..28)
                       mod_base = OTHER
                       note = Phosphorothioate internucleoside linkage
modified_base          order(4,6,10..14,18,20,22)
                       mod_base = OTHER
                       note = Phosphate internucleoside linkage
SEQUENCE: 292
cccagcagct tcagttcctt tctcntcgat                                  30

SEQ ID NO: 293         moltype = RNA  length = 30
FEATURE                Location/Qualifiers
source                 1..30
                       mol_type = other RNA
                       organism = synthetic construct
modified_base          order(1..4,6,7,10..14,16,18,20,22,26,28..30)
                       mod_base = OTHER
                       note = 2-Prime-methoxyribose nucleotides
modified_base          order(5,8,9,15,17,19,21,27)
                       mod_base = OTHER
                       note = 2-Prime-deoxy-2-Prime-fluororibose nucleotides
modified_base          25
                       mod_base = OTHER
                       note = Deoxyribose
modified_base          25
                       mod_base = i
modified_base          24
                       mod_base = OTHER
                       note = Beta-homoDNA
modified_base          23
                       mod_base = OTHER
                       note = Deoxyribose Thymidine
modified_base          order(1,7,9,11,29)
                       mod_base = OTHER
                       note = Mesyl phosphroamidate internucleoside linkage
modified_base          order(2..3,5,8,15..17,19,21,23..28)
                       mod_base = OTHER
                       note = Phosphorothioate internucleoside linkage
modified_base          order(4,6,10,12..14,18,20,22)
                       mod_base = OTHER
                       note = Phosphate internucleoside linkage
SEQUENCE: 293
cccagcagct tcagttcctt tctcntcgat                                  30

SEQ ID NO: 294         moltype = RNA  length = 30
FEATURE                Location/Qualifiers
source                 1..30
                       mol_type = other RNA
                       organism = synthetic construct
modified_base          order(1..4,6,7,10..14,16,18,20,22,26,28..30)
                       mod_base = OTHER
                       note = 2-Prime-methoxyribose nucleotides
modified_base          order(5,8,9,15,17,19,21,27)
                       mod_base = OTHER
                       note = 2-Prime-deoxy-2-Prime-fluororibose nucleotides
modified_base          25
                       mod_base = OTHER
                       note = Deoxyribose
modified_base          25
                       mod_base = i
modified_base          24
                       mod_base = OTHER
                       note = Beta-homoDNA
modified_base          23
                       mod_base = OTHER
                       note = Deoxyribose Thymidine
modified_base          order(1,11,13,15,29)
                       mod_base = OTHER
                       note = Mesyl phosphroamidate internucleoside linkage
modified_base          order(2..3,5,8..9,16..17,19,21,23..28)
                       mod_base = OTHER
                       note = Phosphorothioate internucleoside linkage
modified_base          order(4,6..7,10,12,14,18,20,22)
                       mod_base = OTHER
                       note = Phosphate internucleoside linkage
SEQUENCE: 294
cccagcagct tcagttcctt tctcntcgat                                  30

SEQ ID NO: 295         moltype = RNA  length = 30
FEATURE                Location/Qualifiers
```

```
source                  1..30
                        mol_type = other RNA
                        organism = synthetic construct
modified_base           order(5,8,9,15,17,19,21,27)
                        mod_base = OTHER
                        note = 2-Prime-deoxy-2-Prime-fluororibose nucleotides
modified_base           order(1..4,6,7,10..14,16,18,20,22,26,28..30)
                        mod_base = OTHER
                        note = 2-Prime-methoxyribose nucleotides
modified_base           25
                        mod_base = OTHER
                        note = Deoxyribose
modified_base           25
                        mod_base = i
modified_base           24
                        mod_base = OTHER
                        note = Beta-homoDNA
modified_base           23
                        mod_base = OTHER
                        note = Deoxyribose Thymidine
modified_base           order(1,15,17,19,29)
                        mod_base = OTHER
                        note = Mesyl phosphroamidate internucleoside linkage
modified_base           order(2..3,5,8..9,16,21,23..28)
                        mod_base = OTHER
                        note = Phosphorothioate internucleoside linkage
modified_base           order(4,6..7,10..14,18,20,22)
                        mod_base = OTHER
                        note = Phosphate internucleoside linkage
SEQUENCE: 295
cccagcagct tcagttcctt tctcntcgat                                   30

SEQ ID NO: 296          moltype = RNA  length = 30
FEATURE                 Location/Qualifiers
source                  1..30
                        mol_type = other RNA
                        organism = synthetic construct
modified_base           order(1..4,6,7,10..14,16,18,20,22,26,28..30)
                        mod_base = OTHER
                        note = 2-Prime-methoxyribose nucleotides
modified_base           order(5,8,9,15,17,19,21,27)
                        mod_base = OTHER
                        note = 2-Prime-deoxy-2-Prime-fluororibose nucleotides
modified_base           25
                        mod_base = OTHER
                        note = Deoxyribose
modified_base           25
                        mod_base = i
modified_base           24
                        mod_base = OTHER
                        note = Beta-homoDNA
modified_base           23
                        mod_base = OTHER
                        note = Deoxyribose Thymidine
modified_base           order(1,19,21,25,29)
                        mod_base = OTHER
                        note = Mesyl phosphroamidate internucleoside linkage
modified_base           order(2..3,5,8..9,15..17,23..24,26..28)
                        mod_base = OTHER
                        note = Phosphorothioate internucleoside linkage
modified_base           order(4,6..7,10..14,18,20,22)
                        mod_base = OTHER
                        note = Phosphate internucleoside linkage
SEQUENCE: 296
cccagcagct tcagttcctt tctcntcgat                                   30

SEQ ID NO: 297          moltype = RNA  length = 30
FEATURE                 Location/Qualifiers
source                  1..30
                        mol_type = other RNA
                        organism = synthetic construct
modified_base           order(1..4,6,7,10..14,16,18,20,22,26,28..30)
                        mod_base = OTHER
                        note = 2-Prime-methoxyribose nucleotides
modified_base           order(5,8,9,15,17,19,21,27)
                        mod_base = OTHER
                        note = 2-Prime-deoxy-2-Prime-fluororibose nucleotides
modified_base           25
                        mod_base = OTHER
```

```
                        note = Deoxyribose
modified_base           25
                        mod_base = i
modified_base           24
                        mod_base = OTHER
                        note = Beta-homoDNA
modified_base           23
                        mod_base = OTHER
                        note = Deoxyribose Thymidine
modified_base           order(1,5,7,9,29)
                        mod_base = OTHER
                        note = Mesyl phosphroamidate internucleoside linkage
modified_base           order(2..3,8,15..17,19,21,23..28)
                        mod_base = OTHER
                        note = Phosphorothioate internucleoside linkage
modified_base           order(4,6,10..14,18,20,22)
                        mod_base = OTHER
                        note = Phosphate internucleoside linkage
SEQUENCE: 297
cccagcagct tcagttcctt tctcntcgat                                   30

SEQ ID NO: 298          moltype = RNA  length = 30
FEATURE                 Location/Qualifiers
source                  1..30
                        mol_type = other RNA
                        organism = synthetic construct
modified_base           order(1..3,6,7,10..14,16,18,20,22,26,28..30)
                        mod_base = OTHER
                        note = 2-Prime-methoxyribose nucleotides
modified_base           order(4,5,8,9,15,17,19,21,27)
                        mod_base = OTHER
                        note = 2-Prime-deoxy-2-Prime-fluororibose nucleotides
modified_base           23
                        mod_base = OTHER
                        note = Deoxyribose Thymidine
modified_base           24
                        mod_base = OTHER
                        note = Beta-homoDNA
modified_base           25
                        mod_base = OTHER
                        note = Deoxyribose
modified_base           25
                        mod_base = i
modified_base           order(1,3,8,15,25,29)
                        mod_base = OTHER
                        note = Mesyl phosphroamidate internucleoside linkage
modified_base           order(2,4..5,9,17,19,21,23..24,27..28)
                        mod_base = OTHER
                        note = Phosphorothioate internucleoside linkage
modified_base           order(6..7,10..14,16,18,20,22,26)
                        mod_base = OTHER
                        note = Phosphate internucleoside linkage
SEQUENCE: 298
cccagcagct tcagttcctt tctcntcgat                                   30

SEQ ID NO: 299          moltype = RNA  length = 30
FEATURE                 Location/Qualifiers
source                  1..30
                        mol_type = other RNA
                        organism = synthetic construct
modified_base           order(1..3,5..7,10..14,16,18,20,22,26,28..30)
                        mod_base = OTHER
                        note = 2-Prime-methoxyribose nucleotides
modified_base           order(4,8,9,15,17,19,21,27)
                        mod_base = OTHER
                        note = 2-Prime-deoxy-2-Prime-fluororibose nucleotides
modified_base           23
                        mod_base = OTHER
                        note = Deoxyribose Thymidine
modified_base           24
                        mod_base = OTHER
                        note = Beta-homoDNA
modified_base           25
                        mod_base = OTHER
                        note = Deoxyribose
modified_base           25
                        mod_base = i
modified_base           order(1,3,8,15,25,29)
                        mod_base = OTHER
```

```
                        note = Mesyl phosphroamidate internucleoside linkage
modified_base           order(2,4,9,17,19,21,23..24,27..28)
                        mod_base = OTHER
                        note = Phosphorothioate internucleoside linkage
modified_base           order(5..7,10..14,16,18,20,22,26)
                        mod_base = OTHER
                        note = Phosphate internucleoside linkage
SEQUENCE: 299
cccagcagct tcagttcctt tctcntcgat                                   30

SEQ ID NO: 300          moltype = RNA  length = 30
FEATURE                 Location/Qualifiers
source                  1..30
                        mol_type = other RNA
                        organism = synthetic construct
modified_base           order(1..4,6,7,10..14,16,18,20,22,26,28..30)
                        mod_base = OTHER
                        note = 2-Prime-methoxyribose nucleotides
modified_base           order(5,8,9,15,17,19,21,27)
                        mod_base = OTHER
                        note = 2-Prime-deoxy-2-Prime-fluororibose nucleotides
modified_base           25
                        mod_base = OTHER
                        note = Deoxyribose
modified_base           25
                        mod_base = i
modified_base           24
                        mod_base = OTHER
                        note = Beta-homoDNA
modified_base           23
                        mod_base = OTHER
                        note = Deoxyribose Thymidine
modified_base           order(1,13,15,24..25,29)
                        mod_base = OTHER
                        note = Mesyl phosphroamidate internucleoside linkage
modified_base           order(2..3,5,8..9,16..17,19,21,23,26..28)
                        mod_base = OTHER
                        note = Phosphorothioate internucleoside linkage
modified_base           order(4,6..7,10..12,14,18,20,22)
                        mod_base = OTHER
                        note = Phosphate internucleoside linkage
SEQUENCE: 300
cccagcagct tcagttcctt tctcntcgat                                   30

SEQ ID NO: 301          moltype = RNA  length = 30
FEATURE                 Location/Qualifiers
source                  1..30
                        mol_type = other RNA
                        organism = synthetic construct
modified_base           order(1..4,6,7,10..14,16,18,20,22,26,28..30)
                        mod_base = OTHER
                        note = 2-Prime-methoxyribose nucleotides
modified_base           order(5,8,9,15,17,19,21,27)
                        mod_base = OTHER
                        note = 2-Prime-deoxy-2-Prime-fluororibose nucleotides
modified_base           23
                        mod_base = OTHER
                        note = Deoxyribose Thymidine
modified_base           24
                        mod_base = OTHER
                        note = Beta-homoDNA
modified_base           25
                        mod_base = OTHER
                        note = Deoxyribose
modified_base           25
                        mod_base = i
modified_base           order(1,3,13,15,24..25,29)
                        mod_base = OTHER
                        note = Mesyl phosphroamidate internucleoside linkage
modified_base           order(2,5,8..9,16..17,19,21,23,26..28)
                        mod_base = OTHER
                        note = Phosphorothioate internucleoside linkage
modified_base           order(4,6..7,10..12,14,18,20,22)
                        mod_base = OTHER
                        note = Phosphate internucleoside linkage
SEQUENCE: 301
cccagcagct tcagttcctt tctcntcgat                                   30

SEQ ID NO: 302          moltype = RNA  length = 42
```

```
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = OTHER
                        note = 2-Prime-fluroarabinose nucleotide
modified_base           33
                        mod_base = i
modified_base           order(1..10,12..13,15..16,18..19,22..27,29,31..35,38..41)
                        mod_base = OTHER
                        note = Phosphorothioate internucleoside linkage
modified_base           order(11,14,17,20..21,28,30,36..37)
                        mod_base = OTHER
                        note = Phosphate internucleoside linkage
SEQUENCE: 302
aacatggccc cagcagcttc agtccctttc tcntcgatgg tc                     42

SEQ ID NO: 303          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
                        mod_base = i
modified_base           33
                        mod_base = OTHER
                        note = 2-Prime-fluroarabinose nucleotide
modified_base           order(1..2,4..12,14..18,21..35,39..41)
                        mod_base = OTHER
                        note = Phosphorothioate internucleoside linkage
modified_base           order(3,13,19..20,36..38)
                        mod_base = OTHER
                        note = Phosphate internucleoside linkage
SEQUENCE: 303
aacatggccc cagcagcttc agtccctttc tcntcgatgg tc                     42

SEQ ID NO: 304          moltype = RNA  length = 42
FEATURE                 Location/Qualifiers
source                  1..42
                        mol_type = other RNA
                        organism = synthetic construct
modified_base           order(3,4,9,11,13,14,17,19..21,24,28,30,34,36..39,42)
                        mod_base = OTHER
                        note = 2-Prime-methoxyribose nucleotides
modified_base           order(1,2,5..8,10,12,15,16,18,22,23,25..27,29,35,40,41)
                        mod_base = OTHER
                        note = 2-Prime-deoxy-2-Prime-fluororibose nucleotides
modified_base           31
                        mod_base = OTHER
                        note = Deoxyribose Thymidine
modified_base           32
                        mod_base = OTHER
                        note = Beta-homoDNA
modified_base           33
```

```
                        mod_base = OTHER
                        note = 2-Prime-fluroarabinose nucleotides
modified_base           33
                        mod_base = i
modified_base           order(1,21,23,33,41)
                        mod_base = OTHER
                        note = Mesyl phosphroamidate internucleoside linkage
modified_base           order(2,4..12,14..18,22,24..32,34..35,39..40)
                        mod_base = OTHER
                        note = Phosphorothioate internucleoside linkage
modified_base           order(3,13,19..20,36..38)
                        mod_base = OTHER
                        note = Phosphate internucleoside linkage
SEQUENCE: 304
aacatggccc cagcagcttc agtccctttc tcntcgatgg tc                    42

SEQ ID NO: 305          moltype = DNA  length = 23
FEATURE                 Location/Qualifiers
source                  1..23
                        mol_type = other DNA
                        organism = synthetic construct
SEQUENCE: 305
cagggcatgg agatatctat gct                                         23

SEQ ID NO: 306          moltype = DNA  length = 23
FEATURE                 Location/Qualifiers
source                  1..23
                        mol_type = other DNA
                        organism = synthetic construct
SEQUENCE: 306
tcccaccctt aacatctgct cgt                                         23

SEQ ID NO: 307          moltype = DNA  length = 24
FEATURE                 Location/Qualifiers
source                  1..24
                        mol_type = other DNA
                        organism = synthetic construct
SEQUENCE: 307
cgaaaaggaa agacaagagc aact                                        24

SEQ ID NO: 308          moltype = DNA  length = 22
FEATURE                 Location/Qualifiers
source                  1..22
                        mol_type = other DNA
                        organism = synthetic construct
SEQUENCE: 308
tgtgggcaac ctgggagtag ct                                          22

SEQ ID NO: 309          moltype = RNA  length = 30
FEATURE                 Location/Qualifiers
source                  1..30
                        mol_type = other RNA
                        organism = synthetic construct
modified_base           order(1..4,6,7,10..14,16,18,20,22,26,28..30)
                        mod_base = OTHER
                        note = 2-Prime-methoxyribose nucleotides
modified_base           order(5,8,9,15,17,19,21,27)
                        mod_base = OTHER
                        note = 2-Prime-deoxy-2-Prime-fluororibose nucleotides
modified_base           23
                        mod_base = OTHER
                        note = Deoxyribose Thymidine
modified_base           24
                        mod_base = OTHER
                        note = Beta-homoDNA
modified_base           25
                        mod_base = OTHER
                        note = Deoxyribose
modified_base           25
                        mod_base = i
modified_base           order(1,13,15,25,29)
                        mod_base = OTHER
                        note = Mesyl phosphroamidate internucleoside linkage
modified_base           order(2..3,5,8..9,16..17,19,21,23..24,26..28)
                        mod_base = OTHER
                        note = Phosphorothioate internucleoside linkage
```

-continued

```
modified_base          order(4,6..7,10..12,14,18,20,22)
                       mod_base = OTHER
                       note = Phosphate internucleoside linkage
SEQUENCE: 309
cccagcagct tcagttcctt tctcntcgat                            30
```

RNA-EDITING OLIGONUCLEOTIDES AND USES THEREOF

INCORPORATION BY REFERENCE OF MATERIALS SUBMITTED ELECTRONICALLY

This application contains, as a separate part of the disclosure, a Sequence Listing in computer readable form (Filename: 50004_SubSeqListing.xml; Size: 1,596,294 bytes; Created: Sep. 5, 2024), which is incorporated by reference in its entirety.

BACKGROUND

Adenosine deaminases acting on RNA (ADAR) are enzymes which bind to double-stranded RNA (dsRNA) and convert adenosine to inosine through deamination. In RNA, inosine functions similarly to guanosine for translation and replication. Thus, conversion of adenosine to inosine in an mRNA can result in a codon change that may lead to changes to the encoded protein and its functions. There are three known ADAR proteins expressed in humans, ADAR1, ADAR2, and ADAR3. ADAR1 and ADAR2 are expressed throughout the body whereas ADAR3 is expressed only in the brain. ADAR1 and ADAR2 are catalytically active, while ADAR3 is thought to be inactive.

Synthetic single-stranded oligonucleotides have been shown capable of utilizing the ADAR proteins to edit target RNAs by deaminating particular adenosines in the target RNA. The oligonucleotides are complementary to the target RNA with the exception of at least one mismatch opposite the adenosine to be deaminated. However, the previously disclosed methods have not been shown to have the required selectivity and/or stability to allow for their use as therapies. Accordingly, new oligonucleotides capable of utilizing the ADAR proteins to selectively edit target RNAs in a therapeutically effective manner are needed.

SUMMARY

The disclosure provides oligonucleotides, compositions and methods to deaminate adenosine in target RNAs, e.g., an adenosine which may be deaminated to produce a therapeutic result, e.g., in a subject in need thereof. In some embodiments, the target RNA is a mRNA.

Adenosine deaminases that act on RNA (ADARs) are editing enzymes that recognize certain structural motifs of double-stranded RNA (dsRNA) and edit adenosine to inosine, resulting in recoding of amino acid codons that may lead to changes to the encoded protein and its function. The nucleobases surrounding the editing site, especially the one immediately 5' of the editing site and one immediately 3' to the editing site, which together with the editing site are termed the triplet, play an important role in the deamination of adenosine. A preference for U at the 5' position and G at the 3' position relative to the editing site, was revealed from the analysis of yeast RNAs efficiently edited by overexpressed human ADAR2 and ADAR1. See Wang et al., (2018) Biochemistry, 57: 1640-1651, Eifler et al., (2013) Biochemistry, 52: 7857-7869, and Eggington et al., (2011) Nat. Commun., 319: 1-9. Recruiting ADAR to specific sites of selected transcripts and deamination of adenosine regardless of neighboring bases holds great promise for the treatment of disease. Based on structural and modeling studies of the editing site of dsRNA/ADAR complexes, several structural features that could be incorporated into guide oligonucleotides have been identified, whose properties could increase the recruitment of ADAR and increase the efficiency of editing of target RNA. Novel oligonucleotides with chemical modifications such as α-homo-DNA capable of recruiting ADAR proteins and deaminating adenosine with different surrounding base compositions in target RNA are shown. In addition, structure-activity relationship (SAR) studies revealed that a 2'-O-methyl (2'-OMe) modification of the ribose of some, but not all, nucleosides in the guide oligonucleotide, in addition to triplet modifications, are compatible with efficient ADAR engagement and editing.

In one aspect, described herein is an oligonucleotide comprising the structure:

$$[A_m]—X^1—X^2—X^3—[B_n]$$

wherein m+n is 24 to 50, n is at least 4, and m is at least 20;

$-X^1-X^2-X^3-$ is a Central Triplet of the oligonucleotide;

$X^1$ is position −1 of the oligonucleotide, $X^2$ is position 0 of the oligonucleotide, and $X^3$ is position +1 of the oligonucleotide;

$[A]_m$ is a first domain at positions −(m+1) to −2 of the oligonucleotide;

$[B]_n$ is a second domain at positions +2 to +(n+1) of the oligonucleotide;

each A and B is a nucleotide comprising a nucleobase, a sugar ("an A/B sugar"), and an internucleotide linkage;

each $X^1$, $X^2$, and $X^3$ comprises a nucleobase, a sugar ("an X sugar"), and an internucleotide linkage;

the A/B sugars and the $X^3$ sugar are selected from 2'-methoxy-ribose, 2'-MOE-ribose, 2'-deoxy-2'-fluororibose, 2'-fluoro-arabinose, 2-methoxy-arabinose, 2'deoxyribose and a locked nucleic acid (LNA);

the $X^1$ sugar is 2'-deoxy-2'-fluororibose or 2'deoxyribose;

the $X^2$ sugar is selected from 2'-methoxy-ribose, 2'-MOE-ribose, 2'-deoxy-2'-fluororibose, 2'-fluoro-arabinose, 2-methoxy-arabinose, 2'deoxyribose, a locked nucleic acid (LNA), and a beta-homo-DNA sugar;

the A/B sugars and the X sugars, collectively, are 10-70% 2'-deoxy-2'-fluoro-ribose;

the internucleotide linkages of the oligonucleotide are 30-100% phosphorothioate and phosphoramidate linkages, and 3 to 20 internucleotide linkages are phosphoramidate linkages;

the internucleotide linkage (i) between the nucleotide at position −(m+1) and the nucleotide at position −(m) (the 5'end), (ii) between the nucleotide at position +(n) and the nucleotide at position +(n+1) (the 3'-end), or (iii) at each the 5'-end and 3'-end of the oligonucleotide is a phosphoramidate linkage; and the internucleotide linkage between the nucleotide at position −(m) and the nucleotide at position −(m−1) and the internucleotide linkage between the nucleotide at position +(n−1) and the nucleotide at position +(n) are independently a phosphorothioate or a phosphoramidate linkage.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Definitions

For convenience, the meaning of some terms and phrases used in the specification, examples, and appended claims are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

In this application, unless otherwise clear from context, (i) the term "a" may be understood to mean "at least one"; (ii) the term "or" may be understood to mean "and/or"; and (iii) the terms "including" and "comprising" may be understood to encompass itemized components or steps whether presented by themselves or together with one or more additional components or steps.

As used herein, the terms "about" and "approximately" refer to a value that is within 10% above or below the value being described. For example, the term "about 5 nM" indicates a range of from 4.5 to 5.5 nM.

The term "at least" prior to a number or series of numbers is understood to include the number adjacent to the term "at least", and all subsequent numbers or integers that could logically be included, as clear from context. For example, the number of nucleotides in a nucleic acid molecule must be an integer. For example, "at least 18 nucleotides of a 21-nucleotide nucleic acid molecule" means that 18, 19, 20, or 21 nucleotides have the indicated property. When at least is present before a series of numbers or a range, it is understood that "at least" can modify each of the numbers in the series or range.

As used herein, "no more than" or "less than" is understood as the value adjacent to the phrase and logical lower values or integers, as logical from context, to zero. For example, an oligonucleotide with "no more than 5 unmodified nucleotides" has 5, 4, 3, 2, 1, or 0 unmodified nucleotides. When "no more than" is present before a series of numbers or a range, it is understood that "no more than" can modify each of the numbers in the series or range.

As used herein, the term "administration" refers to the administration of a composition (e.g., a compound or a preparation that includes a compound as described herein) to a subject or system. Administration to an animal subject (e.g., to a human) may be by any appropriate route, such as the one described herein.

The term "oligonucleotide" as used herein, is a molecule including two or more nucleotides. The term "nucleotide" refers to a nucleobase, a sugar moiety, and an internucleotide linkage. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide described herein may be man-made, and is chemically synthesized, and is typically purified or isolated. Oligonucleotide is also intended to include (i) compounds that have one or more furanose moieties that are replaced by furanose derivatives or by any structure, cyclic or acyclic, that may be used as a point of covalent attachment for the base moiety, (ii) compounds that have one or more phosphodiester linkages that are either modified, as in the case of phosphoramidate or phosphorothioate linkages, or completely replaced by a suitable linking moiety as in the case of formacetal or riboacetal linkages, and/or (iii) compounds that have one or more linked sugar-phosphodiester linkage moieties replaced by any structure, cyclic or acyclic, that may be used as a point of covalent attachment for the nucleobase moiety. The oligonucleotide described herein may include one or more alternative nucleotides (e.g., including those described herein). It is also understood that oligonucleotide includes compositions lacking a sugar moiety or nucleobase but is still capable of forming a pairing with or hybridizing to a target sequence. Oligonucleotides as used herein comprise 100 or fewer nucleotides.

The terms "nucleobase" and "base" include the purine (e.g., adenine and guanine) and pyrimidine (e.g. uracil, thymine, and cytosine) moiety present in nucleosides and nucleotides that form hydrogen bonds in nucleic acid hybridization. The term nucleobase also encompasses alternative nucleobases that may differ from naturally-occurring nucleobases but are functional during nucleic acid hybridization. In this context, "nucleobase" refers to both naturally occurring nucleobases such as adenine, guanine, cytosine, thymidine, uracil, xanthine, and hypoxanthine, as well as alternative nucleobases. Such variants are for example described in Hirao et al (2012) Accounts of Chemical Research vol 45, page 2055 and Bergstrom (2009) Current Protocols in Nucleic Acid Chemistry Suppl. 37 1.4.1.

"G," "C," "A," "T," and "U" each generally stand for a naturally-occurring nucleotide that contains guanine, cytosine, adenine, thymidine, and uracil as a nucleobase, respectively. However, G, C, A, T and U can also refer to the guanine, cytosine, adenine, thymidine, and uracil nucleobase with a sugar moiety other than ribose (or deoxyribose). Such alternate sugar moieties are discussed herein.

In a some embodiments, the nucleobase moiety is modified by changing the purine or pyrimidine into a modified purine or pyrimidine, such as substituted purine or substituted pyrimidine, such as an "alternative nucleobase" selected from isocytosine, pseudoisocytosine, 5-methylcytosine, 5-thiazolo-cytosine, 5-propynylcytosine, 5-propynyl-uracil, 5-bromouracil, 5-thiazolo-uracil, 2-thio-uracil, pseudouracil, 1-methylpseudouracil, 5-methoxyuracil, 2'-thio-thymine, hypoxanthine, diaminopurine, 6-aminopurine, 2-aminopurine, 2,6-diaminopurine, and 2-chloro-6-aminopurine.

The nucleobase moieties may be indicated by the letter code for each corresponding nucleobase, e.g. A, T, G, C, or U, wherein each letter may optionally include alternative nucleobases of equivalent function.

A "sugar" or "sugar moiety," includes sugars having a furanose ring (e.g., ribose, deoxyribose, arabinose). A sugar also includes an "alternative sugar," defined as a structure that is capable of replacing the furanose ring of a nucleoside. In certain embodiments, alternative sugars are non-furanose (or 4'-substituted furanose) rings or ring systems or open systems. Such structures include a six-membered ring (e.g., a pyranose ring), or non-ring moieties such as those used in peptide nucleic acids. Alternative sugars may also include a morpholino, a pyranyl, or hexitol ring system. Sugar moieties useful in the preparation of oligonucleotides having motifs include, without limitation, β-D-ribose, β-D-2'-deoxyribose, methoxy-substituted sugars (e.g., β-D-2'methoxyribose), MOE-substituted sugars (e.g., β-D-2'methoxyethylribose), fluoro substituted sugars (e.g., 2'-deoxy-2-fluororibose and β-D-2'-deoxy-2'-fluoroarabinofurose, also referred to herein as 2'-fluoroarabinose), substituted sugars (such as 2', 5' and bis substituted sugars), 4'-S-sugars (such as 4'-S-ribose, 4'-S-2'-deoxyribose and 4'-S-2'-substituted ribose), bicyclic alternative sugars (such as locked nucleic acid (LNA) having a 2'-O—$CH_2$-4' or 2'-O—$(CH_2)_2$-4' bridged ribose derived bicyclic sugar) and sugar surrogates (such as when the ribose ring has been replaced with a morpholino, a pyran, or a hexitol ring system, such as a β-D-homoDNA). A β-D-homoDNA sugar moiety is a pyran ring substituted as shown in this structure (where N is the nucleobase):

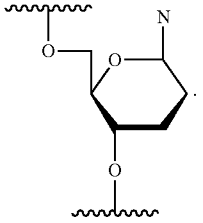

The internucleotide linkage of the nucleotide can be a phosphate linkage. Other internucleotide linkages are known in the art, including, but not limited to, phosphorothioate or boronophosphate. Other internucleotide linkages include phosphotriester, phosphorothionate, phosphoramidate, and other variants of the phosphate backbone.

The term "nucleoside" refers to a monomeric unit of an oligonucleotide or a polynucleotide having a nucleobase and a sugar moiety.

The oligonucleotide may be of any length that permits base modification of a target nucleobase (e.g., deamination of a target adenosine) on a desired target RNA through an ADAR-mediated pathway, and may range from about 27-50 base pairs in length, e.g., about 30-45 base pairs in length or about 35-45 base pairs in length, for example, about 27, 28, 29, 30, 31, 32, 33, 34, 35, 36, 37, 38, 39, 40, 41, 42, 43, 44, 45, 46, 47, 48, 49, or 50 base pairs in length. Ranges intermediate to the above recited ranges are also contemplated to be part of the oligonucleotides described herein.

As used herein, and unless otherwise indicated, the term "complementary," when used to describe a first nucleotide or nucleoside sequence in relation to a second nucleotide or nucleoside sequence, refers to the ability of an oligonucleotide or polynucleotide including the first nucleotide or nucleoside sequence to hybridize and form a duplex structure under certain conditions with an oligonucleotide or polynucleotide including the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C., or 70° C., for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides or nucleosides.

"Complementary" sequences, as used herein, can also include, or be formed entirely from, non-Watson-Crick base pairs and/or base pairs formed from non-natural and alternative nucleotides, in so far as the above requirements with respect to their ability to hybridize are fulfilled. Such non-Watson-Crick base pairs include, but are not limited to, G:U Wobble or Hoogstein base pairing. Complementary sequences between an oligonucleotide and a target sequence as described herein, include base-pairing of the oligonucleotide or polynucleotide including a first nucleotide sequence to an oligonucleotide or polynucleotide including a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally no more than 5, 4, 3 or 2 mismatched base pairs upon hybridization for a duplex up to 30 base pairs, while retaining the ability to hybridize under the conditions most relevant to their ultimate application, e.g., deamination of an adenosine. "Substantially complementary" can also refer to an oligonucleotide that is substantially complementary to a contiguous portion of the mRNA of interest (e.g., an mRNA having a target adenosine). For example, an oligonucleotide is complementary to at least a part of the mRNA of interest if the sequence is substantially complementary to a non-interrupted portion of the mRNA of interest.

As used herein, the term "region of complementarity" refers to the region on the oligonucleotide that is substantially complementary to all or a portion of a gene, primary transcript, a sequence (e.g., a target sequence; e.g., a target sequence having a target nucleobase, e.g., adenosine), or processed mRNA, so as to interfere with expression of the endogenous gene. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- and/or 3'-terminus of the oligonucleotide.

The phrase "contacting a cell with an oligonucleotide," such as an oligonucleotide as described herein, includes contacting a cell by any possible means. Contacting a cell with an oligonucleotide includes contacting a cell in vitro with the oligonucleotide or contacting a cell in vivo with the oligonucleotide. The contacting may be done directly or indirectly. Thus, for example, the oligonucleotide may be put into physical contact with the cell by the individual performing the method, or alternatively, the oligonucleotide agent may be put into a situation that will permit or cause it to subsequently come into contact with the cell.

Contacting a cell in vitro may be done, for example, by incubating the cell with the oligonucleotide. Contacting a cell in vivo may be done, for example, by injecting the oligonucleotide into or near the tissue where the cell is located, or by injecting the oligonucleotide agent into another area, e.g., the bloodstream or the subcutaneous space, such that the agent will subsequently reach the tissue where the cell to be contacted is located. For example, the oligonucleotide may contain and/or be coupled to a ligand, e.g., GalNAc3, that directs the oligonucleotide to a site of interest, e.g., the liver. Combinations of in vitro and in vivo methods of contacting are also possible. For example, a cell may also be contacted in vitro with an oligonucleotide and subsequently transplanted into a subject.

In one embodiment, contacting a cell with an oligonucleotide includes "introducing" or "delivering the oligonucleotide into the cell" by facilitating or effecting uptake or absorption into the cell. Absorption or uptake of an oligonucleotide can occur through unaided diffusive or active cellular processes, or by auxiliary agents or devices. Introducing an oligonucleotide into a cell may be in vitro and/or in vivo. For example, for in vivo introduction, oligonucleotide s can be injected into a tissue site or administered systemically. In vitro introduction into a cell includes methods known in the art such as electroporation and lipofection. Further approaches are described herein below and/or are known in the art.

As used herein, "lipid nanoparticle" or "LNP" is a vesicle including a lipid layer encapsulating a pharmaceutically active molecule, such as a nucleic acid molecule, e.g., an oligonucleotide. LNP refers to a stable nucleic acid-lipid particle. LNPs typically contain a cationic, ionizable lipid, a non-cationic lipid, and a lipid that prevents aggregation of the particle (e.g., a PEG-lipid conjugate). LNPs are described in, for example, U.S. Pat. Nos. 6,858,225; 6,815,432; 8,158,601; and 8,058,069, the entire contents of which are hereby incorporated herein by reference.

As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the oligonucleotide composition. The lipophilic material isolates the aqueous interior from an aqueous exterior, which typically does not include the oligonucleotide composition, although in some examples, it may. Liposomes also include "sterically stabilized" liposomes, a term which, as used herein, refers to liposomes including one or more specialized lipids that, when incorporated into liposomes, result in enhanced circulation lifetimes relative to liposomes lacking such specialized lipids.

"Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

As used herein, the terms "effective amount," "therapeutically effective amount," and "a "sufficient amount" of an agent that results in a therapeutic effect (e.g., in a cell or a subject) described herein refer to a quantity sufficient to, when administered to the subject, including a human, effect beneficial or desired results, including clinical results, and, as such, an "effective amount" or synonym thereto depends on the context in which it is being applied. For example, in the context of treating a disorder, it is an amount of the agent that is sufficient to achieve a treatment response as compared to the response obtained without administration. The amount of a given agent will vary depending upon various factors, such as the given agent, the pharmaceutical formulation, the route of administration, the type of disease or disorder, the identity of the subject (e.g., age, sex, and/or weight) or host being treated, and the like, but can nevertheless be routinely determined by one of skill in the art. Also, as used herein, a "therapeutically effective amount" of an agent is an amount that results in a beneficial or desired result in a subject as compared to a control. As defined herein, a therapeutically effective amount of an agent may be readily determined by one of ordinary skill by routine methods known in the art. Dosage regimen may be adjusted to provide the optimum therapeutic response.

A "therapeutically-effective amount" includes an amount (either administered in a single or in multiple doses) of an oligonucleotide that produces some desired local or systemic effect at a reasonable benefit/risk ratio applicable to any treatment. Oligonucleotides employed in the methods as disclosed herein may be administered in a sufficient amount to produce a reasonable benefit/risk ratio applicable to such treatment.

By "determining the level of a protein" is meant the detection of a protein, or an mRNA encoding the protein, by methods known in the art either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third-party laboratory that directly acquired the physical entity or value). Methods to measure protein level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure mRNA levels are known in the art.

"Percent (%) sequence identity" with respect to a reference polynucleotide or polypeptide sequence is defined as the percentage of nucleotides or amino acids in a candidate sequence that are identical to the nucleotides or amino acids in the reference polynucleotide or polypeptide sequence, after aligning the sequences and introducing gaps, if necessary, to achieve the maximum percent sequence identity. Alignment for purposes of determining percent sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values may be generated using the sequence comparison computer program BLAST. As an illustration, the percent sequence identity of a given sequence, A, to, with, or against a given sequence, B, (which can alternatively be phrased as a given sequence, A that has a certain percent sequence identity to, with, or against a given sequence, B) is calculated as follows:

$$100 \text{ multiplied by } (\text{the fraction } X/Y)$$

where X is the number of nucleotides or amino acids scored as identical matches by a sequence alignment program (e.g., BLAST) in that program's alignment of A and B, and where Y is the total number of nucleotides or amino acids in B. It will be appreciated that where the length of sequence A is not equal to the length of sequence B, the percent sequence identity of A to B will not equal the percent sequence identity of B to A.

By "level" is meant a level or activity of a protein, or mRNA encoding the protein, as compared to a reference. The reference can be any useful reference, as defined herein. By a "decreased level" or an "increased level" of a protein is meant a decrease or increase in protein level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a protein may be expressed in mass/vol (e.g., g/dL, mg/mL, μg/mL, ng/mL) or percentage relative to total protein or mRNA in a sample.

The term "pharmaceutical composition," as used herein, represents a composition containing a compound described herein formulated with a pharmaceutically acceptable excipient, and preferably manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); for intrathecal injection; for intracerebroventricular injections; for intraparenchymal injection; or in any other pharmaceutically acceptable formulation.

A "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

As used herein, the term "pharmaceutically acceptable salt" means any pharmaceutically acceptable salt of an oligonucleotide as described herein. For example, pharmaceutically acceptable salts include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid.

Pharmaceutically acceptable salts may be acid addition salts involving inorganic or organic acids or the salts maybe prepared from inorganic or organic bases. Frequently, pharmaceutically acceptable salts are prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

By a "reference" is meant any useful reference used to compare protein or mRNA levels or activity. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound described herein; a sample from a subject that has been treated by a compound described herein; or a sample of a purified protein (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder; a subject that has been treated with a compound described herein. In preferred embodiments, the reference sample, standard, or level is matched to the sample subject sample by at least one of the following criteria: age, weight, sex, disease stage, and overall health. A standard curve of levels of a purified protein, e.g., any described herein, within the normal reference range can also be used as a reference.

As used herein, the term "subject" refers to any organism to which a composition in accordance with the disclosure may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material.

The details of one or more embodiments described herein are set forth in the description below. Other features, objects, and advantages described herein will be apparent from the description and from the claims.

DETAILED DESCRIPTION

Figure 1:
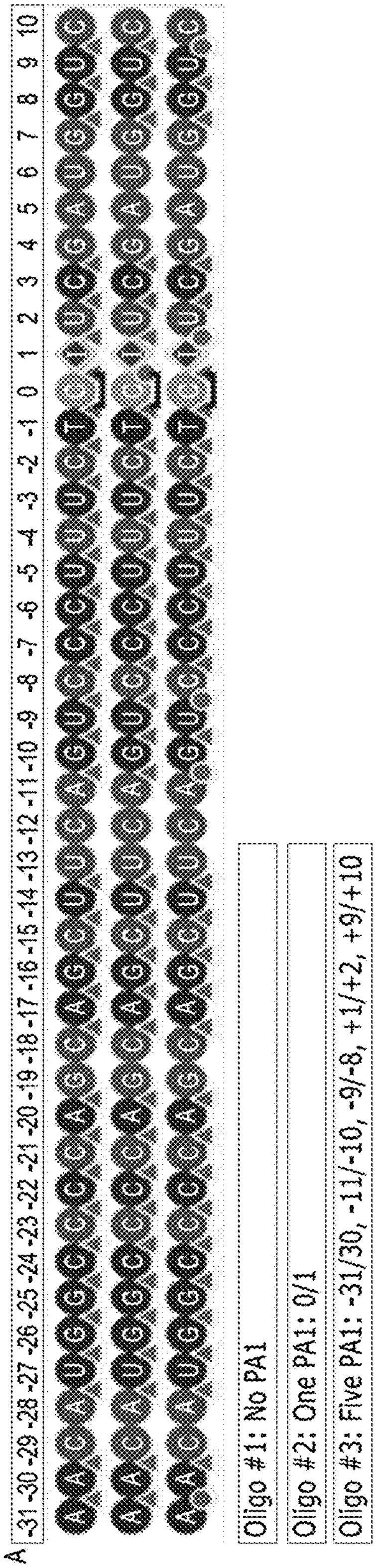
FIG. 1. (A) Schematics of 42mer oligonucleotides designed to test the effect of PA-1 linkages (Oligos #1, #2, and #3, SEQ ID NOs: 1, 3, and 4). A circle between nucleobases represents a PA-1 linkage, while a triangle represents a PS linkage; all other linkages between nucleobases not designated with a triangle or circle are phosphate linkages. (B) Chemical structure of PA-1 linkage within the backbone of an oligonucleotide. (C) In vivo editing percentage of E342K SERPINA1 RNA isolated from PiZ mouse livers at days one, four, and seven (n=3 per group).
Figure 1:
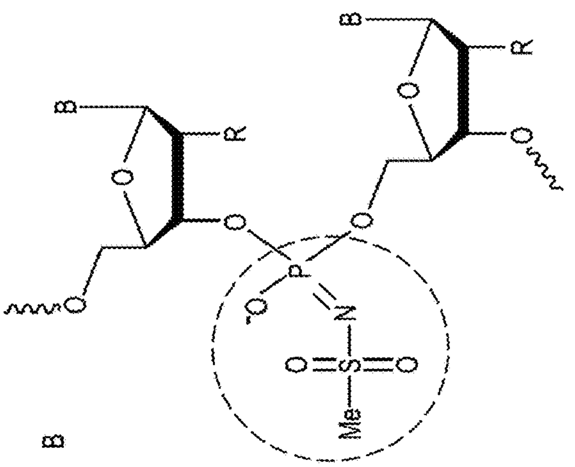
Figure 1:
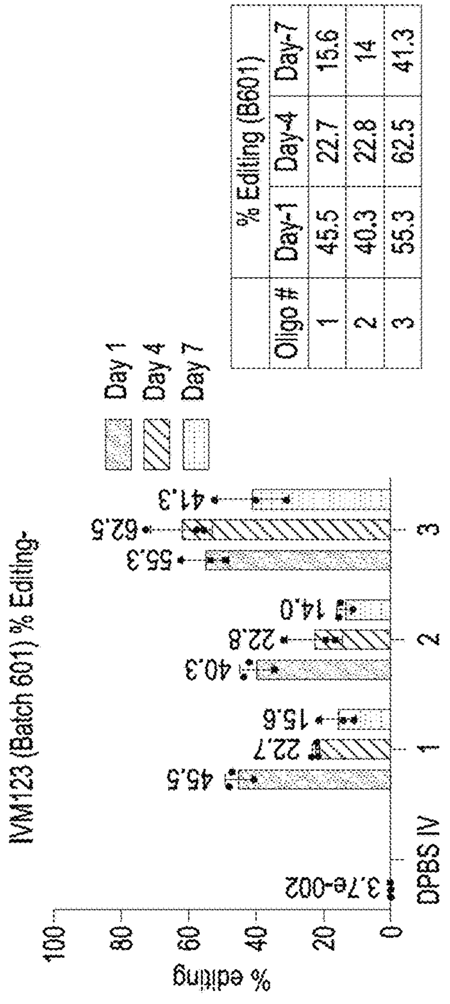

Provided herein are oligonucleotides that can be used to modify a nucleobase on a target RNA. Accordingly, the disclosure provides oligonucleotides, compositions containing the same, and methods to modify a target nucleobase (e.g., deaminate a target adenosine) on RNA, where the modification produces a therapeutic result, e.g., in a subject in need thereof. In some embodiments, the target RNA is a mRNA.

I. Disorders

The disclosure also oligonucleotides for use in a method for making a change in a target RNA sequence in a mammalian, preferably human cell, as described herein. Similarly, the disclosure provides the use of these oligonucleotides in the manufacture of a medicament for making a change in a target RNA sequence in a mammalian, preferably human cell, as described herein. In some embodiments, the target RNA is a mRNA.

The disclosure also relates to a method for the deamination of at least one specific target adenosine present in a target RNA sequence in a cell, said method including the steps of: providing said cell with an oligonucleotide described herein; allowing uptake by the cell of the oligonucleotide; allowing annealing of the oligonucleotide to the target RNA sequence; allowing a mammalian ADAR enzyme to deaminate said target adenosine in the target RNA sequence to an inosine; and optionally identifying the presence of the inosine in the RNA sequence.

In some embodiments, provided herein are oligonucleotides, compositions, and methods wherein two adenosines that are next to each other are co-deaminated by an RNA editing enzyme such as ADAR. In this particular case, the UAA stop codon is converted into a UII Trp-encoding codon. Other examples of modifications resulting from deamination of target adenosines within a target codon are provided in Tables 1 and 2 below.

TABLE 1

| Target Codon | Amino Acid Encoded by Target Codon | Modified Codon | Amino Acid Encoded by Modified Codon |
|---|---|---|---|
| AAA | Lys | IAA | Glu |
| | | AIA | Arg |
| | | IIA | Gly |
| | | AII | Arg |
| | | IAI | Glu |
| | | III | Gly |
| AAC | Asn | IAC | Asp |
| | | AIC | Ser |
| | | IIC | Gly |
| AAG | Lys | IAG | Glu |
| | | AIG | Arg |
| | | IIG | Gly |
| AAU | Arg | IAU | Asp |
| | | AIU | Ser |
| | | IIU | Gly |
| ACA | Thr | ICA | Ala |
| | | ICI | Ala |
| ACC | Thr | ICC | Ala |
| ACG | Thr | ICG | Ala |
| ACU | Thr | ICU | Ala |
| AGA | Arg | IGA | Gly |
| | | IGI | Gly |
| AGC | Ser | IGC | Gly |
| AGG | Arg | IGG | Gly |
| AGU | Ser | IGU | Gly |
| AUA | Ile | IUA | Asp |
| | | AUI | Met |
| | | IUI | Val |
| AUC | Ile | IUC | Val |
| AUG | Met | IUG | Val |
| AUU | Ile | IUU | Val |
| CAA | Gln | CIA | Arg |
| | | CII | Arg |
| CAC | His | CIC | Arg |
| CAG | Gln | CIG | Arg |
| CAU | His | CIU | Arg |
| GAA | Glu | GIA | Gly |
| | | GII | Gly |
| GAC | Asp | GIC | Gly |
| GAG | Glu | GIG | Gly |
| GAU | Asp | GIU | Gly |
| UAA | Stop | UII | Trp |
| UGA | Stop | UGI | Trp |
| UAC | Tyr | UIC | Cys |
| UAG | Stop | UIG | Trp |
| UAU | Tyr | UIU | Cys |

TABLE 2

| Triplet Base Composition and Resulting Edited Triplet | |
|---|---|
| Target Codon | Modified Codon |
| AAA | AIA |
| AAC | AIC |
| AAG | AIG |
| AAU | AIU |
| CAA | CIA |
| CAC | CIC |
| CAG | CIG |
| CAU | CIU |
| GAA | GIA |
| GAC | GIC |
| GAG | GIG |
| GAU | GIU |
| UAA | UIA |
| UAC | UIC |
| UAG | UIG |
| UAU | UIU |

Because the deamination of the adenosine to an inosine may result in a protein that is no longer suffering from the mutated A at the target position, the identification of the deamination into inosine may be a functional read-out, for instance an assessment on whether a functional protein is present, or even the assessment that a disease that is caused by the presence of the adenosine is (partly) reversed. The functional assessment for each of the diseases mentioned herein will generally be according to methods known to the skilled person. When the presence of a target adenosine causes aberrant splicing, the read-out may be the assessment of whether the aberrant splicing is still taking place, or not, or taking place less often. On the other hand, when the deamination of a target adenosine is wanted to introduce a splice site, then similar approaches can be used to check whether the required type of splicing is indeed taking place. A suitable manner to identify the presence of an inosine after deamination of the target adenosine is RT-PCR and sequencing, using methods that are well-known to the person skilled in the art.

In general, mutations in any target RNA that can be reversed using oligonucleotide constructs as disclosed herein are G-to-A mutations, and oligonucleotide constructs can be designed accordingly. Mutations that may be targeted using oligonucleotide constructs also include C to A, U to A (T to A on the DNA level) in the case of recruiting adenosine deaminases. Although RNA editing in the latter circumstances may not necessarily revert the mutation to wild-type, the edited nucleotide may give rise to an improvement over the original mutation. For example, a mutation that causes an in frame stop codon—giving rise to a truncated protein, upon translation—may be changed into a codon coding for an amino acid that may not be the original amino acid in that position, but that gives rise to a (full length) protein with at least some functionality, at least more functionality than the truncated protein.

The oligonucleotides described herein particularly suitable for treating genetic diseases, such as cystic fibrosis, albinism, alpha-1-antitrypsin (A1AT) deficiency, Alzheimer disease, amyotrophic lateral sclerosis, asthma, 11-thalassemia, Cadasil syndrome, Charcot-Marie-Tooth disease, chronic obstructive pulmonary disease (COPD), distal spinal muscular atrophy (DSMA), Duchenne/Becker muscular dystrophy, dystrophic epidermolysis bullosa, epidermylosis bullosa, Fabry disease, Factor V Leiden associated disorders, familial adenomatous, polyposis, galactosemia, Gaucher's disease, glucose-6-phosphate dehydrogenase deficiency, haemophilia, hereditary hematochromatosis, Hunter syndrome, Huntington's disease, Hurler syndrome, inflammatory bowel disease (IBD), inherited polyagglutination syndrome, Leber congenital amaurosis, Lesch-Nyhan syndrome, Lynch syndrome, Marfan syndrome, mucopolysaccharidosis, muscular dystrophy, myotonic dystrophy types I and II, neurofibromatosis, Niemann-Pick disease type A, B and C, NY-ESO-1 related cancer, Parkinson's disease, Peutz-Jeghers syndrome, phenylketonuria, Pompe's disease, primary ciliary disease, prothrombin mutation related disorders (e.g., prothrombin G20210A mutation), pulmonary hypertension, retinitis pigmentosa, Sandhoff disease, severe combined immune deficiency syndrome (SCID), sickle cell anemia, spinal muscular atrophy, Stargardt's disease, Tay-Sachs disease, Usher syndrome, X-linked immunodeficiency, Sturge-Weber syndrome, Rett syndrome, and various forms of cancer (e.g. BRCA1 and 2 linked breast cancer and ovarian cancer).

Oligonucleotides described herein may deaminate the adenosine mutation resulting in an increase in protein activity.

In certain embodiments, treatment is performed on a subject who has been diagnosed with a mutation in a gene, but does not yet have disease symptoms (e.g., an infant such as a subject that is 1 month to 12 months old or subject under the age of 2). In other embodiments, treatment is performed on an individual who has at least one symptom.

Treatment may be performed in a subject of any age, starting from infancy to adulthood. Subjects may begin treatment, for example, at birth, six months, or 1, 2, 3, 4, 5, 6, 7, 8, 9, 10, 11, 12, 13, 15, or 18 years of age.

In certain embodiments, the oligonucleotide increases (e.g., an increase by 10%, 20%, 30%, 40%, 50%, 60%, 70%, 80%, 90%, 100%, 150%, 200%, 300%, 400%, 500%, 600%, 700%, 800%, 900%, 1000% or more, or an increase by more than 1.2-fold, 1.4-fold, 1.5-fold, 1.8-fold, 2.0-fold, 3.0-fold, 3.5-fold, 4.5-fold, 5.0-fold, 10-fold, 15-fold, 20-fold, 30-fold, 40-fold, 50-fold, 100-fold, 1000-fold, or more) protein activity in vitro and/or in vivo.

In some embodiments, the oligonucleotide increases (e.g., an increase by 10%, 20%, 30%, 40%, 50%, 60%, 70%, 80%, 90%, 100%, 150%, 200%, 300%, 400%, 500%, 600%, 700%, 800%, 900%, 1000% or more, or an increase by more than 1.2-fold, 1.4-fold, 1.5-fold, 1.8-fold, 2.0-fold, 3.0-fold, 3.5-fold, 4.5-fold, 5.0-fold, 10-fold, 15-fold, 20-fold, 30-fold, 40-fold, 50-fold, 100-fold, 1000-fold, or more) protein activity in the brain.

II. Oligonucleotides

The oligonucleotides described herein are complementary to target RNA and are capable of recruiting ADAR enzymes used to edit a target nucleobase on the target RNA, e.g., to deaminate a target adenosine on the target RNA. In some embodiments, only one nucleobase (e.g., one adenosine) is edited (e.g., deaminated). In some embodiments, 1, 2, or 3 nucleobases are edited. In some embodiments, the oligonucleotide includes at least one mismatch, wobble, insertion or deletion. In some cases, the oligonucleotide includes a mismatch opposite the target nucleobase, e.g., at $X^2$ (see structure below). The oligonucleotides described herein may further include modifications (e.g., alternative nucleotides) to increase stability and/or increase deamination efficiency. In some embodiments, the oligonucleotides described herein comprises 1, 2, 3, 4, or 5 mismatches or wobbles or insertions or deletions (or any combination thereof).

In some embodiments, one or more of the nucleobases of an oligonucleotide described herein is chemically modified to enhance stability or other beneficial characteristics. Without being bound by theory, it is believed that certain modification can increase nuclease resistance and/or serum stability or decrease immunogenicity. For example, oligonucleotides described herein may contain nucleotides found to occur naturally in DNA or RNA (e.g., adenine, thymidine, guanosine, cytidine, uridine, or inosine) or may contain nucleotides that have one or more chemical modifications to one or more components of the nucleotide (e.g., the nucleobase, sugar, or internucleotide linkage).

The oligonucleotides described herein comprise the structure:

$$[A_m]—X^1—X^2—X^3—[B_n]$$

wherein m+n is 24 to 50, n is at least 4, and m is at least 20;

$-X^1-X^2-X^3-$ is a Central Triplet of the oligonucleotide;

$X^1$ is position −1 of the oligonucleotide, $X^2$ is position 0 of the oligonucleotide, and $X^3$ is position +1 of the oligonucleotide;

$[A]_m$ is a first domain at positions −(m+1) to −2 of the oligonucleotide;

$[B]_n$ is a second domain at positions +2 to +(n+1) of the oligonucleotide;

each A and B is a nucleotide comprising a nucleobase, a sugar ("an A/B sugar"), and an internucleotide linkage;

each $X^1$, $X^2$, and $X^3$ comprises a nucleobase, a sugar ("an X sugar"), and an internucleotide linkage;

the A/B sugars and the $X^3$ sugar are selected from 2'-methoxy-ribose, 2'-MOE-ribose, 2'-deoxy-2'-fluororibose, 2'-fluoro-arabinose, 2-methoxy-arabinose, 2'deoxyribose and a locked nucleic acid (LNA);

the $X^1$ sugar is 2'-deoxy-2'-fluororibose or 2'deoxyribose;

the $X^2$ sugar is selected from 2'-methoxy-ribose, 2'-MOE-ribose, 2'-deoxy-2'-fluororibose, 2'-fluoro-arabinose, 2-methoxy-arabinose, 2'deoxyribose, a locked nucleic acid (LNA), and a beta-homo-DNA sugar;

the A/B sugars and the X sugars, collectively, are 10-70% 2'-deoxy-2'-fluoro-ribose;

the internucleotide linkages of the oligonucleotide are 30-100% phosphorothioate and phosphoramidate linkages, and 3 to 20 internucleotide linkages are phosphoramidate linkages;

the internucleotide linkage (i) between the nucleotide at position −(m+1) and the nucleotide at position −(m) (the 5'end), (ii) between the nucleotide at position +(n) and the nucleotide at position +(n+1) (the 3'-end), or (iii) at each the 5'-end and 3'-end of the oligonucleotide is a phosphoramidate linkage; and the internucleotide linkage between the nucleotide at position −(m) and the nucleotide at position −(m−1) and the internucleotide linkage between the nucleotide at position +(n−1) and the nucleotide at position +(n) are independently a phosphorothioate or a phosphoramidate linkage.

In some embodiments, the $X^2$ nucleobase is cytosine or isodU. In some embodiments, the $X^3$ nucleobase is guanosine, hypoxanthine, or 7-deazaguanine.

The $X^1$ sugar of the oligonucleotides disclosed herein are a 2'-deoxy-2'-fluororibose (sometimes referred to as 2'-fluororibose)

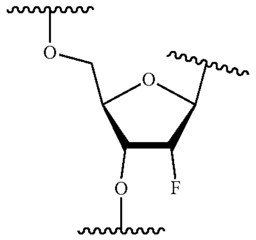

or a 2'-deoxyribose

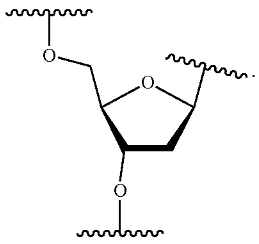 [SMILES: *OC[C@H]1O[C@@H](*)C[C@H]1O*]

The A/B sugars and the $X^3$ sugar of the oligonucleotides disclosed herein are each individually 2'-methoxyribose

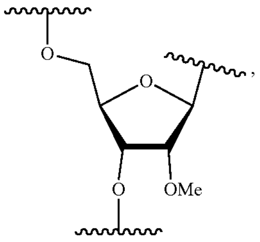

a 2'-deoxy-2'-fluororibose (sometimes referred to as 2'-deoxy-2'-fluororibose)

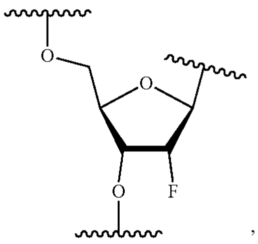

,

2'-methoxyethylribose (sometimes referred to as 2'-MOE-ribose)

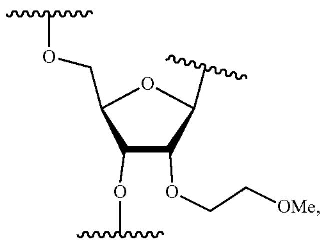

a 2'-fluoroarabinose

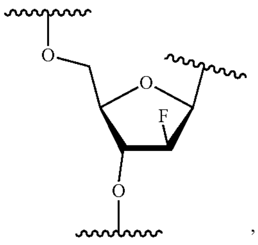

, a 2'-deoxyribose

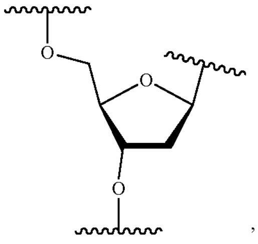 [SMILES: *OC[C@H]1O[C@@H](*)C[C@H]1O*]

, or a locked nucleic acid (LNA).

The $X^2$ sugar of the oligonucleotides disclosed herein are each individually 2'-methoxyribose

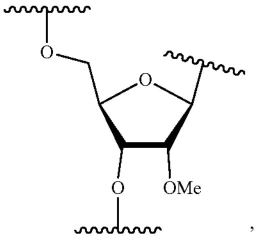

a 2'-deoxy-2'-fluororibose

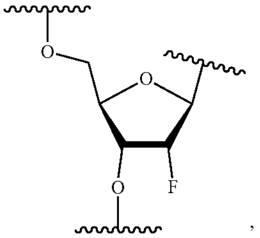

2'-methoxyethylribose

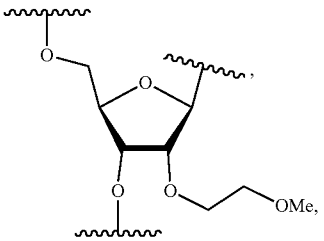

a 2'-fluoroarabinose

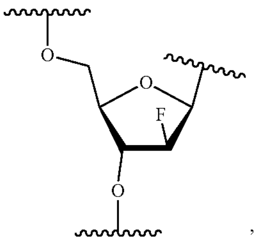

a 2'-deoxyribose

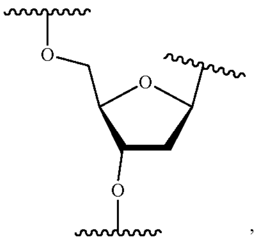 [SMILES: *OC[C@H]1O[C@@H](*)C[C@H]1O*]

a β-D-homoDNA sugar

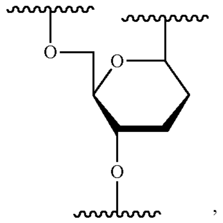

or a locked nucleic acid (LNA).

In some embodiments, 10-70% (e.g., 10%, 11%, 12%, 13%, 14%, 15%, 16%, 17%, 18%, 19%, 20%, 21%, 22%, 23%, 24%, 25%, 26%, 27%, 28%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62% 63% 64%, 65%, 66%, 67%, 68%, 69%, or 70%) of the A/B sugars and the X sugars, collectively, are 2'-deoxy-2'-fluororibose. In some embodiments, 20-50% (e.g., 20%, 21%, 22%, 23%, 24%, 25%, 26%, 27%, 28%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%) of the A/B sugars and the X sugars, collectively, are 2'-deoxy-2'-fluororibose.

In some embodiments, no more than four sequential A/B sugars are 2'-deoxy-2'-fluororibose. In some embodiments, the A/B sugars are selected from 2'-methoxy-ribose, 2'-MOE-ribose, 2'-deoxy-2'-fluororibose, and 2'deoxyribose.

In some embodiments, the A/B sugar at position +3 is a 2'-deoxy-2'-fluororibose. In some embodiments, the A/B sugar at position −5 is a 2'-deoxy-2'-fluororibose. In some embodiments, the A/B sugar at position −16 is a 2'-deoxy-2'-fluororibose. In some embodiments, the A/B sugar at position −20 is a 2'-deoxy-2'-fluororibose. In some embodiments, the A/B sugar at each of positions −5, −16, and −20 is a 2'-deoxy-2'-fluororibose. In some embodiments, the A/B sugar at each of positions +3, −5, −16, and −20 is a 2'-deoxy-2'-fluororibose.

In some embodiments, the $X^1$ sugar is a 2'-fluororibose or a 2-deoxyribose. In some embodiments, the $X^1$ sugar is a 2'-fluororibose. In some embodiments, the $X^1$ sugar is a 2-deoxyribose.

In some embodiments, the $X^2$ nucleobase is a cytosine. In some embodiments, the $X^2$ sugar is a beta-homo-DNA-sugar or a 2'-deoxyribose. In some embodiments, the $X^2$ sugar is a beta-homo-DNA-sugar. In some embodiments, the $X^2$ sugar is a 2'-deoxyribose.

In some embodiments, the $X^3$ nucleobase is hypoxanthine.

In some embodiments, the internucleotide linkage is a phosphoroamidate, phosphorothioate, phosphorodithioate, methylphosphonate, thiophosphate, 3'-thiophosphate, or 5'-thiophosphate.

Phosphoramidate linkages (e.g.,

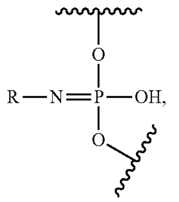

where R is a suitable substituent on the nitrogen, such as an alkyl, sulfoxide, or the like), include mesyl phosphoramidate

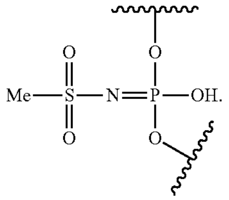 [SMILES: *OP(O)(=NS(C)(=O)=O)O*]

In some embodiments, the phosphoramidite linkage is a mesyl phosphoramidite. In some embodiments, each phosphoroamidate linkage in the oligonucleotide is a mesyl phosphoramidite.

In some embodiments, the internucleotide linkages of the oligonucleotides described herein comprise at least 30% (e.g., at least 30%, 35%, 40%, 45%, 50%, 55%, 60%, 65%, 70%, 75%, 80%, 85%, 90%, 95%, or 100%) phosphoramidate and/or phosphorothioate linkages. In some embodiments, the oligonucleotides described herein have 30-70% (e.g., 30%, 35%, 40%, 45%, 50%, 55%, 60%, 65%, 70%) phosphorothioate and phosphoroamidate linkages. In some embodiments, the oligonucleotides described herein have 40-60% (e.g., 40%, 45%, 50%, 55%, 60%) phosphorothioate and phosphoroamidate linkages.

In some embodiments, the phosphorothioate linkages are Sp phosphorothioate linkages. In other embodiments, the phosphorothioate linkages are Rp phosphorothioate linkages. In some cases, the phosphorothioate linkages are a mixture of Sp and Rp.

In some embodiments, at least 3 (e.g., 3, 4, 5, 6, 7, 8, 9, 10, 11, 12, 13, 14, 15, 16, 17, 18, 19, 20) of the internucleotide linkages of the oligonucleotides described herein are phosphoramidite linkages.

In some embodiments, the internucleotide linkage between $X^1$ and $X^2$ is a phosphorothioate or a phosphodiester linkage. In some embodiments, the internucleotide linkage between $X^1$ and $X^2$ is a phosphorothioate linkage.

In some embodiments, the internucleotide linkage between $X^2$ and $X^3$ is a phosphorothioate or a phosphodiester linkage. In some embodiments, the internucleotide linkage between $X^2$ and $X^3$ is a phosphorothioate linkage.

In some embodiments, the internucleotide linkage between the nucleoside at position −2 and $X^1$ is a phosphorothioate or a phosphodiester linkage. In some embodiments, the internucleotide linkage between the nucleoside at position −2 and $X^1$ is a phosphorothioate linkage.

In some embodiments, the internucleotide linkage between the nucleotide at position −9 and the nucleotide at position −8 is a phosphoramidite linkage.

In some embodiments, the internucleotide linkage between the nucleotide at position −11 and the nucleotide at position −10 is a phosphoramidite linkage.

In some embodiments, the internucleotide linkage between the nucleotide at position +1 and the nucleotide at position +2 is a phosphoramidite linkage.

In some embodiments, the internucleotide linkage between the nucleotide at position +4 and the nucleotide at position +5 is a phosphoramidate linkage. In some embodiments, the internucleotide linkage between the nucleotide at position +5 and the nucleotide at position +6 is a phosphoramidate linkage. In some embodiments, the internucleotide linkage between the nucleotide at position +9 and the nucleotide at position +10 is a phosphoramidate linkage. In some embodiments, the internucleotide linkage between the nucleotide at position +1 and the nucleotide at position +2 and the internucleotide linkage between the nucleotide at position +9 and the nucleotide at position +10 are a phosphoramidate linkage. In some embodiments, the internucleotide linkage between the nucleotide at position +1 and the nucleotide at position +2, the internucleotide linkage between the nucleotide at position +5 and the nucleotide at position +6, and the internucleotide linkage between the nucleotide at position +9 and the nucleotide at position +10 are a phosphoramidate linkage.

In some embodiments, n and m (collectively) is an integer ranging from 24-40 (e.g., 24, 25, 26, 27, 28, 29, 30, 31, 32, 33, 34, 35, 36, 37, 38, 39 or 40). In some embodiments, n and m (collectively) is 27. In some embodiments, n and m (collectively) is 39.

In some embodiments, m is at least 20 (e.g., 21, 22, 23, 24, 25, 26, 27, 28, 29. 30, 31, 32, 33, 34 or 35). In some embodiments, n is at least 4 (e.g., 4, 5, 6, 7, 8, or 9).

In some embodiments, the oligonucleotides described herein have a GalNAc moiety at the 5' end. In some embodiments, the oligonucleotides described herein have a GalNAc moiety at the 3' end.

In some embodiments, n is an integer ranging from 8 to 10. In some embodiments, n is 8, 9, or 10. In some embodiments, n is 9.

Exemplary oligonucleotides described herein are shown in Table 3 below (in Hierarchical Editing Language for Macromolecules (HELM) syntax) (Zhang et al., J. Chem. Inf. Model. 2012, 52, 10, 2796-2806), where each nucleotide is noted by terms between periods (.); the first term indicates the sugar moiety, the next is the nucleobase, and last term is the internucleotide linkage. For clarity, the terms can be separated by punctuation, e.g., brackets and parentheses. Thus, a nucleotide designation of ".f(A)P." means a 2'-deoxy-2'-fluororibose sugar moiety and an adenosine nucleobase that is then linked via a phosphodiester linkage. Sugar moiety designations are "f" for 2'-deoxy-2'-fluororibose, "m" for 2'-methoxyribose, "fana" for 2'-fluoroarabinose, "d" is deoxyribose, "dH" is beta-homoDNA, and "moe: is 2'-MOEribose. For linkages, "msPA" indicates a mesyl phosphoramidate internucleotide linkage, "sP" indicates a phosphorothioate linkage; and "P" indicates a phosphate linkage. Additional chemical modifications are noted by CHEM1{TriGalNAc2}|CHEM2{P}, which indicates a tri-GalNAc conjugated to the 5' end of the oligonucleotide, and CHEM3{P}|CHEM4{TriGalNAc1}, which indicates a tri-GalNAc conjugated to the 3' end.

TABLE 3

<table>
<tr><th colspan="3">Exemplary Oligonucleotides</th></tr>
<tr><th>Oligo No.</th><th>Oligonucleotide sequence</th><th>Base sequence</th></tr>
<tr><td>1.</td><td>{f(A)[sP].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[sP].f(G)[sP].f(U)[sP].m(C)[sP].f(C)[sP].f(C)[sP].f(U)[sP].m(U)[sP].f(U)[sP].m(C)[sP].d(T)[sP].[Dh](C)[sP].[fana](I)[sP].m(U)[sP].f(C)[sP].m(G)P.m(A)P.m(U)P.m(G)[sP].f(G)[sP].f(U)[sP].m(C)} (SEQ ID NO: 1)</td><td>AACAUGGCCCCAGCAGCUUCAGUCCCUUUCTCIUCGAUGGUC (SEQ ID NO: 2)</td></tr>
<tr><td>2.</td><td>{f(A)[sP].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[sP].f(G)[sP].f(U)[sP].m(C)[sP].f(C)[sP].f(C)[sP].f(U)[sP].m(U)[sP].f(U)[sP].m(C)[sP].d(T)[sP].[Dh](C)[msPA].[fana](I)[sP].m(U)[sP].f(C)[sP].m(G)P.m(A)P.m(U)P.m(G)[sP].f(G)[sP].f(U)[sP].m(C)} (SEQ ID NO: 3)</td><td>AACAUGGCCCCAGCAGCUUCAGUCCCUUUCTCIUCGAUGGUC (SEQ ID NO: 2)</td></tr>
<tr><td>3.</td><td>{f(A)[msPA].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[sP]f(U)[sP].m(C)[sP].d(T)[sP].[Dh](C)[sP].[fana](I)[msPA].m(U)[sP].f(C)[sP].m(G)P.m(A)P.m(U)P.m(G)[sP].f(G)[sP].f(U)[msPA].m(C)} (SEQ ID NO: 4)</td><td>AACAUGGCCCCAGCAGCUUCAGUCCCUUUCTCIUCGAUGGUC (SEQ ID NO: 2)</td></tr>
<tr><td>4.</td><td>{m(C)[msPA].f(C)[sP].f(C)[sP].m(C)P.m(A)P.f(G)[sP].m(C)P.f(A)[sP].m(G)P.f(C)[sP].f(U)[sP].m(U)P.m(C)P.m(A)[msPA].f(G)[sP].f(U)[msPA].m(C)P.f(C)[sP].f(C)[sP].m(U)P.m(U)P.f(U)[sP].m(C)P.d(T)[sP].[Dh](C)[P].d(I)[msPA].m(U)P.f(C)[sP].m(G)[msPA].m(A)} (SEQ ID NO: 5)</td><td>CCCCAGCAGCUUCAGUCCCUUUCTCIUCGA (SEQ ID NO: 6)</td></tr>
<tr><td>5.</td><td>{f(C)[msPA].f(C)[sP].f(C)[sP].f(C)[sP].m(A)[sP].m(G)[sP].f(C)[sP].m(A)[sP].m(G)[sP].f(C)[sP].f(U)[sP].f(U)[sP].f(C)[sP].m(A)[msPA].m(G)[sP].f(U)[msPA].f(C)[sP].f(C)[sP].f(C)[sP].f(U)[sP].f(U)[sP].f(U)[sP].f(C)[sP].d(T)[sP].[Dh](C)[sP].d(I)[msPA].f(U)[sP].f(C)[sP].m(G)[msPA].m(A)} (SEQ ID NO: 7)</td><td>CCCCAGCAGCUUCAGUCCCUUUCTCIUCGA (SEQ ID NO: 6)</td></tr>
<tr><td>6.</td><td>{m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].f(U)[sP].[Dh](C)[P].d(I)[msPA].m(U)[sP].f(C)[sP].m(G)[msPA].m(A)} (SEQ ID NO: 8)</td><td>CCCCAGCAGCUUCAGUCCCUUUCUCIUCGA (SEQ ID NO: 9)</td></tr>
<tr><td>7.</td><td>CHEM1{TriGalNAc2}|CHEM2{P}{f(A)[msPA].f(C)[sP].f(A)[sP].f(U)[sP].f(A)[sP].f(A)[sP].f(U)[sP].f(U)[sP].f(U)[sP].f(A)[sP].f(C)[sP].f(A)[sP].f(C)[sP].f(G)[msPA].f(A)[sP].m(A)[msPA].m(A)[sP].m(G)[sP].m(C)[sP].m(A)[sP].m(A)[sP].m(U)[sP].m(G)[sP].f(C)[sP].d(C)[sP].d(A)[msPA].m(U)[sP].m(C)[sP].m(A)[msPA].m(C)} (SEQ ID NO: 10)</td><td>ACAUAAUUUACACGAAAGCAAUGCCAUCAC (SEQ ID NO: 11)</td></tr>
<tr><td>8.</td><td>{f(A)[msPA].f(C)[sP].f(A)[sP].f(U)[sP].f(A)[sP].f(A)[sP].f(U)[sP].f(U)[sP].f(U)[sP].f(A)[sP].f(C)[sP].f(A)[sP].f(C)[sP].f(G)[msPA].f(A)[sP].m(A)[msPA].m(A)[sP].m(G)[sP].m(C)[sP].m(A)[sP].m(A)[sP].m(U)[sP].m(G)[sP].f(C)[P].d(C)[sP].d(A)[msPA].m(U)[sP].m(C)[sP].m(A)[msPA].m(C)}|CHEM3{P}|CHEM4{TriGalNAc1} (SEQ ID NO: 12)</td><td>ACAUAAUUUACACGAAAGCAAUGCCAUCAC (SEQ ID NO: 11)</td></tr>
<tr><td>9.</td><td>CHEM1{TriGalNAc2}|CHEM2{P}|{f(A)[sP].f(C)[sP].f(A)[sP].f(U)[sP].f(A)[sP].f(A)[sP].f(U)[sP].f(U)[sP].f(U)[sP].f(A)[sP].f(C)[sP].f(A)[sP].f(C)[sP].f(G)[sP].f(A)[sP].m(A)[sP].m(A)[sP].m(G)[sP].m(C)[sP].m(A)[sP].m(A)[sP].m(U)[sP].m(G)[sP].f(C)[sP].d(C)[sP].d(A)[sP].m(U)[sP].m(C)[sP].m(A)[sP].m(C)} SEQ ID NO: 13)</td><td>ACAUAAUUUACACGAAAGCAAUGCCAUCAC (SEQ ID NO: 11)</td></tr>
<tr><td>10.</td><td>{f(A)[sP].f(C)[sP].f(A)[sP].f(U)[sP].f(A)[sP].f(A)[sP].f(U)[sP].f(U)[sP].f(U)[sP].f(A)[sP].f(C)[sP].f(A)[sP].f(C)[sP].f(G)[sP].f(A)[sP].m(A)[sP].m(A)[sP].m(G)[sP].m(C)[sP].m(A)[sP].m(A)[sP].m(U)[sP].m(G)[sP].f(C)[sP].d(C)[sP].d(A)[sP].m(U)[sP].m(C)[sP].m(A)[sP].m(C)}|CHEM3{P}|CHEM4{TriGalNAc1} (SEQ ID NO: 14)</td><td>ACAUAAUUUACACGAAAGCAAUGCCAUCAC (SEQ ID NO: 11)</td></tr>
</table>

TABLE 3-continued

Exemplary Oligonucleotides

| Oligo No. | Oligonucleotide sequence | Base sequence |
|---|---|---|
| 11. | CHEM1{TriGalNAc2}\|CHEM2{P}\|{f(G)[msPA].f(U)[sP].f(C)[sP]f(U)[sP].f(A)[sP].f(C)[sP].f(U)[sP].f(G)[sP].f(U)[sP].f(A)[sP].f(C)[sP].f(A)[P].f(G)[sP].f(A)[msPA].f(A)[P].m(U)[msPA].m(A)[sP].m(C)[sP].m(U)[sP].m(G)[sP].m(C)[sP].m(C)[sP].m(G)[sP].f(C)[sP].d(C)[sP].d(A)[msPA].m(G)[sP].m(C)[sP].m(U)[msPA].m(G)} (SERQ ID NO: 15) | GUCUACUGUACAGAAUACUGCCGCCAGCUG (SEQ ID NO: 16) |
| 12. | {f(G)[msPA].f(U)[sP].f(C)[sP].f(U)[sP].f(A)[sP].f(C)[P].f(U)[sP].f(G)[sP].f(U)[sP].f(A)[sP].f(C)[sP].f(A)[sP].f(G)[sP].f(A)[msPA].f(A)[sP].m(U)[msPA].m(A)[sP].m(C)[P].m(U)[sP].m(G)[sP].m(C)[sP].m(C)[sP].m(G)[sP].f(C)[P].d(C)[sP].d(A)[msPA].m(G)[sP].m(C)[sP].m(U)[msPA].m(G)}\|CHEM3{P}\|CHEM4{TriGaINAc1} (SEQ Id NO: 17) | GUCUACUGUACAGAAUACUGCCGCCAGCUG (SEQ ID NO: 16) |
| 13. | CHEM1{TriGalNAc2}\|CHEM2{P}\|{f(G)[sP].f(U)[sP].f(C)[sP].f(U)[sP].f(A)[sP].f(C)[sP].f(U)[sP].f(G)[sP].f(U)[sP].f(A)[sP].f(C)[sP].f(A)[sP].f(G)[sP].f(A)[sP].f(A)[P].m(U)[sP].m(A)[sP].m(C)[sP].m(U)[sP].m(G)[sP].m(C)[sP].m(C)[sP].m(G)[sP].f(C)[sP].d(C)[sP].d(A)[sP].m(G)[sP].m(C)[sP].m(U)[sP].m(G)} (SEQ ID NO: 18) | GUCUACUGUACAGAAUACUGCCGCCAGCUG (SEQ ID NO: 16) |
| 14. | {f(G)[sP].f(U)[sP].f(C)[sP].f(U)[sP].f(A)[sP].f(C)[sP].f(U)[sP].f(G)[sP].f(U)[sP].f(A)[sP].f(C)[sP].f(A)[sP].f(G)[sP].f(A)[sP].f(A)[sP].m(U)[sP].m(A)[sP].m(C)[P].m(U)[sP].m(G)[sP].m(C)[sP].m(C)[sP].m(G)[sP].f(C)[sP].d(C)[sP].d(A)[sP].m(G)[sP].m(C)[sP].m(U)[sP].m(G)}\|CHEM3{P}\|CHEM4{TriGalNAc1} (SEQ ID NO: 19) | GUCUACUGUACAGAAUACUGCCGCCAGCUG (SEQ ID NO: 16) |
| 15. | CHEM1{TriGalNAc2}\|CHEM2{P}\|{m(C)[msPA].m(C)[P].m(C)[sP].f(A)[sP].f(G)[sP].[moe]([m5C])P.[moe](A)P.f(G)[P].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[Dh](C)[sP].d(I)[msPA].m(U)P.f(C)[sP].m(G)[sP].m(A)[msPA].m(U)} (SEQ ID NO: 20) | CCCAGAGCTCAGUCCCUTTCTCIUCGAU (SEQ ID NO: 21) |
| 16. | CHEM1{TriGalNAc2}\|CHEM2{P}{m(C)[msPA].m(C)[sP].m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[msPA].m(A)} (SEQ ID NO: 22) | CCCAGAGCTCAGUCCCUTTCTCIUCGA (SEQ ID NO: 23) |
| 17. | CHEM1{TriGalNAc2}\|CHEM2{P}\|{m(C)[msPA].m(C)[sP].m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C[sP].f(C)[sP].f(C)[sP].f(U)[sP].[moe](T)P.[moe](T)P.f(C)[sP].d(T)[sP].[hd](C)[sP].d(I)[msPA].m(U)[sP].f(C)[msPA].m(G)} (SEQ ID NO: 24) | CCCAGAGCTCAGUCCCUTTCTCIUCG (SEQ ID NO: 25) |
| 18. | CHEM1{TriGalNAc2}\|CHEM2{P}\|{m(C)[msPA].m(A)[sP].m(U)[sP].m(G)[sP].m(G)P.m(C)P.m(C)P.m(C)P.m(C)P.f(A)[sP].f(G)[sP].[moe]([m5C])P.[moe](A)P.f(G)[P].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 26) | CAUGGCCCCAGAGCTCAGUCCCUTTCTCIUCGAU (SEQ ID NO: 27) |
| 19. | CHEM1{TriGalNAc2}\|CHEM2{P}\|{m(A)[msPA].m(U)[sP].m(G)[sP].m(G)[sP].m(C)P.m(C)P.m(C)P.m(C)P.f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[P].d(I)[msPA].m(U)P.f(C)[sP].m(G)[sP].m(A)[msPA].m(U)} (SEQ ID NO: 28) | AUGGCCCCAGAGCTCAGUCCCUTTCTCIUCGAU (SEQ ID NO: 29) |
| 20. | CHEM1{TriGalNAc2}\|CHEM2{P}\|{m(U)[msPA].m(G)[sP].m(G)[sP].m(C)[sP].m(C)P.m(C)P.m(C)P.f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 30) | UGGCCCCAGAGCTCAGUCCCUTTCTCIUCGAU (SEQ ID NO: 31) |

TABLE 3-continued

<table>
<tr><th colspan="3">Exemplary Oligonucleotides</th></tr>
<tr><th>Oligo No.</th><th>Oligonucleotide sequence</th><th>Base sequence</th></tr>
<tr><td>21.</td><td>CHEM1{TriGalNAc2}|CHEM2{P}|{m(C)[msPA].m(G)[sP].m(C)[sP].m(C)[sP].m(C)P.m(C)P.f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[P].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 32)</td><td>CGCCCCAGAGCTUCAGUCCCUTTCTCIUCGAU (SEQ ID NO: 33)</td></tr>
<tr><td>22.</td><td>CHEM1{TriGalNAc2}|CHEM2{P}|{m(G)[msPA].m(C)[sP].m(C)[sP].m(C)[sP].m(C)P.f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[P].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 34)</td><td>GCCCCAGAGCTUCAGUCCCUTTCTCIUCGAU (SEQ ID NO: 35)</td></tr>
<tr><td>23.</td><td>CHEM1{TriGalNAc2}|CHEM2{P}|{m(C)[msPA].m(C)[sP].m(C)[sP].m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 36)</td><td>CCCCAGAGCTUCAGUCCCUTTCTCIUCGAU (SEQ ID NO: 37)</td></tr>
<tr><td>24.</td><td>CHEM1{TriGalNAc2}|CHEM2{P}|{m(C)[msPA].m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 38)</td><td>CCAGAGCTUCAGUCCCUTTCTCIUCGAU (SEQ ID NO: 39)</td></tr>
<tr><td>25.</td><td>CHEM1{TriGalNAc2}|CHEM2{P}|{m(C)[msPA].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[P].d(T)[sP].[hd](C)[sP].d(I)[msPA].m(U)P.f(C)[sP].m(G)[sP].m(A)[msPA].m(U)} (SEQ ID NO: 40)</td><td>CAGAGCTUCAGUCCCUTTCTCIUCGAU (SEQ ID NO: 41)</td></tr>
<tr><td>26.</td><td>CHEM1{TriGalNAc2}|CHEM2{P}|{f(A)[msPA].f(G)[sP].[moe]([m5C])[sP].[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 42)</td><td>AGAGCTUCAGUCCCUTTCTCIUCGAU (SEQ ID NO: 43)</td></tr>
<tr><td>27.</td><td>CHEM1{TriGalNAc2}|CHEM2{P}|{f(G)[msPA].[moe]([m5C])[sP].[moe](A)[sP].f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 44)</td><td>GAGCTUCAGUCCCUTTCTCIUCGAU (SEQ ID NO: 45)</td></tr>
<tr><td>28.</td><td>CHEM1{TriGalNAc2}|CHEM2{P}|{[moe]([m5C])[msPA].[moe](A)[sP].f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 46)</td><td>AGCTUCAGUCCCUTTCTCIUCGAU (SEQ ID NO: 47)</td></tr>
<tr><td>29.</td><td>CHEM1{TriGalNAc2}|CHEM2{P}|{[moe](A)[msPA].f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 48)</td><td>AGCTUCAGUCCCUTTCTCIUCGAU (SEQ ID NO: 49)</td></tr>
<tr><td>30.</td><td>CHEM1{TriGalNAc2}|CHEM2{P}|{f(G)[msPA].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 50)</td><td>GCTUCAGUCCCUTTCTCIUCGAU (SEQ ID NO: 51)</td></tr>
<tr><td>31.</td><td>CHEM1{TriGalNAc2}|CHEM2{P}|{m(C)[msPA].m(C)[sP].m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[msPA].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 52)</td><td>CCCAGCAGCTUCAGUCCCUTCTCIUCGAU (SEQ ID NO: 53)</td></tr>
</table>

TABLE 3-continued

| Exemplary Oligonucleotides | | |
|---|---|---|
| Oligo No. | Oligonucleotide sequence | Base sequence |
| 32. | CHEM1{TriGalNAc2}\|CHEM2{P}\|{m(C)[sP].m(C)[sP].m(C)[sP].f(A)[sP].f(G)[sP].[moe]([m5C])P.[moe](A)P.f(G)[sP].f(C)[sP].[moe](T)P.f(U)[sP].m(C)P.f(A)[sP].m(G)[P].f(U)P.m(C)[sP].f(C)[sP].f(C)[sP].f(U)[sP].[moe](T)P.[moe](T)P.f(C)[sP].d(T)[sP].[hd](C)[sP].d(I)[sP].m(U)P.f(C)[sP].m(G)[sP].m(A)[sP].m(U)} (SEQ ID NO: 54) | CCCAGCAGCTUCAGUCCCUTTCTCIUCGAU (SEQ ID NO: 53) |
| 33. | CHEM1{TriGalNAc2}\|CHEM2{P}\|{m(C)[msPA].m(C)[sP].m(C)[sP].f(A)[sP].f(G)[sP].[moe]([m5C])[sP].[moe](A)[sP].f(G)[sP].f(C)[sP].[moe](T)[sP].f(U)[msPA].m(C)[P].f(A)[sP].m(G)[msPA].f(U)[sP].m(C)[sP].f(C)[sP].f(C)[sP].f(U)[sP].[moe](T)[sP].[moe](T)[sP].f(C)[sP].d(T)[sP].[hd](C)[sP].d(I)[msPA].m(U)[sP].f(C)[sP].m(G)[sP].m(A)[msPA].m(U)} (SEQ ID NO: 55) | CCCAGCAGCTUCAGUCCCUTTCTCIUCGAU (SEQ ID NO: 53) |
| 34. | CHEM1{TriGalNAc2}\|CHEM2{P}\|{m(C)[msPA].m(C)[sP].m(C)[sP].f(A)[sP].f(G)[sP].[moe]([m5C])P.[moe](A)P.f(G)[sP].f(C)[sP].[moe](T)[msPA].f(U)[sP].m(C)[msPA].f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 56) | CCCAGCAGCTUCAGUCCCUTTCTCIUCGAU (SEQ ID NO: 53) |
| 35. | CHEM1{TriGalNAc2}\|CHEM2{P}{m(C)[sP].m(C)[sP].m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[P].m(A)[msPA].m(U)} (SEQ ID NO: 57) | CCCAGCAGCTUCAGUCCCUTTCTCIUCGAU (SEQ ID NO: 53) |
| 36. | CHEM1{TriGalNAc2}\|CHEM2{P}\|{m(C)[msPA].m(C)[sP].m(C)[sP].f(A)[sP].f(G)[sP].[moe]([m5C])P.[moe](A)P.f(G)[sP].f(C)[sP].[moe](T)P.f(U)[sP].m(C)P.f(A)[sP].m(G)[msPA].f(U)P.m(C)[sP].f(C)[sP].f(C)[P].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 58) | CCCAGCAGCTUCAGUCCCUTTCTCIUCGAU (SEQ ID NO: 53) |
| 37. | CHEM1{TriGalNAc2}\|CHEM2{P}\|{m(C)[msPA].m(C)[sP].m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[sP].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 59) | CCCAGCAGCTUCAGUCCCUTTCTCIUCGAU (SEQ ID NO: 53) |
| 38. | CHEM1{TriGalNAc2}\|CHEM2{P}\|{m(C)[msPA].m(C)[sP].m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[sP].m(U)P.f(C)[sP].m(G)[sP].m(A)[msPA].m(U)} (SEQ ID NO: 60) | CCCAGCAGCTUCAGUCCCUTTCTCIUCGAU (SEQ ID NO: 53) |
| 39. | CHEM1{TriGalNAc2}\|CHEM2{P}\|{m(C)[msPA].m(C)[sP].m(C)[sP].f(A)[sP].f(G)[sP].[moe]([m5C])P.[moe](A)P.f(G)[P].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[sP].m(U)} (SEQ ID NO: 61) | CCCAGCAGCTUCAGUCCCUTTCTCIUCGAU (SEQ ID NO: 53) |
| 40. | CHEM1{TriGalNAc2}\|CHEM2{P}\|{m(C)[msPA].m(C)[msPA].m(C)[sP].f(A)[sP].f(G)[sP].[moe]([m5C])P.[moe](A)P.f(G)[sP].f(C)[sP].[moe](T)P.f(U)[msPA].m(C)P.f(A)[P].m(G)[msPA].f(U)P.m(C)[sP].f(C)[P].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 62) | CCCAGCAGCTUCAGUCCCUTTCTCIUCGAU (SEQ ID NO: 53) |
| 41. | CHEM1{TriGalNAc2}\|CHEM2{P}\|{m(C)[msPA].m(C)[sP].m(C)[msPA].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[P].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 63) | CCCAGCAGCTUCAGUCCCUTTCTCIUCGAU (SEQ ID NO: 53) |
| 42. | CHEM1{TriGalNAc2}\|CHEM2{P}\|{m(C)[msPA].m(C)[sP].m(C)[sP].f(A)[msPA].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[s | CCCAGCAGCTUCAGUCCCUTTCTCIUCGAU (SEQ ID NO: 53) |

TABLE 3-continued

| Oligo No. | Oligonucleotide sequence | Base sequence |
|---|---|---|
| | Exemplary Oligonucleotides | |
| | P].d(T)[sP].[hd](C)[sP].d(I)[msPA].m(U)P.f(C)[sP].m(G)[sP].m(A)[msPA].m(U)} (SEQ ID NO: 64) | |
| 43. | CHEM1{TriGalNAc2}\|CHEM2{P}\|{m(C)[msPA].m(C)[sP].m(C)[sP].f(A)[sP].f(G)[msPA].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 65) | CCCAGCAGCTUCAGUCCCUTTCTCIUCGAU (SEQ ID NO: 53) |
| 44. | CHEM1{TriGalNAc2}\|CHEM2{P}{m(C)[msPA].m(C)[sP].m(C)[sP].f(A)[sP].f(G)[sP].[moe]([m5C])[msPA].[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 66) | CCCAGCAGCTUCAGUCCCUTTCTCIUCGAU (SEQ ID NO: 53) |
| 45. | CHEM1{TriGalNAc2}\|CHEM2{P}{m(C)[msPA].m(C)[sP].m(C)[sP].f(A)[sP].f(G)[sP].[moe]([m5C])P.[moe](A)[msPA].f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 67) | CCCAGCAGCTUCAGUCCCUTTCTCIUCGAU (SEQ ID NO: 53) |
| 46. | CHEM1{TriGalNAc2}\|CHEM2{P}\|{m(C)[msPA].m(C)[sP].m(C)[sP].f(A)[sP].f(G)[sP].[moe]([m5C])P.[moe](A)P.f(G)[msPA].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 68) | CCCAGCAGCTUCAGUCCCUTTCTCIUCGAU (SEQ ID NO: 53) |
| 47. | CHEM1{TriGalNAc2}\|CHEM2{P}\|{m(C)[msPA].m(C)[sP].m(C)[sP].f(A)[sP].f(G)[sP].[moe]([m5C])P.[moe](A)P.f(G)[sP].f(C)[msPA].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 69) | CCCAGCAGCTUCAGUCCCUTTCTCIUCGAU (SEQ ID NO: 53) |
| 48. | CHEM1{TriGalNAc2}\|CHEM2{P}\|{m(C)[msPA].m(C)[sP].m(C)[sP].f(A)[sP].f(G)[sP].[moe]([m5C])P.[moe](A)P.f(G)[sP].f(C)[sP].[moe](T)[msPA].f(U)[msPA].m(C)P.f(A)[sP].m(G)[msPA].f(U)P.m(C)[sP].f(C)[P].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 70) | CCCAGCAGCTUCAGUCCCUTTCTCIUCGAU (SEQ ID NO: 53) |
| 49. | CHEM1{TriGalNAc2}\|CHEM2{P}\|{m(C)[msPA].m(C)[sP].m(C)[sP].f(A)[sP].f(G)[sP].[moe]([m5C])P.[moe](A)P.f(G)[P].f(C)[sP].[moe](T)P.f(U)[msPA].m(C)[msPA].f(A)[sP].m(G)[msPA].f(U)P.m(C)[sP].f(C)[sP].f(C)[P].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 71) | CCCAGCAGCTUCAGUCCCUTTCTCIUCGAU (SEQ ID NO: 53) |
| 50. | CHEM1{TriGalNAc2}\|CHEM2{P}\|{m(C)[msPA].m(C)[sP].m(C)[sP].f(A)[sP].f(G)[sP].[moe]([m5C])P.[moe](A)P.f(G)[sP].f(C)[sP].[moe](T)P.f(U)[msPA].m(C)P.f(A)[msPA].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 72) | CCCAGCAGCTUCAGUCCCUTTCTCIUCGAU (SEQ ID NO: 53) |
| 51. | CHEM1{TriGalNAc2}\|CHEM2{P}\|{m(C)[msPA].m(C)[sP].m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)[msPA].m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 73) | CCCAGCAGCTUCAGUCCCUTTCTCIUCGAU (SEQ ID NO: 53) |
| 52. | CHEM1{TriGalNAc2}\|CHEM2{P}\|{m(C)[msPA].m(C)[sP].m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[msPA].f(C)[P].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 74) | CCCAGCAGCTUCAGUCCCUTTCTCIUCGAU (SEQ ID NO: 53) |

TABLE 3-continued

<table>
<tr><th colspan="3">Exemplary Oligonucleotides</th></tr>
<tr><th>Oligo No.</th><th>Oligonucleotide sequence</th><th>Base sequence</th></tr>
<tr><td>53.</td><td>CHEM1{TriGalNAc2}|CHEM2{P}|{m(C)[msPA].m(C)[sP].m(C)<br>[sP].f(A)[sP].f(G)[sP].[moe]([m5C])P.[moe](A)P.f(G)[sP].f(C)[sP].<br>[moe](T)P.f(U)[msPA].m(C)P.f(A)[sP].m(G)[msPA].f(U)P.m(C)<br>[sP].f(C)[msPA].f(C)[sP].f(U)[sP].[moe](T)P.[moe](T)P.f(C)[sP].<br>d(T)[sP].[hd](C)[sP].d(I)[msPA].m(U)P.f(C)[sP].m(G)[P].m(A)<br>[msPA].m(U)} (SEQ ID NO: 75)</td><td>CCCAGCAGCTUCAGUCCCUT<br>TCTCIUCGAU (SEQ ID<br>NO: 53)</td></tr>
<tr><td>54.</td><td>CHEM1{TriGalNAc2}|CHEM2{P}|{m(C)[msPA].m(C)[sP].m(C)<br>[sP].f(A)[sP].f(G)[sP].[moe]([m5C])P.[moe](A)P.f(G)[sP].f(C)<br>[sP].[moe](T)P.f(U)[msPA].m(C)P.f(A)[sP].m(G)[msPA].f(U)P.m<br>(C)[sP].f(C)[sP].f(C)[msPA].f(U)[sP].[moe](T)P.[moe](T)P.f(C)<br>[sP].d(T)[sP].[hd](C)[sP].d(I)[msPA].m(U)P.f(C)[sP].m(G)[sP].m<br>(A)[msPA].m(U)} (SEQ ID NO: 76)</td><td>CCCAGCAGCTUCAGUCCCUT<br>TCTCIUCGAU (SEQ ID<br>NO: 53)</td></tr>
<tr><td>55.</td><td>CHEM1{TriGalNAc2}|CHEM2{P}|{m(C)[msPA].m(C)[sP].m(C)<br>[sP].f(A)[sP].f(G)[sP].[moe]([m5C])P.[moe](A)P.f(G)[sP].f(C)<br>[sP].[moe](T)P.f(U)[msPA].m(C)P.f(A)[sP].m(G)[msPA].f(U)P.m(C)<br>[sP].f(C)[sP].f(C)[sP].f(U)[sP].[moe](T)[msPA].[moe](T)P.f(C)<br>[sP].d(T)[sP].[hd](C)[sP].d(I)[msPA].m(U)P.f(C)[sP].m(G)[sP].<br>m(A)[msPA].m(U)} (SEQ ID NO: 77)</td><td>CCCAGCAGCTUCAGUCCCUT<br>TCTCIUCGAU (SEQ ID<br>NO: 53)</td></tr>
<tr><td>56.</td><td>CHEM1{TriGalNAc2}|CHEM2{P}|{m(C)[msPA].m(C)[sP].m(C)<br>[sP].f(A)[sP].f(G)[sP].[moe]([m5C])P.[moe](A)P.f(G)[sP].f(C)<br>[sP].[moe](T)P.f(U)[msPA].m(C)P.f(A)[sP].m(G)[msPA].f(U)P.m(C<br>[sP].f(C)[sP].f(C)[sP].f(U)[sP].[moe](T)P.[moe](T)[msPA].f(C)<br>[sP].d(T)[sP].[hd](C)[sP].d(I)[msPA].m(U)P.f(C)[sP].m(G)[sP].<br>m(A)[msPA].m(U)} (SEQ ID NO: 78)</td><td>CCCAGCAGCTUCAGUCCCUT<br>TCTCIUCGAU (SEQ ID<br>NO: 53)</td></tr>
<tr><td>57.</td><td>CHEM1{TriGalNAc2}|CHEM2{P}{m(C)[msPA].m(C)[P].m(C)<br>[sP].f(A)[sP].f(G)[sP].[moe]([m5C])P.[moe](A)P.f(G)[sP].f(C)<br>[sP].[moe](T)P.f(U)[msPA].m(C)P.f(A)[sP].m(G)[msPA].f(U)P.m(C)<br>[sP].f(C)[sP].f(C)[sP].f(U)[sP].[moe](T)P.[moe](T)P.f(C)[msPA].<br>d(T)[sP].[hd](C)[sP].d(I)[msPA].m(U)P.f(C)[sP].m(G)[sP].m(A)<br>[msPA].m(U)} (SEQ ID NO: 79)</td><td>CCCAGCAGCTUCAGUCCCUT<br>TCTCIUCGAU (SEQ ID<br>NO: 53)</td></tr>
<tr><td>58.</td><td>CHEM1{TriGalNAc2}|CHEM2{P}|{m(C)[msPA].m(C)[sP].m(C)<br>[sP].f(A)[sP].f(G)[sP].[moe]([m5C])P.[moe](A)P.f(G)[sP].f(C)<br>[sP].[moe](T)P.f(U)[msPA].m(C)P.f(A)[sP].m(G)[msPA].f(U)P.m(C)<br>[sP].f(C)[sP].f(C)[P].f(U)[sP].[moe](T)P.[moe](T)P.f(C)[sP].d<br>(T)[sP].[hd](C)[sP].d(I)[msPA].m(U)[msPA].f(C)[sP].m(G)[sP].m<br>(A)[msPA].m(U)} (SEQ ID NO: 80)</td><td>CCCAGCAGCTUCAGUCCCUT<br>TCTCIUCGAU (SEQ ID<br>NO: 53)</td></tr>
<tr><td>59.</td><td>CHEM1{TriGalNAc2}|CHEM2{P}|{m(C)[msPA].m(C)[sP].m(C)<br>[sP].f(A)[sP].f(G)[sP].[moe]([m5C])P.[moe](A)P.f(G)[P].f(C)<br>[sP].[moe](T)P.f(U)[msPA].m(C)P.f(A)[sP].m(G)[msPA].f(U)P.m(C)<br>[sP].f(C)[sP].f(C)[P].f(U)[sP].[moe](T)P.[moe](T)P.f(C)[sP].d<br>(T)[sP].[hd](C)[sP].d(I)[msPA].m(U)P.f(C)[msPA].m(G)[sP].m(A)<br>[msPA].m(U)} (SEQ ID NO: 81)</td><td>CCCAGCAGCTUCAGUCCCUT<br>TCTCIUCGAU (SEQ ID<br>NO: 53)</td></tr>
<tr><td>60.</td><td>CHEM1{TriGalNAc2}|CHEM2{P}|{m(C)[msPA].m(C)[sP].m(C)<br>[sP].f(A)[sP].f(G)[sP].[moe]([m5C])P.[moe](A)P.f(G)[sP].f(C)<br>[sP].[moe](T)P.f(U)[msPA].m(C)P.f(A)[sP].m(G)[msPA].f(U)P.m(C)<br>[sP].f(C)[sP].f(C)[sP].f(U)[sP].[moe](T)P. [moe](T)P.f(C)[sP].d<br>(T)[sP].[hd](C)[sP].d(I)[msPA].m(U)P.f(C)[sP].m(G)[msPA].m(A)<br>[msPA].m(U)} (SEQ ID NO: 82)</td><td>CCCAGCAGCTUCAGUCCCUT<br>TCTCIUCGAU (SEQ ID<br>NO: 53)</td></tr>
<tr><td>61.</td><td>CHEM1{TriGalNAc2}|CHEM2{P}|{m(C)[msPA].m(C)[sP].m(C)<br>[sP].m(A)[sP].f(G)[sP].[moe]([m5C])P.[moe](A)P.f(G)[P].f(C)[s<br>P].[moe](T)P.f(U)[msPA].m(C)P.f(A)[sP].m(G)[msPA].f(U)P.m<br>(C)[sP].f(C)[sP].f(C)[sP].f(U)[sP].[moe](T)P.[moe](T)P.f(C)[sP].<br>d(T)[sP].[hd](C)[sP].d(I)[msPA].m(U)P.f(C)[sP].m(G)[sP].m(A)<br>[msPA].m(U)} (SEQ ID NO: 83)</td><td>CCCAGCAGCTUCAGUCCCUT<br>TCTCIUCGAU (SEQ ID<br>NO: 53)</td></tr>
<tr><td>62.</td><td>CHEM1{TriGalNAc2}|CHEM2{P}|{m(C)[msPA].m(C)[sP].m(C)<br>[sP].f(A)[sP].m(G)[sP].[moe]([m5C])P.[moe](A)P.f(G)[sP].f(C)[s<br>P].[moe](T)P.f(U)[msPA].m(C)P.f(A)[sP].m(G)[msPA].f(U)P.m(<br>C)[sP].f(C)[sP].f(C)[sP].f(U)[sP].[moe](T)P.[moe](T)P.f(C)[sP].<br>d(T)[sP].[hd](C)[sP].d(I)[msPA].m(U)P.f(C)[sP].m(G)[sP].m(A)<br>[msPA].m(U)} (SEQ ID NO: 84)</td><td>CCCAGCAGCTUCAGUCCCUT<br>TCTCIUCGAU (SEQ ID<br>NO: 53)</td></tr>
<tr><td>63.</td><td>CHEM1{TriGalNAc2}|CHEM2{P}|{m(C)[msPA].m(C)[sP].m(C)<br>[sP].f(A)[sP].f(G)[sP].m(C)P.[moe](A)P.f(G)[sP].f(C)[sP].[moe]<br>(T)P.f(U)[msPA].m(C)P.f(A)[sP].m(G)[msPA].f(U)P.m(C)[sP].f<br>(C)[sP].f(C)[sP].f(U)[sP].[moe](T)P.[moe](T)P.f(C)[sP].d(T)[sP].</td><td>CCCAGCAGCTUCAGUCCCUT<br>TCTCIUCGAU (SEQ ID<br>NO: 53)</td></tr>
</table>

TABLE 3-continued

<table>
<tr><th colspan="3">Exemplary Oligonucleotides</th></tr>
<tr><th>Oligo No.</th><th>Oligonucleotide sequence</th><th>Base sequence</th></tr>
<tr><td></td><td>[hd](C)[sP].d(I)[msPA].m(U)P.f(C)[sP].m(G)[sP].m(A)[msPA].m(U)} (SEQ ID NO: 85)</td><td></td></tr>
<tr><td>64.</td><td>CHEM1{TriGalNAc2}|CHEM2{P}|{m(C)[msPA].m(C)[sP].m(C)[sP].f(A)[sP].f(G)[sP].[moe]([m5C])P.m(A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 86)</td><td>CCCAGCAGCTUCAGUCCCUTTCTCIUCGAU (SEQ ID NO: 53)</td></tr>
<tr><td>65.</td><td>CHEM1{TriGalNAc2}|CHEM2{P}|{m(C)[msPA].m(C)[sP].m(C)[sP].f(A)[sP].f(G)[sP].[moe]([m5C])P.[moe](A)P.m(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 87)</td><td>CCCAGCAGCTUCAGUCCCUTTCTCIUCGAU (SEQ ID NO: 53)</td></tr>
<tr><td>66.</td><td>CHEM1{TriGalNAc2}|CHEM2{P}|{m(C)[msPA].m(C)[sP].m(C)[sP].f(A)[sP].f(G)[sP].[moe]([m5C])P.[moe](A)P.f(G)[sP].m(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 88)</td><td>CCCAGCAGCTUCAGUCCCUTTCTCIUCGAU (SEQ ID NO: 53)</td></tr>
<tr><td>67.</td><td>CHEM1{TriGalNAc2}|CHEM2{P}{m(C)[msPA].m(C)[sP].m(C)[sP].f(A)[sP].f(G)[sP].[moe]([m5C])P.[moe](A)P.f(G)[sP].f(C)[sP1.m(U)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 89)</td><td>CCCAGCAGCTUCAGUCCCUTTCTCIUCGAU (SEQ ID NO: 53)</td></tr>
<tr><td>68.</td><td>CHEM1{TriGalNAc2}|CHEM2{P}|{m(C)[msPA].m(C)[sP].m(C)[sP].f(A)[sP].f(G)[sP].[moe]([m5C])P.[moe](A)P.f(G)[sP].f(C)[sP].[moe](T)P.m(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 90)</td><td>CCCAGCAGCTUCAGUCCCUTTCTCIUCGAU (SEQ ID NO: 53)</td></tr>
<tr><td>69.</td><td>CHEM1{TriGalNAc2}|CHEM2{P}|{m(C)[msPA].m(C)[sP].m(C)[sP].f(A)[sP].f(G)[sP].[moe]([m5C])P.[moe](A)P.f(G)[P].f(C)[sP].[moe](T)P.f(U)[msPA].m(C)P.m(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[P].m(G)[sP].m(A)[msPA].m(U)} (SEQ ID NO: 91)</td><td>CCCAGCAGCTUCAGUCCCUTTCTCIUCGAU (SEQ ID NO: 53)</td></tr>
<tr><td>70.</td><td>CHEM1{TriGalNAc2}|CHEM2{P}|{m(C)[msPA].m(C)[sP].m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].m(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 92)</td><td>CCCAGCAGCTUCAGUCCCUTTCTCIUCGAU (SEQ ID NO: 53)</td></tr>
<tr><td>71.</td><td>CHEM1{TriGalNAc2}|CHEM2{P}{m(C)[msPA].m(C)[sP].m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].m(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 93)</td><td>CCCAGCAGCTUCAGUCCCUTTCTCIUCGAU (SEQ ID NO: 53)</td></tr>
<tr><td>72.</td><td>CHEM1{TriGalNAc2}|CHEM2{P}|{m(C)[msPA].m(C)[sP].m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[sP].m(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 94)</td><td>CCCAGCAGCTUCAGUCCCUTTCTCIUCGAU (SEQ ID NO: 53)</td></tr>
<tr><td>73.</td><td>CHEM1{TriGalNAc2}|CHEM2{P}|{m(C)[msPA].m(C)[sP].m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].m(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 95)</td><td>CCCAGCAGCTUCAGUCCCUTTCTCIUCGAU (SEQ ID NO: 53)</td></tr>
</table>

TABLE 3-continued

<table>
<tr><th colspan="3">Exemplary Oligonucleotides</th></tr>
<tr><th>Oligo No.</th><th>Oligonucleotide sequence</th><th>Base sequence</th></tr>
<tr><td>74.</td><td>CHEM1{TriGalNAc2}|CHEM2{P}|{m(C)[msPA].m(C)[sP].m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].m(U)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 96)</td><td>CCCACGAGCTUCAGUCCCUUTCTCIUCGAU (SEQ ID NO: 97)</td></tr>
<tr><td>75.</td><td>CHEM1{TriGalNAc2}|CHEM2{P}|{m(C)[msPA].m(C)[sP].m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.m(U)P.f(C)[sP].d(T)[sP].[hd](C)[sP].d(I)[msPA].m(U)P.f(C)[sP].m(G)[sP].m(A)[msPA].m(U)} (SEQ ID NO: 98)</td><td>CCCACGAGCTUCAGUCCCUTUCTCIUCGAU (SEQ ID NO: 99)</td></tr>
<tr><td>76.</td><td>CHEM1{TriGalNAc2}|CHEM2{P}|{m(C)[msPA].m(C)[sP].m(C)[[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.m(C)[sP].d(T)[sP].[hd](C)[sP].d(I)[msPA].m(U)P.f(C)[sP].m(G)[sP].m(A)[msPA].m(U)} (SEQ ID NO: 100)</td><td>CCCAGCAGCTUCAGUCCCUTTCTCIUCGAU (SEQ ID NO: 53)</td></tr>
<tr><td>77.</td><td>CHEM1{TriGalNAc2}|CHEM2{P}|{m(C)[msPA].m(C)[sP].m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.m(C)[sP].m(G)[sP].m(A)[msPA].m(U)} (SEQ ID NO: 101)</td><td>CCCACGAGCTUCAGUCCCUTTCTCIUCGAU (SEQ ID 53)</td></tr>
<tr><td>78.</td><td>CHEM1{TriGalNAc2}|CHEM2{P}[{m(C)[msPA].m(C)[sP].m(C)[sP].m(A)[sP].m(G)[sP].m(C)P.m(A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 102)</td><td>CCCAGCAGCTUCAGUCCCUTTCTCIUCGAU (SEQ ID NO: 53)</td></tr>
<tr><td>79.</td><td>CHEM1{TriGalNAc2}|CHEM2{P}|{m(C)[msPA].m(C)[sP].m(C)[sP].f(A)[sP].f(G)[sP].[moe]([m5C])P.[moe](A)P.m(G)[sP].m(C)[sP].m(U)P.m(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 103)</td><td>CCCAGCAGCTUCAGUCCCUTTCTCIUCGAU (SEQ ID NO: 53)</td></tr>
<tr><td>80.</td><td>CHEM1{TriGalNAc2}|CHEM2{P}|{m(C)[msPA].m(C)[sP].m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].m(C)[sP].m(C)[sP].m(U)[sP].[moe](T)P.[moe](T)P.f(C)[sP].d(T)[sP].[hd](C)[sP].d(I)[msPA].m(U)P.f(C)[sP].m(G)[sP].m(A)[msPA].m(U)} (SEQ ID NO: 104)</td><td>CCCAGCAGCTUCAGUCCCUTTCTCIUCGAU (SEQ ID NO: 53)</td></tr>
<tr><td>81.</td><td>CHEM1{TriGalNAc2}|CHEM2{P}|{m(C)[msPA].m(C)[sP].m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].m(U)P.m(U)P.m(C)[sP].d(T)[sP].[hd](C)[sP].d(I)[msPA].m(U)P.f(C)[sP].m(G)[sP].m(A)[msPA].m(U)} (SEQ ID NO: 105)</td><td>CCCAGCAGCTUCAGUCCCUUUCTCIUCGAU (SEQ ID NO: 106)</td></tr>
<tr><td>82.</td><td>CHEM1{TriGalNAc2}|CHEM2{P}|{m(C)[msPA].m(C)[sP].m(C)[sP].f(A)[sP].f(G)[sP].m(C)P.m(A)P.f(G)[sP].f(C)[sP].m(U)P.f(U)[msPA].m(C)P.f(A)[sP].m(G)[msPA].f(U)P.m(C)[sP].f(C)[sP].f(C)[sP].f(U)[sP].m(U)P.m(U)P.f(C)[sP].d(T)[sP].[hd](C)[sP].d(I)[msPA].m(U)P.f(C)[sP].m(G)[sP].m(A)[msPA].m(U)} (SEQ ID NO: 107)</td><td>CCCAGCAGCUUCAGUCCCUUUCTCIUCGAU (SEQ ID NO: 108)</td></tr>
<tr><td>83.</td><td>{f(A)[msPA].f(A)[msPA].m(C)P.m(A)[sP].f(U)[P].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[sP].f(U)[sP].m(C)[sP].d(T)[sP].[hd](C)[sP].[fana](I)[msPA].m(U)[sP].f(C)[sP].m(G)P.m(A)P.m(U)P.m(G)[P].f(G)[sP].f(U)[msPA].m(C)} (SEQ ID NO: 109)</td><td>AACAUGGCCCCAGCAGCUUCAGUCCCUUUCTCIUCGAUGGUC (SEQ ID NO: 2)</td></tr>
<tr><td>84.</td><td>{f(A)[msPA].f(A)[sP].m(C)[msPA].m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)</td><td>AACAUGGCCCCAGCAGCUUCAGUCCCUUUCTCIUCGAUGGUC (SEQ ID NO: 2)</td></tr>
</table>

TABLE 3-continued

Exemplary Oligonucleotides

| Oligo No. | Oligonucleotide sequence | Base sequence |
|---|---|---|
| | [msPA].f(G)[sP].f(U)[msPA].m(C)[sP].f(C)[sP].f(C)[sP].f(U)[sP].m(U)[sP].f(U)[sP].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} (SEQ ID NO: 110) | |
| 85. | {f(A)[msPA].f(A)[sP].m(C)P.m(A)[msPA].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[P].f(C)[sP].f(U)[sP].m(U)[sP].f(U)[sP].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} (SEQ ID NO: 111) | AACAUGGCCCCAGCAGCUUCAGUCCCUUUCTCIUCGAUGGUC (SEQ ID NO: 2) |
| 86. | {f(A)[msPA].f(A)[sP].m(C)P.m(A)[sP].f(U)[msPA].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[P].m(U)P.m(C)P.m(A)[msPA].f(G)[sP].f(U)[msPA].m(C)[P].f(C)[sP].f(C)[sP].f(U)[sP].m(U)[P].f(U)[sP].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} (SEQ ID NO: 112) | AACAUGGCCCCAGCAGCUUCAGUCCCUUUCTCIUCGAUGGUC (SEQ ID NO: 2) |
| 87. | {f(A)[msPA].f(A)[sP].m(C)P.m(A)[sP].f(U)[sP].f(G)[msPA].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[sP].f(U)[sP].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} (SEQ ID NO: 113) | AACAUGGCCCCAGCAGCUUCAGUCCCUUUCTCIUCGAUGGUC (SEQ ID NO: 2) |
| 88. | {f(A)[msPA].f(A)[sP].m(C)P.m(A)[P].f(U)[sP].f(G)[sP].f(G)[msPA].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[sP].f(U)[sP].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} (SEQ ID NO: 114) | AACAUGGCCCCAGCAGCUUCAGUCCCUUUCTCIUCGAUGGUC (SEQ ID NO: 2) |
| 89. | {f(A)[msPA].f(A)[sP].m(C)P.m(A)[sP].f(U)[sP].f(G)[sP].f(G)[sP].f(C)[msPA].m(C)[sP].f(C)[sP].m(C)[sP].f(A)[P].m(G)P.m(C)[sP].f(A)[sP].f(G)[sP].m(C)[P].f(U)[sP].m(U)P.m(C)P.m(A)[msPA].f(G)[sP].f(U)[msPA].m(C)[sP].f(C)[sP].f(C)[sP].f(U)[sP].m(U)[sP].f(U)[sP].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} (SEQ ID NO: 115) | AACAUGGCCCCAGCAGCUUCAGUCCCUUUCTCIUCGAUGGUC (SEQ ID NO: 2) |
| 90. | {f(A)[msPA].f(A)[sP].m(C)P.m(A)[sP].f(U)[sP].f(G)[sP].f(G)[sP].f(C)[sP].m(C)[msPA].f(C)[sP].m(C)[sP].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[sP].f(U)[sP].m(C)[sP].d(T)[sP].[hd](C)[sP].[fana](I)[msPA].m(U)[sP].f(C)[sP].m(G)P.m(A)P.m(U)P.m(G)[P].f(G)[sP].f(U)[msPA].m(C)} (SEQ ID NO: 116) | AACAUGGCCCCAGCAGCUUCAGUCCCUUUCTCIUCGAUGGUC (SEQ ID NO: 2) |
| 91. | {f(A)[msPA].f(A)[sP].m(C)P.m(A)[sP].f(U)[sP].f(G)[sP].f(G)[sP].f(C)[sP].m(C)[sP].f(C)[msPA].m(C)[sP].f(A)[sP].m(G)P.m(C)[sP].f(A)[sP].f(G)[sP].m(C)[P].f(U)[sP].m(U)P.m(C)P.m(A)[msPA].f(G)[sP].f(U)[msPA].m(C)[sP].f(C)[sP].f(C)[sP].f(U)[sP].m(U)[sP].f(U)[sP].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} (SEQ ID NO: 117) | AACAUGGCCCCAGCAGCUUCAGUCCCUUUCTCIUCGAUGGUC (SEQ ID NO: 2) |
| 92. | {f(A)[msPA].f(A)[sP].m(C)P.m(A)[sP].f(U)[sP].f(G)[sP].f(G)[sP].f(C)[sP].m(C)[sP].f(C)[sP].m(C)[msPA].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[P].f(U)[sP].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} (SEQ ID NO: 118) | AACAUGGCCCCAGCAGCUUCAGUCCCUUUCTCIUCGAUGGUC (SEQ ID NO: 2) |
| 93. | {f(A)[msPA].f(A)[sP].m(C)P.m(A)[sP].f(U)[sP].f(G)[sP].f(G)[P].f(C)[sP].m(C)[sP].f(C)[sP].m(C)[sP].f(A)[msPA].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[P].f(C)[sP].f(U)[sP].m(U) | AACAUGGCCCCAGCAGCUUCAGUCCCUUUCTCIUCGAUGGUC (SEQ ID NO: 2) |

TABLE 3-continued

| Oligo No. | Exemplary Oligonucleotides<br>Oligonucleotide sequence | Base sequence |
|---|---|---|
| | [sP].f(U)[sP].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} (SEQ ID NO: 119) | |
| 94. | {f(A)[msPA].f(A)[sP].m(C)P.m(A)[sP].f(U)[P].f(G)[sP].f(G)[sP].f(C)[sP].m(C)[sP].f(C)[sP].m(C)[sP].f(A)[P].m(G)[msPA].m(C)[sP].f(A)[sP].f(G)[P].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[sP].f(U)[sP].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} (SEQ ID NO: 120) | AACAUGGCCCCAGCAGCUUCAGUCCCUUUCTCIUCGAUGGUC (SEQ ID NO: 2) |
| 95. | {f(A)[msPA].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[msPA].f(A)[sP].f(G)[sP].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[sP].f(U)[sP].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} (SEQ ID NO: 121) | AACAUGGCCCCAGCAGCUUCAGUCCCUUUCTCIUCGAUGGUC (SEQ ID NO: 2) |
| 96. | {f(A)[msPA].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[msPA].f(G)[sP].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[sP].f(U)[sP].m(C)[sP].d(T)[sP].[hd](C)[sP].[fana](I)[msPA].m(U)[sP].f(C)[sP].m(G)P.m(A)P.m(U)P.m(G)[P].f(G)[sP].f(U)[msPA].m(C)} (SEQ ID NO: 122) | AACAUGGCCCCAGCAGCUUCAGUCCCUUUCTCIUCGAUGGUC (SEQ ID NO: 2) |
| 97. | {f(A)[msPA].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[msPA].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[sP].f(U)[sP].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} (SEQ ID NO: 123) | AACAUGGCCCCAGCAGCUUCAGUCCCUUUCTCIUCGAUGGUC (SEQ ID NO: 2) |
| 98. | {f(A)[msPA].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[P].m(C)[msPA].f(U)[sP].m(U)P.m(C)P.m(A)[msPA].f(G)[sP].f(U)[msPA].m(C)[sP].f(C)[sP].f(C)[sP].f(U)[sP].m(U)[sP].f(U)[sP].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} (SEQ Id NO: 124) | AACAUGGCCCCAGCAGCUUCAGUCCCUUUCTCIUCGAUGGUC (SEQ ID NO: 2) |
| 99. | {f(A)[msPA].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[msPA].m(U)P.m(C)P.m(A)[msPA].f(G)[sP].f(U)[msPA].m(C)[sP].f(C)[P].f(C)[sP].f(U)[sP].m(U)[sP].f(U)[sP].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} (SEQ ID NO: 125) | AACAUGGCCCCAGCAGCUUCAGUCCCUUUCTCIUCGAUGGUC (SEQ ID NO: 2) |
| 100. | {f(A)[msPA].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)[msPA].m(C)P.m(A)[msPA].f(G)[sP].f(U)[msPA].m(C)[P].f(C)[sP].f(C)[sP].f(U)[sP].m(U)[sP].f(U)[sP].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} (SEQ ID NO: 126) | AACAUGGCCCCAGCAGCUUCAGUCCCUUUCTCIUCGAUGGUC (SEQ ID NO: 2) |
| 101. | {f(A)[msPA].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)[msPA].m(A)[msPA].f(G)[sP].f(U)[msPA].m(C)[sP].f(C)[sP].f(C)[sP].f(U)[sP].m(U)[sP].f(U)[sP].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} (SEQ ID NO: 127) | AACAUGGCCCCAGCAGCUUCAGUCCCUUUCTCIUCGAUGGUC (SEQ ID NO: 2) |
| 102. | {f(A)[msPA].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[msPA].f(G)[msPA].f(U)[msPA].m(C)[sP].f(C)[sP].f(C)[sP].f(U)[sP].m(U)[sP].f(U)[sP].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} (SEQ ID NO: 128) | AACAUGGCCCCAGCAGCUUCAGUCCCUUUCTCIUCGAUGGUC (SEQ ID NO: 2) |

TABLE 3-continued

Exemplary Oligonucleotides

| Oligo No. | Oligonucleotide sequence | Base sequence |
|---|---|---|
| 103. | {f(A)[msPA].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[msPA].f(C)[sP].f(C)[sP].f(U)[sP].m(U)[sP].f(U)[sP].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} (SEQ ID NO: 129) | AACAUGGCCCCAGCAGCUUCAGUCCCUUUCTCIUCGAUGGUC (SEQ ID NO: 2) |
| 104. | {f(A)[msPA].f(A)[sP].m(C)P.m(A)[sP].f(U)[sP].f(G)[sP].f(G)[sP].f(C)[sP].m(C)[sP].f(C)[sP].m(C)[P].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[msPA].f(C)[sP].f(U)[sP].m(U)[sP].f(U)[sP].m(C)[sP].d(T)[sP].[hd](C)[sP].[fana](I)[msPA].m(U)[sP].f(C)[P].m(G)P.m(A)P.m(U)P.m(G)[sP].f(G)[sP].f(U)[msPA].m(C)} (SEQ ID NO: 130) | AACAUGGCCCCAGCAGCUUCAGUCCCUUUCTCIUCGAUGGUC (SEQ ID NO: 2) |
| 105. | {f(A)[msPA].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[sP].f(C)[msPA].f(U)[sP].m(U)[sP].f(U)[sP].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} (SEQ ID NO: 131) | AACAUGGCCCCAGCAGCUUCAGUCCCUUUCTCIUCGAUGGUC (SEQ ID NO: 2) |
| 106. | {f(A)[msPA].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[sP].f(C)[P].f(U)[msPA].m(U)[sP].f(U)[sP].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} SEQ ID NO: 132) | AACAUGGCCCCAGCAGCUUCAGUCCCUUUCTCIUCGAUGGUC (SEQ ID NO: 2) |
| 107. | {f(A)[msPA].f(A)[sP].m(C)P.m(A)[sP].f(U)[sP].f(G)[sP].f(G)[sP].f(C)[sP].m(C)[sP].f(C)[sP].m(C)[P].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[msPA].f(U)[sP].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} (SEQ ID NO: 133) | AACAUGGCCCCAGCAGCUUCAGUCCCUUUCTCIUCGAUGGUC (SEQ ID NO: 2) |
| 108. | {f(A)[msPA].f(A)[sP].m(C)P.m(A)[sP].f(U)[sP].f(G)[sP].f(G)[sP].f(C)[sP].m(C)[sP].f(C)[sP].m(C)[P].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[sP].f(U)[msPA].m(C)[sP].d(T)[sP].[hd](C)[sP].[fana](I)[msPA].m(U)[sP].f(C)[sP].m(G)P.m(A)P.m(U)P.m(G)[sP].f(G)[sP].f(U)[msPA].m(C)} (SEQ ID NO: 134) | AACAUGGCCCCAGCAGCUUCAGUCCCUUUCTCIUCGAUGGUC (SEQ ID NO: 2) |
| 109. | {f(A)[msPA].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[sP]f(U)[sP].m(C)[msPA].d(T)[sP].[hd](C)[sP].[fana](I)[msPA].m(U)[sP].f(C)[sP].m(G)P.m(A)P.m(U)P.m(G)[sP].f(G)[P].f(U)[msPA].m(C)} (SEQ ID NO: 135) | AACAUGGCCCCAGCAGCUUCAGUCCCUUUCTCIUCGAUGGUC (SEQ ID NO: 2) |
| 110. | {f(A)[msPA].f(A)[P].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[sP]f(U)[sP].m(C)[sP].d(T)[msPA].[hd](C)[sP].[fana](I)[msPA].m(U)[sP].f(C)[P].m(G)P.m(A)P.m(U)P.m(G)[sP].f(G)[sP].f(U)[msPA].m(C)} (SEQ ID NO: 136) | AACAUGGCCCCAGCAGCUUCAGUCCCUUUCTCIUCGAUGGUC (SEQ ID NO: 2) |
| 111. | {f(A)[msPA].f(A)[sP].m(C)P.m(A)[P].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[sP]f(U)[sP].m(C)[sP].d(T)[sP].[hd](C)[msPA].[fana](I)[msPA].m(U)[sP].f(C)[sP].m(G)P.m(A)P.m(U)P.m(G)[sP].f(G)[sP].f(U)[msPA].m(C)} (SEQ ID NO: 137) | AACAUGGCCCCAGCAGCUUCAGUCCCUUUCTCIUCGAUGGUC (SEQ ID NO: 2) |

TABLE 3-continued

| Oligo No. | Oligonucleotide sequence | Base sequence |
|---|---|---|
| | Exemplary Oligonucleotides | |
| 112. | {f(A)[msPA].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[sP]f(U)[sP].m(C)[sP].d(T)[sP].[hd](C)[sP].[fana](I)[msPA].m(U)[msPA].f(C)[sP].m(G)P.m(A)P.m(U)P.m(G)[sP].f(G)[sP].f(U)[msPA].m(C)} (SEQ ID NO: 138) | AACAUGGCCCCAGCAGCUUCAGUCCCUUUCTCIUCGAUGGUC (SEQ ID NO: 2) |
| 113. | {f(A)[msPA].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[sP]f(U)[sP].m(C)[sP].d(T)[sP].[hd](C)[sP].[fana](I)[msPA].m(U)[sP].f(C)[msPA].m(G)P.m(A)P.m(U)P.m(G)[sP].f(G)[sP].f(U)[msPA].m(C)} (SEQ ID NO: 139) | AACAUGGCCCCAGCAGCUUCAGUCCCUUUCTCIUCGAUGGUC (SEQ ID NO: 2) |
| 114. | {f(A)[msPA].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[sP].f(U)[sP].m(C)[sP].d(T)[sP].[hd](C)[sP].[fana](I)[msPA].m(U)[sP].f(C)[sP].m(G)[msPA].m(A)P.m(U)P.m(G)[sP].f(G)[sP].f(U)[msPA].m(C)} (SEQ ID NO: 140) | AACAUGGCCCCAGCAGCUUCAGUCCCUUUCTCIUCGAUGGUC (SEQ ID NO: 2) |
| 115. | {f(A)[msPA].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[sP]f(U)[sP].m(C)[sP].d(T)[sP].[hd](C)[sP].[fana](I)[msPA].m(U)[sP].f(C)[sP].m(G)P.m(A)[msPA].m(U)P.m(G)[sP].f(G)[sP].f(U)[msPA].m(C)} (SEQ ID NO: 141) | AACAUGGCCCCAGCAGCUUCAGUCCCUUUCTCIUCGAUGGUC (SEQ ID NO: 2) |
| 116. | {f(A)[msPA].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[P].f(U)[sP].m(U)P.m(C)P.m(A)[msPA].f(G)[sP].f(U)[msPA].m(C)[sP].f(C)[sP].f(C)[sP].f(U)[sP].m(U)[sP].f(U)[sP].m(C)[sP].d(T)[sP].[hd](C)[sP].[fana](I)[msPA].m(U)[sP].f(C)[sP].m(G)P.m(A)P.m(U)[msPA].m(G)[sP].f(G)[sP].f(U)[msPA].m(C)} (SEQ ID NO: 142) | AACAUGGCCCCAGCAGCUUCAGUCCCUUUCTCIUCGAUGGUC (SEQ ID NO: 2) |
| 117. | {f(A)[msPA].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[sP]f(U)[sP].m(C)[sP].d(T)[sP].[hd](C)[sP].[fana](I)[msPA].m(U)[sP].f(C)[sP].m(G)P.m(A)P.m(U)P.m(G)[msPA].f(G)[sP].f(U)[msPA].m(C)} (SEQ ID NO: 143) | AACAUGGCCCCAGCAGCUUCAGUCCCUUUCTCIUCGAUGGUC (SEQ ID NO: 2) |
| 118. | {f(A)[msPA].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[sP]f(U)[sP].m(C)[sP].d(T)[sP].[hd](C)[P].[fana](I)[msPA].m(U)[sP].f(C)[sP].m(G)P.m(A)P.m(U)P.m(G)[sP].f(G)[msPA].f(U)[msPA].m(C)} (SEQ ID NO: 144) | AACAUGGCCCCAGCAGCUUCAGUCCCUUUCTCIUCGAUGGUC (SEQ ID NO: 2) |
| 119. | {m(U)[sP].f(U)[sP].m(G)[sP].m(C)[sP].f(A)[sP].f(G)[sP].f(U)[sP]f(A)[sP].m(C)P.m(A)P.m(U)P.f(A)[sP].m(A)[sP].m(U)P.f(U)[sP].f(U)[sP].f(A)[sP].m(C)[sP].f(A)[sP].m(C)[sP].m(A)P.f(G)[sP].f(A)[sP].m(A)[sP].m(G)P.f(C)[sP].f(A)[sP].f(A)[sP].f(U)[sP].m(G)P.d(C)[sP].[Dh](C)[sP].d(I)[sP].m(U)P.f(C)[sP].m(A)P.m(C)P.m(C)[sP].m(U)[sP].m(U)[sP].f(C)[sP].m(C)}\|CHEM3{P}\|CHEM4{TriGalNAc1} (SEQ ID NO: 145) | UUGCAGUACAUAAUUUACACAGAAGCAAUGCCIUCACCUUCC (SEQ ID NO: 146) |
| 120. | {m(U)[msPA].f(U)[sP].m(G)[sP].m(C)[sP].f(A)[sP].f(G)[sP].f(U)[sP].f(A)[sP].m(C)P.m(A)P.m(U)P.f(A)[sP].m(A)[sP].m(U)P.f(U)[sP].f(U)[sP].f(A)[sP].m(C)[sP].f(A)[sP].m(C)[sP].m(A)P.f(G)[sP].f(A)[sP].m(A)[sP].m(G)P.f(C)[sP].f(A)[sP].f(A)[sP].f(U)[sP].m(G)P.d(C)[sP].[Dh](C)[sP].d(I)[sP].m(U)P.f(C)[sP].m(A)P.m(C)P.m(C)[sP].m(U)[sP].m(U)[sP].f(C)[msPA].m(C)}\|CHEM3{P}\|CHEM4{TriGalNAc1} (SEQ ID NO: 147) | UUGCAGUACAUAAUUUACACAGAAGCAAUGCCIUCACCUUCC (SEQ ID NO: 146) |

TABLE 3-continued

<table>
<tr><th colspan="3">Exemplary Oligonucleotides</th></tr>
<tr><th>Oligo No.</th><th>Oligonucleotide sequence</th><th>Base sequence</th></tr>
<tr><td>121.</td><td>{m(U)[msPA].f(U)[sP].m(G)[sP].m(C)[sP].f(A)[sP].f(G)[sP].f(U)[sP].f(A)[sP].m(C)P.m(A)P.m(U)P.f(A)[sP].m(A)[sP].m(U)P.f(U)[sP].f(U)[sP].f(A)[sP].m(C)[sP].f(A)[sP].m(C)[sP].m(A)[msPA].f(G)[sP].f(A)[msPA].m(A)[sP].m(G)P.f(C)[sP].f(A)[sP].f(A)[sP].f(U)[sP].m(G)P.d(C)[sP].[Dh](C)[sP].d(I)[msPA].m(U)P.f(C)[sP].m(A)P.m(C)P.m(C)[sP].m(U)[sP].m(U)[sP].f(C)[msPA].m(C)}|CHEM3{P}|CHEM4{TriGalNAc1} (SEQ ID NO: 148)</td><td>UUGCAGUACAUAAUUUACACAGAAGCAAUGCCIUCACCUUCC (SEQ ID NO: 146)</td></tr>
<tr><td>122.</td><td>CHEM1{TriGalNAc1}|CHEM2{P}|{f(A)[sP].m(C)[sP].f(A)[sP].m(U)[P].f(A)[sP].f(A)[sP].m(U)[sP].m(U)[sP].m(U)[sP].f(A)[sP].m(C)[sP].f(A)[sP].m(C)[sP].f(A)[sP].f(G)[sP].f(A)[sP].f(A)[sP].f(G)[sP].m(C)[sP].f(A)[sP].f(A)[sP].m(U)[sP].f(G)[sP].d(C)[sP].[Dh](C)[sP].d(I)[sP].m(U)[sP].f(C)[sP].m(A)[sP].m(C)} (SEQ ID NO: 149)</td><td>ACAUAAUUUACACAGAAGCAAUGCCIUCAC (SEQ ID NO: 150)</td></tr>
<tr><td>123.</td><td>CHEM1{TriGalNAc1}|CHEM2{P}|{f(A)[msPA].m(C)[sP].f(A)[sP].m(U)[sP].f(A)[sP].f(A)[sP].m(U)[sP].m(U)[sP].m(U)[sP].f(A)[sP].m(C)[sP].f(A)[sP].m(C)[sP].f(A)[msPA].f(G)[sP].f(A)[msPA].f(A)[sP].f(G)[sP].m(C)[sP].f(A)[sP].f(A)[sP].m(U)[sP].f(G)[sP].d(C)[sP].[Dh](C)[sP].d(I)[msPA].m(U)[sP].f(C)[P].m(A)[msPA].m(C)} (SEQ ID NO: 151)</td><td>ACAUAAUUUACACAGAAGCAAUGCCIUCAC (SEQ ID NO: 150)</td></tr>
<tr><td>124.</td><td>m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[msPA].f(G)[sP].f(U)[msPA].m(C)[sP].f(C)[sP].f(C)[P].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 162)</td><td>CCCCAGCAGCUUCAGUCCCUUUCTCIUCGA (SEQ ID NO: 163)</td></tr>
<tr><td>125.</td><td>m(C)[sP].f(C)[sP].f(C)[sP].f(C)[P].m(A)[sP].f(G)[sP].f(C)[sP].f(A)[sP].m(G)[sP].f(C)[sP].f(U)[sP].f(U)[sP].m(C)[sP].f(A)[sP].f(G)[sP].f(U)[sP].m(C)[sP].f(C)[sP].f(C)[P].f(U)[sP].m(U)[sP].f(U)[sP].f(C)[sP].d(T)[sP].[Dh](C)[sP].d(I)[sP].m(U)[sP].f(C)[sP].m(G)[sP].m(A) (SEQ ID NO: 164)</td><td>CCCCAGCAGCUUCAGUCCCUUUCTCIUCGA (SEQ ID NO: 163)</td></tr>
<tr><td>126.</td><td>m(C)[sP].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[msPA]f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 165)</td><td>CCCCAGCAGCUUCAGUCCCUUUCTCIUCGA (SEQ ID NO: 163)</td></tr>
<tr><td>127.</td><td>m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[sP].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 166)</td><td>CCCCAGCAGCUUCAGUCCCUUUCTCIUCGA (SEQ ID NO: 163)</td></tr>
<tr><td>128.</td><td>m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[mSPA].f(G)[sP].f(U)[sP].m(C)[sP].f(C)[sP].f(C)[P].f(U)[sP].m(U)[[sP].f(U)[sP].f(C)[sP].d(T)[sP].[Dh](C)[sP].d(I)[msPA].m(U)[sP].f(C)[sP].m(G)[msPA].m(A) (SEQ ID NO: 167)</td><td>CCCCAGCAGCUUCAGUCCCUUUCTCIUCGA (SEQ ID NO: 163)</td></tr>
<tr><td>129.</td><td>m(C)[msPA].f(C)[sP].f(C)[sP].f(C)[P].m(A)[sP].f(G)[sP].f(C)[sP].f(A)[sP].m(G)[sP].f(C)[sP].f(U)[sP].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[sP].m(U)[sP].f(C)[sP].m(G)[msPA].m(A) (SEQ ID NO: 168)</td><td>CCCCAGCAGCUUCAGUCCCUUUCTCIUCGA (SEQ ID NO: 163)</td></tr>
<tr><td>130.</td><td>m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[msPA].f(G)[sP].f(U)[msPA].m(C)[sP].f(C)[sP].f(C)[P].f(U)[sP].m(U)[sP].f(U)[sP].f(C)[sP].d(T)[P].[Dh](C)[sP].d(I)[msPA].m(U)[sP].f(C)[sP].m(G)[sP].m(A) (SEQ ID NO: 169)</td><td>CCCCAGCAGCUUCAGUCCCUUUCTCIUCGA (SEQ ID NO: 163)</td></tr>
<tr><td>131.</td><td>m(C)[msPA].f(C)[msPA].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[P].d(I)[msPA].m(U)[P].f(C)[sP].m(G)[msPA].m(A) (SEQ ID NO: 170)</td><td>CCCCAGCAGCUUCAGUCCCUUUCTCIUCGA (SEQ ID NO: 163)</td></tr>
</table>

TABLE 3-continued

Exemplary Oligonucleotides

| Oligo No. | Oligonucleotide sequence | Base sequence |
| --- | --- | --- |
| 132. | m(C)[msPA].f(C)[sP].f(C)[msPA].f(C)[sP].m(A)[sP].f(G)[sP].f(C)[sP].f(A)[sP].m(G)[sP].f(C)[sP].f(U)[sP].f(U)[sP].m(C)[sP].f(A)[msPA].f(G)[sP].f(U)[msPA].m(C)[sP].f(C)[P].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 171) | CCCCAGCAGCUUCAGUCCCUUUCTCIUCGA (SEQ ID NO: 163) |
| 133. | m(C)[msPA].f(C)[sP].f(C)[sP].f(C)[msPA].m(A)[sP].f(G)[sP].f(C)[sP].f(A)[sP].m(G)[sP].f(C)[sP].f(U)[sP].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 172) | CCCCAGCAGCUUCAGUCCCUUUCTCIUCGA (SEQ ID NO: 163) |
| 134. | m(C)[msPA].f(C)[sP].f(C)[sP].f(C)[sP].m(A)[msPA].f(G)[sP].f(C)[sP].f(A)[sP].m(G)[sP].f(C)[sP].f(U)[sP].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 173) | CCCCAGCAGCUUCAGUCCCUUUCTCIUCGA (SEQ ID NO: 163) |
| 135. | m(C)[msPA].f(C)[sP].f(C)[P].f(C)[sP].m(A)[sP].f(G)[msPA].f(C)[sP].f(A)[sP].m(G)[sP].f(C)[sP].f(U)[sP].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 174) | CCCCAGCAGCUUCAGUCCCUUUCTCIUCGA (SEQ ID NO: 163) |
| 136. | m(C)[msPA].f(C)[sP].f(C)[sP].f(C)[sP].m(A)[sP].f(G)[sP].f(C)[msPA].f(A)[sP].m(G)[sP].f(C)[sP].f(U)[sP].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 175) | CCCCAGCAGCUUCAGUCCCUUUCTCIUCGA (SEQ ID NO: 163) |
| 137. | m(C)[msPA].f(C)[sP].f(C)[sP].f(C)[sP].m(A)[sP].f(G)[sP].f(C)[sP].f(A)[msPA].m(G)[sP].f(C)[sP].f(U)[sP].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 176) | CCCCAGCAGCUUCAGUCCCUUUCTCIUCGA (SEQ ID NO: 163) |
| 138. | m(C)[msPA].f(C)[sP].f(C)[sP].f(C)[sP].m(A)[P].f(G)[sP].f(C)[sP].f(A)[sP].m(G)[msPA].f(C)[sP].f(U)[sP].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[P].[Dh](C)[sP].d(I)[msPA].m(U)[sP].f(C)[sP].m(G)[msPA].m(A) (SEQ ID NO: 177) | CCCCAGCAGCUUCAGUCCCUUUCTCIUCGA (SEQ ID NO: 163) |
| 139. | m(C)[msPA].f(C)[sP].f(C)[sP].f(C)[sP].m(A)[sP].f(G)[sP].f(C)[sP].f(A)[sP].m(G)[sP].f(C)[msPA].f(U)[sP].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 178) | CCCCAGCAGCUUCAGUCCCUUUCTCIUCGA (SEQ ID NO: 163) |
| 140. | m(C)[msPA].f(C)[sP].f(C)[sP].f(C)[sP].m(A)[sP].f(G)[sP].f(C)[sP].f(A)[sP].m(G)[sP].f(C)[sP].f(U)[msPA].f(U)[sP].m(C)[sP].f(A)[msPA].f(G)[sP].f(U)[msPA].m(C)[P].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 179) | CCCCAGCAGCUUCAGUCCCUUUCTCIUCGA (SEQ ID NO: 163) |
| 141. | m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[msPA].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 180) | CCCCAGCAGCUUCAGUCCCUUUCTCIUCGA (SEQ ID NO: 163) |
| 142. | m(C)[msPA].f(C)[P].f(C)[sP].f(C)[sP].m(A)[sP].f(G)[sP].f(C)[sP].f(A)[sP].m(G)[sP].f(C)[sP].f(U)[sP].f(U)[sP].m(C)[msPA].f(A)[msPA].f(G)[sP].f(U)[msPA].m(C)[sP].f(C)[sP].f(C)[sP].f(U)[P].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 181) | CCCCAGCAGCUUCAGUCCCUUUCTCIUCGA (SEQ ID NO: 163) |
| 143. | m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[mSPA].f(G)[msPA].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 182) | CCCCAGCAGCUUCAGUCCCUUUCTCIUCGA (SEQ ID NO: 163) |

TABLE 3-continued

Exemplary Oligonucleotides

| Oligo No. | Oligonucleotide sequence | Base sequence |
|---|---|---|
| 144. | m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[msPA].f(G)[sP].f(U)[msPA].m(C)[msPA].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 183) | CCCCAGCAGCUUCAGUCCCUUUCTCIUCGA (SEQ ID NO: 163) |
| 145. | m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[msPA].f(G)[sP].f(U)[msPA].m(C)[sP].f(C)[msPA].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 184) | CCCCAGCAGCUUCAGUCCCUUUCTCIUCGA (SEQ ID NO: 163) |
| 146. | m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[mSPA].f(G)[sP].f(U)[msPA].m(C)[sP].f(C)[sP].f(C)[msPA].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 185) | CCCCAGCAGCUUCAGUCCCUUUCTCIUCGA (SEQ ID NO: 163) |
| 147. | m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[mSPA].f(G)[sP].f(U)[msPA].m(C)[sP].f(C)[sP].f(C)[sP].f(U)[msPA].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 186) | CCCCAGCAGCUUCAGUCCCUUUCTCIUCGA (SEQ ID NO: 163) |
| 148. | m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[mSPA].f(G)[sP].f(U)[msPA].m(C)[sP].f(C)[P].f(C)[P].f(U)[sP].m(U)[msPA].f(U)[sP].f(C)[sP].d(T)[sP].[Dh](C)[sP].d(I)[msPA].m(U)[sP].f(C)[sP].m(G)[msPA].m(A) (SEQ ID NO: 187) | CCCCAGCAGCUUCAGUCCCUUUCTCIUCGA (SEQ ID NO: 163) |
| 149. | m(C)[msPA].f(C)[sP].f(C)[sP].f(C)[sP].m(A)[sP].f(G)[sP].f(C)[sP].f(A)[sP].m(G)[sP].f(C)[sP].f(U)[P].f(U)[sP].m(C)[sP].f(A)[mSPA].f(G)[sP].f(U)[msPA].m(C)[sP].f(C)[sP].f(C)[sP].f(U)[sP].m(U)[sP].f(U)[msPA].f(C)[sP].d(T)[sP].[Dh](C)[sP].d(I)[msPA].m(U)[sP].f(C)[sP].m(G)[msPA].m(A) (SEQ ID NO: 188) | CCCCAGCAGCUUCAGUCCCUUUCTCIUCGA (SEQ ID NO: 163) |
| 150. | m(C)[msPA].f(C)[sP].f(C)[sP].f(C)[sP].m(A)[sP].f(G)[sP].f(C)[sP].f(A)[sP].m(G)[sP].f(C)[P].f(U)[sP].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[msPA].d(T)[sP].[Dh](C)[sP].d(I)[msPA].m(U)[sP].f(C)[sP].m(G)[msPA].m(A) (SEQ ID NO: 189) | CCCCAGCAGCUUCAGUCCCUUUCTCIUCGA (SEQ ID NO: 163) |
| 151. | m(C)[msPA].f(C)[sP].f(C)[sP].f(C)[sP].m(A)[sP].f(G)[sP].f(C)[sP].f(A)[sP].m(G)[sP].f(C)[sP].f(U)[P].f(U)[sP].m(C)[P].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[msPA].f(C)[sP].m(G)[msPA].m(A) (SEQ ID NO: 190) | CCCCAGCAGCUUCAGUCCCUUUCTCIUCGA (SEQ ID NO: 163) |
| 152. | m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[msPA].m(G)[msPA].m(A) (SEQ ID NO: 191) | CCCCAGCAGCUUCAGUCCCUUUCTCIUCGA (SEQ ID NO: 163) |
| 153. | f(C)[msPA].f(C)[sP].f(C)[sP].f(C)[P].m(A)[sP].f(G)[sP].f(C)[sP].f(A)[sP].m(G)[P].f(C)[sP].f(U)[sP].f(U)[sP].m(C)[sP].f(A)[msPA].f(G)[sP].f(U)[msPA].m(C)[sP].f(C)[P].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 192) | CCCCAGCAGCUUCAGUCCCUUUCTCIUCGA (SEQ ID NO: 163) |
| 154. | m(C)[msPA].m(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 193) | CCCCAGCAGCUUCAGUCCCUUUCTCIUCGA (SEQ ID NO: 163) |
| 155. | m(C)[msPA].m(C)[sP].f(C)[sP].m(C)[sP].m(A)[sP].f(G)[sP].f(C)[sP].f(A)[sP].m(G)[P].f(C)[sP].f(U)[P].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 194) | CCCCAGCAGCUUCAGUCCCUUUCTCIUCGA (SEQ ID NO: 163) |

TABLE 3-continued

| Exemplary Oligonucleotides | | |
|---|---|---|
| Oligo No. | Oligonucleotide sequence | Base sequence |
| 156. | m(C)[msPA].f(C)[sP].f(C)[sP].m(C)[sP].m(A)[sP].f(G)[sP].f(C)[sP].f(A)[sP].m(G)[sP].f(C)[sP].f(U)[sP].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[P].d(I)[msPA].m(U)[sP].f(C)[sP].m(G)[msPA].m(A) (SEQ ID NO: 195) | CCCCAGCAGCUUCAGUCCCUUUCTCIUCGA (SEQ ID NO: 163) |
| 157. | m(C)[msPA].f(C)[sP].f(C)[sP].f(C)[sP].f(A)[sP].f(G)[sP].f(C)[sP].f(A)[sP].m(G)[sP].f(C)[sP].f(U)[sP].f(U)[sP].m(C)[sP].f(A)[msPA].f(G)[sP].f(U)[msPA].m(C)[sP].f(C)[sP].f(C)[sP].f(U)[sP].m(U)[P].f(U)[sP].f(C)[sP].d(T)[sP].[Dh](C)[sP].d(I)[msPA].m(U)[sP].]f(C)[sP].m(G)[msPA].m(A) (SEQ ID NO: 196) | CCCCAGCAGCUUCAGUCCCUUUCTCIUCGA (SEQ ID NO: 163) |
| 158. | m(C)[msPA].f(C)[P].f(C)[sP].f(C)[sP].m(A)[sP].m(G)[sP].f(C)[sP].f(A)[sP].m(G)[sP].f(C)[sP].f(U)[sP].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 197) | CCCCAGCAGCUUCAGUCCCUUUCTCIUCGA (SEQ ID NO: 163) |
| 159. | m(C)[msPA].f(C)[sP].f(C)[sP].f(C)[sP].m(A)[sP].f(G)[sP].m(C)[sP].f(A)[sP].m(G)[sP].f(C)[sP].f(U)[sP].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 198) | CCCCAGCAGCUUCAGUCCCUUUCTCIUCGA (SEQ ID NO: 163) |
| 160. | m(C)[msPA].f(C)[sP].f(C)[sP].f(C)[P].m(A)[sP].f(G)[sP].f(C)[sP].m(A)[sP].m(G)[sP].f(C)[sP].f(U)[P].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 199 | CCCCAGCAGCUUCAGUCCCUUUCTCIUCGA (SEQ ID NO: 163) |
| 161. | m(C)[msPA].f(C)[sP].f(C)[sP].f(C)[sP].m(A)[sP].f(G)[sP].f(C)[sP].f(A)[sP].f(G)[sP].f(C)[sP].f(U)[sP].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 200) | CCCCAGCAGCUUCAGUCCCUUUCTCIUCGA (SEQ ID NO: 163) |
| 162. | m(C)[msPA].f(C)[sP].f(C)[P].f(C)[sP].m(A)[sP].f(G)[sP].f(C)[sP].f(A)[sP].m(G)[sP].m(C)[sP].f(U)[P].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 201) | CCCCAGCAGCUUCAGUCCCUUUCTCIUCGA (SEQ ID NO: 163) |
| 163. | m(C)[msPA].f(C)[sP].f(C)[sP].f(C)[sP].m(A)[sP].f(G)[sP].f(C)[sP].f(A)[sP].m(G)[sP].f(C)[sP].m(U)[sP].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 202) | CCCCAGCAGCUUCAGUCCCUUUCTCIUCGA (SEQ ID NO: 163) |
| 164. | m(C)[msPA].f(C)[sP].f(C)[sP].f(C)[sP].m(A)[sP].f(G)[sP].f(C)[sP].f(A)[sP].m(G)[sP].f(C)[sP].f(U)[sP].m(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 203) | CCCCAGCAGCUUCAGUCCCUUUCTCIUCGA (SEQ ID NO: 163) |
| 165. | m(C)[msPA].f(C)[P].f(C)[sP].f(C)[sP].m(A)[sP].f(G)[sP].f(C)[sP].f(A)[sP].m(G)[sP].f(C)[sP].f(U)[sP].f(U)[sP].f(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 204) | CCCCAGCAGCUUCAGUCCCUUUCTCIUCGA (SEQ ID NO: 163) |
| 166. | m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].m(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 205) | CCCCAGCAGCUUCAGUCCCUUUCTCIUCGA (SEQ ID NO: 163) |
| 167. | m(C)[msPA].f(C)[sP].f(C)[sP].f(C)[sP].m(A)[sP].f(G)[sP].f(C)[sP].f(A)[sP].m(G)[sP].f(C)[sP].f(U)[P].f(U)[sP].m(C)[sP].f(A)[msPA].m(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 206) | CCCCAGCAGCUUCAGUCCCUUUCTCIUCGA (SEQ ID NO: 163) |

TABLE 3-continued

Exemplary Oligonucleotides

| Oligo No. | Oligonucleotide sequence | Base sequence |
|---|---|---|
| 168. | m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[P].f(A)[mSPA].f(G)[sP].m(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 207) | CCCCAGCAGCUUCAGUCCCUUUCTCIUCGA (SEQ ID NO: 163) |
| 169. | m(C)[msPA].f(C)[sP].f(C)[P].f(C)[sP].m(A)[sP].f(G)[sP].f(C)[sP].f(A)[sP].m(G)[sP].f(C)[sP].f(U)[sP].f(U)[sP].m(C)[sP].f(A)[mSPA].f(G)[sP].f(U)[msPA].f(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 208) | CCCCAGCAGCUUCAGUCCCUUUCTCIUCGA (SEQ ID NO: 163) |
| 170. | m(C)[msPA].f(C)[sP].f(C)[sP].f(C)[sP].m(A)[sP].f(G)[sP].f(C)[sP].f(A)[sP].m(G)[P].f(C)[sP].f(U)[sP].f(U)[sP].m(C)[sP].f(A)[mSPA].f(G)[sP].f(U)[msPA].m(C)[sP].m(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 209) | CCCCAGCAGCUUCAGUCCCUUUCTCIUCGA (SEQ ID NO: 163) |
| 171. | m(C)[msPA].f(C)[sP].f(C)[sP].f(C)[P].m(A)[sP].f(G)[sP].f(C)[sP].f(A)[sP].m(G)[P].f(C)[sP].f(U)[sP].f(U)[sP].m(C)[sP].f(A)[mSPA].f(G)[sP].f(U)[msPA].m(C)[sP].f(C)[sP].m(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 210) | CCCCAGCAGCUUCAGUCCCUUUCTCIUCGA (SEQ ID NO: 163) |
| 172. | m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[mSPA].f(G)[sP].f(U)[msPA].m(C)[sP].f(C)[sP].f(C)[sP].m(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 211) | CCCCAGCAGCUUCAGUCCCUUUCTCIUCGA (SEQ ID NO: 163) |
| 173. | m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[msPA].f(G)[sP].f(U)[msPA].m(C)[sP].f(C)[sP].f(C)[sP].f(U)[sP].f(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 212) | CCCCAGCAGCUUCAGUCCCUUUCTCIUCGA (SEQ ID NO: 163) |
| 174. | m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[mSPA].f(G)[sP].f(U)[msPA].m(C)[sP].f(C)[sP].f(C)[sP].f(U)[sP].m(U)[sP].m(U)[sP].f(C)[sP].d(T)[sP].[Dh](C)[sP].d(I)[msPA].m(U)[sP].f(C)[sP].m(G)[msPA].m(A) (SEQ ID NO: 213) | CCCCAGCAGCUUCAGUCCCUUUCTCIUCGA (SEQ ID NO: 163) |
| 175. | m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[mSPA].f(G)[sP].f(U)[msPA].m(C)[sP].f(C)[sP].f(C)[sP].f(U)[sP].m(U)[sP].f(U)[sP].m(C)[sP].d(T)[sP].[Dh](C)[sP].d(I)[msPA].m(U[sP].f(C)[sP].m(G)[msPA].m(A) (SEQ ID NO: 214) | CCCCAGCAGCUUCAGUCCCUUUCTCIUCGA (SEQ ID NO: 163) |
| 176. | m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[mSPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].f(U)[sP].f(C)[sP].m(G)[msPA].m(A) (SEQ ID NO: 215) | CCCCAGCAGCUUCAGUCCCUUUCTCIUCGA (SEQ ID NO: 163) |
| 177. | m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[mSPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].m(C)[sP].m(G)[msPA].m(A) (SEQ ID NO: 216) | CCCCAGCAGCUUCAGUCCCUUUCTCIUCGA (SEQ ID NO: 163) |
| 178. | m(C)[msPA].f(C)[sP].f(C)[sP].f(C)[sP].m(A)[sP].f(G)[P].f(C)[sP].f(A)[sP].m(G)[sP].f(C)[sP].f(U)[sP].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[[sP].f(C)[sP].f(G)[msPA].m(A) (SEQ ID NO: 217) | CCCCAGCAGCUUCAGUCCCUUUCTCIUCGA (SEQ ID NO: 163) |
| 179. | m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].f(A) (SEQ ID NO: 218) | CCCCAGCAGCUUCAGUCCCUUUCTCIUCGA (SEQ ID NO: 163) |

TABLE 3-continued

| Exemplary Oligonucleotides | | |
|---|---|---|
| Oligo No. | Oligonucleotide sequence | Base sequence |
| 180. | m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[msPA].m(C)[sP].f(A)[sP].f(G)[msPA].f(U)[sP].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 219) | CCCCAGCAGCUUCAGUCCCUUUCTCIUCGA (SEQ ID NO: 163) |
| 181. | m(C)[msPA].f(C)[sP].f(C)[P].f(C)[sP].m(A)[sP].f(G)[sP].f(C)[sP].f(A)[sP].m(G)[sP].f(C)[sP].f(U)[sP].f(U)[msPA].m(C)[sP].f(A)[sP].f(G)[msPA].f(U)[sP].m(C)[sP].f(C)[sP].f(C)[sP].f(U)[msPA].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 220) | CCCCAGCAGCUUCAGUCCCUUUCTCIUCGA (SEQ ID NO: 163) |
| 182. | m(C)[msPA].f(C)[sP].f(C)[P].f(C)[sP].m(A)P.f(G)[sP].f(C)[sP].f(A)[sP].m(G)P.f(C)[sP].f(U)[sP].f(U)[sP].m(C)P.f(A)[msPA].f(G)[sP].f(U)[msPA].m(C)P.f(C)[sP].f(C)[sP].f(U)[sP].m(U)P.f(U)[sP].f(C)[sP].d(T)[sP].[Dh](C)[sP].d(I)[msPA].m(U)[sP].f(C)[sP].m(G)[msPA].m(A) (SEQ ID NO: 221) | CCCCAGCAGCUUCAGUCCCUUUCTCIUCGA (SEQ ID NO: 163) |
| 183. | m(C)[msPA].m(C)[sP].m(C)[sP].m(C)[sP].m(A)[sP].f(G)[sP].f(C)[sP].f(A)[sP].m(G)[sP].f(C)[sP].f(U)[sP].f(U)[sP].m(C)[sP].f(A)[msPA].f(G)[P].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 222) | CCCCAGCAGCUUCAGUCCCUUUCTCIUCGA (SEQ ID NO: 163) |
| 184. | m(C)[msPA].f(C)[sP].f(C)[sP].f(C)[sP].m(A)[sP].m(G)[sP].m(C)[sP].m(A)[sP].m(G)[sP].f(C)[sP].f(U)[sP].f(U)[sP].m(C)[sP].f(A)[msPA].f(G)[sP].f(U)[msPA].m(C)[sP].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 223) | CCCCAGCAGCUUCAGUCCCUUUCTCIUCGA (SEQ ID NO: 163) |
| 185. | m(C)[msPA].f(C)[sP].f(C)[P].f(C)[sP].m(A)[sP].f(G)[P].f(C)[sP].f(A)[sP].m(G)[P].f(C)[sP].f(U)[sP].f(U)[sP].m(C)[sP].m(A)[msPA].m(G)[sP].m(U)[msPA].m(C)[sP].f(C)[sP].f(C)[sP].f(U)[sP].m(U)[sP].f(U)[P].f(C)[sP].d(T)[sP].[Dh](C)[sP].d(I)[msPA].m(U)[sP].f(C)[sP].m(G)[msPA].m(A) (SEQ ID NO: 224) | CCCCAGCAGCUUCAGUCCCUUUCTCIUCGA (SEQ ID NO: 163) |
| 186. | m(C)[msPA].f(C)[sP].f(C)[sP].f(C)[sP].m(A)[sP].f(G)[sP].f(C)[sP].f(A)[sP].m(G)[sP].f(C)[P].f(U)[sP].f(U)[sP].m(C)[sP].f(A)[msPA].f(G)[sP].f(U)[msPA].m(C)[sP].m(C)[sP].m(C)[sP].m(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 225) | CCCCAGCAGCUUCAGUCCCUUUCTCIUCGA (SEQ ID NO: 163) |
| 187. | m(C)[msPA].f(C)[sP].f(C)[sP].f(C)[sP].m(A)[sP].f(G)[sP].f(C)[sP].f(A)[sP].m(G)[sP].f(C)[sP].f(U)[sP].f(U)[sP].m(C)[sP].f(A)[msPA].f(G)[sP].f(U)[msPA].m(C)[sP].f(C)[sP].f(C)[sP].f(U)[sP].m(U)[sP].m(U)[sP].m(C)[sP].d(T)[sP].[Dh](C)[sP].d(I)[msPA].m(U)[sP].f(C)[sP].m(G)[msPA].m(A) (SEQ ID NO: 226) | CCCCAGCAGCUUCAGUCCCUUUCTCIUCGA (SEQ ID NO: 163) |
| 188. | m(C)[msPA].m(C)[sP].m(C)[sP].m(C)[sP].m(A)P.f(G)[sP].f(C)[sP].f(A)[sP].m(G)P.f(C)[sP].f(U)[sP].f(U)[sP].m(C)P.f(A)[msPA].f(G)[sP].f(U)[msPA].m(C)P.f(C)[sP].f(C)[sP].f(U)[sP].m(U)P.f(U)[sP].f(C)[sP].d(T)[sP].[Dh](C)[sP].d(I)[msPA].m(U)[sP].f(C)[sP].m(G)[msPA].m(A) (SEQ ID NO: 227) | CCCCAGCAGCUUCAGUCCCUUUCTCIUCGA (SEQ ID NO: 163) |
| 189. | m(C)[msPA].f(C)[sP].f(C)[sP].f(C)[sP].m(A)P.m(G)P.m(C)P.m(A)P.m(G)P.f(C)[sP].f(U)[sP].f(U)[sP].m(C)P.f(A)[msPA].f(G)[sP].f(U)[msPA].m(C)P.f(C)[sP].f(C)[sP].f(U)[sP].m(U)P.f(U)[sP].f(C)[sP].d(T)[sP].[Dh](C)[sP].d(I)[msPA].m(U)[sP].f(C)[sP].m(G)[msPA].m(A) (SEQ ID NO: 228) | CCCCAGCAGCUUCAGUCCCUUUCTCIUCGA (SEQ ID NO: 163) |
| 190. | m(C)[msPA].f(C)[sP].f(C)[sP].f(C)[sP].m(A)P.f(G)[sP].f(C)[sP].f(A)[sP].m(G)P.m(C)P.m(U)P.m(U)P.m(C)P.f(A)[msPA].f(G)[sP].f(U)[msPA].m(C)P.f(C)[sP].f(C)[sP].f(U)[sP].m(U)P.f(U)[sP].f(C)[sP].d(T)[sP].[Dh](C)[sP].d(I)[msPA].m(U)[sP].f(C)[sP].m(G)[msPA].m(A) (SEQ ID NO: 229) | CCCCAGCAGCUUCAGUCCCUUUCTCIUCGA (SEQ ID NO: 163) |
| 191. | m(C)[msPA].f(C)[sP].f(C)[sP].f(C)[sP].m(A)P.f(G)[sP].f(C)[sP].f(A)[sP].m(G)P.f(C)[sP].f(U)[sP].f(U)[sP].m(C)P.m(A)[msPA].m(G)P.m(U)[msPA].m(C)P.f(C)[sP].f(C)[sP].f(U)[sP].m(U)P.f(U)[sP].f(C)[sP].d(T)[sP].[Dh](C)[sP].d(I)[msPA].m(U)[sP].f(C)[sP].m(G)[msPA].m(A) (SEQ ID NO: 230) | CCCCAGCAGCUUCAGUCCCUUUCTCIUCGA (SEQ ID NO: 163) |

TABLE 3-continued

Exemplary Oligonucleotides

| Oligo No. | Oligonucleotide sequence | Base sequence |
|---|---|---|
| 192. | m(C)[msPA].f(C)[sP].f(C)[sP].f(C)[P].m(A)P.f(G)[sP].f(C)[sP].f(A)[sP].m(G)P.f(C)[sP].f(U)[sP].f(U)[sP].m(C)P.f(A)[msPA].f(G)[sP].f(U)[msPA].m(C)P.m(C)P.m(C)P.m(U)P.m(U)P.f(U)[sP].f(C)[sP].d(T)[sP].[Dh](C)[sP].d(I)[msPA].m(U)[sP].f(C)[sP].m(G)[msPA].m(A) (SEQ ID NO: 231) | CCCCAGCAGCUUCAGUCCCUUUCTCIUCGA (SEQ ID NO: 163) |
| 193. | m(C)[msPA].f(C)[sP].f(C)[sP].f(C)[sP].m(A)P.f(G)[sP].f(C)[sP].f(A)[sP].m(G)P.f(C)[sP].f(U)[sP].f(U)[sP].m(C)P.f(A)[msPA].f(G)[sP].f(U)[msPA].m(C)P.f(C)[sP].f(C)[sP].f(U)[sP].m(U)P.m(U)P.m(C)P.d(T)[sP].[Dh](C)[sP].d(I)[msPA].m(U)[sP].f(C)[sP].m(G)[msPA].m(A) (SEQ ID NO: 232) | CCCCAGCAGCUUCAGUCCCUUUCTCIUCGA (SEQ ID NO: 163) |
| 194. | m(C)[msPA].f(C)[sP].f(C)[sP].f(C)[sP].m(A)[P].f(G)[sP].f(C)[sP].f(A)[sP].m(G)[P].f(C)[sP].f(U)[P].f(U)[sP].m(C)[sP].f(A)[msPA].f(G)[sP].f(U)[msPA].m(C)[P].f(C)[sP].f(C)[sP].f(U)[sP].m(U)[sP].f(U)[sP].f(C)[sP].d(T)[sP].[Dh](C)[sP].d(I)[msPA].m(U)[sP].f(C)[sP].m(G)[msPA].m(A) (SEQ ID NO: 233) | CCCCAGCAGCUUCAGUCCCUUUCTCIUCGA (SEQ ID NO: 163) |
| 195. | m(U)[sP].f(U)[sP].m(G)[sP].m(C)[sP].f(A)[sP].f(G)[sP].f(U)[sP].f(A)[sP].m(C)P.m(A)P.m(U)P.f(A)[sP].m(A)[sP].m(U)P.f(U)[sP].f(U)[sP].f(A)[sP].m(C)[sP].f(A)[sP].m(C)[sP].m(A)P.f(G)[sP].f(A)[sP].m(A)[sP].m(G)P.f(C)[sP].f(A)[sP].f(A)[sP].f(U)[sP].m(G)P.d(C)[sP].d(C)[sP].d(G)[sP].m(U)P.f(C)[sP].m(A)P.m(C)P.m(C)[sP].m(U)[sP].m(U)[sP].f(C)[sP].m(C) (SEQ ID NO: 244) | UUGCAGUACAUAAUUUACACAGAAGCAAUGCCGUCACCUUCC (SEQ ID NO: 234) |
| 196. | m(U)[msPA].f(U)[sP].m(G)[sP].m(C)[sP].f(A)[sP].f(G)[sP].f(U)[sP].f(A)[sP].m(C)P.m(A)P.m(U)P.f(A)[sP].m(A)[sP].m(U)P.f(U)[sP].f(U)[sP].f(A)[sP].m(C)[sP].f(A)[sP].m(C)[sP].m(A)[msPA].f(G)[sP].f(A)[msPA].m(A)[sP].m(G)P.f(C)[sP].m(A)[sP].f(A)[sP].f(U)[sP].m(G)P.d(C)[P].[Dh](C)[sP].d(I)[msPA].m(U)P.f(C)[sP].m(A)P.m(C)P.m(C)[sP].m(U)[sP].m(U)[sP].f(C)[msPA].m(C)}\| (SEQ ID NO: 245) | UUGCAGUACAUAAUUUACACAGAAGCAAUGCCIUCACCUUCC (SEQ ID NO: 235) |
| 197. | m(C)[msPA].f(A)[sP].m(U)[sP].f(A)[sP].f(A)[sP].m(U)[P].m(U)[sP].m(U)[sP].f(A)[sP].m(C)[sP].f(A)[msPA].m(C)[sP].f(A)[sP].f(G)[msPA].f(A)[sP].f(A)[sP].f(G)[sP].m(C)[P].f(A)[sP].f(A)[sP].m(U)[sP].f(G)[sP].d(C)[sP].[Dh](C)[sP].d(I)[msPA].m(U)[sP].f(C)[sP].m(A)[sP].m(C)[msPA].m(C)}\| (SEQ ID NO: 246) | CAUAAUUUACACAGAAGCAAUGCCIUCACC (SEQ ID NO: 236) |
| 198. | m(U)[sP].f(A)[sP].m(U)[sP].m(A)[sP].f(C)[sP].f(A)[sP].f(G)[sP].f(A)[sP].m(U)P.m(C)P.m(C)P.f(A)[sP].m(C)[sP].m(U)P.f(G)[sP].f(U)[sP].f(G)[sP].m(G)[sP].f(C)[sP].m(A)[sP].m(C) .f(C)[sP].f(C)[sP].m(A)[sP].m(G)P.f(A)[sP].f(U)[sP].f(U)[sP].f(A)[sP].m(U)P.d(C)[sP].[Dh](C)[sP].d(A)[sP].m(U)P.f(G)[sP].m(U)P.m(U)P.m(A)[sP].m(G)[sP].m(A)[sP].f(C)[sP].m(A)} (SEQ ID NO: 247) | UAUACAGAUCCACUGUGGCACCCAGAUUAUCCAUGUUAGACA (SEQ ID NO: 237) |
| 199. | m(U)[msPA].f(A)[sP].m(U)[sP].m(A)[sP].f(C)[sP].f(A)[sP].f(G)[sP].f(A)[sP].m(U)P.m(C)P.m(C)P.f(A)[sP].m(C)[sP].m(U)P.f(G)[sP].f(U)[sP].f(G)[sP].m(G)[sP].f(C)[sP].m(A)[sP].m(C)[msPA].f(C)[sP].f(C)[msPA].m(A)[sP].m(G)P.f(A)[sP].f(U)[sP].f(U)[sP].f(A)[sP].m(U)P.d(C)[sP].[Dh](C)[sP].d(A)[msPA].m(U)P.f(G)[sP].m(U)P.m(U)P.m(A)[sP].m(G)[sP].m(A)[sP].f(C)[msPA].m(A) (SEQ ID NO: 248) | UAUACAGAUCCACUGUGGCACCCAGAUUAUCCAUGUUAGACA (SEQ ID NO: 237) |
| 200. | m(U)[msPA].f(A)[sP].m(U)[sP].m(A)[sP].f(C)[sP].f(A)[sP].f(G)[sP].f(A)[sP].m(U)P.m(C)P.m(C)P.f(A)[sP].m(C)[sP].m(U)P.f(G)[sP].f(U)[sP].f(G)[sP].m(G)[sP].f(C)[sP].m(A)[sP].m(C)[msPA].f(C)[sP].f(C)[msPA].m(A)[sP].m(G)P.f(A)[sP].f(U)[msPA].f(U)[sP].f(A)[sP].m(U)P.d(C)[sP].[Dh](C)[sP].d(A)[msPA].m(U)P.f(G)[sP].m(U)P.m(U)P.m(A)[sP].m(G)[sP].m(A)[sP].f(C)[msPA].m(A) (SEQ ID : 249) | UAUACAGAUCCACUGUGGCACCCAGAUUAUCCAUGUUAGACA (SEQ ID NO: 237) |
| 201. | m(U)[msPA].f(A)[sP].m(U)[sP].m(A)[sP].f(C)[sP].f(A)[sP].f(G)[msPA].f(A)[sP].m(U)P.m(C)P.m(C)P.f(A)[sP].m(C)[sP].m(U)P.f(G)[sP].f(U)[sP].f(G)[sP].m(G)[P].f(C)[sP].m(A)[sP].m(C)[msPA].f(C)[sP].f(C)[msPA].m(A)[sP].m(G)P.f(A)[sP].f(U)[sP].f(U)[sP].f(A)[sP].m(U)P.d(C)[sP].[Dh](C)[P].d(A)[msPA].m(U)P.f(G)[sP].m(U)P.m(U)P.m(A)[sP].m(G)[sP].m(A)[sP].f(C)[msPA].m(A)} (SEQ ID NO: 250) | UAUACAGAUCCACUGUGGCACCCAGAUUAUCCAUGUUAGACA (SEQ ID NO: 237) |
| 202. | m(U)[msPA].f(A)[sP].m(U)[sP].m(A)[sP].f(C)[sP].f(A)[sP].f(G)[sP].f(A)[sP].m(U)P.m(C)[msPA].m(C)P.f(A)[P].m(C)[msPA].m(U)P.f(G)[P].f(U)[sP].f(G)[sP].m(G)[sP].f(C)[sP].m(A)[sP].m(C)[msPA].f(C)[sP].f(C)[msPA].m(A)[sP].m(G)P.f(A)[sP].f(U)[sP].f | UAUACAGAUCCACUGUGGCACCCAGAUUAUCCAUGUUAGACA (SEQ ID NO: 237) |

TABLE 3-continued

| Exemplary Oligonucleotides | | |
|---|---|---|
| Oligo No. | Oligonucleotide sequence | Base sequence |
| | (U)[sP].f(A)[sP].m(U)P.d(C)[sP].[Dh](C)[sP].d(A)[msPA].m(U)P.f(G)[sP].m(U)P.m(U)P.m(A)[sP].m(G)[sP].m(A)[sP].f(C)[msPA].m(A)} (SEQ ID NO: 251) | |
| 203. | m(U)[msPA].f(A)[sP].m(U)[sP].m(A)[sP].f(C)[sP].f(A)[sP].f(G)[msPA].f(A)[sP].m(U)P.m(C)P.m(C)P.f(A)[sP].m(C)[sP].m(U)P.f(G)[sP].f(U)[sP].f(G)[sP].m(G)[sP].f(C)[sP].m(A)[sP].m(C)[msPA].f(C)[sP].f(C)[msPA].m(A)[sP].m(G)P.f(A)[sP].f(U)[sP].f(U)[sP].f(A)[sP].m(U)P.d(C)[sP].[Dh](C)[sP].d(A)[msPA].m(U)P.f(G)[sP].m(U)P.m(U)[msPA].m(A)[sP].m(G)[sP].m(A)[sP].f(C)[msPA].m(A) (SEQ ID NO: 252) | UAUACAGAUCCACUGUGGCACCCAGAUUAUCCAUGUUAGACA (SEQ ID NO: 237) |
| 204. | m(U)[msPA].f(A)[sP].m(U)[sP].m(A)[sP].f(C)[sP].f(A)[sP].f(G)[msPA].f(A)[sP].m(U)P.m(C)P.m(C)P.f(A)[sP].m(C)[msPA].m(U)P.f(G)[sP].f(U)[sP].f(G)[sP].m(G)[sP].f(C)[sP].m(A)[sP].m(C)[msPA].f(C)[sP].f(C)[msPA].m(A)[sP].m(G)P.f(A)[sP].f(U)[sP].f(U)[sP].f(A)[sP].m(U)P.d(C)[sP].[Dh](C)[sP].d(A)[msPA].m(U)P.f(G)[sP].m(U)P.m(U)[msPA].m(A)[sP].m(G)[sP].m(A)[sP].f(C)[msPA].m(A)} (SEQ ID NO: 253) | UAUACAGAUCCACUGUGGCACCCAGAUUAUCCAUGUUAGACA (SEQ ID NO: 237) |
| 205. | m(U)[msPA].f(A)[sP].m(U)[sP].m(A)[sP].f(C)[sP].f(A)[sP].f(G)[msPA].f(A)[sP].m(U)P.m(C)[msPA].m(C)P.f(A)[P].m(C)[sP].m(U)P.f(G)[P].f(U)[sP].f(G)[sP].m(G)[sP].f(C)[sP].m(A)[sP].m(C)[msPA].f(C)[sP].f(C)[msPA].m(A)[sP].m(G)P.f(A)[sP].f(U)[mSPA].f(U)[sP].f(A)[sP].m(U)P.d(C)[sP].[Dh](C)[sP].d(A)[msPA].m(U)P.f(G)[sP].m(U)P.m(U)P.m(A)[sP].m(G)[P].m(A)[sP].f(C)msPA].m(A) (SEQ ID NO: 254) | UAUACAGAUCCACUGUGGCACCCAGAUUAUCCAUGUUAGACA (SEQ ID NO: 237) |
| 206. | m(U)[msPA].f(A)[sP].m(U)[sP].m(A)[sP].f(C)[sP].f(A)[sP].f(G)[sP].f(A)[sP].m(U)P.m(C)P.m(C)P.f(A)[sP].m(C)[sP].m(U)P.f(G)[sP].f(U)[sP].f(G)[sP].m(G)[sP].f(C)[sP].m(A)[msPA].m(C)P.f(C)[sP].f(C)[sP].m(A)[sP].m(G)[msPA].f(A)[sP].f(U)[sP].f(U)[sP].f(A)[sP].m(U)P.d(C)[sP].[Dh](C)[sP].d(A)[msPA].m(U)P.f(G)[P].m(U)P.m(U)P.m(A)[sP].m(G)[sP].m(A)[sP].f(C)[msPA].m(A) (SEQ ID NO: 255) | UAUACAGAUCCACUGUGGCACCCAGAUUAUCCAUGUUAGACA (SEQ ID NO: 237) |
| 207. | m(U)[msPA].f(A)[sP].m(U)[sP].m(A)[sP].f(C)[sP].f(A)[sP].f(G)[sP].f(A)[sP].m(U)[sP].m(C)[sP].m(C)[sP].f(A)[sP].m(C)[sP].m(U)[sP].f(G)[sP].f(U)[P].f(G)[sP].m(G)[sP].f(C)[sP].m(A)[sP].m(C)[msPA].f(C)[sP].f(C)[msPA].m(A)[sP].m(G)[sP].f(A)[sP].f(U)[sP].f(U)[sP].f(A)[sP].m(U)[sP].d(C)[sP].[Dh](C)[sP].d(A)[msPA].m(U)[sP].f(G)[sP].m(U)[sP].m(U)[sP].m(A)[sP].m(G)[sP].m(A)[sP].f(C)[msPA].m(A) (SEQ ID NO: 256) | UAUACAGAUCCACUGUGGCACCCAGAUUAUCCAUGUUAGACA (SEQ ID NO: 237) |
| 208. | m(U)[msPA].f(A)[sP].m(U)[sP].m(A)[sP].f(C)[sP].f(A)[sP].f(G)[sP].f(A)[sP].m(U)[P].m(C)P.m(C)P.f(A)[sP].m(C)[P].m(U)P.f(G)[sP].f(U)[sP].f(G)[sP].m(G)[sP].f(C)[sP].m(A)[sP].m(C)[msPA].f(C)[sP].f(C)[msPA].m(A)[sP].m(G)[sP].f(A)[sP].f(U)[sP].f(U)[sP].f(A)[sP].m(U)P.d(C)[sP].[Dh](C)[sP].d(A)[msPA].m(U)P.f(G)[sP].m(U)[sP].m(U)P.m(A)[sP].m(G)[sP].m(A)[sP].f(C)[msPA].m(A) (SEQ ID NO: 257) | UAUACAGAUCCACUGUGGCACCCAGAUUAUCCAUGUUAGACA (SEQ ID NO: 237) |
| 209. | m(U)[msPA].f(A)[sP].m(U)[sP].m(A)[sP].f(C)[sP].f(A)[sP].f(G)[sP].f(A)[sP].m(U)P.m(C)[sP].m(C)P.f(A)[sP].m(C)[sP].m(U)P.f(G)[P].f(U)[sP].f(G)[sP].m(G)[sP].f(C)[sP].m(A)[sP].m(C)[msPA].f(C)[sP].f(C)[msPA].m(A)[sP].m(G)[sP].f(A)[sP].f(U)[sP].f(U)[sP].f(A)[sP].m(U)P.d(C)[sP].[Dh](C)[sP].d(A)[msPA].m(U)P.f(G)[sP].m(U)P.m(U)[sP].m(A)[sP].m(G)[sP].m(A)[sP].f(C)[msPA].m(A)} (SEQ ID NO: 258) | UAUACAGAUCCACUGUGGCACCCAGAUUAUCCAUGUUAGACA (SEQ ID NO: 237) |
| 210. | m(U)[msPA].f(A)[sP].m(U)[sP].m(A)[sP].f(C)[sP].f(A)[sP].f(G)[sP].f(A)[sP].m(U)P.m(C)P.m(C)[sP].f(A)[sP].m(C)[sP].m(U)[sP].f(G)[sP].f(U)[sP].f(G)[sP].m(G)[sP].f(C)[sP].m(A)[sP].m(C)[msPA].f(C)[sP].f(C)[msPA].m(A)[sP].m(G)P.f(A)[sP].f(U)[sP].f(U)[sP].f(A)[sP].m(U)P.d(C)[sP].[Dh](C)[sP].d(A)[msPA].m(U)P.f(G)[sP].m(U)[sP].m(U)P.m(A)[sP].m(G)[sP].m(A)[sP].f(C)[msPA].m(A)} (SEQ ID NO: 259) | UAUACAGAUCCACUGUGGCACCCAGAUUAUCCAUGUUAGACA (SEQ ID NO: 237) |
| 211. | m(U)[msPA].f(A)[sP].m(U)P.m(A)[sP].f(C)[sP].f(A)[sP].f(G)[sP].f(A)[sP].m(U)P.m(C)P.m(C)P.f(A)[sP].m(C)[sP].m(U)P.f(G)[sP].f(U)P.f(G)[sP].m(G)[sP].f(C)[sP].m(A)P.m(C)[msPA].f(C)[sP].f(C)[msPA].m(A)P.m(G)P.f(A)[sP].f(U)P.f(U)[sP].f(A)[sP].m(U)P.d(C)[sP].[Dh](C)[sP].d(A)[msPA].m(U)P.f(G)[sP].m(U)P.m(U)P.m(A)[sP].m(G)P.m(A)[sP].f(C)[msPA].m(A)} (SEQ ID NO: 260) | UAUACAGAUCCACUGUGGCACCCAGAUUAUCCAUGUUAGACA (SEQ ID NO: 237) |

TABLE 3-continued

Exemplary Oligonucleotides

| Oligo No. | Oligonucleotide sequence | Base sequence |
|---|---|---|
| 212. | m(U)[msPA].f(A)[sP].m(U)[sP].m(A)P.f(C)[sP].f(A)[sP].f(G)[sP].f(A)[sP].m(U)P.m(C)P.m(C)P.f(A)[sP].m(C)[P].m(U)P.f(G)P.f(U)[sP].f(G)[sP].m(G)[sP].f(C)[sP].m(A)P.m(C)[msPA].f(C)[sP].f(C)[msPA].m(A)P.m(G)P.f(A)[sP].f(U)[sP].f(U)P.f(A)[sP].m(U)P.d(C)[sP].[Dh](C)[sP].d(A)[msPA].m(U)P.f(G)[sP].m(U)P.m(U)P.m(A)P.m(G)[sP].m(A)[sP].f(C)[msPA].m(A)} (SEQ ID NO: 261) | UAUACAGAUCCACUGUGGCACCCAGAUUAUCCAUGUUAGACA (SEQ ID NO: 237) |
| 213. | m(U)[msPA].f(A)[sP].m(U)[sP].m(A)[sP].f(C)P.f(A)[sP].f(G)[sP]f(A)[sP].m(U)P.m(C)P.m(C)P.f(A)[sP].m(C)[sP].m(U)P.f(G)[sPl.f(U)[sP].f(G)P.m(G)[sP].f(C)[sP].m(A)P.m(C)[msPA].f(C)[sP].f(C)[msPA].m(A)P.m(G)P.f(A)[sP].f(U)[sP].f(U)[sP].f(A)P.m(U)P.d(C)[sP].[Dh](C)[sP].d(A)[msPA].m(U)P.f(G)[sP].m(U)P.m(U)P.m(A)[sP].m(G)[sP].m(A)P.f(C)[msPA].m(A)} (SEQ ID NO: 262) | UAUACAGAUCCACUGUGGCACCCAGAUUAUCCAUGUUAGACA (SEQ ID NO: 237) |
| 214. | m(U)[msPA].f(A)[P].m(U)P.m(A)P.f(C)[sP].f(A)[sP].f(G)P.f(A)[sP].m(U)P.m(C)P.m(C)P.f(A)[sP].m(C)P.m(U)P.f(G)[sP].f(U)P.f(G)[sP].m(G)[P].f(C)P.m(A)[sP].m(C)[msPA].f(C)[P].f(C)[msPA].m(A)P.m(G)P.f(A)P.f(U)[sP].f(U)P.f(A)[sP].m(U)P.d(C)[sP][Dh](C)[sP].d(A)[msPA].m(U)P.f(G)[sP].m(U)P.m(U)P.m(A)[sP].m(G)P.m(A)[sP].f(C)[msPA].m(A)} (SEQ ID NO: 263) | UAUACAGAUCCACUGUGGCACCCAGAUUAUCCAUGUUAGACA (SEQ ID NO: 237) |
| 215. | m(U)[msPA].f(A)[sP].m(U)P.m(A)P.f(C)[sP].f(A)P.f(G)[sP].f(A)P.m(U)P.m(C)P.m(C)P.f(A)[sP].m(C)P.m(U)P.f(G)[sP].f(U)[sP].f(G)[sP].m(G)P.f(C)[sP].m(A)[sP].m(C)[msPA].f(C)[sP].f(C)[mSPA].m(A)P.m(G)P.f(A)[sP].f(U)P.f(U)[sP].f(A)P.m(U)P.d(C)[sP].[Dh](C)[sP].d(A)[msPA].m(U)P.f(G)[sP].m(U)P.m(U)P.m(A)[sP].m(G)P.m(A)[sP].f(C)[msPA].m(A) (SEQ ID NO: 264) | UAUACAGAUCCACUGUGGCACCCAGAUUAUCCAUGUUAGACA (SEQ ID NO: 237) |
| 216. | m(U)[msPA].f(A)[sP].m(U)P.m(A)P.f(C)P.f(A)[sP].f(G)[sP].f(A)P.m(U)P.m(C)P.m(C)P.f(A)[sP].m(C)P.m(U)P.f(G)[sP].f(U)[sP]f(G)P.m(G)[sP].f(C)[sP].m(A)[sP].m(C)[msPA].f(C)[sP].f(C)[msPA].m(A)P.m(G)P.f(A)P.f(U)[sP].f(U)[sP].f(A)P.m(U)P.d(C)[sP].[Dh](C)[sP].d(A)[msPA].m(U)P.f(G)[sP].m(U)P.m(U)P.m(A)P.m(G)[sP].m(A)[sP].f(C)[msPA].m(A)} (SEQ ID NO: 265) | UAUACAGAUCCACUGUGGCACCCAGAUUAUCCAUGUUAGACA (SEQ ID NO: 237) |
| 217. | m(G)[sP].f(C)[sP].m(U)[sP].f(G)[sP].f(A)[sP].m(A)P.m(U)P.f(U)[sP].m(G)P.f(G)[sP].m(G)P.f(A)[sP].f(G)[sP].m(A)P.m(A)P.m(A)P.d(T)[sP].d(C)[sP].d(C)[sP].f(A)[sP].f(C)[sP].m(C)P.m(U)P.f(G)[sP].m(U)P.d(C)[sP].[Dh](C)[sP].d(I)[sP].m(U)P.f(U)[sP].m(C)P.m(A)P.f(U)[sP].f(C)[P].m(U)[sP].f(A)[sP].f(G)[sP].m(U)} (SEQ ID NO: 266) | GCUGAAUUGGGAGAAATCCACCUGUCCIUUCAUCUAGU (SEQ ID NO: 238) |
| 218. | m(G)[msPA].f(C)[sP].m(U)[sP].f(G)[sP].f(A)[sP].m(A)P.m(U)P.f(U)[sP].m(G)P.f(G)[sP].m(G)P.f(A)[sP].f(G)[sP].m(A)P.m(A)P.m(A)[msPA].d(T)[sP].d(C)[msPA].d(C)[sP].f(A)[sP].f(C)[sP].m(C)P.m(U)P.f(G)[sP].m(U)P.d(C)[sP].[Dh](C)[sP].d(I)[msPA].m(U)P.f(U)[sP].m(C)P.m(A)P.f(U)[sP].f(C)[sP].m(U)[sP].f(A)[sP].f(G)[msPA].m(U)} (SEQ ID NO: 267) | GCUGAAUUGGGAGAAATCCACCUGUCCIUUCAUCUAGU (SEQ ID NO: 238) |
| 219. | m(G)[msPA].f(C)[sP].m(U)[sP].f(G)[sP].f(A)[sP].m(A)P.m(U)P.f(U)[sP].m(G)P.f(G)[sP].m(G)P.f(A)[sP].f(G)[sP].m(A)P.m(A)P.m(A)P.d(T)[sP].d(C)[sP].d(C)[sP].f(A)[sP].f(C)[sP].m(C)P.m(U)P.f(G)[sP].m(U)P.d(C)[sP].[Dh](C)[sP].d(I)[msPA].m(U)P.f(U)[sP].m(C)P.m(A)P.f(U)[sP].f(C)[sP].m(U)[sP].f(A)[sP].f(G)[msPA].m(U)} (SEQ ID NO: 268) | GCUGAAUUGGGAGAAATCCACCUGUCCIUUCAUCUAGU (SEQ ID NO: 238) |
| 220. | m(G)[msPA].f(C)[sP].m(U)[sP].f(G)[sP].f(A)[sP].m(A)P.m(U)P.f(U)[sP].m(G)P.f(G)[sP].m(G)P.f(A)[sP].f(G)[sP].m(A)P.m(A)P.m(A)P.d(T)[sP].d(C)[sP].d(C)[sP].f(A)[sP].f(C)[sP].m(C)P.m(U)P.f(G)[sP].m(U)P.d(C)[sP].[Dh](C)[sP].d(I)[sP].m(U)P.f(U)[sP].m(C)P.m(A)P.f(U)[sP].f(C)[sP].m(U)[sP].f(A)[sP].f(G)[msPA].m(U)} (SEQ ID NO: 269) | GCUGAAUUGGGAGAAATCCACCUGUCCIUUCAUCUAGU (SEQ ID NO: 238) |
| 221. | m(G)[msPA].f(C)[sP].m(U)[sP].f(G)[sP].f(A)[sP].m(A)P.m(U)P.f(U)[sP].m(G)P.f(G)[sP].m(G)P.f(A)[sP].f(G)[sP].m(A)P.m(A)P.m(A)P.d(T)[sP].d(C)[sP].d(C)[sP].f(A)[sP].f(C)[sP].m(C)P.m(U)P.f(G)[sP].m(U)P.d(C)[sP].[Dh](C)[sP].d(I)[sP].m(U)P.f(U)[sP].m(C)P.m(A)P.f(U)[sP].f(C)[sP].m(U)[sP].f(A)[sP].f(G)[sP].m(U)} (SEQ ID NO: 270) | GCUGAAUUGGGAGAAATCCACCUGUCCIUUCAUCUAGU (SEQ ID NO: 238) |

TABLE 3-continued

Exemplary Oligonucleotides

| Oligo No. | Oligonucleotide sequence | Base sequence |
|---|---|---|
| 222. | m(G)[sP].f(C)[sP].m(U)[sP].f(G)[sP].f(A)[sP].m(A)P.m(U)P.f(U)[sP].m(G)P.f(G)[sP].m(G)P.f(A)[sP].f(G)[sP].m(A)P.m(A)P.m(A)P.d(T)[sP].d(C)[sP].d(C)[sP].f(A)[sP].f(C)[sP].m(C)P.m(U)P.f(G)[sP].m(U)P.d(C)[sP].[Dh](C)[sP].d(I)[msPA].m(U)P.f(U)[sP].m(C)P.m(A)P.f(U)[sP].f(C)[sP].m(U)[sP].f(A)[sP].f(G)[sP].m(U)} (SEQ ID NO: 271) | GCUGAAUUGGGAGAAATCCACCUGUCCIUUCAUCUAGU (SEQ ID NO: 238) |
| 223. | m(G)[sP].f(C)[sP].m(U)[sP].f(G)[sP].f(A)[sP].m(A)P.m(U)P.f(U)[sP].m(G)P.f(G)[sP].m(G)P.f(A)[sP].f(G)[sP].m(A)P.m(A)P.m(A)P.d(T)[sP].d(C)[sP].d(C)[sP].f(A)[sP].f(C)[sP].m(C)P.m(U)P.f(G)[sP].m(U)P.d(C)[sP].[Dh](C)[sP].d(I)[sP].m(U)P.f(U)[sP].m(C)P.m(A)P.f(U)[sP].f(C)[sP].m(U)[sP].f(A)[sP].f(G)[msPA].m(U)} (SEQ ID NO: 272) | GCUGAAUUGGGAGAAATCCACCUGUCCIUUCAUCUAGU (SEQ ID NO: 238) |
| 224. | m(A)[msPA].m(A)[sP].m(C)[sP].m(A)P.m(U)P.m(G)P.m(G)P.m(C)P.m(C)P.m(C)P.m(C)[sP].f(A)[sP].f(G)[sP].m(C)P.m(A)P.f(G)[sP].f(C)P.m(U)[sP].f(U)[msPA].m(C)P.f(A)[sP].f(G)[msPA].f(U)P.m(C)[sP].f(C)[sP].m(C)P.f(U)[sP].m(U)P.m(U)P.f(C)[sP].d(T)[sP].[Dh](C)[P].d(I)[msPA].m(U)P.f(C)[sP].m(G)P.m(A)P.m(U)P.m(G)[sP].m(G)[sP].m(U)[msPA].m(C) (SEQ ID NO: 273) | AACAUGGCCCCAGCAGCUUCAGUCCCUUUCTCIUCGAUGGUC (SEQ ID NO: 239) |
| 225. | m(A)[msPA].m(A)[sP].m(C)[sP].f(A)[sP].m(U)P.f(G)[sP].m(G)P.m(C)P.m(C)P.m(C)[sP].f(A)[sP].f(G)[sP].m(C)P.m(A)P f(G)[sP].f(C)P.m(U)[sP].f(U)[msPA].m(C)P.f(A)[sP].f(G)[msPA].f(U)P.m(C)[sP].f(C)[sP].m(C)P.f(U)[sP].m(U)P.m(U)P.f(C)[sP].d(T)[sP].[Dh](C)[sP].d(I)[msPA].m(U)P.f(C)[sP].m(G)P.m(A)P.m(U)P.m(G)[sP].f(G)[sP].f(U)[msPA].m(C)} (SEQ ID NO: 274) | AACAUGGCCCCAGCAGCUUCAGUCCCUUUCTCIUCGAUGGUC (SEQ ID NO: 239) |
| 226. | m(A)[msPA].m(A)[sP].m(C)[sP].m(A)[sP].m(U)P.d(G)[sP].f(G)[sP].f(C)[sP].m(C)P.m(C)[sP].m(C)[sP].f(A)[sP].f(G)[sP].m(C)P.m(A)P.f(G)[sP].f(C)P.m(U)[sP].f(U)[msPA].m(C)P.f(A)[sP].f(G)[msPA].f(U)P.m(C)[sP].f(C)[sP].m(C)P.f(U)[sP].m(U)P.m(U)P.f(C)[sP].d(T)[sP].[Dh](C)[sP].d(I)[msPA].m(U)P.f(C)[sP].m(G)P.m(A)P.m(U)[sP].m(G)[sP].m(G)[sP].d(T)[msPA].m(C)} (SEQ ID NO: 275) | AACAUGGCCCCAGCAGCUUCAGUCCCUUUCTCIUCGAUGGTC (SEQ ID NO: 239) |
| 227. | m(A)[sP].m(A)[sP].m(C)[sP].m(A)P.m(U)P.m(G)P.m(G)P.m(C)P.m(C)P.m(C)P.m(C)[sP].f(A)[sP].f(G)[sP].m(C)P.m(A)P.f(G)[sP].f(C)P.m(U)[sP].f(U)[sP].m(C)P.f(A)[sP].f(G)[sP].f(U)P.m(C[sP].f(C)[sP].m(C)P.f(U)[sP].m(U)P.m(U)P.f(C)[sP].d(T)[sP].[Dh](C)[sP].d(I)[sP].m(U)P.f(C)[sP].m(G)P.m(A)P.m(U)P.m(G)[sP].m(G)[sP].m(U)[sP].m(C)} (SEQ ID NO: 276) | AACAUGGCCCCAGCAGCUUCAGUCCCUUUCTCIUCGAUGGUC (SEQ ID NO: 239) |
| 228. | m(A)[sP].m(A)[sP].m(C)[sP].f(A)[sP].m(U)P.f(G)[sP].m(G)P.m(C)P.m(C)P.m(C)P.m(C)[P].f(A)[sP].f(G)[sP].m(C)P.m(A)P.f(G)[sP].f(C)P.m(U)[sP].f(U)[sP].m(C)P.f(A)[sP].f(G)[sP].f(U)P.m(C)[sP].f(C)[sP].m(C)P.f(U)[sP].m(U)P.m(U)P.f(C)[sP].d(T)[sP].[Dh](C)[sP].d(I)[sP].m(U)P.f(C)[sP].m(G)P.m(A)P.m(U)P.m(G)[sP].f(G)[sP].f(U)[sP].m(C) (SEQ ID NO: 277) | AACAUGGCCCCAGCAGCUUCAGUCCCUUUCTCIUCGAUGGUC (SEQ ID NO: 239) |
| 229. | m(A)[sP].m(A)[sP].m(C)[sP].m(A)[sP].m(U)P.d(G)[sP].f(G)[sP]f(C)[sP].m(C)P.m(C)P.m(C)[sP].f(A)[sP].f(G)[sP].m(C)P.m(A)P.f(G)[sP].f(C)P.m(U)[sP].f(U)[sP].m(C)P.f(A)[sP].f(G)[sP].f(U)P.m(C)[sP].f(C)[sP].m(C)P.f(U)[sP].m(U)P.m(U)P.f(C)[sP].d(T)[sP].[Dh](C)[sP].d(I)[sP].m(U)P.f(C)[sP].m(G)P.m(A)P.m(U)[sPl.m(G)[sP].m(G)[sP].d(T)[sP].m(C)} (SEQ ID NO: 278) | AACAUGGCCCCAGCAGCUUCAGUCCCUUUCTCIUCGAUGGTC (SEQ ID NO: 239) |
| 230. | m(A)[msPA].m(A)[sP].m(C)[sP].m(A)P.m(U)P.m(G)P.m(G)P.m(C)P.m(C)P.m(C)P.m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[Dh](C)[sP].d(I)[msPA].m(U)P.f(C)[sP].m(G)P.m(A)P.m(U)P.m(G)[sP].m(G)[sP].m(U)[mSPA].m(C)} (SEQ ID NO: 279) | AACAUGGCCCCAGCAGCTUCAGUCCCUTTCTCIUCGAUGGUC (SEQ ID NO: 240) |
| 231. | m(A)[msPA].m(A)[sP].m(C)[sP].f(A)[sP].m(U)P.f(G)[sP].m(G)P.m(C)P.m(C)P.m(C)P.m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[P].f(C)[P].f(C)[P].f(U)[sP].[moe](T)P.[moe](T)P.f(C)[sP].d(T)[sP].[Dh](C)[sP].d(I)[msPA].m(U)P.f(C)[sP].m(G)P.m(A)P.m(U)P.m(G)[sP].f(G)[sP].f(U)[msPA].m(C)} (SEQ ID NO: 280) | AACAUGGCCCCAGCAGCTUCAGUCCCUTTCTCIUCGAUGGUC (SEQ ID NO: 240) |

TABLE 3-continued

Exemplary Oligonucleotides

| Oligo No. | Oligonucleotide sequence | Base sequence |
|---|---|---|
| 232. | m(A)[msPA].m(A)[sP].m(C)[sP].m(A)[sP].m(U)P.d(G)[sP].f(G)[sP].f(C)[sP].m(C)P.m(C)P.m(C)[sP].f(A)[sP].f(G)[sP].[moe]([m5C])P.[moe](A)P.f(G)[sP].f(C)[sP].[moe](T)P.f(U)[msPA].m(C)P.f(A)[sP].m(G)[msPA].f(U)P.m(C)[sP].f(C)[sP].f(C)[sP].f(U)[sP].[moe](T)P.[moe](T)P.f(C)[sP].d(T)[sP].[Dh](C)[P].d(I)[msPA].m(U)P.f(C)[sP].m(G)P.m(A)P.m(U)[sP].m(G)[sP].m(G)[sP].d(T)[msPA].m(C) (SEQ ID NO: 281) | AACAUGGCCCCAGCAGCTUCAGUCCCUTTCTCIUCGAUGGTC (SEQ ID NO: 241) |
| 233. | m(A)[sP].m(A)[sP].m(C)[sP].m(A)P.m(U)P.m(G)P.m(G)P.m(C)P.m(C)P.m(C)P.m(C)[sP].f(A)[sP].f(G)[sP].[moe]([m5C])P.[moe](A)P.f(G)[sP].f(C)[sP].[moe](T)P.f(U)[sP].m(C)P.f(A)[sP].m(G)[sP].f(U)P.m(C)[sP].f(C)[sP].f(C)[sP].f(U)[sP].[moe](T)P.[moe](T)P.f(C)[sP].d(T)[sP].[Dh](C)[sP].d(I)[sP].m(U)P.f(C)[sP].m(G)P.m(A)P.m(U)P.m(G)[sP].m(G)[sP].m(U)[sP].m(C) (SEQ ID NO: 282) | AACAUGGCCCCAGCAGCTUCAGUCCCUTTCTCIUCGAUGGUC (SEQ ID NO: 240) |
| 234. | m(A)[sP].m(A)[sP].m(C)[sP].f(A)[sP].m(U)P.f(G)[sP].m(G)P.m(C)P.m(C)P.m(C)P.m(C)[sP].f(A)[sP].f(G)[sP].[moe]([m5C])P.[moe](A)P.f(G)[sP].f(C)[sP].[moe](T)P.f(U)[sP].m(C)P.f(A)[sP].m(G)[sP].f(U)P.m(C)[sP].f(C)[sP].f(C)[sP].f(U)[sP].[moe](T)P.[moe](T)P.f(C)[sP].d(T)[sP].[Dh](C)[sP].d(I)[sP].m(U)P.f(C)[sP].m(G)P.m(A)P.m(U)P.m(G)[sP].f(G)[sP].f(U)[sP].m(C) (SEQ ID NO: 283) | AACAUGGCCCCAGCAGCTUCAGUCCCUTTCTCIUCGAUGGUC (SEQ ID NO: 240) |
| 235. | m(A)[sP].m(A)[sP].m(C)[sP].m(A)[sP].m(U)P.d(G)[sP].f(G)[sP]f(C)[sP].m(C)P.m(C)P.m(C)[sP].f(A)[sP].f(G)[sP].[moe]([m5C])P.[moe](A)P.f(G)[sP].f(C)[sP].[moe](T)P.f(U)[sP].m(C)P.f(A)[sP].m(G)[sP].f(U)P.m(C)[sP].f(C)[sP].f(C)[sP].f(U)[sP].[moe](T)P.[moe](T)P.f(C)[sP].d(T)[sP].[Dh](C)[sP].d(I)[sP].m(U)P.f(C)[sP].m(G)P.m(A)P.m(U)[sP].m(G)[sP].m(G)[sP].d(T)[sP].m(C) SEQ ID NO: 284) | AACAUGGCCCCAGCAGCTUCAGUCCCUTTCTCIUCGAUGGTC (SEQ ID NO: 241) |
| 236. | m(C)[msPA].m(C)[sP].m(C)[sP].m(A)P.f(G)[sP].m(C)P.m(A)P.f(G)[sP].f(C)[sP].m(U)P.m(U)P.m(C)P.m(A)[msPA].m(G)P.f(U)[msPA].m(U)[sP].f(C)[sP].m(C)P.f(U)[sP].m(U)P.f(U)[sP].m(C)P.d(T)[sP].[Dh](C)[P].d(I)[msPA].m(U)[sP].f(C)[sP].m(G)[sP].m(A)[msPA].m(U) (SEQ ID NO: 284) | CCCAGCAGCUUCAGUUCCUUUCTCIUCGAU (SEQ ID NO: 242) |
| 237. | m(C)[msPA].m(C)[sP].m(C)[sP].m(A)P.f(G)[sP].m(C)P.m(A)P.f(G)[sP].f(C)[sP].m(U)P.m(U)P.m(C)P.m(A)[msPA].m(G)P.f(U)[msPA].m(U)P.f(C)[sP].m(C)P.f(U)[sP].m(U)P.f(U)[sP].m(C)P.d(T)[sP].[Dh](C)[sP].d(I)[msPA].m(U)P.f(C)[sP].m(G)[P].m(A)[msPA].m(U) (SEQ ID NO: 285) | CCCAGCAGCUUCAGUUCCUUUCTCIUCGAU (SEQ ID NO: 242) |
| 238. | m(C)[msPA].m(C)[sP].m(C)[msPA].m(A)P.f(G)[sP].m(C)P.m(A)P.f(G)[msPA].f(C)[sP].m(U)P.m(U)P.m(C)P.m(A)P.m(G)P.f(U)[msPA].m(U)P.f(C)[sP].m(C)P.f(U)[sP].m(U)P.f(U)[sP].m(C)P.d(T)[sP].[Dh](C)[P].d(I)[msPA].m(U)P.f(C)[sP].m(G)[sP].m(A)[msPA].m(U) (SEQ ID NO: 286) | CCCAGCAGCUUCAGUUCCUUUCTCIUCGAU (SEQ ID NO: 242) |
| 239. | m(C)[msPA].m(C)[sP].m(C)[sP].m(A)P.f(G)[msPA].m(C)P.m(A)P.f(G)[msPA].f(C)[sP].m(U)P.m(U)P.m(C)P.m(A)P.m(G)P.f(U)[msPA].m(U)P.f(C)[sP].m(C)P.f(U)[sP].m(U)P.f(U)[sP].m(C)P.d(T)[sP].[Dh](C)[sP].d(I)[msPA].m(U)P.f(C)[sP].m(G)[sP].m(A)[msPA].m(U) (SEQ ID NO: 287) | CCCAGCAGCUUCAGUUCCUUUCTCIUCGAU (SEQ ID NO: 242) |
| 240. | m(C)[msPA].m(C)[sP].m(C)P.m(A)P.f(G)[msPA].m(C)P.m(A)P.f(G)[msPA].f(C)[sP].m(U)P.m(U)P.m(C)P.m(A)P.m(G)P.f(U)[msPA].m(U)P.f(C)[sP].m(C)P.f(U)[sP].m(U)P.f(U)[sP].m(C)P.d(T)[sP].[Dh](C)[sP].d(I)[msPA].m(U)P.f(C)[sP].m(G)[sP].m(A)[msPA].m(U) (SEQ ID NO: 288) | CCCAGCAGCUUCAGUUCCUUUCTCIUCGAU (SEQ ID NO: 242) |
| 241. | m(C)[msPA].m(C)[sP].m(C)[msPA].m(A)P.f(G)[msPA].m(C)P.m(A)P.f(G)[msPA].f(C)[sP].m(U)P.m(U)P.m(C)P.m(A)P.m(G)P.f(U)[msPA].m(U)P.f(C)[sP].m(C)P.f(U)[sP].m(U)P.f(U)[sP].m(C)P.d(T)[sP].[Dh](C)[sP].d(I)[msPA].m(U)P.f(C)[sP].m(G)[sP].m(A)[msPA].m(U) (SEQ ID NO: 289) | CCCAGCAGCUUCAGUUCCUUUCTCIUCGAU (SEQ ID NO: 242) |
| 242. | m(C)[msPA].m(C)[sP].m(C)[msPA].m(A)P.f(G)[msPA].m(C)P.m(A)P.f(G)[msPA].f(C)[sP].m(U)P.m(U)P.m(C)P.m(A)P.m(G)P.f(U)[msPA].m(U)P.f(C)[sP].m(C)P.f(U)[msPA].m(U)P.f(U)[sP].m(C)P.d(T)[sP].[Dh](C)[sP].d(I)[msPA].m(U)P.f(C)[sP].m(G)[sP].m(A)[msPA].m(U) (SEQ ID NO: 290) | CCCAGCAGCUUCAGUUCCUUUCTCIUCGAU (SEQ ID NO: 242) |

TABLE 3-continued

Exemplary Oligonucleotides

| Oligo No. | Oligonucleotide sequence | Base sequence |
|---|---|---|
| 243. | m(C)[msPA].m(C)[sP].m(C)[sP].m(A)P.f(G)[P].m(C)P.m(A)P.f(G)[sP].f(C)[sP].m(U)P.m(U)P.m(C)P.m(A)P.m(G)P.f(U)[sP].m(U)[sP].f(C)[sP].m(C)P.f(U)[sP].m(U)P.f(U)[sP].m(C)P.d(T)[sP].[Dh](C)[sP].d(I)[sP].m(U)[sP].f(C)[sP].m(G)[sP].m(A)[msPA]m(U) (SEQ ID NO: 291) | CCCAGCAGCUUCAGUUCCUUUCTCIUCGAU (SEQ ID NO: 242) |
| 244. | m(C)[msPA].m(C)[P].m(C)[msPA].m(A)P.f(G)[msPA].m(C)P.m(A)[msPA].f(G)[P].f(C)[sP].m(U)P.m(U)P.m(C)P.m(A)P.m(G)P.f(U)[sP].m(U)[sP].f(C)[sP].m(C)P.f(U)[sP].m(U)P.f(U)[sP].m(C)P.d(T)[sP].[Dh](C)[sP].d(I)[sP].m(U)[sP].f(C)[sP].m(G)[sP].m(A)[msPA].m(U) (SEQ ID NO: 292) | CCCAGCAGCUUCAGUUCCUUUCTCIUCGAU (SEQ ID NO: 242) |
| 245. | m(C)[msPA].m(C)[sP].m(C)[sP].m(A)P.f(G)[sP].m(C)P.m(A)[msPA].f(G)[sP].f(C)[msPA].m(U)P.m(U)[msPA].m(C)P.m(A)P.m(G)P.f(U)[sP].m(U)[sP].f(C)[sP].m(C)P.f(U)[sP].m(U)P.f(U)[sP].m(C)P.d(T)[sP].[Dh](C)[sP].d(I)[P].m(U)[sP].f(C)[P].m(G)[sP].m(A)[msPA].m(U) (SEQ ID NO: 293) | CCCAGCAGCUUCAGUUCCUUUCTCIUCGAU (SEQ ID NO: 242) |
| 246. | m(C)[msPA].m(C)[sP].m(C)[sP].m(A)P.f(G)[sP].m(C)P.m(A)P.f(G)[sP].f(C)[sP].m(U)P.m(U)[msPA].m(C)P.m(A)[msPA].m(G)P.f(U)[msPA].m(U)[sP].f(C)[sP].m(C)P.f(U)[sP].m(U)P.f(U)[sP].m(C)P.d(T)[sP].[Dh](C)[sP].d(I)[sP].m(U)[sP].f(C)[sP].m(G)[sP].m(A)[msPA].m(U)} (SEQ ID NO: 294) | CCCAGCAGCUUCAGUUCCUUUCTCIUCGAU (SEQ ID NO: 242) |
| 247. | m(C)[msPA].m(C)[sP].m(C)[sP].m(A)P.f(G)[sP].m(C)P.m(A)P.f(G)[sP].f(C)[sP].m(U)P.m(U)P.m(C)P.m(A)P.m(G)P.f(U)[msPA].m(U)[sP].f(C)[msPA].m(C)P.f(U)[msPA].m(U)P.f(U)[sP].m(C)P.d(T)[sP].[Dh](C)[sP].d(I)[sP].m(U)[sP].f(C)[sP].m(G)[sP].m(A)[msPA].m(U)} (SEQ ID NO: 295) | CCCAGCAGCUUCAGUUCCUUUCTCIUCGAU (SEQ ID NO: 242) |
| 248. | m(C)[msPA].m(C)[sP].m(C)[sP].m(A)P.f(G)[sP].m(C)P.m(A)P.f(G)[sP].f(C)[sP].m(U)P.m(U)P.m(C)P.m(A)P.m(G)P.f(U)[sP].m(U)[sP].f(C)[sP].m(C)P.f(U)[msPA].m(U)P.f(U)[msPA].m(C)P.d(T)[sP].[Dh](C)[sP].d(I)[msPA].m(U)[P].f(C)[sP].m(G)[sP].m(A)[msPA].m(U) (SEQ ID NO: 296) | CCCAGCAGCUUCAGUUCCUUUCTCIUCGAU (SEQ ID NO: 242) |
| 249. | m(C)[msPA].m(C)[sP].m(C)[sP].m(A)P.f(G)[msPA].m(C)P.m(A)[msPA].f(G)[sP].f(C)[msPA].m(U)P.m(U)P.m(C)P.m(A)P.m(G)P.f(U)[sP].m(U)[sP].f(C)[sP].m(C)P.f(U)[sP].m(U)P.f(U)[sP].m(C)P.d(T)[sP].[Dh](C)[sP].d(I)[sP].m(U)[sP].f(C)[sP].m(G)[sP].m(A)[msPA].m(U) (SEQ ID NO: 297) | CCCAGCAGCUUCAGUUCCUUUCTCIUCGAU (SEQ ID NO: 242) |
| 250. | m(C)[msPA].m(C)[sP].m(C)[msPA].f(A)[sP].f(G)[P].m(C)P.m(A)P.f(G)[msPA].f(C)[sP].m(U)P.m(U)P.m(C)P.m(A)P.m(G)P.f(U)[msPA].m(C)P.f(C)[sP].m(C)P.f(U)[sP].m(U)P.f(U)[sP].m(C)P.d(T)[sP].[Dh](C)[sP].d(I)[msPA].m(U)P.f(C)[sP].m(G)[sP].m(A)[msPA].m(U) (SEQ ID NO: 298) | CCCAGCAGCUUCAGUUCCUUUCTCIUCGAU (SEQ ID NO: 242) |
| 251. | m(C)[msPA].m(C)[sP].m(C)[msPA].f(A)[sP].m(G)P.m(C)P.m(A)P.f(G)[msPA].f(C)[sP].m(U)P.m(U)P.m(C)P.m(A)P.m(G)P.f(U)[msPA].m(C)P.f(C)[sP].m(C)P.f(U)[sP].m(U)P.f(U)[sP].m(C)P.d(T)[sP].[Dh](C)[sP].d(I)[msPA].m(U)P.f(C)[P].m(G)[sP].m(A)[msPA].m(U) (SEQ ID NO: 299) | CCCAGCAGCUUCAGUUCCUUUCTCIUCGAU (SEQ ID NO: 242) |
| 252. | m(C)[msPA].m(C)[sP].m(C)[sP].m(A)P.f(G)[sP].m(C)P.m(A)P.f(G)[sP].f(C)[sP].m(U)P.m(U)P.m(C)P.m(A)[msPA].m(G)P.f(U)[msPA].m(U)[sP].f(C)[sP].m(C)P.f(U)[sP].m(U)P.f(U)[sP].m(C)P.d(T)[sP].[Dh](C)[msPA].d(I)[msPA].m(U)[sP].f(C)[sP].m(G)[sP].m(A)[msPA].m(U) (SEQ ID NO: 300) | CCCAGCAGCUUCAGUUCCUUUCTCIUCGAU (SEQ ID NO: 242) |
| 253. | m(C)[msPA].m(C)[sP].m(C)[msPA].m(A)P.f(G)[sP].m(C)P.m(A)P.f(G)[sP].f(C)[sP].m(U)P.m(U)P.m(C)P.m(A)[msPA].m(G)P.f(U)[msPA].m(U)[sP].f(C)[sP].m(C)P.f(U)[sP].m(U)P.f(U)[sP].m(C)P.d(T)[sP].[Dh](C)[msPA].d(I)[msPA].m(U)[sP].f(C)[sP].m(G)[sP].m(A)[msPA].m(U) (SEQ ID NO: 301) | CCCAGCAGCUUCAGUUCCUUUCTCIUCGAU (SEQ ID NO: 242) |
| 254. | f(A)[sP].f(A)[sP].m(C)[sP].m(A)[sP].f(U)[sP].f(G)[sP].f(G)[sP].f(C)[sP].m(C)[sP].f(C)[sP].m(C)P.f(A)[sP].m(G)[sP].m(C)P.f(A)[sP].f(G)[sP].m(C)P.f(U)[sP].m(U)[sP].m(C)P.m(A)P.f(G)[sP].f(U)[sP].m(C)[sP].f(C)[sP].f(C)[sP].f(U)[sP].m(U)P.f(U)[sP].m(C)P.d(T)[sP].[Dh](C)[sP].[fana](I)[sP].m(U)[sP].f(C)[sP].m(G)P.m(A)P.m(U)[sP].m(G)[sP].f(G)[sP].f(U)[sP].m(C) (SEQ ID NO: 302) | AACAUGGCCCCAGCAGCUUCAGUCCCUUUCTCIUCGAUGGUC (SEQ ID NO: 243) |

TABLE 3-continued

Exemplary Oligonucleotides

| Oligo No. | Oligonucleotide sequence | Base sequence |
|---|---|---|
| 255. | f(A)[sP].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[sP].f(G)[sP]f(U)[sP].m(C)[sP].f(C)[sP].f(C)[sP].f(U)[sP].m(U)[sP].f(U)[sP].m(C)[sP].d(T)[sP].[Dh](C)[sP].[fana](I)[P].m(U)[sP].f(C)[sP].m(G)P.m(A)P.m(U)P.m(G)[sP].f(G)[sP].f(U)[sP].m(C) (SEQ ID NO: 303) | AACAUGGCCCCAGCAGCUUCAGUCCCUUUCTCIUCGAUGGUC (SEQ ID NO: 243) |
| 256. | f(A)[msPA].f(A)[sP].m(C)P.m(A)[sP].f(U)[sP].f(G)[sP].f(G)[sP].f(C)[sP].m(C)[sP].f(C)[sP].m(C)[sP].f(A)[sP].m(G)P.m(C)[sP].f(A)[sP].f(G)[sP].m(C)[sP].f(U)[sP].m(U)P.m(C)P.m(A)[msPA].f(G)[sP].f(U)[msPA].m(C)[sP].f(C)[sP].f(C)[sP].f(U)[sP].m(U)[sP].f(U)[sP].m(C)[sP].d(T)[sP].[Dh](C)[sP].[fana](I)[msPA].m(U)[sP].f(C)[sP].m(G)P.m(A)P.m(U)P.m(G)[sP].f(G)[sP].f(U)[msPA].m(C) (SEQ ID NO: 304) | AACAUGGCCCCAGCAGCUUCAGUCCCUUUCTCIUCGAUGGUC (SEQ ID NO: 243) |

In some embodiments, the oligonucleotides disclosed herein do not include a stem-loop structure.

In some embodiments, the oligonucleotides disclose herein include a stem loop structure. Stem loop structures can act as a recruitment domain for the ADAR enzyme (e.g., an ADAR-recruiting domain), yet the oligonucleotides as disclosed herein can affect ADAR recruitment and activity against a target adenosine in a target RNA without such a stem loop structure.

In some embodiments, the oligonucleotides described herein may further include a 5' cap structure. In some embodiments, the 5' cap structure is a 2,2,7-trimethyl-guanosine cap.

In some embodiments the oligonucleotides described herein include a GalNAc moiety at the 5' end of the oligonucleotide. In some embodiments the oligonucleotides described herein include a GalNAc moiety at the 3' end of the oligonucleotide.

Oligonucleotides described herein can be synthesized by standard methods known in the art as further discussed below, e.g., by use of an automated DNA synthesizer, such as are commercially available from, for example, Biosearch, Applied Biosystems, Inc.

The oligonucleotide can be prepared using solution-phase or solid-phase organic synthesis or both. Organic synthesis offers the advantage that the oligonucleotide including unnatural or alternative nucleotides can be easily prepared. Single-stranded oligonucleotides described herein can be prepared using solution-phase or solid-phase organic synthesis or both.

It is contemplated that for any sequence identified herein, further optimization could be achieved by systematically either adding or removing linked nucleosides to generate longer or shorter sequences. Such optimized sequences can be adjusted by, e.g., the introduction of alternative nucleosides, alternative sugar moieties, and/or alternative internucleotide linkages as described herein or as known in the art, including alternative nucleosides, alternative sugar moieties, and/or alternative internucleotide linkages as known in the art and/or discussed herein to further optimize the molecule (e.g., increasing serum stability or circulating half-life, increasing thermal stability, enhancing transmembrane delivery, targeting to a particular location or cell type, and/or increasing interaction with RNA editing enzymes (e.g., ADAR)).

The oligonucleotides described herein are synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Representative U.S. patents that teach the preparation of the oligonucleosides include, but are not limited to, U.S. Pat. Nos. 5,034,506; 5,166,315; 5,185,444; 5,214,134; 5,216,141; 5,235,033; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and 5,677,439, the entire contents of each of which are hereby incorporated herein by reference.

Some embodiments include oligonucleotides with phosphorothioate backbones, and/or oligonucleotides with heteroatom backbones, and in particular $—CH_2—NH—CH_2—$, $—CH_2—N(CH_3)—O—CH_2$-[known as a methylene (methylimino) or MMI backbone], $—CH_2—O—N(CH_3)—CH_2—$, $—CH_2—N(CH_3)—N(CH_3)—CH_2—$ and $—N(CH_3)—CH_2—CH_2$-[wherein the native phosphodiester backbone is represented as $—O—PO—CH_2—$] of the above-referenced U.S. Pat. No. 5,489,677, and the amide backbones of the above-referenced U.S. Pat. No. 5,602,240. In some embodiments, the oligonucleotides featured herein have morpholino backbone structures of the above-referenced U.S. Pat. No. 5,034,506. In some embodiments, the oligonucleotides described herein include phosphorodiamidate morpholino oligomers (PMO), in which the deoxyribose moiety is replaced by a morpholine ring, and the charged phosphodiester inter-subunit linkage is replaced by an uncharged phosphorodiamidate linkage, as described in Summerton, et al., Antisense Nucleic Acid Drug Dev. 1997, 7:63-70.

Various modifications can be introduced to a sugar and/or nucleobase in accordance with the present disclosure. For example, in some embodiments, a modification is a modification described in U.S. Pat. No. 9,006,198. In some embodiments, a modification is a modification described in U.S. Pat. Nos. 9,394,333, 9,744,183, 9,605,019, 9,982,257, US 20170037399, US 20180216108, US 20180216107, U.S. Pat. No. 9,598,458, WO 2017/062862, WO 2018/067973, WO 2017/160741, WO 2017/192679, WO 2017/210647, WO 2018/098264, WO 2018/022473, WO 2018/223056, WO 2018/223073, WO 2018/223081, WO 2018/237194, WO 2019/032607, WO 2019/032612, WO 2019/

055951, WO 2019/075357, WO 2019/200185, WO 2019/217784, WO 2019/032612, WO 2020/191252, and/or WO 2021/071858, the sugars, bases, and internucleotide linkages of each of which are independently incorporated herein by reference.

Alternative nucleotides and nucleosides include those with modifications including, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. The nucleobase may also be an isonucleoside in which the nucleobase is moved from the C1 position of the sugar moiety to a different position (e.g. C2, C3, C4, or C5). Specific examples of oligonucleotide compounds useful in the embodiments described herein include but are not limited to alternative nucleosides containing modified backbones or no natural internucleotide linkages. Nucleotides and nucleosides having modified backbones include, among others, those that do not have a phosphorus atom in the backbone. For the purposes of this specification, and as sometimes referenced in the art, alternative RNAs that do not have a phosphorus atom in their internucleoside backbone can also be considered to be oligonucleosides. In some embodiments, an oligonucleotide will have a phosphorus atom in its internucleoside backbone.

Alternative internucleotide linkages include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boronophosphates having normal 3'-5' linkages, 2'-5-linked analogs of these, and those having inverted polarity wherein the adjacent pairs of nucleoside units are linked 3'-5' to 5'-3' or 2'-5' to 5'-2'. Various salts, mixed salts, and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Alternative internucleotide linkages that do not include a phosphorus atom therein have backbones that are formed by short chain alkyl or cycloalkyl internucleotide linkages, mixed heteroatoms and alkyl or cycloalkyl internucleotide linkages, or one or more short chain heteroatomic or heterocyclic internucleotide linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable oligonucleotides include those in which both the sugar and the internucleotide linkage, i.e., the backbone, of the nucleotide units are replaced. The base units are maintained for hybridization with an appropriate nucleic acid target compound. One such oligomeric compound, a mimetic that has been shown to have excellent hybridization properties, is referred to as a peptide nucleic acid (PNA). In PNA compounds, the sugar of a nucleoside is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the oligonucleotides described herein are disclosed in, for example, in Nielsen et al., Science, 1991, 254, 1497-1500.

Alternative nucleosides and nucleotides can also contain one or more substituted sugar moieties. The oligonucleotides, e.g., oligonucleotides, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $—O[(CH_2)_nO]_mCH_3$, $—O(CH_2)_nOCH_3$, $—O(CH_2)_n—NH_2$, $—O(CH_2)_nCH_3$, $—O(CH_2)_n—ONH_2$, and $—O(CH_2)_n—ON[(CH_2)_nCH_3]_2$, where n and m are from 1 to about 10. In other embodiments, oligonucleotides include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In some embodiments, the modification includes a 2'-methoxyethoxy (2'-O—$CH_2CH_2OCH_3$, also known as 2'-O-(2-methoxyethyl) or 2'-O-MOE) (Martin et al., Helv. Chin. Acta, 1995, 78:486-504) i.e., an alkoxy-alkoxy group. 2'-O-MOE nucleosides confer several beneficial properties to oligonucleotides including, but not limited to, increased nuclease resistance, improved pharmacokinetics properties, reduced non-specific protein binding, reduced toxicity, reduced immunostimulatory properties, and enhanced target affinity as compared to unmodified oligonucleotides.

Another exemplary alternative contains 2'-dimethylaminooxyethoxy, i.e., a —$O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$(CH_2)_2$—O—$(CH_2)_2$—$N(CH_3)_2$. Further exemplary alternatives include: 5'-Me-2'-F nucleotides, 5'-Me-2'-OMe nucleotides, 5'-Me-2'-deoxynucleotides, (both R and S isomers in these three families); 2'-alkoxyalkyl; and 2'-NMA (N-methylacetamide).

Other alternatives include 2'-methoxy (2'-$OCH_3$), 2'-aminopropoxy (2'-$OCH_2CH_2CH_2NH_2$) and 2'-fluoro (2'-F). Similar modifications can also be made at other positions on the nucleosides and nucleotides of an oligonucleotide, particularly the 3' position of the sugar on the 3' terminal nucleotide or in 2'-5' linked oligonucleotides and the 5' position of 5' terminal nucleotide. Oligonucleotides can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

Oligonucleotides described herein can also include nucleobase (often referred to in the art simply as "base") alternatives (e.g., modifications or substitutions). Unmodified or natural nucleobases include the purine bases adenine (A) and guanine (G), and the pyrimidine bases thymine (T), cytosine (C) and uracil (U). Alternative nucleobases include other synthetic and natural nucleobases such as 5-methylcytosine, 5-hydroxymethylcytosine, 5-formylcytosine, 5-carboxycytosine, pyrrolocytosine, dideoxycytosine, uracil, 5-methoxyuracil, 5-hydroxydeoxyuracil, dihydrouracil, 4-thiouracil, pseudouracil, 1-methyl-pseudouracil, deoxyuracil, 5-hydroxybutynl-2'-deoxyuracil, xanthine, hypoxanthine, 7-deaza-xanthine, thienoguanine, 8-aza-7-deazaguanine, 7-methylguanine, 7-deazaguanine, 6-aminomethyl-7-deazaguanine, 8-aminoguanine, 2,2,7-trimethylguanine, 8-methyladenine, 8-azidoadenine, 7-methyladenine, 7-deazaadenine, 3-deazaadenine, 2,6-diaminopurine, 2-aminopurine, 7-deaza-8-aza-adenine, 8-amino-adenine, thymine, dideoxythymine, 5-nitroindole, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 8-azaguanine and 8-azaadenine, and 3-deazaguanine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., (1991) Angewandte Chemie, International Edition, 30:613, and those disclosed by Sanghvi, Y S., Chapter 15, Antisense Research and Applications, pages 289-302, Crooke, S. T. and Lebleu, B., Ed., CRC Press, 1993. Certain of these nucleobases are particularly useful for increasing the binding affinity of the oligomeric compounds described herein. These include 5-substituted pyrimidines, 6-azapyrimidines, and N-2, N-6 and 0-6 substituted purines, including 2-aminopropyladenine, 5-propynyluracil, and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., Antisense Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted alternative nucleobases as well as other alternative nucleobases include, but are not limited to, the above noted U.S. Pat. Nos. 3,687,808, 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

In other embodiments, the sugar moiety in the nucleotide may be a ribose molecule, optionally having a 2'-O-methyl, 2'-O-MOE, 2'-F, 2'-amino, 2'-O-propyl, 2'-aminopropyl, or 2'-OH modification.

In some embodiments, oligonucleotides described herein include one or more bicyclic sugar moieties. A "bicyclic sugar" is a furanosyl ring modified by the bridging of two atoms. A "bicyclic nucleoside" ("BNA") is a nucleoside having a sugar moiety including a bridge connecting two carbon atoms of the sugar ring, thereby forming a bicyclic ring system. In certain embodiments, the bridge connects the 4'-carbon and the 2'-carbon of the sugar ring. Thus, in some embodiments, oligonucleotides described herein may include one or more locked nucleosides. A locked nucleoside is a nucleoside having a modified ribose moiety in which the ribose moiety includes an extra bridge connecting the 2' and 4' carbons. In other words, a locked nucleoside is a nucleoside including a bicyclic sugar moiety including a 4'-$CH_2$—O-2' bridge. This structure effectively "locks" the ribose in the 3'-endo structural conformation. The addition of locked nucleosides to oligonucleotides has been shown to increase oligonucleotide stability in serum, and to reduce off-target effects (Grunweller, A. et al., (2003) Nucleic Acids Research 31(12):3185-3193). Examples of bicyclic nucleosides include without limitation nucleosides including a bridge between the 4' and the 2' ribosyl ring atoms. In certain embodiments, oligonucleotides include one or more bicyclic nucleosides including a 4' to 2' bridge. Examples of such 4' to 2' bridged bicyclic nucleosides, include but are not limited to 4'-$(CH_2)$—O-2' (LNA); 4'-$(CH_2)$—S-2'; 4'-$(CH_2)_2$—O-2' (ENA); 4'-$CH(CH_3)$—O-2' (also referred to as "constrained ethyl" or "cEt") and 4'-$CH(CH_2OCH_3)$—O-2' (and analogs thereof; see, e.g., U.S. Pat. No. 7,399,845); 4'-$C(CH_3)(CH_3)$—O-2' (and analogs thereof; see e.g., U.S. Pat. No. 8,278,283); 4'-$CH_2$—$N(OCH_3)$-2' (and analogs thereof; see e.g., U.S. Pat. No. 8,278,425); 4'-$CH_2$—O—$N(CH_3)_2$-2' (see, e.g., U.S. Patent Publication No. 2004/0171570); 4'-$CH_2$—N(R)—O-2', wherein R is H, $C_1$-$C_{12}$ alkyl, or a protecting group (see, e.g., U.S. Pat. No. 7,427,672); 4'-$CH_2$—$C(H)(CH_3)$-2' (see, e.g., Chattopadhyaya et al., J. Org. Chem., 2009, 74, 118-134); and 4'-$CH_2$—$C(=CH_2)$-2' (and analogs thereof; see, e.g., U.S. Pat. No. 8,278,426). The entire contents of each of the foregoing are hereby incorporated herein by reference.

Additional representative U.S. Patents and US Patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

Oligonucleotides described herein can also be modified to include one or more constrained ethyl nucleotides. As used herein, a "constrained ethyl nucleotide" or "cEt" is a locked nucleic acid including a bicyclic sugar moiety including a 4'-CH(CH3)-O-2' bridge. In one embodiment, a constrained ethyl nucleotide is in the S conformation referred to herein as "S-cEt."

Oligonucleotides described herein may also include one or more "conformationally restricted nucleotides" ("CRN"). CRN are nucleotide analogs with a linker connecting the C2' and C4' carbons of ribose or the C3 and —C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, US Patent Publication No. 2013/0190383; and PCT publication WO 2013/036868, the entire contents of each of which are hereby incorporated herein by reference.

In some embodiments, the oligonucleotides described herein include one or more monomers that are UNA (unlocked nucleic acid) nucleotides. UNA is unlocked acyclic nucleic acid, wherein any of the bonds of the sugar has been removed, forming an unlocked "sugar" residue. In one example, UNA also encompasses monomer with bonds between C1'-C4' have been removed (i.e. the covalent carbon-oxygen-carbon bond between the C1' and C4' carbons). In another example, the C2'-C3' bond (i.e. the covalent carbon-carbon bond between the C2' and C3' carbons) of the sugar has been removed (see Nuc. Acids Symp. Series, 52, 133-134 (2008) and Fluiter et al., Mol. Biosyst., 2009, 10, 1039 hereby incorporated by reference).

Representative U.S. publications that teach the preparation of UNA include, but are not limited to, U.S. Pat. No. 8,314,227; and US Patent Publication Nos. 2013/0096289; 2013/0011922; and 2011/0313020, the entire contents of each of which are hereby incorporated herein by reference.

The ribose molecule may also be modified with a cyclopropane ring to produce a tricyclodeoxynucleic acid (tricyclo DNA). The ribose moiety may be substituted for another sugar such as 1,5-anhydrohexitol, threose to produce a threose nucleoside (TNA), or arabinose to produce an arabino nucleoside. The ribose molecule can also be replaced with non-sugars such as cyclohexene to produce cyclohexene nucleoside or glycol to produce glycol nucleosides.

The ribose molecule can also be replaced with non-sugars such as cyclohexene to produce cyclohexene nucleic acid (CeNA) or glycol to produce glycol nucleic acids (GNA). Potentially stabilizing modifications to the ends of nucleotide molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

Other alternatives chemistries of the oligonucleotides described herein include a 5' phosphate or 5' phosphate mimic, e.g., a 5'-terminal phosphate or phosphate mimic of an oligonucleotide. Suitable phosphate mimics are disclosed in, for example US Patent Publication No. 2012/0157511, the entire contents of which are incorporated herein by reference.

Exemplary oligonucleotides described herein include sugar-modified nucleosides and may also include DNA or RNA nucleosides. In some embodiments, the oligonucleotide includes sugar-modified nucleosides and DNA nucleosides. Incorporation of alternative nucleosides into the oligonucleotides described herein may enhance the affinity of the oligonucleotide for the target nucleic acid. In that case, the alternative nucleosides can be referred to as affinity enhancing alternative nucleotides.

In some embodiments, the oligonucleotides described herein includes at least 1 alternative nucleoside, such as at least 2, at least 3, at least 4, at least 5, at least 6, at least 7, at least 8, at least 9, at least 10, at least 11, at least 12, at least 13, at least 14, at least 15 or at least 16 alternative nucleosides. In other embodiments, the oligonucleotides include from 1 to 10 alternative nucleosides, such as from 2 to 9 alternative nucleosides, such as from 3 to 8 alternative nucleosides, such as from 4 to 7 alternative nucleosides, such as 6 or 7 alternative nucleosides. In an embodiment, the oligonucleotides described herein may include alternatives, which are independently selected from these three types of alternative (alternative sugar moiety, alternative nucleobase, and alternative internucleotide linkage), or a combination thereof. Preferably the oligonucleotide includes one or more nucleosides including alternative sugar moieties, e.g., 2' sugar alternative nucleosides. In some embodiments, the oligonucleotides described herein include the one or more 2' sugar alternative nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, ANA, 2'-fluoro-ANA, and BNA (e.g., LNA) nucleosides. In some embodiments, the one or more alternative nucleoside is a BNA.

Oligonucleotide Conjugated to Ligands

Oligonucleotides described herein may be chemically linked to one or more ligands, moieties, or conjugates that enhance the activity, cellular distribution, or cellular uptake of the oligonucleotide. Such moieties include but are not limited to lipid moieties such as a cholesterol moiety (Letsinger et al., (1989) Proc. Natl. Acid. Sci. USA, 86: 6553-6556), cholic acid (Manoharan et al., (1994) Biorg. Med. Chem. Let., 4:1053-1060), a thioether, e.g., beryl-S-tritylthiol (Manoharan et al., (1992) Ann. N.Y. Acad. Sci., 660:306-309; Manoharan et al., (1993) Biorg. Med. Chem. Let., 3:2765-2770), a thiocholesterol (Oberhauser et al., (1992) Nucl. Acids Res., 20:533-538), an aliphatic chain, e.g., dodecandiol or undecyl residues (Saison-Behmoaras et al., (1991) EMBO J, 10:1111-1118; Kabanov et al., (1990) FEBS Lett., 259:327-330; Svinarchuk et al., (1993) Biochimie, 75:49-54), a phospholipid, e.g., di-hexadecyl-rac-glycerol or triethyl-ammonium 1,2-di-O-hexadecyl-rac-glycero-3-phosphonate (Manoharan et al., (1995) Tetrahedron Lett., 36:3651-3654; Shea et al., (1990) Nucl. Acids Res., 18:3777-3783), a polyamine or a polyethylene glycol chain (Manoharan et al., (1995) Nucleosides & Nucleotides, 14:969-973), or adamantane acetic acid (Manoharan et al., (1995) Tetrahedron Lett., 36:3651-3654), a palmityl moiety (Mishra et al., (1995) Biochim. Biophys. Acta, 1264:229-237), or an octadecylamine or hexylamino-carbonyloxycholesterol moiety (Crooke et al., (1996) J. Pharmacol. Exp. Ther., 277:923-937).

In one embodiment, a ligand alters the distribution, targeting, or lifetime of an oligonucleotide agent into which it is incorporated. In some embodiments, a ligand provides an enhanced affinity for a selected target, e.g., molecule, cell or cell type, compartment, e.g., a cellular or organ compartment, tissue, organ, or region of the body, as, e.g., compared to a species absent such a ligand.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylglucosamine, N-acetylgalactosamine, or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e.g. acridines), cross-linkers (e.g. psoralen, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose.

The ligand can be a substance, e.g., a drug, which can increase the uptake of the oligonucleotide agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to oligonucleotides described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that include a number of phosphorothioate linkages are also known to bind to serum protein, thus short oligonucleotides, e.g., oligonucleotides of about 5 bases, 10 bases, 15 bases, or 20 bases, including multiple of phosphorothioate linkages in the backbone are also amenable to oligonucleotides disclosed herein as ligands (e.g. as PK modulating ligands). In addition, aptamers that bind serum components (e.g. serum proteins) are also suitable for use as PK modulating ligands in the embodiments described herein.

Ligand-conjugated oligonucleotides described herein may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates described herein may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

In the ligand-conjugated oligonucleotides described herein, such as the ligand-molecule bearing sequence-specific linked nucleosides of the oligonucleotides described herein, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides described herein are synthesized by an automated synthesizer using phosphoramidites derived from ligand-nucleoside conjugates in addition to the standard phosphoramidites and non-standard phosphoramidites that are commercially available and routinely used in oligonucleotide synthesis.

Lipid Conjugates

In some embodiments, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid-based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In some embodiments, the ligand is a moiety, e.g., a vitamin, which is taken up by a target cell, e.g., a proliferating cell. Exemplary vitamins include vitamin A, E, and K.

Cell Permeation Agents

In some embodiments, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the oligonucleotide, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp, or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 152). An RFGF analogue (e.g., amino acid sequence AALLPVLLAAP (SEQ ID NO: 153) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ; SEQ ID NO: 154) and the Drosophila Antennapedia protein (RQIKIWFQNRRMKWKK; SEQ ID NO: 155) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to an oligonucleotide agent via an incorporated monomer unit for cell targeting purposes is an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods described herein may be linear or cyclic, and may be modified, e.g., glycosylated or methylated, to facilitate targeting to a specific tissue(s). RGD-containing peptides and peptidomimetics may include D-amino acids, as well as synthetic RGD mimics. In addition to RGD, one can use other moieties that target the integrin ligand. Some conjugates of this ligand target PECAM-1 or VEGF.

A cell permeation peptide is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin, or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

Carbohydrate Conjugates

In some embodiments, oligonucleotides described herein further includes a carbohydrate. The carbohydrate conjugated oligonucleotide is advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In some embodiments, a carbohydrate conjugate is a monosaccharide.

In some embodiments, the carbohydrate conjugate further includes one or more additional ligands as described above, such as, but not limited to, a PK modulator and/or a cell permeation peptide.

Additional carbohydrate conjugates (and linkers) suitable for use in the oligonucleotides described herein include those described in PCT Publication Nos. WO 2014/179620 and WO 2014/179627, the entire contents of each of which are incorporated herein by reference.

Linkers

In some embodiments, the conjugate or ligand described herein can be attached to an oligonucleotide with various linkers that can be cleavable or non-cleavable.

Linkers typically include a direct bond or an atom such as oxygen or sulfur, a unit such as $NR_8$, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, $N(R_8)$, C(O), substituted or unsubstituted aryl, substituted or unsubstituted heteroaryl, substituted or unsubstituted heterocyclic; where $R_8$ is hydrogen, acyl, aliphatic or substituted aliphatic. In one embodiment, the linker is between about 1-24 atoms, 2-24, 3-24, 4-24, 5-24, 6-24, 6-18, 7-18, 8-18 atoms, 7-17, 8-17, 6-16, 7-17, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times, or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential, or the presence of degradative molecules. Generally, cleavage agents are more prevalent or found at higher levels or activities inside cells than in serum or blood. Examples of such degradative agents include: redox agents which are selective for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissues. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In some embodiments, useful candidate compounds are cleaved at least about 2, 4, 10, 20, 30, 40, 50, 60, 70, 80, 90, or about 100 times faster in the cell (or under in vitro conditions selected to mimic intracellular conditions) as compared to blood or serum (or under in vitro conditions selected to mimic extracellular conditions).

Redox Cleavable Linking Groups

In one embodiment, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular oligonucleotide moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one embodiment, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

In another embodiment, a cleavable linker includes a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, O P(S)(ORk) O—, —O—P(S)(SRk)-O—, —S—P(O)(ORk)-O—, —O—P(O)(ORk)-S—, —S—P(O)(ORk)-S—, O P(S)(ORk) S, —S—P(S)(ORk)-O—, —O—P(O)(Rk)-O—, —O—P(S)(Rk)-O—, —S—P(O)(Rk)-O—, —S—P(S)(Rk)-O—, S P(O)(Rk)-S—, —O—P(S)(Rk)-S—. These candidates can be evaluated using methods analogous to those described above.

Acid Cleavable Linking Groups

In another embodiment, a cleavable linker includes an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C═NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

In another embodiment, a cleavable linker includes an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Groups

In yet another embodiment, a cleavable linker includes a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene, or alkynelene. A peptide bond is a special type of amide bond formed between amino acids to yield peptides and proteins. The peptide-based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above.

In one embodiment, oligonucleotides described herein are conjugated to a carbohydrate through a linker. Linkers include bivalent and trivalent branched linker groups. Exemplary oligonucleotide carbohydrate conjugates with linkers include, but are not limited to, those described in formulas 24-35 of PCT Publication No. WO 2018/195165.

Representative U.S. patents that teach the preparation of oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; 8,106,022, the entire contents of each of which are hereby incorporated herein by reference.

In certain instances, the oligonucleotide described herein can be modified by a non-ligand group. A number of non-ligand molecules have been conjugated to oligonucleotides in order to enhance the activity, cellular distribution, or cellular uptake of the oligonucleotide, and procedures for performing such conjugations are available in the scientific literature. Such non-ligand moieties have included lipid moieties, such as cholesterol (Kubo, T. et al., Biochem. Biophys. Res. Comm, 2007, 365(1):54-61; Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-S-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such oligonucleotide conjugates have been listed above. Typical conjugation protocols involve the synthesis of an oligonucleotide bearing an aminolinker at one or more positions of the sequence. The amino group is then reacted with the molecule being conjugated using appropriate coupling or activating reagents. The conjugation reaction can be performed either with the oligonucleotide still bound to the solid support or following cleavage of the oligonucleotide, in solution phase. Purification of the oligonucleotide conjugate by HPLC typically affords the pure conjugate.

III. Pharmaceutical Uses

The oligonucleotides described herein may be used to treat any disorder which may be treated through deamination of an adenosine. For example, any disorder which is caused by a guanosine to adenosine mutation, the introduction of a premature stop codon, or expression of an undesired protein. In some embodiments, the oligonucleotides described herein, when administered to a subject, can result in correction of a guanosine to adenosine mutation. In some embodiments, the oligonucleotides described herein can result in turning off of a premature stop codon so that a desired protein is expressed. In some embodiments, the oligonucleotides described herein can result in inhibition of expression of an undesired protein.

Particularly interesting target adenosines for editing using oligonucleotides described herein are those that are part of codons for amino acid residues that define key functions, or characteristics, such as catalytic sites, binding sites for other proteins, binding by substrates, localization domains, for co- or post-translational modification, such as glycosylation, hydroxylation, myristoylation, and protein cleavage by proteases (to mature the protein and/or as part of the intracellular routing).

A host of genetic diseases are caused by G-to-A mutations, and these are possible diseases to be treated by oligonucleotides described herein because adenosine deamination at the mutated target adenosine will reverse the mutation to wild-type. However, reversal to wild-type may not always be necessary to obtain a beneficial effect. Modification of an A to a G in a target may also be beneficial if the wild-type nucleotide is other than a G. In certain circumstances this may be predicted to be the case, in others this may require some testing. In certain circumstances, the modification from an A in a target RNA to a G where the wild-type is not a G may be silent (not translated into a different amino acid), or otherwise non-consequential (for example an amino acid is substituted but it constitutes a conservative substitution that does not disrupt protein structure and function), or the amino acid is part of a functional domain that has a certain robustness for change. If the A-to-G transition brought about by editing is in a non-coding RNA, or a non-coding part of an RNA, the consequence may also be inconsequential or less severe than the original mutation. Those of ordinary skill in the art will understand that the applicability of the methods described herein is very wide and is not even limited to preventing or treating disease. The methods described herein may also be used to modify transcripts to study the effect thereof, even if, or particularly when, such modification induces a diseased state, for example in a cell or a non-human animal model.

Examples of genetic diseases that can be prevented and/or treated with oligonucleotides described herein are any disease where the modification of one or more adenosines in a target RNA will bring about a (potentially) beneficial change.

The present disclosure is not limited to correcting mutations, as it may instead be useful to change a wildtype sequence into a mutated sequence by applying oligonucleotides described herein. One example where it may be advantageous to modify a wild-type adenosine is to bring about skipping of an exon, for example by modifying an adenosine that happens to be a branch site required for splicing of said exon. Another example is where the adenosine defines or is part of a recognition sequence for protein binding, or is involved in secondary structure defining the stability of the RNA. As noted above, therefore, the oligonucleotides and methods described herein can be used to provide research tools for diseases, to introduce new mutations which are less deleterious than an existing mutation. Deamination of an adenosine using the oligonucleotides disclosed herein includes any level of adenosine deamination, e.g., at least 1 deaminated adenosine within a target sequence (e.g., at least, 1, 2, 3, or more deaminated adenosines in a target sequence).

Adenosine deamination may be assessed by a decrease in an absolute or relative level of adenosines within a target sequence compared with a control level. The control level may be any type of control level that is utilized in the art, e.g., pre-dose baseline level, or a level determined from a similar subject, cell, or sample that is untreated or treated with a control (such as, e.g., buffer only control or inactive agent control).

Because the enzymatic activity of ADAR converts adenosines to inosines, adenosine deamination can alternatively be assessed by an increase in an absolute or relative level of inosines within a target sequence compared with a control level. Similarly, the control level may be any type of control level that is utilized in the art, e.g., pre-dose baseline level, or a level determined from a similar subject, cell, or sample that is untreated or treated with a control (such as, e.g., buffer only control or inactive agent control).

The levels of adenosines and/or inosines within a target sequence can be assessed using any of the methods known in the art for determining the nucleotide composition of a polynucleotide sequence. For example, the relative or absolute levels of adenosines or inosines within a target sequence can be assessed using nucleic acid sequencing technologies including but not limited to Sanger sequencing methods, Next Generation Sequencing (NGS; e.g., pyrosequencing, sequencing by reversible terminator chemistry, sequencing by ligation, and real-time sequencing) such as those offered on commercially available platforms (e.g., Illumina, Qiagen, Pacific Biosciences, Thermo Fisher, Roche, and Oxford Nanopore Technologies). Clonal amplification of target sequences for NGS may be performed using real-time polymerase chain reaction (also known as qPCR) on commercially available platforms from Applied Biosystems, Roche, Stratagene, Cepheid, Eppendorf, or Bio-Rad Laboratories. Additionally or alternatively, emulsion PCR methods can be used for amplification of target sequences using commercially available platforms such as Droplet Digital PCR by Bio-Rad Laboratories.

In certain embodiments, surrogate markers can be used to detect adenosine deamination within a target sequence. For example, effective treatment of a subject having a genetic disorder involving G-to-A mutations with an oligonucleotide of the present disclosure, as demonstrated by an acceptable diagnostic and monitoring criteria can be understood to demonstrate a clinically relevant adenosine deamination. In certain embodiments, the methods include a clinically relevant adenosine deamination, e.g., as demonstrated by a clinically relevant outcome after treatment of a subject with an oligonucleotide of the present disclosure.

Adenosine deamination in a gene of interest may be manifested by an increase or decrease in the levels of mRNA expressed by a first cell or group of cells (such cells may be present, for example, in a sample derived from a subject) in which a gene of interest is transcribed and which has or have been treated (e.g., by contacting the cell or cells with an oligonucleotide of the present disclosure, or by administering an oligonucleotide described herein to a subject in which the cells are or were present) such that the expression of the gene of interest is increased or decreased, as compared to a second cell or group of cells substantially identical to the first cell or group of cells but which has not or have not been so treated (control cell(s) not treated with an oligonucleotide or not treated with an oligonucleotide targeted to the gene of interest). The degree of increase or decrease in the levels of mRNA of a gene of interest (e.g., SERPINA1) may be expressed in terms of:

$$\frac{(mRNA \text{ in control cells}) - (mRNA \text{ in treated cells})}{(mRNA \text{ in control cells})} \times 100\%$$

In other embodiments, change in the levels of a gene may be assessed in terms of a reduction of a parameter that is functionally linked to the expression of a gene of interest, e.g., protein expression of the gene of interest or signaling downstream of the protein. A change in the levels of the gene of interest may be determined in any cell expressing the gene of interest, either endogenous or heterologous from an expression construct, and by any assay known in the art.

A change in the level of expression of a gene of interest may be manifested by an increase or decrease in the level of the protein produced by the gene of interest that is expressed by a cell or group of cells (e.g., the level of protein expressed in a sample derived from a subject). As explained above, for the assessment of mRNA suppression, the change in the level of protein expression in a treated cell or group of cells may similarly be expressed as a percentage of the level of protein in a control cell or group of cells.

A control cell or group of cells that may be used to assess the change in the expression of a 3 gene of interest includes a cell or group of cells that has not yet been contacted with an oligonucleotide of the present disclosure. For example, the control cell or group of cells may be derived from an individual subject (e.g., a human or animal subject) prior to treatment of the subject with an oligonucleotide.

The level of mRNA of a gene of interest that is expressed by a cell or group of cells may be determined using any method known in the art for assessing mRNA expression. In one embodiment, the level of expression of a gene of interest in a sample is determined by detecting a transcribed polynucleotide, or portion thereof, e.g., mRNA of the gene of interest. RNA may be extracted from cells using RNA extraction techniques including, for example, using acid phenol/guanidine isothiocyanate extraction (RNAzol B; Biogenesis), RNEASY™ RNA preparation kits (Qiagen) or PAXgene (PreAnalytix, Switzerland). Typical assay formats utilizing ribonucleic acid hybridization include nuclear run-on assays, RT-PCR, RNase protection assays, northern blotting, in situ hybridization, and microarray analysis. Circulating mRNA of the gene of interest may be detected using methods the described in PCT Publication WO2012/177906, the entire contents of which are hereby incorporated herein by reference. In some embodiments, the level of expression of the gene of interest is determined using a nucleic acid probe. The term "probe," as used herein, refers to any molecule that is capable of selectively binding to a specific sequence, e.g. to an mRNA or polypeptide. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or northern analyses, polymerase chain reaction (PCR) analyses, and probe arrays. One method for the determination of mRNA levels involves contacting the isolated mRNA with a nucleic acid molecule (probe) that can hybridize to the mRNA of a gene of interest. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an AFFYMETRIX gene chip array. A skilled artisan can readily adapt known mRNA detection methods for use in determining the level of mRNA of a gene of interest.

An alternative method for determining the level of expression of a gene of interest in a sample involves the process of nucleic acid amplification and/or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) Proc. Natl. Acad. Sci. USA 88:189-193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In some embodiments, the level of expression of a gene of interest is determined by quantitative fluorogenic RT-PCR (i.e., the TAQMAN™ System) or the DUAL-GLO® Luciferase assay.

The expression levels of mRNA of a gene of interest may be monitored using a membrane blot (such as used in hybridization analysis such as northern, Southern, dot, and the like), or microwells, sample tubes, gels, beads or fibers (or any solid support including bound nucleic acids). See U.S. Pat. Nos. 5,770,722; 5,874,219; 5,744,305; 5,677,195; and 5,445,934, which are incorporated herein by reference. The determination of gene expression level may also include using nucleic acid probes in solution.

In some embodiments, the level of mRNA expression is assessed using branched DNA (bDNA) assays or real time PCR (qPCR). The use of this PCR method is described and exemplified in the Examples presented herein. Such methods can also be used for the detection of nucleic acids of the gene of interest.

The level of protein produced by the expression of a gene of interest may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, western blotting, radioimmunoassay (RIA), enzyme-linked immunosorbent assays (ELISAs), immunofluorescent assays, electrochemiluminescence assays, and the like. Such assays can also be used for the detection of proteins indicative of the presence or replication of proteins produced by the gene of interest. Additionally, the above assays may be used to report a change in the mRNA sequence of interest that results in the recovery or change in protein function thereby providing a therapeutic effect and benefit to the subject, treating a disorder in a subject, and/or reducing of symptoms of a disorder in the subject.

In some embodiments, the oligonucleotides described herein are administered to a subject such that the oligonucleotide is delivered to a specific site within the subject. The change in the expression of the gene of interest may be assessed using measurements of the level or change in the level of mRNA or protein produced by the gene of interest in a sample derived from a specific site within the subject.

In other embodiments, the oligonucleotide is administered in an amount and for a time effective to result in one of (or more, e.g., two or more, three or more, four or more of): (a) decrease the number of adenosines within a target sequence of the gene of interest, (b) delayed onset of the disorder, (c) increased survival of subject, (d) increased progression free survival of a subject, (e) recovery or change in protein function, and (f) reduction in symptoms.

Treating disorders associated with G-to-A mutations can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with a compound or pharmaceutically acceptable salt of a compound described herein. A decrease in the mortality rate of a population may also be measured, for example, by calculating for a population the average number of disease-related deaths per unit time following completion of a first round of treatment with a compound or pharmaceutically acceptable salt of a compound described herein.

A. Delivery of Oligonucleotides

The delivery of oligonucleotides described herein to a cell e.g., a cell within a subject, such as a human subject (e.g., a subject in need thereof, such as a subject having a disorder) can be achieved in a number of different ways. For example, delivery may be performed by contacting a cell with an oligonucleotide described herein either ex vivo, in vitro or in vivo. In vivo delivery may also be performed directly by administering a composition including an oligonucleotide to a subject. Alternatively, in vivo delivery may be performed indirectly by administering one or more vectors that encode and direct the expression of the oligonucleotide. Combinations of in vitro and in vivo methods of contacting a cell are also possible. Contacting a cell may be direct or indirect, as discussed above. Furthermore, contacting a cell may be accomplished via a targeting ligand, including any ligand described herein or known in the art. In some embodiments, the targeting ligand is a carbohydrate moiety, e.g., a GalNAc$_3$ ligand, or any other ligand that directs the oligonucleotide to a site of interest. Cells can include those of the central nervous system, or muscle cells. These alternatives are discussed further below.

Contacting of a cell with an oligonucleotide may be done in vitro or in vivo. For in vivo delivery, factors to consider in order to deliver an oligonucleotide molecule include, for example, biological stability of the delivered molecule, prevention of non-specific effects, and accumulation of the delivered molecule in the target tissue. The non-specific effects of an oligonucleotide can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the oligonucleotide molecule to be administered.

For administering an oligonucleotide systemically for the treatment of a disease, the oligonucleotide can include alternative nucleobases, alternative sugar moieties, and/or alternative internucleotide linkages, or alternatively delivered using a drug delivery system; both methods act to prevent the rapid degradation of the oligonucleotide by endo- and exo-nucleases in vivo. Modification of the oligonucleotide or the pharmaceutical carrier can also permit targeting of the oligonucleotide composition to the target tissue and avoid undesirable off-target effects. Oligonucleotide molecules can be modified by chemical conjugation to lipophilic groups such as cholesterol to enhance cellular uptake and prevent degradation. In an alternative embodiment, the oligonucleotide can be delivered using drug delivery systems such as a nanoparticle, a lipid nanoparticle, a polyplex nanoparticle, a lipoplex nanoparticle, a dendrimer, a polymer, liposomes, or a cationic delivery system. Positively charged cationic delivery systems facilitate binding of an oligonucleotide molecule (negatively charged) and also enhance interactions at the negatively charged cell membrane to permit efficient uptake of an oligonucleotide by the cell. Cationic lipids, dendrimers, or polymers can either be bound to an oligonucleotide, or induced to form a vesicle or micelle that encases an oligonucleotide. The formation of vesicles or micelles further prevents degradation of the oligonucleotide when administered systemically. In general, any methods of delivery of nucleic acids known in the art may be adaptable to the delivery of the oligonucleotides described herein. Methods for making and administering cationic oligonucleotide complexes are well within the abilities of one skilled in the art (see e.g., Sorensen, D R., et al. (2003) J. Mol. Biol 327:761-766; Verma, U N. et al., (2003) Clin. Cancer Res. 9:1291-1300; Arnold, A S et al., (2007) J. Hypertens. 25:197-205, which are incorporated herein by reference in their entirety). Some non-limiting examples of drug delivery systems useful for systemic delivery of oligonucleotides include DOTAP (Sorensen, D R., et al (2003), supra; Verma, U N. et al., (2003), supra), Oligofectamine, "solid nucleic acid lipid particles" (Zimmermann, T S. et al., (2006) Nature 441:111-114), cardiolipin (Chien, P Y. et al., (2005) Cancer Gene Ther. 12:321-328; Pal, A. et al., (2005) Int J. Oncol. 26:1087-1091), polyethyleneimine (Bonnet M E. et al., (2008) Pharm. Res. August 16 Epub ahead of print; Aigner, A. (2006) J. Biomed. Biotechnol. 71659), Arg-Gly-Asp (RGD) peptides (Liu, S. (2006) Mol. Pharm. 3:472-487), and polyamidoamines (Tomalia, D A. et al., (2007) Biochem. Soc. Trans. 35:61-67; Yoo, H. et al., (1999) Pharm. Res. 16:1799-1804). In some embodiments, an oligonucleotide forms a complex with cyclodextrin for systemic administration. Methods for administration and pharmaceutical compositions of oligonucleotides and cyclodextrins can be found in U.S. Pat. No. 7,427,605, which is herein incorporated by reference in its entirety. In some embodiments the oligonucleotides described herein are delivered by polyplex or lipoplex nanoparticles. Methods for administration and pharmaceutical compositions of oligonucleotides and polyplex nanoparticles and lipoplex nanoparticles can be found in U.S. Patent Application Nos. 2017/0121454; 2016/0369269; 2016/0279256; 2016/0251478; 2016/0230189; 2015/0335764; 2015/0307554; 2015/0174549; 2014/0342003; 2014/0135376; and 2013/0317086, which are herein incorporated by reference in their entirety.

i. Membranous Molecular Assembly Delivery Methods

Oligonucleotides described herein can also be delivered using a variety of membranous molecular assembly delivery methods including polymeric, biodegradable microparticle, or microcapsule delivery devices known in the art. For example, a colloidal dispersion system may be used for targeted delivery an oligonucleotide agent described herein. Colloidal dispersion systems include macromolecule complexes, nanocapsules, microspheres, beads, and lipid-based systems including oil-in-water emulsions, micelles, mixed micelles, and liposomes. Liposomes are artificial membrane vesicles that are useful as delivery vehicles in vitro and in vivo. It has been shown that large unilamellar vesicles (LUV), which range in size from 0.2-4.0 μm can encapsulate a substantial percentage of an aqueous buffer containing large macromolecules. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the oligonucleotide are delivered into the cell where the oligonucleotide can specifically bind to a target RNA and can mediate RNase H-mediated gene silencing. In some cases, the liposomes are also specifically targeted, e.g., to direct the oligonucleotide to particular cell types. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

A liposome containing an oligonucleotide can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The oligonucleotide preparation is then added to the micelles that include the lipid component. The cationic groups on the lipid interact with the oligonucleotide and condense around the oligonucleotide to form a liposome. After condensation, the detergent is removed, e.g., by dialysis, to yield a liposomal preparation of oligonucleotide.

If necessary, a carrier compound that assists in condensation can be added during the condensation reaction, e.g., by controlled addition. For example, the carrier compound can be a polymer other than a nucleic acid (e.g., spermine or spermidine). The pH can also be adjusted to favor condensation.

Methods for producing stable oligonucleotide delivery vehicles, incorporating a oligonucleotide/cationic lipid complex as a structural component of the delivery vehicle, are further described in, e.g., WO 96/37194, the entire contents of which are incorporated herein by reference. Liposome formation can also include one or more aspects of exemplary methods described in Feigner, P. L. et al., (1987) Proc. Natl. Acad. Sci. USA 8:7413-7417; U.S. Pat. Nos. 4,897,355; 5,171,678; Bangham et al., (1965) M. Mol. Biol. 23:238; Olson et al., (1979) Biochim. Biophys. Acta 557:9; Szoka et al., (1978) Proc. Natl. Acad. Sci. 75: 4194; Mayhew et al., (1984) Biochim. Biophys. Acta 775:169; Kim et al., (1983) Biochim. Biophys. Acta 728:339; and Fukunaga et al., (1984) Endocrinol. 115:757. Commonly used techniques for preparing lipid aggregates of appropriate size for use as delivery vehicles include sonication and freeze-thaw plus extrusion (see, e.g., Mayer et al., (1986) Biochim. Biophys. Acta 858:161. Microfluidization can be used when consistently small (50 to 200 nm) and relatively uniform aggregates are desired (Mayhew et al., (1984) Biochim. Biophys. Acta 775:169. These methods are readily adapted to packaging oligonucleotide preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al. (1987) Biochem. Biophys. Res. Commun., 147:980-985).

Liposomes entrap nucleic acids rather than complex with them. Since both the nucleic acid and the lipid are similarly charged, repulsion rather than complex formation occurs. Nevertheless, some nucleic acid is entrapped within the aqueous interior of these liposomes. pH sensitive liposomes have been used to deliver nucleic acids encoding the thymidine kinase gene to cell monolayers in culture. Expression of the exogenous gene was detected in the target cells (Zhou et al. (1992) Journal of Controlled Release, 19:269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. Nos. 5,283,185; 5,171,678; WO 94/00569; WO 93/24640; WO 91/16024; Feigner, (1994) J. Biol. Chem. 269:2550; Nabel, (1993) Proc. Natl. Acad. Sci. 90:11307; Nabel, (1992) Human Gene Ther. 3:649; Gershon, (1993) Biochem. 32:7143; and Strauss, (1992) EMBO J. 11:417.

Non-ionic liposomal systems have also been examined to determine their utility in the delivery of drugs to the skin, in particular systems including non-ionic surfactant and cholesterol. Non-ionic liposomal formulations including NOVASOME™ I (glyceryl dilaurate/cholesterol/polyoxyethylene-10-stearyl ether) and NOVASOME™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al., (1994) S.T.P. Pharma. Sci., 4(6):466).

Liposomes may also be sterically stabilized liposomes, including one or more specialized lipids that result in enhanced circulation lifetimes relative to liposomes lacking such specialized lipids. Examples of sterically stabilized liposomes are those in which part of the vesicle-forming lipid portion of the liposome (A) includes one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., (1987) FEBS Letters, 223:42; Wu et al., (1993) Cancer Research, 53:3765).

Various liposomes including one or more glycolipids are known in the art. Papahadjopoulos et al. (Ann. N.Y. Acad. Sci., (1987), 507:64) reported the ability of monosialoganglio side $G^{M1}$, galactocerebroside sulfate, and phosphatidylinositol to improve blood half-lives of liposomes. These findings were expounded upon by Gabizon et al. (Proc. Natl. Acad. Sci. U.S.A., (1988), 85:6949). U.S. Pat. No. 4,837,028 and WO 88/04924, both to Allen et al., disclose liposomes including (1) sphingomyelin and (2) the ganglioside $G_{M1}$ or a galactocerebroside sulfate ester. U.S. Pat. No. 5,543,152 (Webb et al.) discloses liposomes including sphingomyelin. Liposomes including 1,2-sn-dimyristoylphosphatidylcholine are disclosed in WO 97/13499 (Lim et al).

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver oligonucleotides to macrophages.

Further advantages of liposomes include: liposomes obtained from natural phospholipids are biocompatible and biodegradable; liposomes can incorporate a wide range of water and lipid soluble drugs; liposomes can protect encapsulated oligonucleotides in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of oligonucleotides (see, e.g., Feigner, P. L. et al., (1987) Proc. Natl. Acad. Sci. USA 8:7413-7417, and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. LIPOFECTIN™ Bethesda Research Laboratories, Gaithersburg, Md.) is an effective agent for the delivery of highly anionic nucleic acids into living tissue culture cells that include positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis (oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (TRANSFECTAM™, Promega, Madison, Wis.) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., (1991) Biochim. Biophys. Res. Commun. 179:280). Lipopolylysine, made by conjugating polylysine to DOPE, has been reported to be effective for transfection in the presence of serum (Zhou, X. et al., (1991) Biochim. Biophys. Acta 1065:8). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer oligonucleotides into the skin. In some implementations, liposomes are used for delivering oligonucleotides to epidermal cells and also to enhance the penetration of oligonucleotides into dermal tissues, e.g., into skin. For example, the liposomes can be applied topically. Topical delivery of drugs formulated as liposomes to the skin has been documented (see, e.g., Weiner et al., (1992) Journal of Drug Targeting, vol. 2, 405-410 and du Plessis et al., (1992) Antiviral Research, 18:259-265; Mannino, R. J. and Fould-Fogerite, S., (1998) Biotechniques 6:682-690; Itani, T. et al., (1987) Gene 56:267-276; Nicolau, C. et al. (1987) Meth. Enzymol. 149:157-176; Straubinger, R. M. and Papahadjopoulos, D. (1983) Meth. Enzymol. 101:512-527; Wang, C. Y. and Huang, L., (1987) Proc. Natl. Acad. Sci. USA 84:7851-7855).

Non-ionic liposomal systems have also been examined to determine their utility in the delivery of drugs to the skin, in particular systems including non-ionic surfactant and cholesterol. Non-ionic liposomal formulations including Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with oligonucleotide are useful for treating a dermatological disorder.

The targeting of liposomes is also possible based on, for example, organ-specificity, cell-specificity, and organelle-specificity and is known in the art. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Additional methods are known in the art and are described, for example in U.S. Patent Application Publication No. 20060058255, the linking groups of which are herein incorporated by reference.

Liposomes that include oligonucleotides can be made highly deformable. Such deformability can enable the liposomes to penetrate through pore that are smaller than the average radius of the liposome. For example, transfersomes are yet another type of liposomes, and are highly deformable lipid aggregates which are attractive candidates for drug delivery vehicles. Transfersomes can be described as lipid droplets which are so highly deformable that they are easily able to penetrate through pores which are smaller than the droplet. Transfersomes can be made by adding surface edge activators, usually surfactants, to a standard liposomal composition. Transfersomes that include oligonucleotides can be delivered, for example, subcutaneously by infection in order to deliver oligonucleotides to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transfersomes can be self-optimizing (adaptive to the shape of pores, e.g., in the skin), self-repairing, and can frequently reach their targets without fragmenting, and often self-loading. Transfersomes have been used to deliver serum albumin to the skin. The transfersome-mediated delivery of serum albumin has been shown to be as effective as subcutaneous injection of a solution containing serum albumin.

Other formulations amenable to the disclosed oligonucleotides and methods are described in WO 2009/086558, and WO 2009/088891. WO 2008/042973 also describes formulations that are amenable to the present oligonucleotides and methods.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general, their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines, and phosphatides.

The use of surfactants in drug products, formulations and in emulsions has been reviewed (Rieger, in Pharmaceutical Dosage Forms, Marcel Dekker, Inc., New York, N.Y., 1988, p. 285).

The oligonucleotide for use in the methods described herein can also be provided as micellar formulations. Micelles are a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

ii. Lipid Nanoparticle-Based Delivery Methods

Oligonucleotides described herein may be fully encapsulated in a lipid formulation, e.g., a lipid nanoparticle (LNP), or other nucleic acid-lipid particle. LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in PCT Publication No. WO 00/03683. The particles of the present disclosure typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; U.S. Publication No. 2010/0324120 and PCT Publication No. WO 96/40964.

In one embodiment, the lipid to drug ratio (mass/mass ratio) (e.g., lipid to oligonucleotide ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part described herein.

Non-limiting examples of cationic lipid include N,N-dioleyl-N,N-dimethylammonium chloride (DODAC), N,N-distearyl-N,N-dimethylammonium bromide (DDAB), N—(I-(2,3-dioleoyloxy)propyl)-N,N,N-trimethylammonium chloride (DOTAP), N—(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA·Cl), 1,2-Dilinoleoyl-3-trimethylaminopropane chloride salt (DLin-TAP·Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-

Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyetetrahydro-3aH-cyclopenta[d][1,3]dioxol-5-amine (ALN100), (6Z,9Z,28Z,31Z)-heptatriaconta-6,9,28,31-tetraen-19-yl4-(dimethylamino)bu-tanoate (MC3), 1,1'-(2-(4-(2-((2-(bis(2-hydroxydodecyl)amino)ethyl)(2-hydroxydodecyl)ami-no)ethyl)piperazin-1-yeethylazanediyedidodecan-2-ol (Tech G1), or a mixture thereof. The cationic lipid can include, for example, from about 20 mol % to about 50 mol % or about 40 mol % of the total lipid present in the particle.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be, for example, from about 5 mol % to about 90 mol %, about 10 mol %, or about 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($Ci_2$), a PEG-dimyristyloxypropyl ($Ci_4$), a PEG-dipalmityloxypropyl ($Ci_6$), or a PEG-distearyloxypropyl ($C]_8$). The conjugated lipid that prevents aggregation of particles can be, for example, from 0 mol % to about 20 mol % or about 2 mol % of the total lipid present in the particle.

In some embodiments, the nucleic acid-lipid particle further includes cholesterol at, e.g., about 10 mol % to about 60 mol % or about 50 mol % of the total lipid present in the particle.

IV. Pharmaceutical Compositions

The oligonucleotides described herein are preferably formulated into pharmaceutical compositions for administration to human subjects in a biologically compatible form suitable for administration in vivo.

The oligonucleotides described herein may be administered, for example, by oral, parenteral, intrathecal, intracerebroventricular, intraparenchymal, buccal, sublingual, nasal, rectal, patch, pump, intratumoral, or transdermal administration and the pharmaceutical compositions formulated accordingly. Parenteral administration includes intravenous, intraperitoneal, subcutaneous, intramuscular, transepithelial, nasal, intrapulmonary, intrathecal, intracerebroventricular, intraparenchymal, rectal, and topical modes of administration. Parenteral administration may be by continuous infusion over a selected period of time.

An oligonucleotide described herein may be orally administered, for example, with an inert diluent or with an assimilable edible carrier, or it may be enclosed in hard- or soft-shell gelatin capsules, or it may be compressed into tablets, or it may be incorporated directly with the food of the diet. For oral therapeutic administration, an oligonucleotide described herein may be incorporated with an excipient and used in the form of ingestible tablets, buccal tablets, troches, capsules, elixirs, suspensions, syrups, and wafers. An oligonucleotide described herein may also be administered parenterally. Solutions of an oligonucleotide described herein can be prepared in water suitably mixed with a surfactant, such as hydroxypropylcellulose. Dispersions can also be prepared in glycerol, liquid polyethylene glycols, DMSO, and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2012, 22nd ed.) and in The United States Pharmacopeia: The National Formulary (USP 41 NF 36), published in 2018. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe. Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form includes an aerosol dispenser, it will contain a propellant, which can be a compressed gas, such as compressed air or an organic propellant, such as fluorochlorohydrocarbon. The aerosol dosage forms can also take the form of a pump-atomizer. Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter. An oligonucleotide described herein may be administered intratumorally, for example, as an intratumoral injection. Intratumoral injection is injection directly into the tumor vasculature and is specifically contemplated for discrete, solid, accessible tumors. Local, regional, or systemic administration also may be appropriate.

The oligonucleotides described herein may be administered to an animal, e.g., a human, alone or in combination with pharmaceutically acceptable carriers, as noted herein, the proportion of which is determined by the solubility and chemical nature of the oligonucleotide, chosen route of administration, and standard pharmaceutical practice.

V. Dosages

The dosage of the compositions (e.g., a composition including an oligonucleotide) described herein, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compositions described herein may be administered initially in a suitable dosage that may be adjusted as required, depending on the clinical response. In some embodiments, the dosage of a composition (e.g., a composition including an oligonucleotide) is a prophylactically or a therapeutically effective amount.

VI. Kit

Provided herein are kits including (a) a pharmaceutical composition including an oligonucleotide that results in deamination of an adenosine in an mRNA in a cell or subject described herein, and (b) a package insert with instructions to perform any of the methods described herein. In some embodiments, the kit includes (a) a pharmaceutical composition including an oligonucleotide that results in deamination of an adenosine in an mRNA in a cell or subject described herein, (b) an additional therapeutic agent, and (c) a package insert with instructions to perform any of the methods described herein.

EMBODIMENTS

1. An oligonucleotide comprising the structure:

$$[A_m]—X^1—X^2—X^3—[B_n]$$

wherein m+n is 24 to 50, n is at least 4, and m is at least 20;

$-X^1-X^2-X^3-$ is a Central Triplet of the oligonucleotide;

$X^1$ is position −1 of the oligonucleotide, $X^2$ is position 0 of the oligonucleotide, and $X^3$ is position +1 of the oligonucleotide;

$[A]_m$ is a first domain at positions −(m+1) to −2 of the oligonucleotide;

$[B]_n$ is a second domain at positions +2 to +(n+1) of the oligonucleotide;

each A and B is a nucleotide comprising a nucleobase, a sugar ("an A/B sugar"), and an internucleotide linkage;

each $X^1$, $X^2$, and $X^3$ comprises a nucleobase, a sugar ("an X sugar"), and an internucleotide linkage;

the A/B sugars and the $X^3$ sugar are selected from 2'-methoxy-ribose, 2'-MOE-ribose, 2'-deoxy-2'-fluororibose, 2'-fluoro-arabinose, 2-methoxy-arabinose, 2'deoxyribose and a locked nucleic acid (LNA);

the $X^1$ sugar is 2'-deoxy-2'-fluororibose or 2'deoxyribose;

the $X^2$ sugar is selected from 2'-methoxy-ribose, 2'-MOE-ribose, 2'-deoxy-2'-fluororibose, 2'-fluoro-arabinose, 2-methoxy-arabinose, 2'deoxyribose, a locked nucleic acid (LNA), and a beta-homo-DNA sugar;

the A/B sugars and the X sugars, collectively, are 10-70% 2'-deoxy-2'-fluoro-ribose;

the internucleotide linkages of the oligonucleotide are 30-100% phosphorothioate and phosphoramidate linkages, and 3 to 20 internucleotide linkages are phosphoramidate linkages;

the internucleotide linkage (i) between the nucleotide at position −(m+1) and the nucleotide at position −(m) (the 5'end), (ii) between the nucleotide at position +(n) and the nucleotide at position +(n+1) (the 3'-end), or (iii) at each the 5'-end and 3'-end of the oligonucleotide is a phosphoramidate linkage; and the internucleotide linkage between the nucleotide at position −(m) and the nucleotide at position −(m−1) and the internucleotide linkage between the nucleotide at position +(n−1) and the nucleotide at position +(n) are independently a phosphorothioate or a phosphoramidate linkage.

2. The oligonucleotide of embodiment 1, wherein the $X^2$ nucleobase is cytosine or isodU.

3. The oligonucleotide of embodiment 1 or embodiment 2, wherein the $X^3$ nucleobase is guanosine, hypoxanthine, or 7-deazaguanine;

4. The oligonucleotide of any one of embodiments 1 to 3, wherein no more than four sequential A/B sugars are 2'-deoxy-2'-fluororibose.

5. The oligonucleotide of any one of embodiments 1 to 4 wherein the A/B sugars and X sugars, collectively, are 20-50% 2'-deoxy-2'-fluororibose.

6. The oligonucleotide of any one of embodiments 1 to 5, wherein the A/B sugars are selected from 2'-methoxy-ribose, 2'-MOE-ribose, 2'-deoxy-2'-fluororibose, and 2'deoxyribose.

7. The oligonucleotide of any one of embodiments 1 to 6, wherein the $X^2$ nucleobase is cytosine.

8. The oligonucleotide of any one of embodiments 1 to 7, wherein the $X^2$ sugar is a beta-homo-DNA sugar.

9. The oligonucleotide of any one of embodiments 1 to 7, wherein the $X^2$ sugar is a 2'-deoxyribose.

10. The oligonucleotide of any one to embodiments 1 to 9, wherein the $X^1$ sugar is 2'-deoxy-2'-fluororibose.

11. The oligonucleotide of any one to embodiments 1 to 9, wherein the $X^1$ sugar is 2-deoxyribose.

12. The oligonucleotide of any one to embodiments 1 to 11, wherein the $X^3$ nucleobase is hypoxanthine.

13. The oligonucleotide of any one of embodiments 1 to 12, wherein the internucleotide linkage between $X^1$ and $X^2$ is a phosphorothioate or a phosphodiester linkage.

14. The oligonucleotide of embodiment 13, wherein the internucleotide linkage between $X^1$ and $X^2$ is a phosphorothioate.

15. The oligonucleotide of any one of embodiments 1 to 14, wherein the internucleotide linkage between $X^2$ and $X^3$ is a phosphorothioate or a phosphodiester linkage.

16. The oligonucleotide of embodiment 15, wherein the internucleotide linkage between $X^2$ and $X^3$ is a phosphorothioate.

17. The oligonucleotide of any one of embodiments 1 to 16, wherein the internucleotide linkage between the nucleotide at position −2 and $X^1$ is a phosphorothioate or a phosphodiester linkage.

18. The oligonucleotide of embodiment 17, wherein the internucleotide linkage between the nucleotide at position −2 and $X^1$ is a phosphorothioate.

19. The oligonucleotide of any one of embodiments 1 to 18, wherein the internucleotide linkage between the nucleotide at position −9 and the nucleotide at position −8 is a phosphoramidate.

20. The oligonucleotide of any one of embodiments 1 to 19, wherein the internucleotide linkage between the nucleotide at position −11 and the nucleotide at position −10 is a phosphoramidate.

21. The oligonucleotide of any one of embodiments 1 to 20, wherein the internucleotide linkage between the nucleotide at position +1 and the nucleotide at position +2 is a phosphoramidate.

22. The oligonucleotide of any one of embodiments 1 to 21, wherein the internucleotide linkage between the nucleotide at position +4 and the nucleotide at position +5 is a phosphoramidate.

23. The oligonucleotide of any one of embodiments 1 to 22, wherein the internucleotide linkage between the nucleotide at position +5 and the nucleotide at position +6 is a phosphoramidate.
24. The oligonucleotide of any one of embodiments 1 to 23, wherein the internucleotide linkage between the nucleotide at position +9 and the nucleotide at position +10 is a phosphoramidate.
25. The oligonucleotide of embodiment 24, wherein the internucleotide linkage between the nucleotide at position +1 and the nucleotide at position +2 and the internucleotide linkage between the nucleotide at position +9 and the nucleotide at position +10 are a phosphoramidate.
26. The oligonucleotide of embodiment 24 or 25, wherein the internucleotide linkage between the nucleotide at position +1 and the nucleotide at position +2, the internucleotide linkage between the nucleotide at position +5 and the nucleotide at position +6, and the internucleotide linkage between the nucleotide at position +9 and the nucleotide at position +10 are a phosphoramidate.
27. The oligonucleotide of any one of embodiments 1 to 26, having 30-70% phosphorothioate and phosphoramidate linkages.
28. The oligonucleotide of embodiment 27, having 40-60% phosphorothioate and phosphoramidate linkages.
29. The oligonucleotide of any one of embodiments 1 to 28, wherein n+m is 27.
30. The oligonucleotide of any one of embodiments 1 to 28, wherein n+m is 39.
31. The oligonucleotide of any one of embodiments 1 to 30, wherein n is 4, 5, 6, 7, 8, or 9.
32. The oligonucleotide of embodiment 31, wherein n is 4.
33. The oligonucleotide of embodiment 31, wherein n is 5.
34. The oligonucleotide of embodiment 31, wherein n is 9.
35. The oligonucleotide of any one of embodiments 1 to 34, wherein the A/B sugar at position +3 is a 2'-deoxy-2'-fluororibose.
36. The oligonucleotide of any one of embodiments 1 to 35, wherein the A/B sugar at position −5 is a 2'-deoxy-2'-fluororibose.
37. The oligonucleotide of any one of embodiments 1 to 36, wherein the A/B sugar at position −16 is a 2'-deoxy-2'-fluororibose.
38. The oligonucleotide of any one of embodiments 1 to 37, wherein the A/B sugar at position −20 is a 2'-deoxy-2'-fluororibose.
39. The oligonucleotide of any one of embodiments 1-34, wherein the A/B sugar at each of positions −5, −16, and −20 is a 2'-deoxy-2'-fluororibose.
40. The oligonucleotide of any one of embodiments 1 to 34, wherein the A/B sugar at each of positions +3, −5, −16, and −20 is a 2'-deoxy-2'-fluororibose.
41. The oligonucleotide of any one of embodiments 1 to 40, having a GalNAc moiety at the 5' end.
42. The oligonucleotide of any one of embodiments 1 to 41, having a GalNAc moiety at the 3' end.
43. The oligonucleotide of any one of embodiments 1 to 42, wherein at least one phosphoramidate is a mesyl phosphoramidate.
44. The oligonucleotide of embodiment 43, wherein each phosphoramidate is a mesyl phosphoramidate.
45. The oligonucleotide of any one of embodiments 1 to 44, sufficiently complementary to part of a target RNA having a target adenosine and capable of forming a complex with the target RNA.
46. The oligonucleotide of embodiment 45, wherein, upon formation of the complex with the target RNA, the nucleotide of the oligonucleotide opposite the target adenosine is $X^2$.
47. The oligonucleotide of embodiment 45 or 46, capable of binding and recruiting an ADAR enzyme to perform editing on the target adenosine of the target RNA.
48. The oligonucleotide of any one of embodiments 1 to 47, wherein the oligonucleotide does not comprise a portion that is capable of forming an intramolecular stem-loop structure.
49. The oligonucleotide of any one of embodiments 1 to 47, comprising a portion that is capable of forming an intramolecular stem-loop structure.
50. A complex comprising the oligonucleotide of any one of embodiments 1 to 49 and a target RNA, the complex formed by hybridization between the oligonucleotide and the target RNA.
51. The complex of embodiment 50, comprising 1, 2, 3, 4, or 5 mismatches, wobbles, insertions or deletions.
52. A method of editing a target adenosine in a target RNA in a cell comprising contacting the cell with the oligonucleotide of any one of embodiments 1 to 49 to (i) form a complex between the oligonucleotide and the target RNA such that $X^2$ of the oligonucleotide is opposite the target adenosine; and (ii) recruit an ADAR in the cell to the complex such that the ADAR edits the target adenosine.
53. A pharmaceutical composition comprising the oligonucleotide of any one of embodiments 1 to 49 and a pharmaceutically acceptable excipient.
54. The pharmaceutical composition of embodiment 53, wherein the oligonucleotide is encapsulated in a lipid nanoparticle (LNP).

EXAMPLES

General Methods

All guide oligonucleotides were chemically synthesized on an automated RNA/DNA synthesizer using standard β-cyanoethylphosphoramidite chemistry and a universal solid support such as controlled pore glass (CPG). Phosphoramidites of N-protected β-homo-DNA was synthesized utilizing reported procedures. See Matheus Froeyen et al., (2001) Chem. Eur. J., 7: 5183-5794, Herdewijn, (2010) Chem. Biodivers., 7: 1-59, Jabgunde et al., (2019) Tetrahedron, 75: 1107-1114. Other 5'-O-DMT-3'-phosphoramidite RNA, 2'-O-methyl-RNA and DNA monomers, i.e., A, C, G, U, and T, were purchased from commercial sources. All oligonucleotides were synthesized by BioSpring GmbH (Frankfurt, Germany) at a 200 nmol scale. After synthesis, oligonucleotides were cleaved from the solid support, deprotected, and purified by a HPLC system using standard protocols. Oligonucleotides were desalted, dialyzed, and lyophilized. The purity of each lyophilized oligo was ≥95% as determined by analytical reversed-phase HPLC. The sequence integrity of the oligonucleotides was determined by ESI-MS. (The sequences of the various oligonucleotides are provided herein in Tables 3 and 4).

Human ADAR2 sequence (NM_001112.4) was cloned into pcDNA3.1 plasmid under the control of the CMV promoter using BamHI and XbaI restriction sites (Quintara Bio, Berkeley, CA) and the correct insert was sequence verified. This plasmid henceforth will be denoted as ADAR2/pcDNA3.1. For editing experiments, 2 μg of ADAR2/pcDNA3.1 plasmid were transfected into $5\times10^6$ HEK293T cells (ATCC) using 25 μL of Lipofectamine 3000 and 24 μL of P3000 (Life Technologies) per 10 cm dish. After 4 hours, the culture media was replenished with fresh warmed media (DMEM High Glucose; Life Technologies). 12-16 hours after transfection, the transfected HEK293T cells were transfected with guide oligonucleotides such that the final concentration in the each well was 100 nM. All transfections were carried out with Lipofectamine 3000 (0.4 μL/per well) in a 96-well format, according to manufacturer's instructions. 12-16 hours after the second transfection, the cells were washed once with ice cold PBS and total mRNA isolation was performed using Dyna Beads mRNA Direct Kit (Life Technologies) adapted for KingFisher Flex Purification (Life Technologies), according to manufacturer's instructions. The samples were treated with TURBO DNase (Life Technologies) prior to elution. The resultant isolated mRNA was used for cDNA synthesis using SuperScript IV Vilo according to the manufacturer's instructions (Life Technologies). One μl of the cDNA was used as template for PCR (Platinum II Hot-Start PCR Master Mix; Life Technologies) using gene specific primers to generate an amplicon for Sanger sequencing. Sanger sequencing was performed by Quintara Biosciences (Berkeley, CA). Adenosine to guanosine editing yields were quantified by measuring the peak height of adenosine and guanosine and dividing the guanosine peak height by the total peak height measurements of adenosine and guanosine combined.

Example 1—Editing Efficiency of 42-mer Oligonucleotides with PA1 vs. Non-PA1 Linkages Single stranded antisense oligonucleotides ("ASOs") were designed to measure the effect of PA1 linkers on editing of SERPINA1 in mice over time. Guide oligonucleotides were chemically synthesized on an automated RNA/DNA synthesizer using standard β-cyanoethylphosphoramidite chemistry and a universal solid support such as controlled pore glass (CPG). 5'-O-DMT-3'-phosphoramidite RNA, 2'-O-methyl-RNA, 2'-Fluoro-arabinose-RNA (FANA) and DNA monomers, i.e., A, C, G, U, and T, were purchased from commercial sources. PA-1 linkage containing oligos were prepared by methods known in prior art such as described in Anderson, et al. After the synthesis, oligonucleotides were cleaved from the solid support, deprotected, and purified by an HPLC system using standard protocols. Oligonucleotides were desalted, dialyzed, and lyophilized. The purity of each lyophilized oligo was ≥90% as determined by analytical reversed-phase HPLC. The sequence integrity of the oligonucleotides was determined by ESI-MS. Oligos were then formulated in lipid nanoparticles ("LNPs") using microfluidic mixing, using MC3 as the ionizable lipid.

Oligos in LNPs were tested in PiZ mice to measure editing of SERPINA1 in the liver at different timepoints. PiZ transgenic mice with the E342K mutation were injected intravenously with Oligos #1, #2, or #3 in LNPs at a dose of three mg/kg. Livers were isolated from mice on days one, four, or seven after injection, and total RNA was isolated. The isolated RNA was used for cDNA synthesis using SuperScript IV VILO™ according to the manufacturer's instructions (Life Technologies). Ten μl of the cDNA was used for Next Generation Sequencing (NGS), Amplicon Sequencing by Quintara Biosciences. Percent editing of the site of interest was quantified as a percentage of the number of edited nucleotides based on NGS counts. Each oligonucleotide was assayed in at least three replicates. Primer sequences used for NGS are shown below in Table 4.

TABLE 4

| PCR and sequencing primers | |
|---|---|
| Forward primer E342K Site E342K | ACCTATGATCTGAAGAGCGTCCT (SEQ ID NO: 156) |
| Reverse primer E342K Site E342K | TTCAATCATTAAGAAGACAAAGGGT (SEQ ID NO: 157) |

Guide oligonucleotides showed higher levels of editing when PA-1 linkages were present, especially at later timepoints (days four and seven) (FIG. 1C). These data show that the PA-1 linkages on Oligo #3 can increase the durability of responses in vivo compared to PS linkages on Oligo #1. Non-PA1 oligo and ONE PA1 linkage oligo have shown less durability at day-4 and day-7. FIVE PA1 linkages oligo showed ~2.7 folds higher activity compared to non-PA1 oligo after day-4 or day-7.

Example 2—Editing Efficiency of 30-mer Oligonucleotides with Differing Patterns of 2'Sugar Modifications Guide oligonucleotides were designed to measure the effect of different patterns of 2' sugar modifications on SERPINA1 editing in vivo. The 2' modification patterns and PS content were varied for the three oligos (i.e., Oligo #4, #5, and #6), while the length and number of PA1 linkages were held constant. ASOs that were 30 nucleotides in length and contained five PA1 linkages were synthesized and formulated in LNPs as described in Example 1. Testing in mice and subsequent analysis were substantially the same as in Example 1 above. Editing was measured at days one and four.

Figure 2:
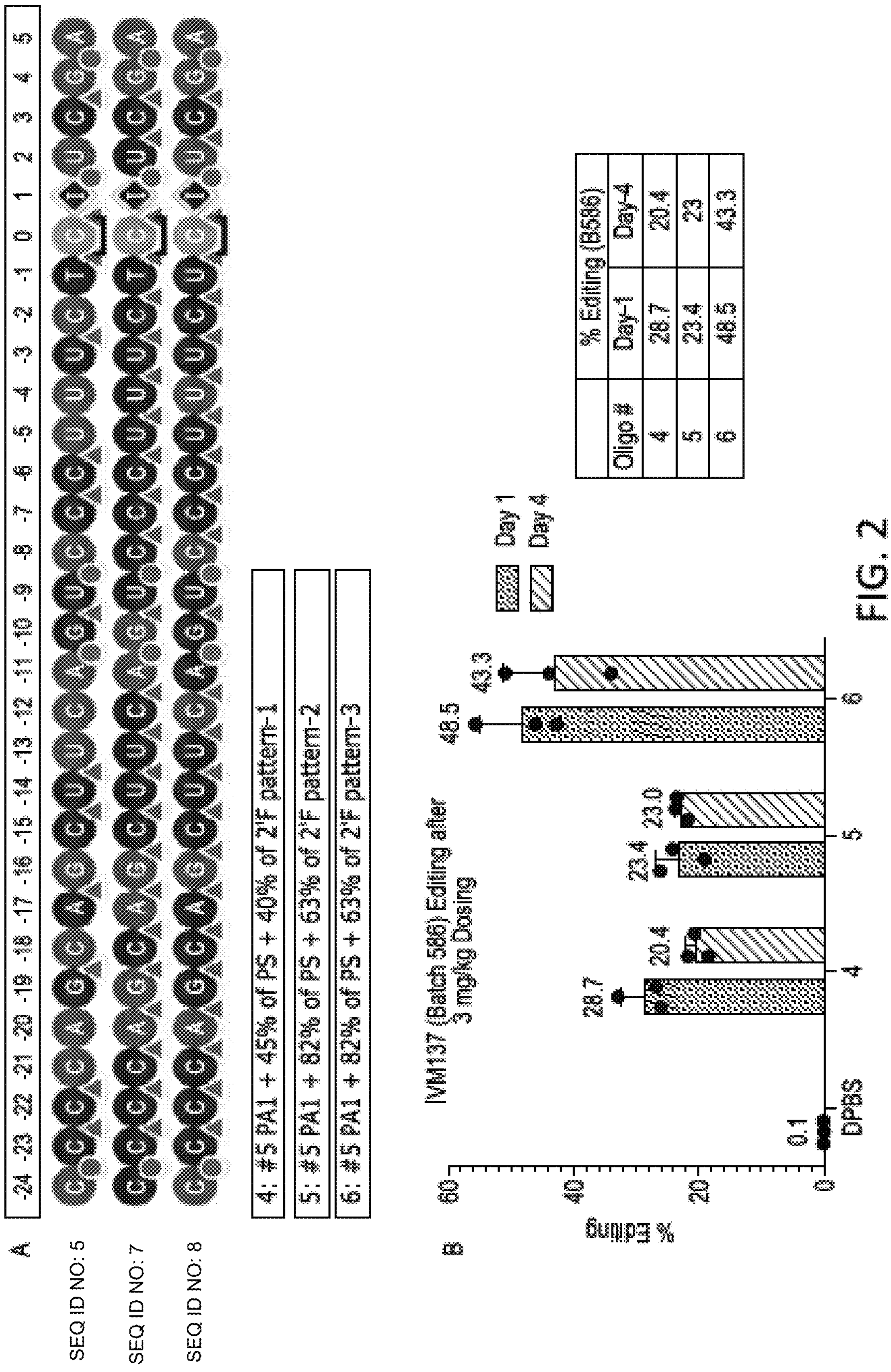
FIG. 2. (A) Schematics of 30mer oligonucleotides designed to test the effect of changing 2' modification pattern. (B) In vivo editing percentage of E342K SERPINA1 RNA isolated from PiZ mouse liver at days one and four (n=3 per group).

Guide oligonucleotides with PA1 linkages showed increased levels of editing when a specific pattern of 2'modifications was used on Oligo #6 (FIG. 2B). Oligos with the same length and number of PA1 linkages (Oligo #4 and #5) showed lower editing, demonstrating the importance of positioning the 2'F modifications. 2'F modification play critical role compared to PS linkages. Pattern of 2'F mods improve ~2× folds in vivo potency (5 vs 6). Percent of 2'F or PS content not influenced to improve the activity (4 vs 5).

Example 3—Editing Efficiency of 30-mer Oligonucleotides with PA1 vs. PS Linkages Guide oligonucleotides were designed to measure the effect of the addition of PA-1 linkages on editing. Guide oligonucleotides were synthesized the same as Example 1. The editing efficiency for oligos was tested primary cynomolgus ("cyno") hepatocytes without interferon alpha. These were tested using RNAiMAX at 10 and 100 nM, as well as without any lipofectamine at 100 and 1000 nM.

Cyno hepatocytes were thawed in a 37° C. water bath in a 50 ml tube of Universal Cryopreservation Recovery Medium (UCRM—Discovery Life Sciences). After centrifugation at 100×g for 5 minutes, supernatant was aspirated and the cell pellet is resuspended in Universal Primary Cell Plating Media (Discovery Life Sciences). Cells were plated on to either 96-well or 384-well collagen-coated tissue culture plates at 40000 cells/well or 10000 cells/well, respectively. Cells were transferred to incubator (37° C.), 4 to 6 hours later media was changed to Hepatocyte Induction Media (Discovery Life Sciences) and cells were transfected with ASOs at desired concentrations, with and without RNAiMax (Life Technologies, CA) according to manufacturer's protocol and placed back into the incubator.

48 hours after the addition of oligo, mRNA was isolated from the cyno hepatocytes using Oligo(dT)25 magnetic beads and relevant buffers from New England BioLabs. The samples were treated with EZ DNase (Life Technologies) after elution. The resultant isolated mRNA was used for cDNA synthesis using SuperScript IV VILO™ according to the manufacturer's instructions (Life Technologies). Ten μl of the cDNA was used for Next Generation Sequencing (NGS), Amplicon Sequencing by Quintara Biosciences.

The DNA amplicons were directly used for Amplicon Next Generation Sequencing (NGS). Percent editing of the site of interest was quantified as a percentage of the number of edited nucleotides based on NGS counts. Each oligonucleotide was assayed in at least three replicates. Primer sequences used for NGS are shown below in Table 5.

TABLE 5

| PCR and sequencing primers | |
|---|---|
| Forward primer Cyno ACTB Site 1 | GATGCATTGTTACAGGAAGTCCCT (SEQ ID NO: 158) |
| Reverse primer Cyno ACTB Site 1 | AGGGGGCATGAAGGCTCATTATTCA (SE ID NO: 159) |

Figure 3:
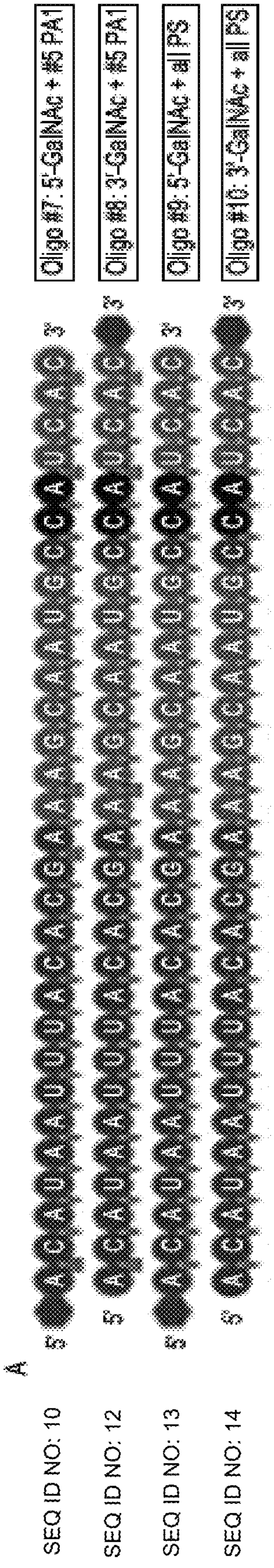
FIG. 3. (A) Schematics of oligonucleotides targeting the 3' UTR region of cyno ACTB. A 5' or 3' tri-GalNAc is represented by a hexagon at either end of the oligonucleotide. Squares between nucleobases represent PA-1 linkages, while triangles represent phosphorothioate linkers. (B) In vitro editing percentage of ACTB RNA in cyno hepatocytes in the presence of RNAiMAX ("LIPO") at 10 and 100 nM of oligonucleotide, or in the absence of transfection reagents (free uptake or "FU") at 100 and 1000 nM (n=4 per group).
Figure 3:
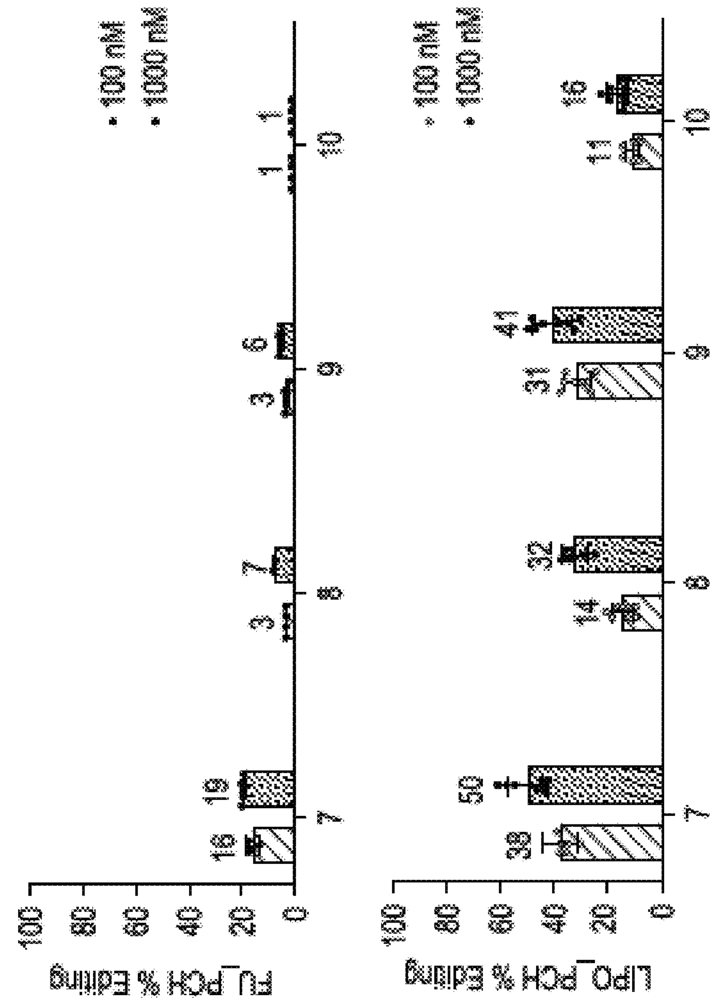

Guide oligos containing PA-1 linkages showed higher editing by both transfection ("Lipo") and free uptake ("FU") in the absence of transfection reagents (FIG. 3B). A 16-fold increase in editing was observed by free uptake when PA-1 linkages were incorporated into the oligo. PA1 in 30mer ACTB oligo (oligo #7) improved ~16× folds higher activity than fully modified PS oligo (oligo #10).

Figure 4:
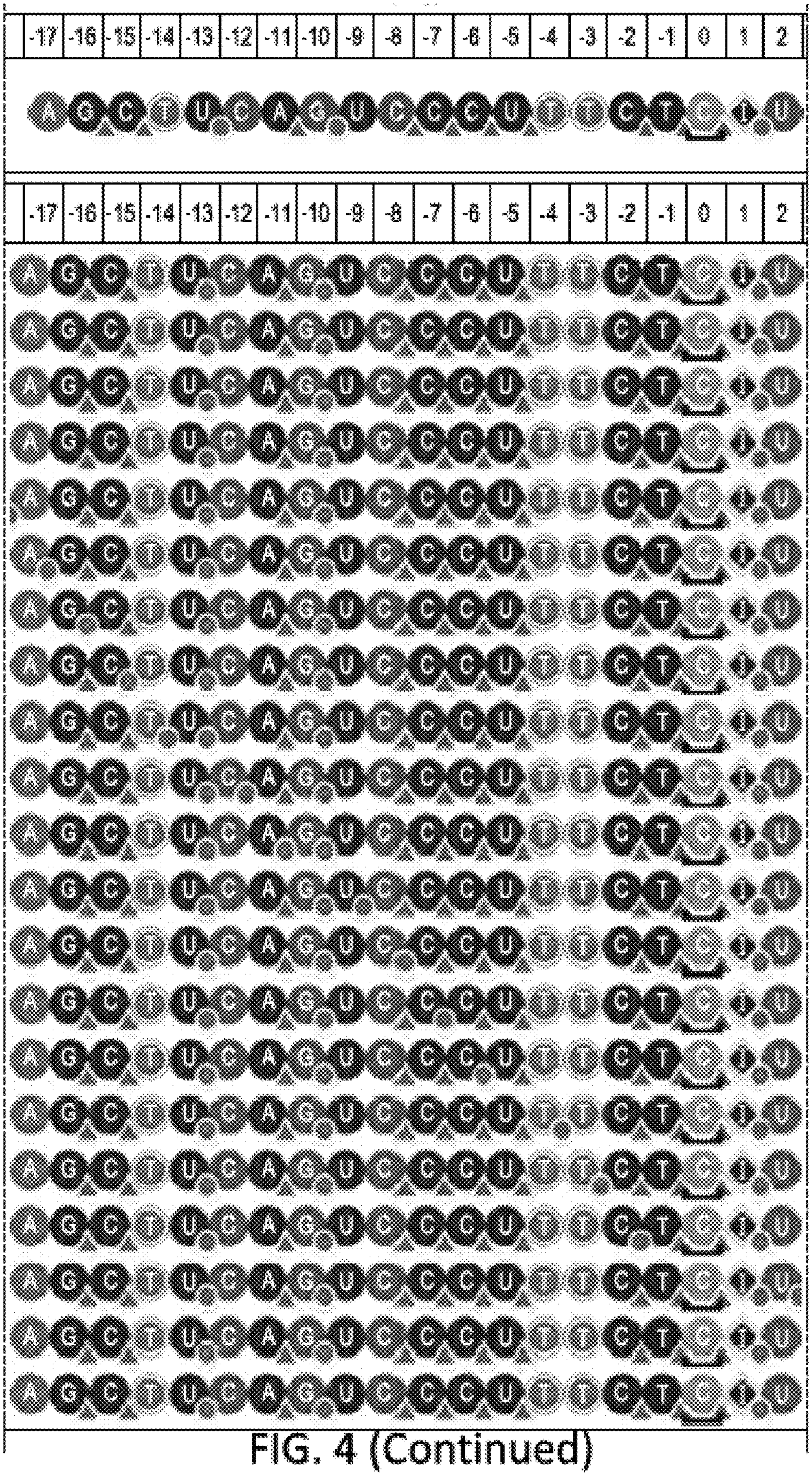
FIG. 4. (A) Schematic of the parental oligonucleotide containing five PA-1 linkages, represented by circles between nucleobases. (B) Schematics of each oligonucleotide containing one additional PA-1 at varying positions in the oligonucleotide (left) and corresponding in vitro percentage editing of E342K SERPINA1 RNA in PiZ mouse hepatocytes at two concentrations, in the absence of lipofectamine (right) (n=3 per group). (C) Analysis of the fold-change in editing (calculated by normalizing the editing levels of the oligonucleotide to the parental oligonucleotide, represented in (A)). X-axis represents the position after which a PA-1 linkage was added. Calculated fold-change in editing and normalized to parent 30mer editing (free uptake either at 10 nM or 100 nM).
Figure 4:
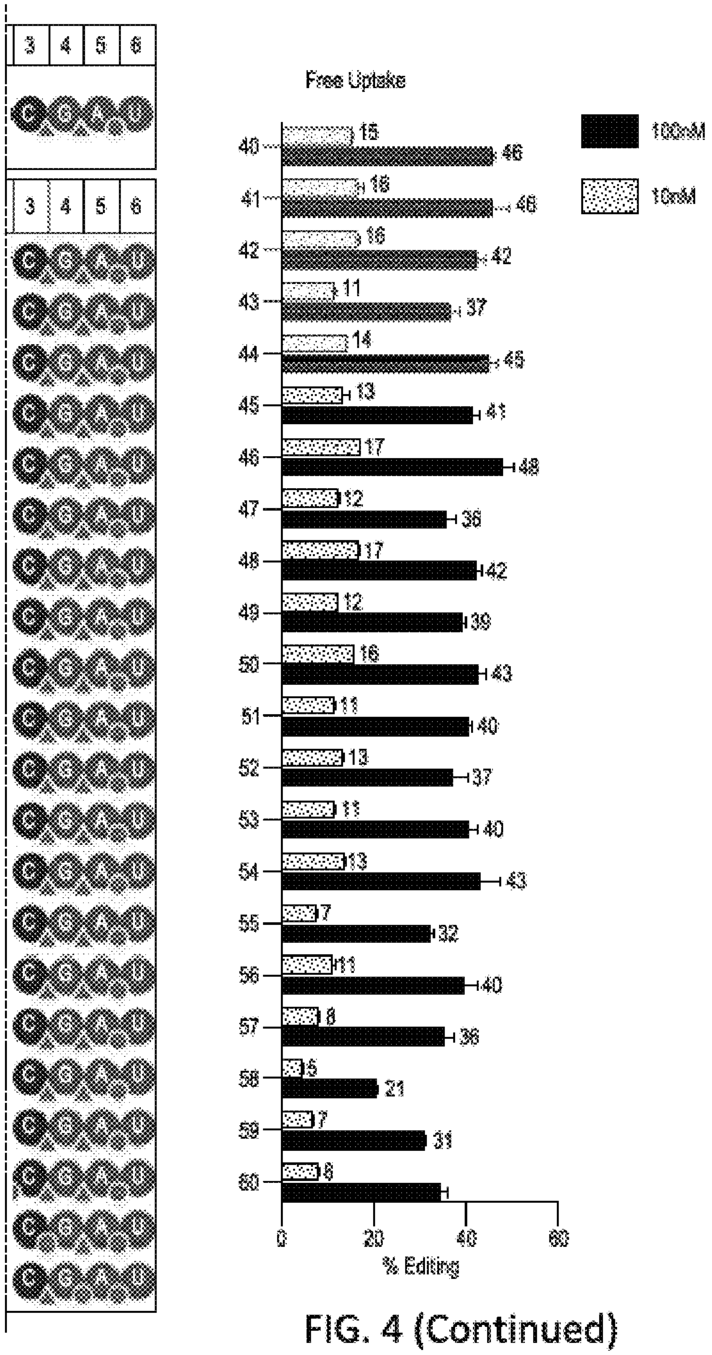
Figure 4:
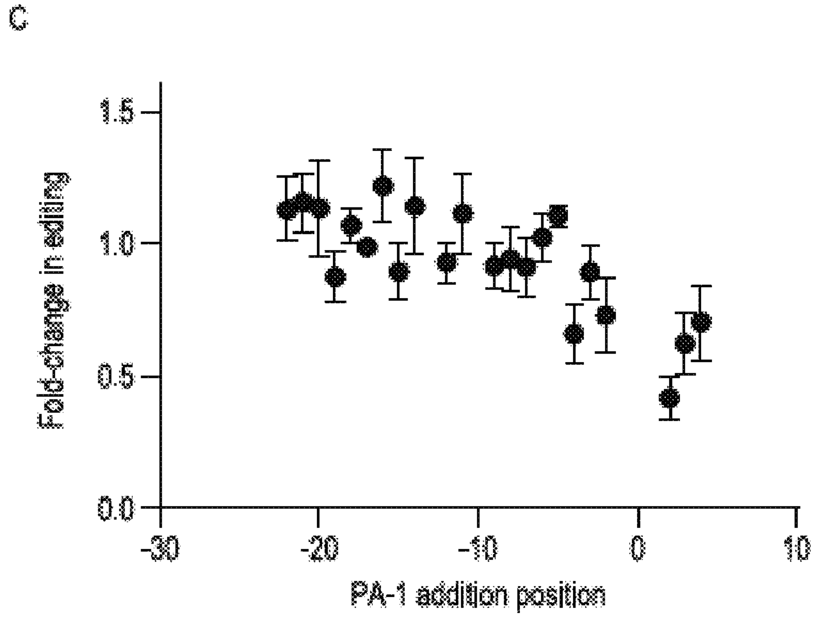
Figure 5:
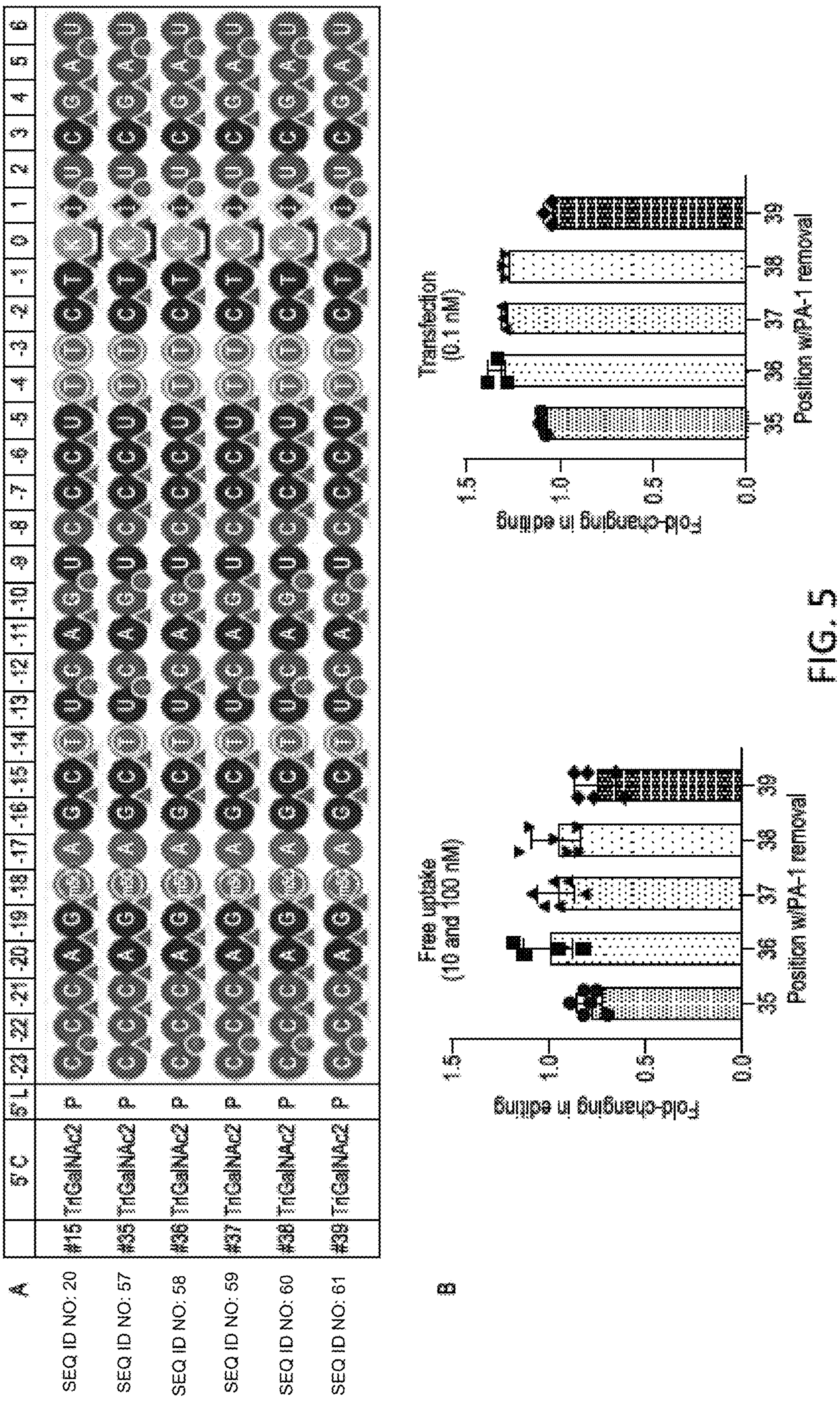
FIG. 5. (A) Schematics of oligonucleotides containing four or five PA-1 linkages, represented by circles between nucleobases. (B) Fold-change in editing of E342K SERPINA1 in the absence of lipofectamine ("Free Uptake") and presence of RNAiMAX ("Transfection") in PiZ mouse hepatocytes (n=3 per group). Fold-change in editing was calculated by dividing the editing level of the oligonucleotide indicated in the X-axis by the editing level of Oligonucleotide 15 (SEQ ID NO: 20).

Example 4—PA-1 Addition and Subtraction Show Positional Importance of PA-1 Linkage Oligonucleotides were designed to contain the addition or removal of a single PA-1 linkage at each position of the guide oligo (FIG. 4A, FIG. 5A). The change in editing was then measured for the oligos with varying positions of PA-1 to determine where editing increased or decreased. Synthesis of the oligonucleotides was performed as described in Example 1.

Editing efficiency of oligos was tested in Piz Mouse Hepatocytes without interferon alpha. These were tested using RNAiMAX, as well as without any lipofectamine at the desired concentrations. Piz Mouse Hepatocytes were thawed in a 37° C. water bath in a 50 ml tube of Cryopreserved Hepatocyte Recovery Medium (CHRM—Life Technologies). After centrifugation at 80×g for 6 minutes, supernatant was aspirated and the cell pellet is resuspended in Hepatocyte Plating Media (MB Bioscience). Cells were plated on to either 96-well collagen-coated tissue culture plates at 20000 cells/well. Cells were transferred to incubator (37° C.), 4 to 6 hours later media was changed to Hepatocyte Maintenance Media (MB Bioscience) and cells were transfected with ASOs at desired concentrations, with and without RNAiMax (Life Technologies, CA) according to manufacturer's protocol and placed back into the incubator.

48 hours after the addition of oligo, mRNA was isolated from the PiZ hepatocytes using Oligo(dT)25 magnetic beads and relevant buffers from New England BioLabs. The samples were treated with EZ DNase (Life Technologies) after elution. The resultant isolated mRNA was used for cDNA synthesis using SuperScript IV VILO™ according to the manufacturer's instructions (Life Technologies). Ten μl of the cDNA was used for Next Generation Sequencing (NGS), Amplicon Sequencing by Quintara Biosciences.

The DNA amplicons were directly used for Amplicon Next Generation Sequencing (NGS). Percent editing of the site of interest was quantified as a percentage of the number of edited nucleotides based on NGS counts. Each oligonucleotide was assayed in at least three replicates. Primers for sequencing were the same as described in Example 1.

Guide oligonucleotides containing PA-1 linkages in positions −23 to −5 showed similar editing, suggesting that PA-1 linkages distant from the triplet were well tolerated (FIG. 4B-C). However, PA-1 linkages closer to the triplet (positions −4 to +4) showed a decrease in editing relative to same oligonucleotide without PA-1 in those positions (FIG. 4B-C). When a PA-1 linkage was removed from Oligo #15 and substitute with a PS linkage, editing decreased when the linkage was at the either ends of the molecules (FIG. 5A-B). These results demonstrate the importance of having a PA-1 linkage at both ends of the molecule.

Example 5—Role of PA-1 Linkage in Editing Efficiency

Figure 6:
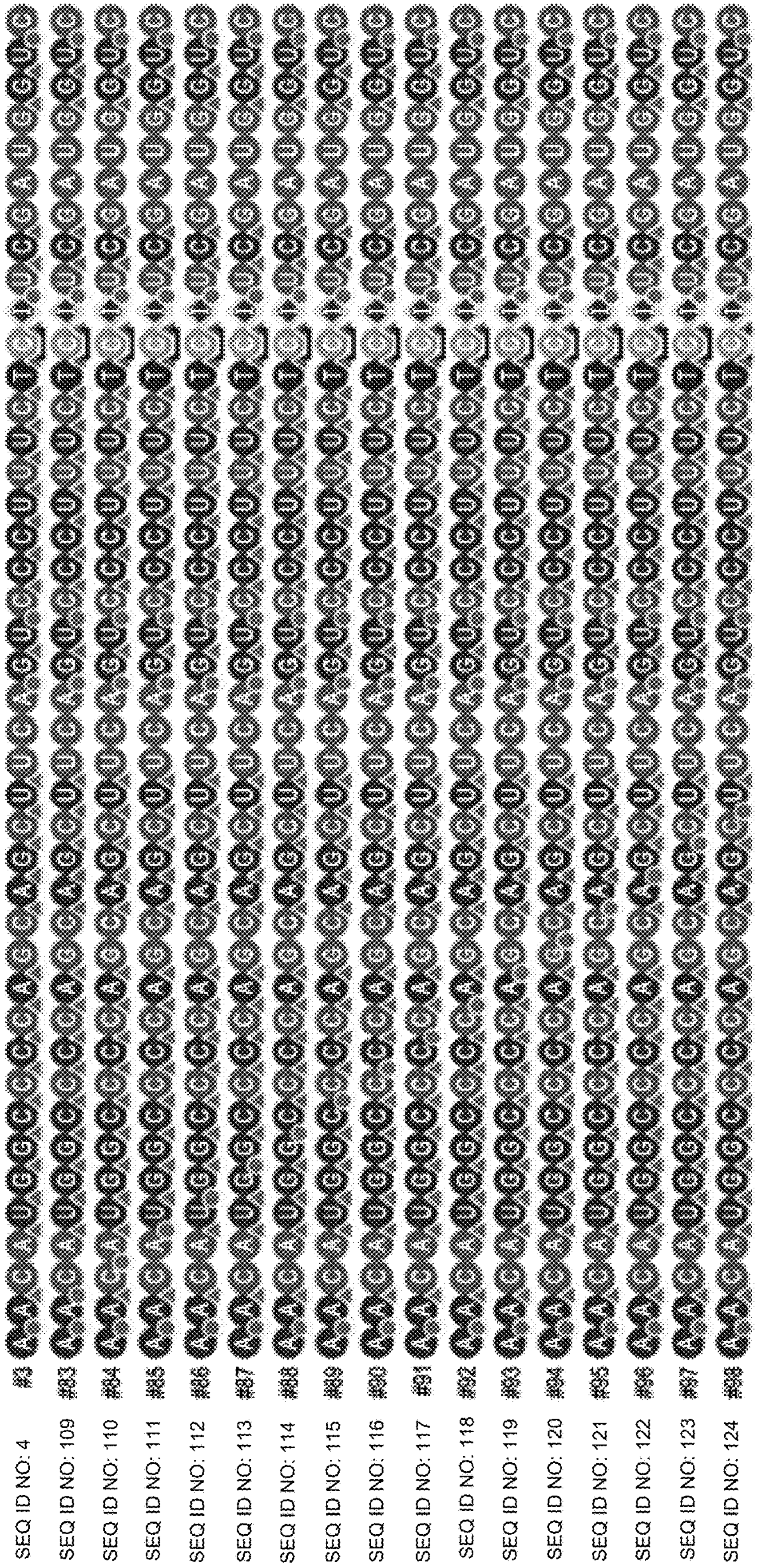
FIG. 6. Schematics of oligonucleotides containing a PA-1 walk on Oligo #3 (SEQ ID NO: 4, left) and corresponding editing of E342K SERPINA1 by those oligonucleotides in ZZ HLCs (right). Each oligonucleotide contains one additional PA-1 linkage at varying positions across the oligonucleotide. Editing in ZZ HLCs was measured at 1, 10, and 100 nM (n=4 per group).
Figure 6:
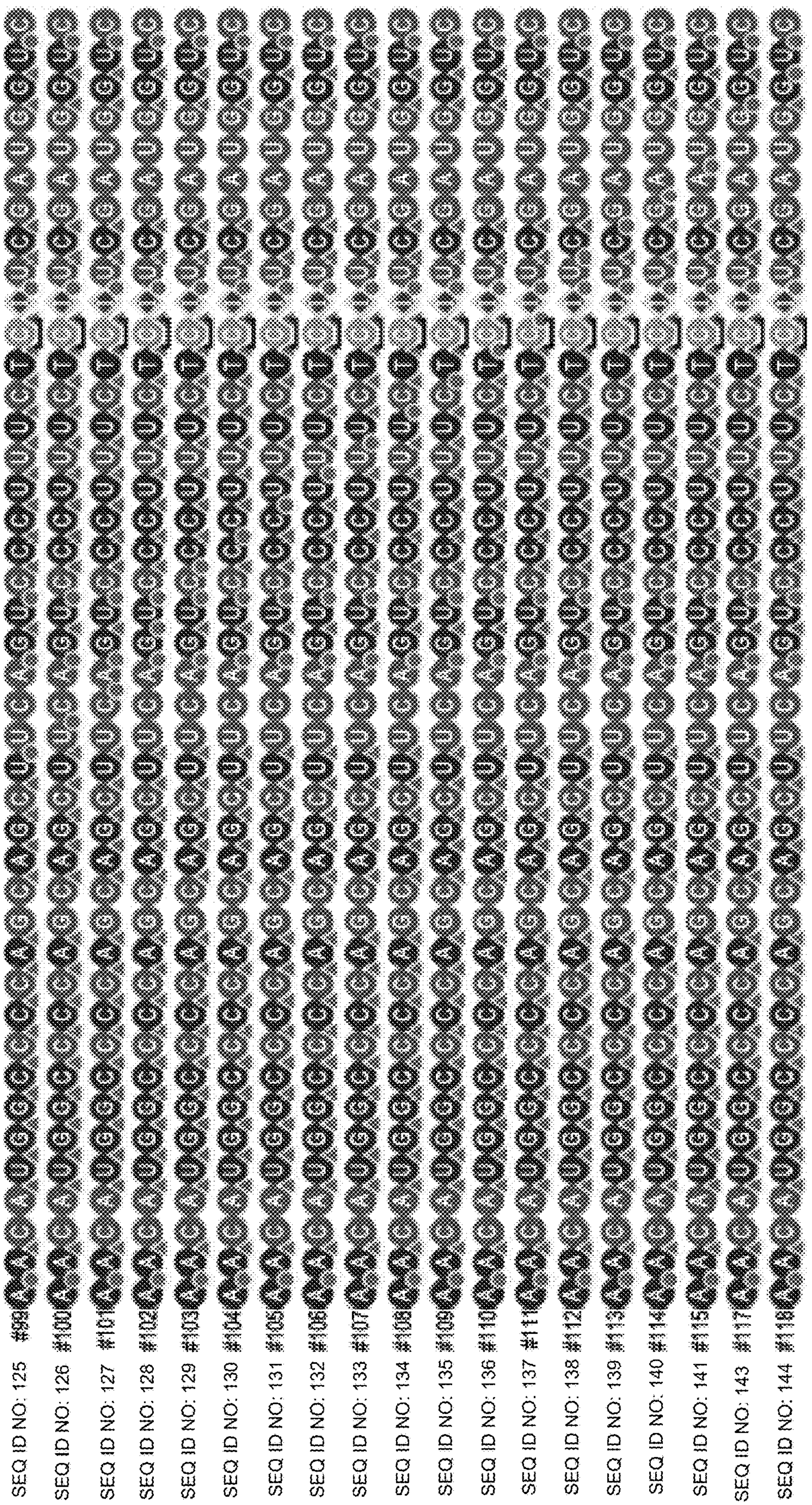
Figure 6:
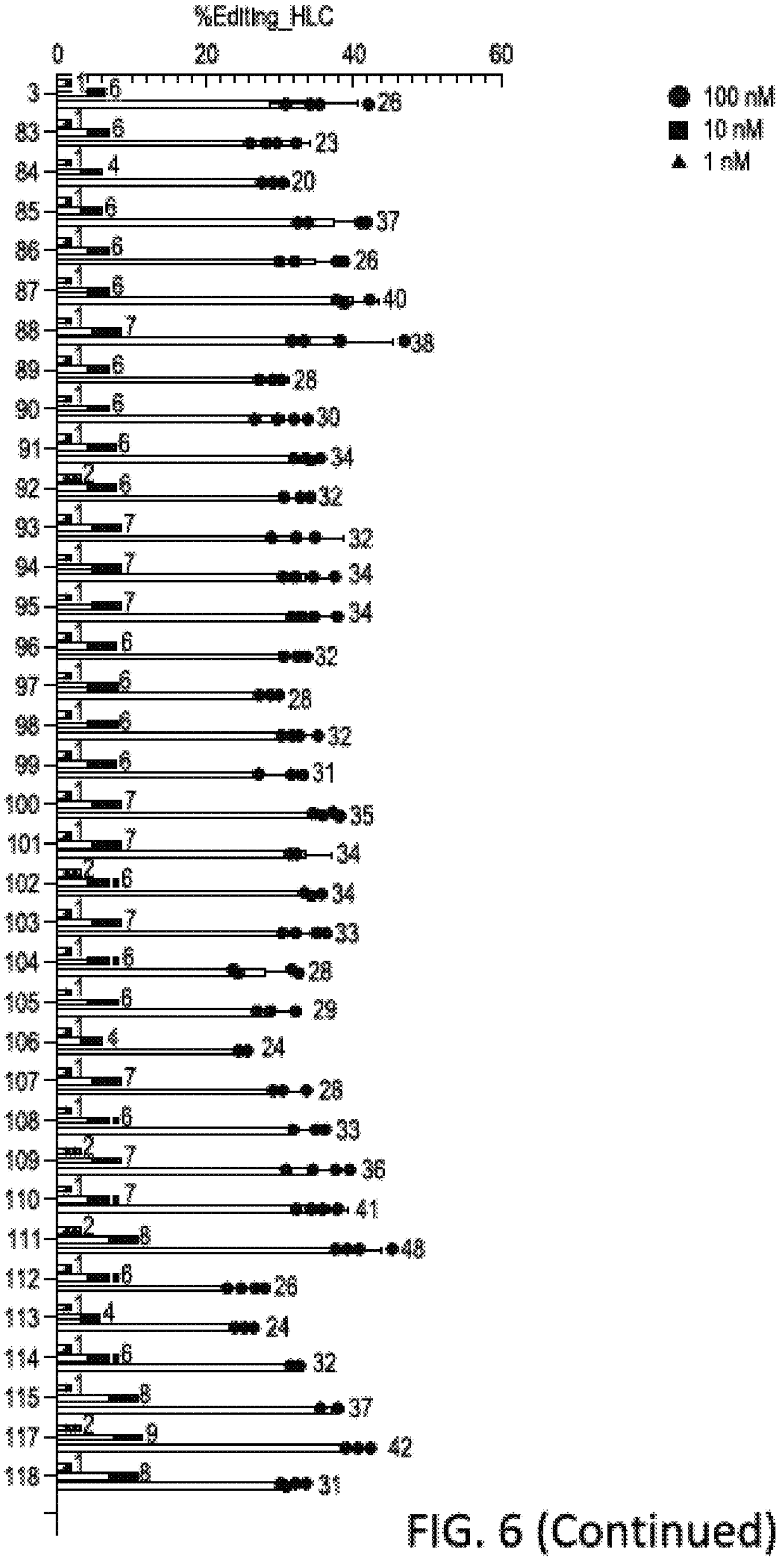

Oligonucleotides were designed to contain the addition or removal of a single PA-1 linkage at each position of the guide oligo (FIG. 6). Like Example 4 but using a 42mer oligonucleotide instead of a 30mer, the PA-1 linkage was substituted in at each position of the oligonucleotide. Synthesis of the oligonucleotides was performed as described in Example 1.

The level of editing efficiency of ASOs was measured in Alpha 1 Antitrypsin Disease ZZ Hepatocyte Like Cells (ZZ HLCs; DefiniGEN) with 1 U/μL interferon alpha at 1, 10 and 100 nM doses. ZZ HLCs were thawed in a 37° C. water bath in a 50 mL tube containing complete Def-Hep Thaw Medium (DTM; DefiniGEN) made according to manufacturer's instructions. After centrifugation at 100×g for 5 minutes, supernatant was aspirated, and the cell pellet was resuspended in Def-Hep Recovery and Maintenance Medium (DefiniGEN) with 1 U/mL Rock Inhibitor (Selleckchem) as per manufacturer's instructions. ZZ HLCs were plated onto 384-well tissue culture treated plates at 15,000 cells per well. Cells were transferred to a hypoxic incubator (37° C., 5% CO2, 6% O2) and re-fed every 48-72 hours for 12-14 days with 40 μLs per well of DTM.

On day 12, 13 or 14, ZZ HLCs were transfected with ASOs at desired concentration(s) using RNAiMax (Life Technologies, CA) according to manufacturer's protocol and placed back into the hypoxic incubator. Further processing was conducted as described in Example 4.

Editing was observed to be generally consistent across the oligos, suggesting the PA-1 linkage was well tolerated in this model (FIG. 6). Increases in editing were observed when a PA-1 linkage was used between the $X^2$ and $X^3$ position, as well as between the +7 and +8 position. Oligo #111 edited significantly higher than Oligo #3 at 10 nM. Oligo #111 edited significantly higher than Oligo #3 at both 100 nM and 10 nM doses.

Figure 7:
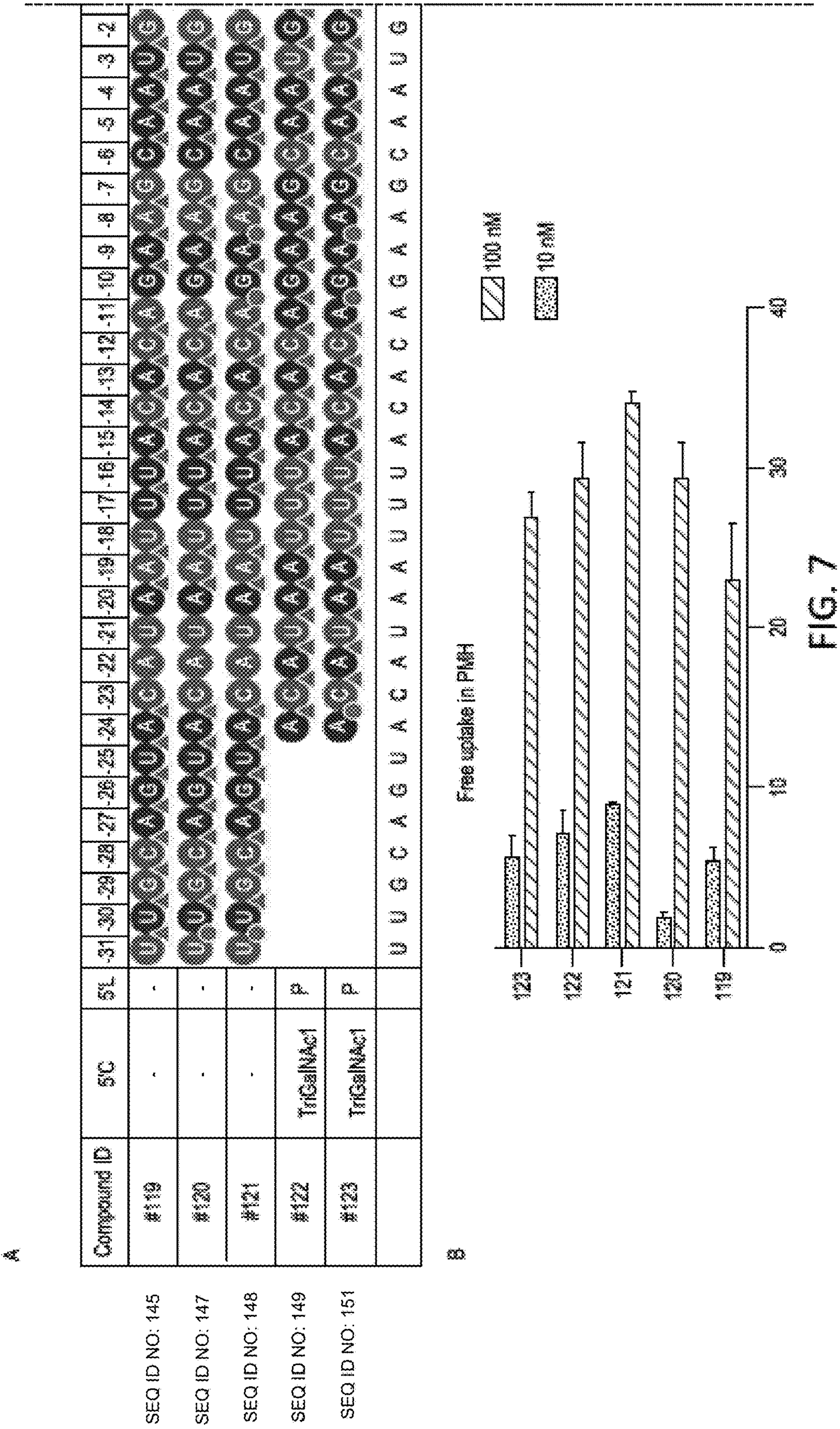
FIG. 7. (A) Schematics of 42mer and 30mer oligonucleotides targeting the 3' UTR region of mouse ACTB. Oligos #120, #121, and #123 (SEQ ID NOs: 147, 148, and 151) contained PA-1 linkages, while oligo #119 (SEQ ID NO: 145) and oligo #122 (SEQ ID NO: 149) did not. (B) Quantification of editing of mouse ACTB RNA in primary mouse hepatocytes ("PMH") at 10 and 100 nM in the absence of lipofectamine.
Figure 7:
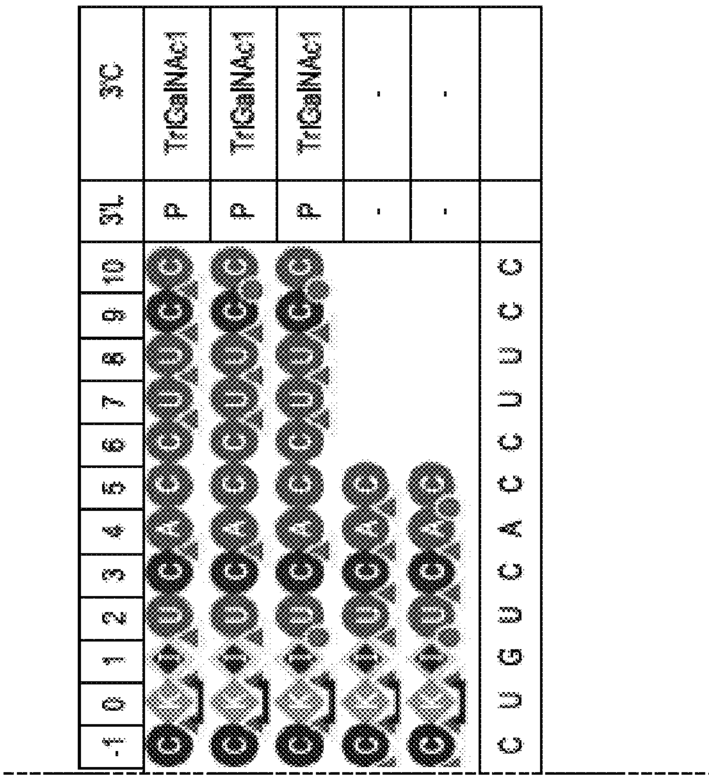

Next, the effect of the addition of PA-1 for oligos of two different lengths was tested against an additional target, mouse ACTB. Oligos that were either 42 or 30 nucleotides in length were synthesized with and without five PA-1 linkages (FIG. 7A). Synthesis of the oligonucleotides was performed as described in Example 1.

Editing was measured in primary mouse hepatocytes. Mouse hepatocytes were thawed in a 37° C. water bath in a 50 ml tube of Lonza rodent cryopreserved hepatocyte thawing media (MCRT50-Lonza). After centrifugation at 100×g for 5 minutes, supernatant was aspirated and the cell pellet is resuspended in Lonza plating media (Lonza). Cells were plated on 96-well collagen-coated tissue culture plates at 20000 cells/well. Cells were transferred to incubator (37° C.), 4 to 6 hours later media was changed to Lonza maintenance media (CC-3198, LonzA) and cells were transfected with ASOs at desired concentrations, with and without RNAiMax (Life Technologies, CA) according to manufacturer's protocol and placed back into the incubator. Subsequent processing was the same as described in Example 3. Primers for NGS are shown below in Table 6.

TABLE 6

| PCR and sequencing primers | |
|---|---|
| Forward primer Mouse ACTB Site 1 | TAAGTGGTTACAGGAAGTCCCTCA (SEQ ID NO: 160) |
| Reverse primer Mouse ACTB Site 1 | GGAGGCCTCAGACCTGGGCCA (SEQ ID NO: 161) |

Figure 10:
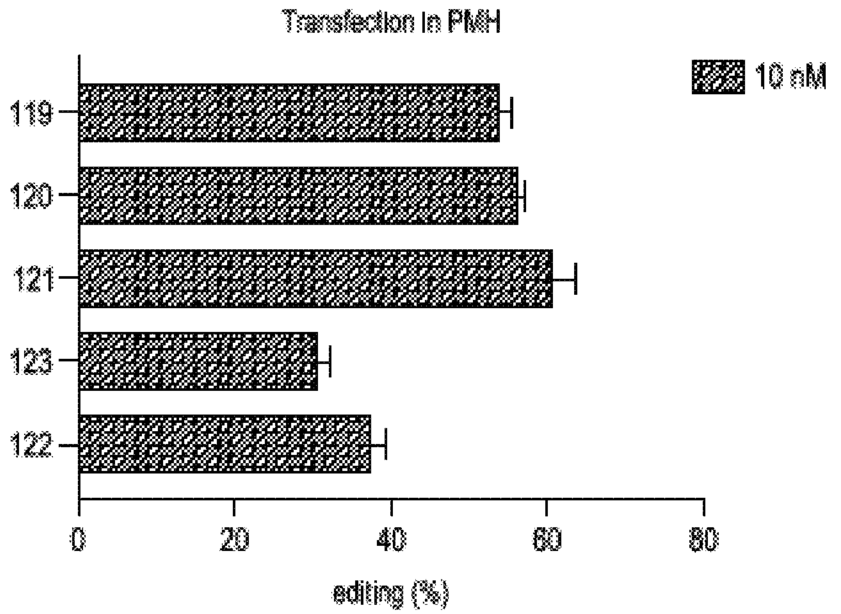
FIG. 10—Quantification of editing mouse ACTB RNA in PMH at 10 nM after transfection of oligonucleotide with lipofectamine (RNAiMax).

Similar to other targets, an increase in editing was observed for oligos containing PA-1 (FIG. 7B). When PA-1 was only included near the 3' and 5' ends of the molecules of the 42mer oligonucleotide, a drop in editing was observed relative to the oligonucleotide with 5 PA-1 linkages, but was still higher than the oligonucleotides where PA-1 was absent. Transfection editing in Piz mouse hepatocytes (PMH) was also increased for oligonucleotides comprising a PA-1 linkage (FIG. 10).

Figure 8:
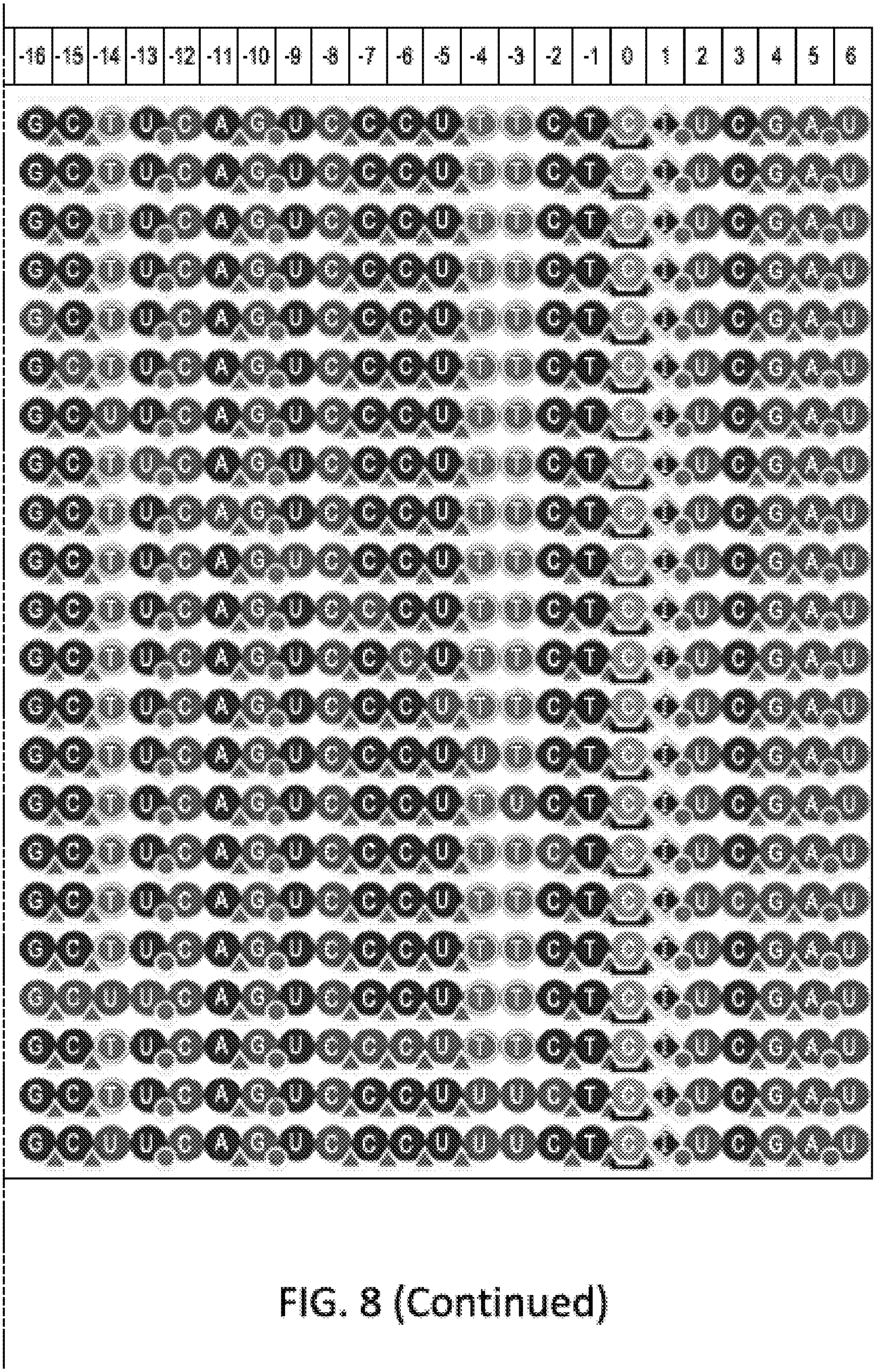
FIG. 8. (A) Schematics of oligonucleotides containing a single substitution of 2'F or 2'MOE with 2'OMe at varying positions across the oligonucleotide. (B) Percent editing of E342K SERPINA1 RNA in PiZ mouse hepatocytes in the presence ("Transfection") and absence ("Free Uptake") of the transfection reagent RNAiMAX.
Figure 8:
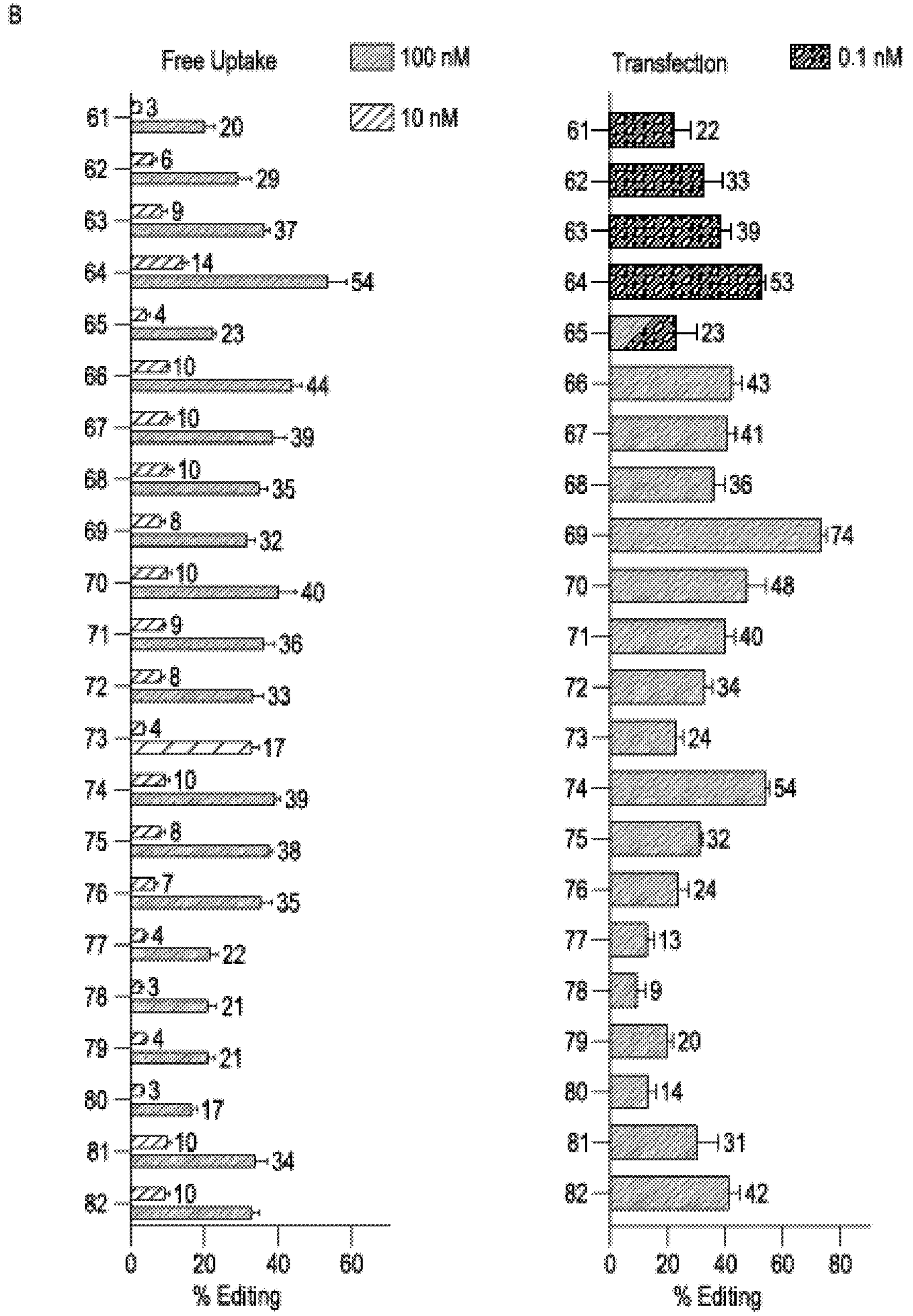
Figure 9:
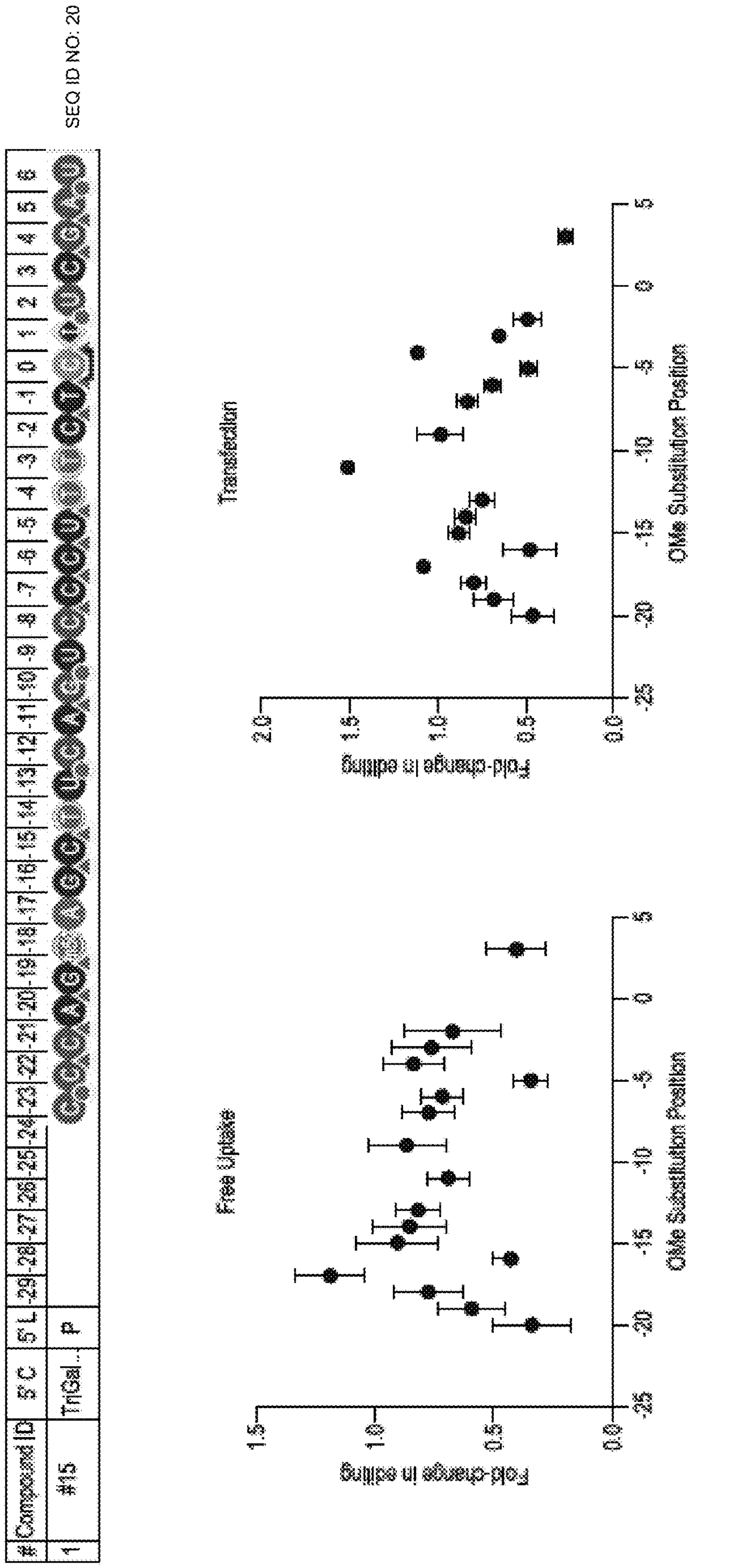
FIG. 9. Top: Schematic of parental oligonucleotide. The circled positions indicate where substitution of a 2'F with a 2'OMe resulted in a drop in editing. Bottom: fold-change in editing in PiZ mouse hepatocytes at varying positions with 2'OMe substitutions show which 2'F residues are critical for editing activity. Fold-change in editing was calculated by dividing the editing activity of the oligonucleotide with the 2'OMe substitution by the parental oligonucleotide lacking the substitution. Editing drops by half with 2'F to 0-Me at +3, −5, −16, −20.

Example 6—Oligonucleotides Having One or More 2'-Modifications and Associated Effect on Editing Efficiency The effect of 2' modification was determined for a 30mer oligonucleotide by substituting each 2'F with a 2'OMe (FIG. 8A). The PA-1 linkages and length were held constant across all of the oligonucleotides. Synthesis of the oligonucleotides was performed as described in Example 1. Editing was measured in PiZ mouse hepatocytes by free uptake and transfection, as described in Example 4.

Several residues showed the importance of 2' modifications. A decrease in editing was observed when a 2'F-ribose was substituted with a 2'OMe-ribose at positions −20, −16, −5, and +3. Some of the highest editors (oligo #63, oligo #64, oligo #67, oligo #74, oligo #75, oligo #81, oligo #82) replace 2'MOE with 2'Ome. Others (oligo #66, oligo #71) break up clusters of 2'F.

Example 7—Editing was Increased for GalNAc-Modified Oligonucleotides

Oligonucleotides containing a triantennary GalNAc were tested in C57BL/6 wild-type mice to measure editing of ACTB in the liver at seven days following the last dose. Mice were injected subcutaneously with oligonucleotides daily for five consecutive days with each dose at 10 mg/kg (QD×5 at 10 mg/kg). Livers were isolated from mice seven days after the final injection, and total RNA was isolated. The isolated RNA was used for cDNA synthesis using SuperScript IV VILO™ according to the manufacturer's instructions (Life Technologies). Ten μl of the cDNA was used for Next Generation Sequencing (NGS), Amplicon Sequencing by Quintara Biosciences. Percent editing of the site of interest was quantified as a percentage of the number of edited nucleotides based on NGS counts. Each oligonucleotide was assayed in at least three replicates. Primer sequences used for NGS are shown below in Table 6.

Figure 11:
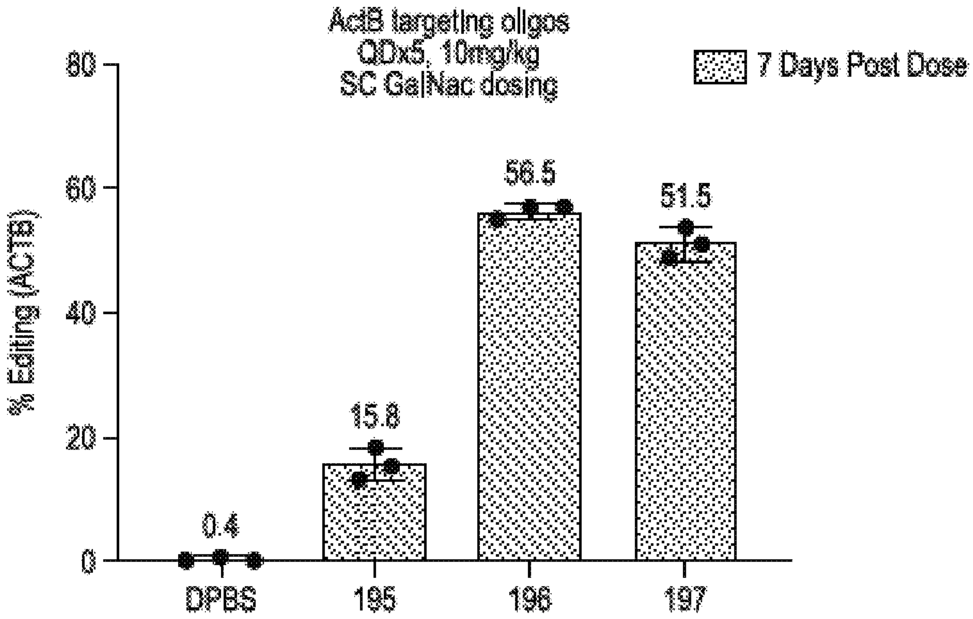
FIG. 11—In vivo editing percentage of ACTB RNA isolated from mouse livers seven days after the final dose (n=3 per group).

Greater than 50% editing was observed for PA-1 oligonucleotides containing a triantennary GalNAc modification (FIG. 11), both in 30-mer and 42-mer oligonucleotides.

Example 8—In Vitro Editing for UGP2

Editing was measured in primary mouse hepatocytes. Mouse hepatocytes were thawed in a 37° C. water bath in a 50 ml tube of Lonza rodent cryopreserved hepatocyte thawing media (MCRT50-Lonza). After centrifugation at 100×g for 5 minutes, supernatant was aspirated and the cell pellet is resuspended in Lonza plating media (Lonza). Cells were plated on 96-well collagen-coated tissue culture plates at 20000 cells/well. Cells were transferred to incubator (37° C.), 4 to 6 hours later media was changed to Lonza maintenance media (CC-3198, LonzA) and cells were transfected with ASOs at desired concentrations, with and without RNAiMax (ThermoFisher Scientific, CA) according to manufacturer's protocol and placed back into the incubator. Subsequent processing was the same as described in Example 3. Primers for NGS are shown below in Table 7.

TABLE 7

| PCR and sequencing primers | |
|---|---|
| Forward primer Mouse UGP2 Site 1 | CAGGGCATGGAGATATCTATGCT (SEQ ID NO: 305) |
| Reverse primer Mouse UGP2 Site 1 | TCCCACCCTTAACATCTGCTCGT (SEQ ID NO: 306) |

Figure 12:
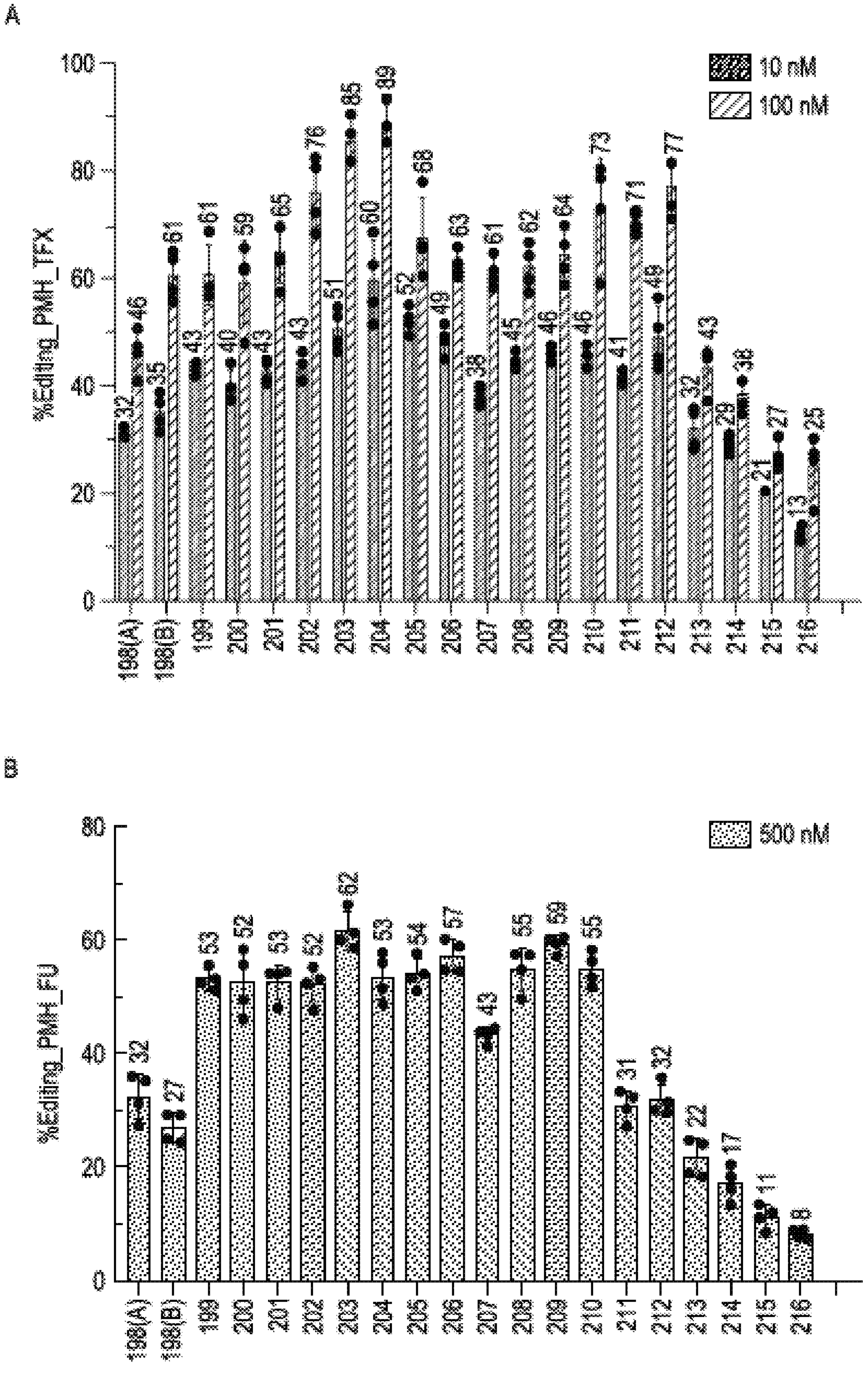
FIG. 12—In vitro editing percentage of UGP2 RNA in mouse hepatocytes in the presence of RNAiMAX ("TFX") at 10 and 100 nM of oligonucleotide (A), or in the absence of transfection reagents (free uptake or "FU") at 500 nM (n=4 per group) (B).

As shown in FIG. 12, PA-1/PS/PO variants of 42mer oligo #198 had the highest editing of the experiment, in all conditions. The presence of PA-1 at the +5 position specifically appeared to be beneficial in this chemotype (see e.g., oligos 203 and 204), in transfection. The best editing was observed for oligos having at least 5 PA-1 linkages, and additional PA-1 linkages did not appear to reduce editing. Further, editing was generally higher in oligos containing 75% PS than in other oligonucleotides.

Example 9—In Vitro Editing for NRF2

Editing was measured in in the human hepatocellular carcinoma cell line Hep3B. Hep3B cells were grown in complete MEM media (Minimum Essential Medium (ThermoFisher Scientific, CA) with 10% fetal bovine serum). On the day transfection, Hep3B cells underwent trypsinization and were washed once in MEM complete media. Cells were then reverse transfected with oligonucleotides by adding resuspended cells in MEM complete media to solutions of oligonucleotide with RNAiMax (ThermoFisher Scientific, CA) on 384-well collagen-coated tissue culture plates at 12000 cells/well. Cells were then transfected for 48 hours at 37° C. Subsequent processing was the same as described in Example 3. Primers for NGS are shown below in Table 8.

TABLE 8

| PCR and sequencing primers | |
|---|---|
| Forward primer Human NRF2 Site 1 | CGAAAAGGAAAGACAAGAGCAACT (SEQ ID NO: 307) |
| Reverse primer Human NRF2 Site 1 | TGTGGGCAACCTGGGAGTAGCT (SEQ ID NO: 308) |

Figure 13:
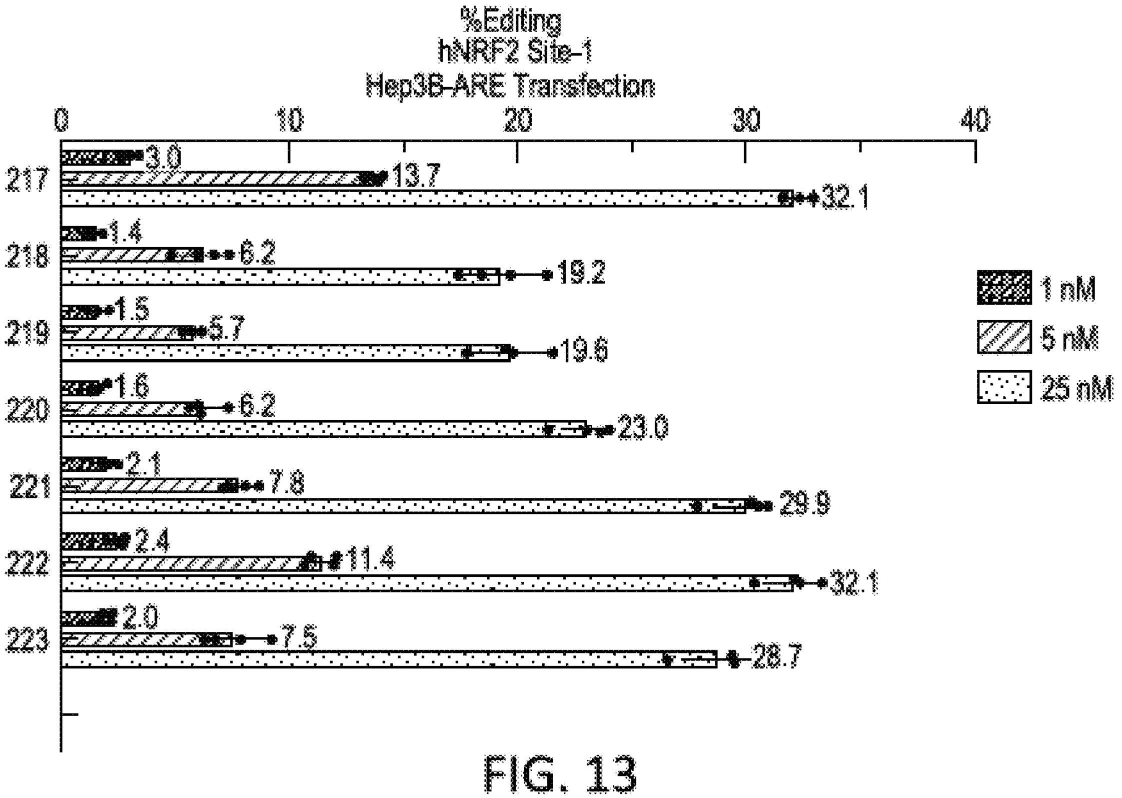
FIG. 13—In vitro editing percentage of NRF2 RNA in mouse hepatocytes in the presence of RNAiMAX ("TFX") at 1, 5, and 25 nM of oligonucleotide.

For variants of KB021602, the oligos with two or more PA-1 (oligo #218, oligo #219, oligo #220) showed a significant decrease in editing. Oligos with 5×PA-1 (oligo #218), 3×PA-1 (oligo #219), and 2×PA-1 (oligo #220) all had similar decreases in editing compared to oligo #217 at all doses tested. For single modification changes compared to oligo #217, a single addition of PA-1 at either the 5' terminus or 3' terminus also decreased editing at the 5 nM dose, and addition of a single PA-1 at the +1 position had the smallest effect on editing. See FIG. 13.

Example 10—In Vitro Editing for A1AT

Oligos were tested in vitro in PiZ hepatocytes, as described in example 4.

Figure 14:
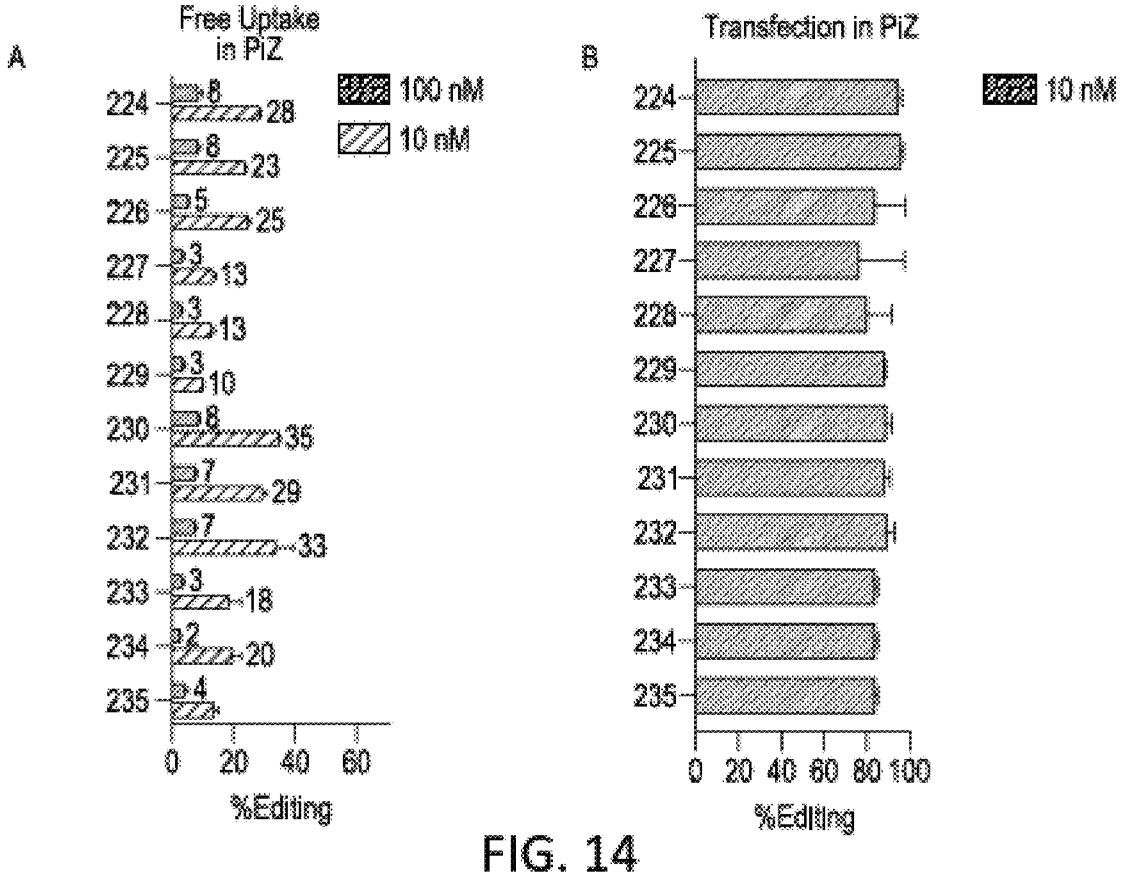
FIG. 14—In vitro editing of E342K SERPINA1 in the absence of lipofectamine ("Free Uptake") (A) and presence of RNAiMAX ("Transfection") (B) in PiZ mouse hepatocytes (n=3 per group).

As shown in FIG. 14, oligos containing PA-1 linkages showed a significant boost in editing by free uptake, and similar editing to PS-only oligos by transfection.

Figure 15:
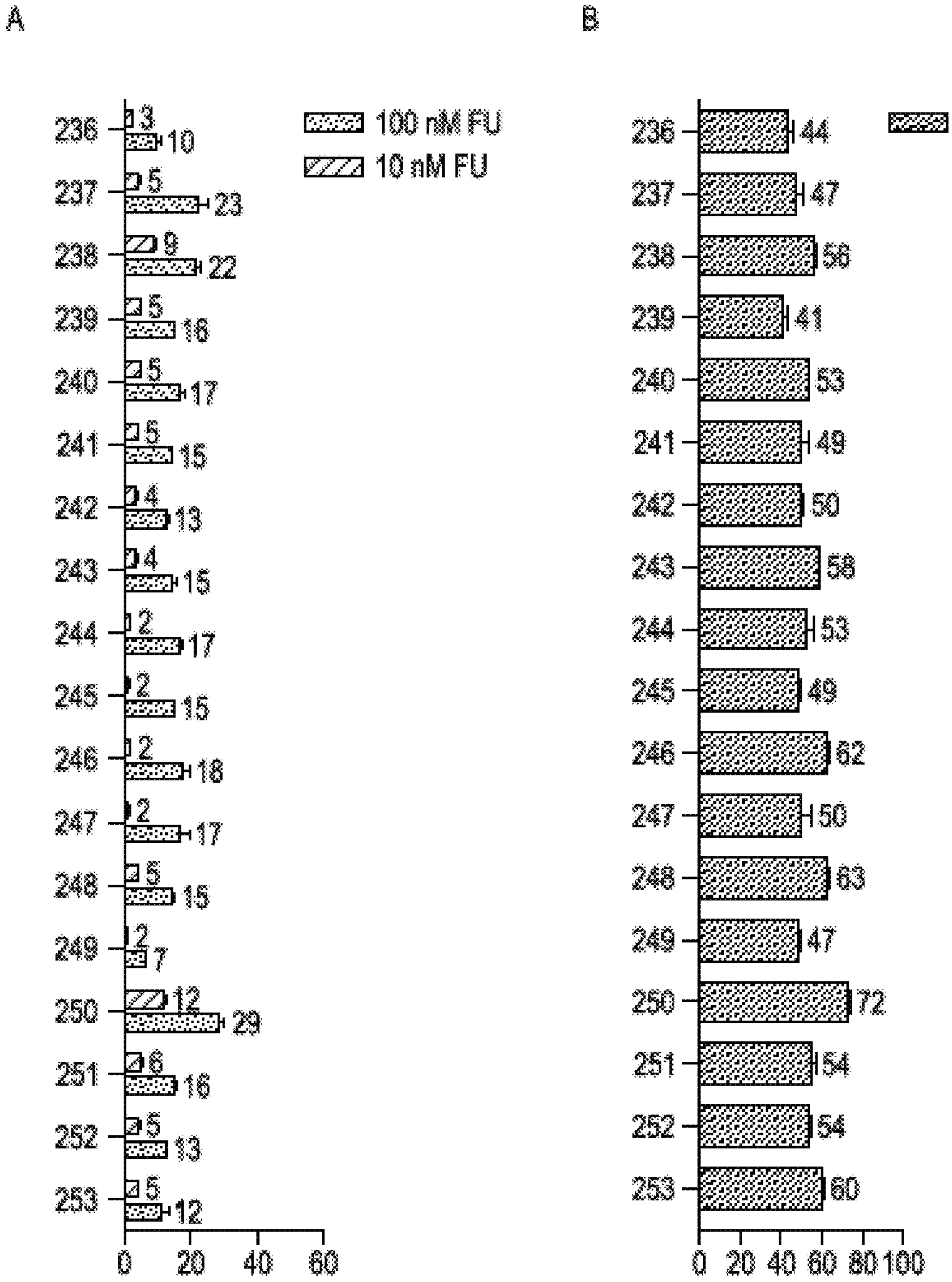
FIG. 15—In vitro editing of E342K SERPINA1 in the absence of lipofectamine ("Free Uptake") (A) and presence of RNAiMAX ("Transfection") (B) in PiZ mouse hepatocytes (n=3 per group).

A screen was conducted to determine optimal PA-1 placement for A1AT editing (FIG. 15). Localization of PA-1 was found to be flexible 5' of the triplet, with the best performing oligos containing internal PA-1 at the −21, −16, −9, and +1 positions. The combination of 2'F sugars at −20 and −19 with PA-1 at −21 yielded the highest editing (FIG. 14).

A time study of PA-1 oligonucleotides administered IV as LNP formulations in mice was conducted. PA-1 containing oligonucleotides exhibited improved editing over oligonucleotides lacking a PA-1 linkage at all time points.

What is claimed is:

1. An oligonucleotide capable of binding and recruiting an ADAR enzyme to perform editing on a target adenosine of a target RNA, the oligonucleotide comprising the structure:

$$[A_m]—X^1—X^2—X^3—[B_n]$$

wherein m+n is 24 to 50, n is at least 4, and m is at least 20;

$-X^1-X^2-X^3-$ is a Central Triplet of the oligonucleotide;

$X^1$ is position −1 of the oligonucleotide, $X^2$ is position 0 of the oligonucleotide, and $X^3$ is position +1 of the oligonucleotide;

$[A]_m$ is a first domain at positions −(m+1) to −2 of the oligonucleotide;

$[B]_n$ is a second domain at positions +2 to +(n+1) of the oligonucleotide;

each A and B is a nucleotide comprising a nucleobase, a sugar ("an A/B sugar"), and an internucleotide linkage;

each $X^1$, $X^2$, and $X^3$ comprises a nucleobase, a sugar ("an X sugar"), and an internucleotide linkage;

the A/B sugars and the $X^3$ sugar are selected from 2'-methoxy-ribose, 2'-MOE-ribose, 2'-deoxy-2'-fluororibose, 2'-fluoro-arabinose, 2-methoxy-arabinose, 2'deoxyribose and a locked nucleic acid (LNA);

the $X^1$ sugar is 2'-deoxy-2'-fluororibose or 2'deoxyribose;

the $X^2$ sugar is a beta-homo-DNA sugar;

the A/B sugars and the X sugars, collectively, are 10-70% 2'-deoxy-2'-fluororibose;

the internucleotide linkages of the oligonucleotide are 30-100% phosphorothioate and mesyl phosphoramidate linkages, and 3, 4, 5, 6, 7, 8, 9, or 10 internucleotide linkages are mesyl phosphoramidate linkages;

the internucleotide linkage (i) between the nucleotide at position −(m+1) and the nucleotide at position −(m) (the 5'end), (ii) between the nucleotide at position +(n) and the nucleotide at position +(n+1) (the 3'-end), or (iii) at each the 5'-end and 3'-end of the oligonucleotide is a mesyl phosphoramidate linkage; and the internucleotide linkage between the nucleotide at position −(m) and the nucleotide at position −(m−1) and the internucleotide linkage between the nucleotide at position +(n−1) and the nucleotide at position +(n) are independently a phosphorothioate or a mesyl phosphoramidate linkage.

2. The oligonucleotide of claim 1, wherein the $X^3$ nucleobase is hypoxanthine.

3. The oligonucleotide of claim 1, wherein no more than four sequential A/B sugars are 2'-deoxy-2'-fluororibose.

4. The oligonucleotide of claim 1, wherein the A/B sugars and X sugars, collectively, are 20-50% 2'-deoxy-2'-fluororibose.

5. The oligonucleotide of claim 1, wherein the A/B sugars are selected from 2'-methoxy-ribose, 2'-deoxy-2'-fluororibose, and 2'deoxyribose.

6. The oligonucleotide of claim 1, wherein the $X^2$ nucleobase is cytosine.

7. The oligonucleotide of claim 1, wherein the $X^1$ sugar is 2-deoxyribose.

8. The oligonucleotide of claim 1, wherein the internucleotide linkage between $X^1$ and $X^2$ is a phosphorothioate.

9. The oligonucleotide of claim 1, wherein the internucleotide linkage between $X^2$ and $X^3$ is a phosphorothioate.

10. The oligonucleotide of claim 1, wherein the internucleotide linkage between the nucleotide at position −2 and $X^1$ is a phosphorothioate.

11. The oligonucleotide of claim 1, wherein the internucleotide linkage between the nucleotide at position −9 and the nucleotide at position −8 is a mesyl phosphoramidate.

12. The oligonucleotide of claim 1, wherein the internucleotide linkage between the nucleotide at position −11 and the nucleotide at position −10 is a mesyl phosphoramidate.

13. The oligonucleotide of claim 1, wherein the internucleotide linkage between the nucleotide at position +1 and the nucleotide at position +2 is a mesyl phosphoramidate.

14. The oligonucleotide of claim 1, wherein the internucleotide linkage between the nucleotide at position +9 and the nucleotide at position +10 is a mesyl phosphoramidate.

15. The oligonucleotide of claim 1, wherein the internucleotide linkage between the nucleotide at position +1 and the nucleotide at position +2 and the internucleotide linkage between the nucleotide at position +9 and the nucleotide at position +10 are a mesyl phosphoramidate.

16. The oligonucleotide of claim 1, having 30-70% phosphorothioate and phosphoramidate linkages.

17. The oligonucleotide of claim 1, having 40-60% phosphorothioate and mesyl phosphoramidate linkages.

18. The oligonucleotide of claim 1, wherein n+m is 39.

19. The oligonucleotide of claim 1, wherein the A/B sugar at position +3 is a 2'-deoxy-2'-fluororibose.

20. The oligonucleotide of claim 1, wherein the A/B sugar at position −5 is a 2'-deoxy-2'-fluororibose.

21. The oligonucleotide of claim 1, wherein the A/B sugar at position −16 is a 2'-deoxy-2'-fluororibose.

22. The oligonucleotide of claim 1, wherein the A/B sugar at position −20 is a 2'-deoxy-2'-fluororibose.

23. The oligonucleotide of claim 1, wherein the A/B sugar at each of positions +3, −5, −16, and −20 is a 2'-deoxy-2'-fluororibose.

24. A pharmaceutical composition comprising the oligonucleotide of claim 1 and a pharmaceutically acceptable excipient.

25. The pharmaceutical composition of claim 24, wherein the oligonucleotide is encapsulated in a lipid nanoparticle (LNP).

26. An oligonucleotide capable of binding and recruiting an ADAR enzyme to perform editing on a target adenosine of a target RNA comprising the structure:

$$[A_m]—X^1—X^2—X^3—[B_n]$$

wherein m+n is 29 to 50, n is at least 9, and m is at least 20;

$-X^1-X^2-X^3-$ is a Central Triplet of the oligonucleotide;

$X^1$ is position −1 of the oligonucleotide, $X^2$ is position 0 of the oligonucleotide, and $X^3$ is position +1 of the oligonucleotide;

$[A]_m$ is a first domain at positions −(m+1) to −2 of the oligonucleotide;

$[B]_n$ is a second domain at positions +2 to +(n+1) of the oligonucleotide;

each A and B is a nucleotide comprising a nucleobase, a sugar ("an A/B sugar"), and an internucleotide linkage;

each $X^1$, $X^2$, and $X^3$ comprises a nucleobase, a sugar ("an X sugar"), and an internucleotide linkage;

the A/B sugars and the $X^3$ sugar are selected from 2'-methoxy-ribose, 2'-MOE-ribose, 2'-deoxy-2'-fluororibose, 2'-fluoro-arabinose, 2-methoxy-arabinose, 2'deoxyribose and a locked nucleic acid (LNA);

the $X^1$ and $X^3$ sugars are 2'deoxyribose;

the $X^2$ sugar is a beta-homo-DNA sugar;

the A/B sugars and the X sugars, collectively, are 10-70% 2'-deoxy-2'-fluororibose;

the internucleotide linkages of the oligonucleotide are 30-100% phosphorothioate and mesyl phosphoramidate linkages, and 5 internucleotide linkages are mesyl phosphoramidate linkages;

the internucleotide linkage between the nucleotide at position −(m+1) and the nucleotide at position −(m) (the 5'end) is a mesyl phosphoramidate linkage, the internucleotide linkage between the nucleotide at position +(n) and the nucleotide at position +(n+1) (the 3'-end) is a mesyl phosphoramidate linkage;

the internucleotide linkage between the nucleotide at position +1 and the nucleotide at position +2 is a mesyl phosphoramidate;

the internucleotide linkage between the nucleotide at position −9 and the nucleotide at position −8 is a mesyl phosphoramidate; and the internucleotide linkage between the nucleotide at position −11 and the nucleotide at position −10 is a mesyl phosphoramidate.

27. The oligonucleotide of claim 26, wherein said oligonucleotide is complementary to a SERPINA1 mRNA transcript.

28. A pharmaceutical composition comprising the oligonucleotide of claim 27 and a pharmaceutically acceptable excipient.

29. The pharmaceutical composition of claim 28, wherein the oligonucleotide is encapsulated in a lipid nanoparticle (LNP).

* * * * *